United States Patent
Guttman et al.

(10) Patent No.: US 10,689,626 B2
(45) Date of Patent: *Jun. 23, 2020

(54) COMPOSITIONS AND METHODS FOR MEASURING BLOOD GLUCOSE LEVELS

(71) Applicant: SmartZyme Innovations Ltd., Ness-Ziona (IL)

(72) Inventors: Chen Haim Guttman, Petah Tiqva (IL); David Baram, Nir-zvi (IL); Dotan Omer, Raanana (IL)

(73) Assignee: SmartZyme Innovations Ltd., Ness-Ziona (IL)

( * ) Notice: Subject to any disclaimer, the term of this patent is extended or adjusted under 35 U.S.C. 154(b) by 190 days.

This patent is subject to a terminal disclaimer.

(21) Appl. No.: 15/532,339

(22) PCT Filed: Dec. 4, 2015

(86) PCT No.: PCT/IB2015/002431
§ 371 (c)(1),
(2) Date: Jun. 1, 2017

(87) PCT Pub. No.: WO2016/087937
PCT Pub. Date: Jun. 9, 2016

(65) Prior Publication Data
US 2018/0282705 A1  Oct. 4, 2018

Related U.S. Application Data

(60) Provisional application No. 62/087,297, filed on Dec. 4, 2014.

(51) Int. Cl.
*C12N 9/04* (2006.01)
*C12Q 1/54* (2006.01)
*C12Q 1/32* (2006.01)

(52) U.S. Cl.
CPC ............ *C12N 9/0006* (2013.01); *C12Q 1/32* (2013.01); *C12Q 1/54* (2013.01); *C12Y 101/01047* (2013.01); *C12Y 101/05* (2013.01); *C12Y 101/9901* (2013.01)

(58) Field of Classification Search
None
See application file for complete search history.

(56) References Cited

U.S. PATENT DOCUMENTS

| | | |
|---|---|---|
| 2004/0023330 A1 | 2/2004 | Sode |
| 2008/0206833 A1 | 8/2008 | Yamaoka |
| 2011/0076707 A1 | 3/2011 | Yamaoka |
| 2012/0107903 A1 | 5/2012 | Sode |
| 2019/0002949 A1 | 1/2019 | Guttman et al. |

FOREIGN PATENT DOCUMENTS

| | | |
|---|---|---|
| EP | 3 162 983 A1 | 5/2017 |
| WO | 2017/013495 A2 | 1/2017 |

OTHER PUBLICATIONS

Witkowski et al., Biochemistry 38:11643-11650, 1999 (Year: 1999).*
Pfutzner et al. "Development of a new glucose dehydrogenase mutant with direct electron transfer and enhanced stability and specificity", Diabetes Technology and Therapeutics vol. 18, Suppl. 1, p. A-78, Abstract No. 194, 2016 (Year: 2016).*
International Search Report for International Application No. PCT/IB2015/002431, dated Jan. 26, 2017.
Yamashita, Yuki et al., Direct electron transfer type disposable sensor strip for glucose sensing employing an engineered FAD glucose dehydrogenase, Enzyme and Microbial Technology, vol. 52, pp. 123-128, 2013.
Supplementary European Search Report from European Patent Application No. 15865878.1 dated May 8, 2018.
"Gluconobacter japonicus fdhS, fdhC, fdhL genes for small subunit of fructose dehydrogenase, cytochrome subunit of fructose dehydrogenase, large subunit of fructose dehydrogenase, complete cds, strain: NBRC 3260"; Nucleotide, GenBank: AB728656.1; Mar. 1, 2013.
Kawai et al., "Heterologous Overexpression and Characterization of a Flavoprotein-Cytochrome c Complex Fructose Dehydrogenase of Gluconobacter japonicus NBRC3260", Applied and Environmental Microbiology, Mar. 2013, vol. 79, No. 5, pp. 1654-1660.
Marx et al., "Electrospun gold nanofiber electrodes for biosensors", Biosensors and Bioelectronics 26 (2011), pp. 2981-2986.
Ferri, et al., "Review of Glucose Oxidases and Glucose Dehydrogenases: A Bird's Eye View of Glucose Sensing Enzymes", Journal of Diabetes Science and Technology, vol. 5, Issue 5, Sep. 2011.
Krasney et al., "Evolution of the Glucose Dehydrogenase Gene in Drosophila", Mol. Biol. Evol. vol. 7, pp. 1-177, 1990.
Wang, Joseph, "Electrochemical Glucose Biosensors", Chem. Rev., vol. 108, pp. 814-825, 2008.
Whisstock et al., Quarterly Reviews of Biophysics, 2003, "Prediction of Protein Function from Protein Sequence and Structure", vol. 36, No. 3, pp. 307-340.

* cited by examiner

*Primary Examiner* — David Steadman
(74) *Attorney, Agent, or Firm* — Greenberg Traurig, LLP

(57) ABSTRACT

In some embodiments, the present invention provides a protein comprising amino acids in the following sequence $L(X)_{n=14}X^3(X)_{n=1}X^1(X)_{n=1}E(X)_{n=4}P(X)_{n=1}NR(X)_{n=3}S(X)_{n=4}D(X)_{n=2}G(X)_{n=7}Y(X)_{n=4}Y\ (X)_{n=32\text{-}34}X^2$ (SEQ ID NO: 128), wherein each X independently represents any naturally occurring amino acid residue and n indicates the number of amino acid residues represented by the respective paranthetical at that position, wherein: a) $X^1$ is selected from the group consisting of S, C, T, M, V, Y, N, P, L, G, Q, A, I, D, W, H, or E, wherein if $X^1$ is L, H or V, then $X^3$ is D; and/or b) $X^2$ is selected from the group consisting of H, L, S or V. In some embodiments, the present invention also provides a protein comprising amino acids in the sequence set forth by SEQ ID NO: 38 or SEQ ID NO: 39, except that: the amino acid at position 406 is an amino acid other than F; and/or the amino acid at position 474 is an amino acid other than N.

7 Claims, 49 Drawing Sheets

Specification includes a Sequence Listing.

| Mutant # | Position | Original AA | Mutated AA |
|---|---|---|---|
| 002 | 318 | M | T |
|  | 369 | R | H |
| 021 | 215 | N | Y |
|  | 487 | A | G |
| 022 | 116 | N | S |
|  | 219 | M | I |
|  | 440 | D | G |
| 023 | 219 | M | V |
| 024 | 330 | S | G |
|  | 257 | P | R |
|  | 474 | N | S |
| 025 | 521 | T | A |

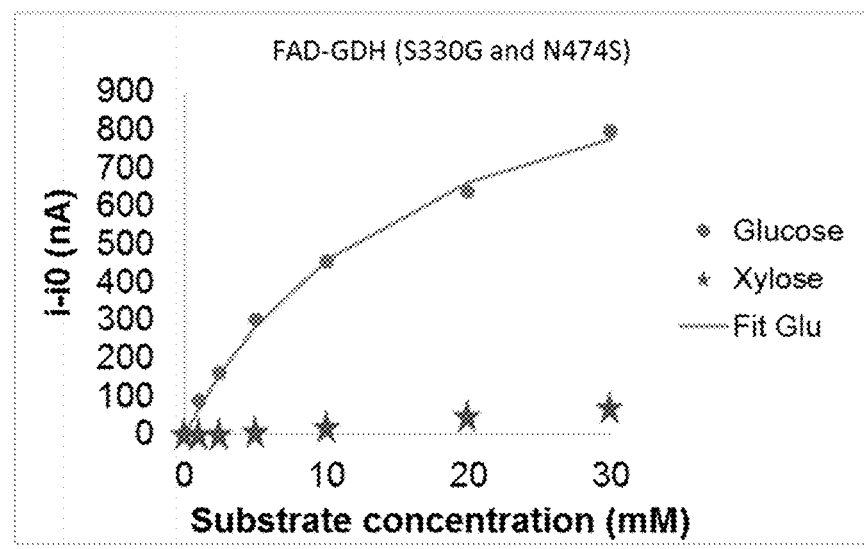
FIG. 6A
| Substrate | Maximum current [nA] | Km [mM] |
|---|---|---|
| Glucose | 1119.1 | 10.87 |
| Xylose | ND | ND |
FIG. 6B
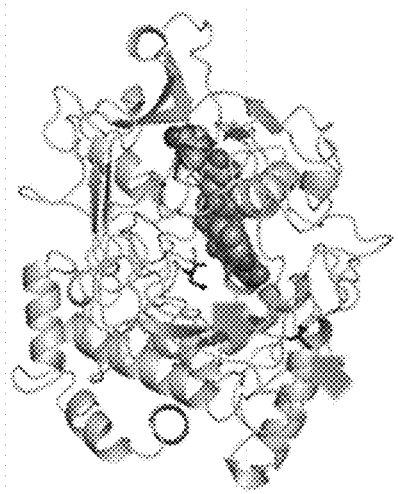
FIG. 6C

| Substrate | Maximum current [nA] | Km [mM] |
|---|---|---|
| Glucose | 685.2 | 3.37 |
| Xylose | ND | ND |

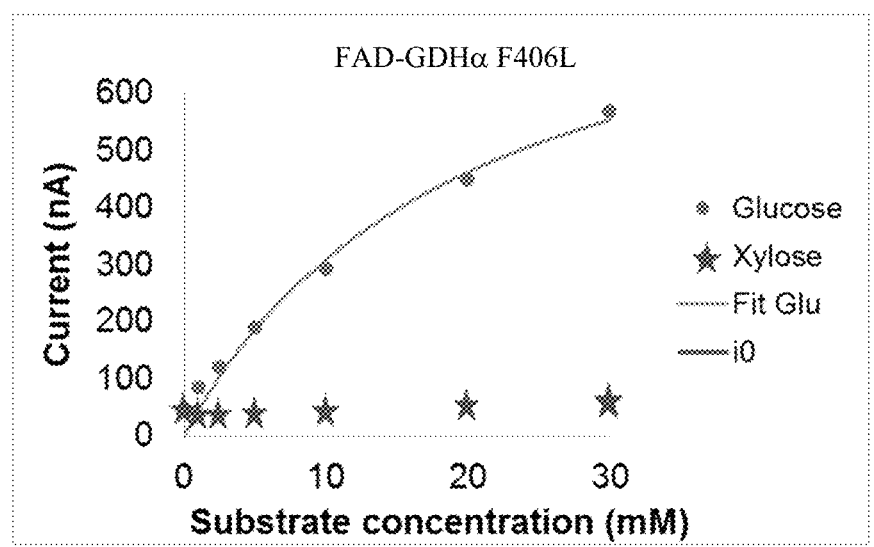
FIG. 8A
| Substrate | Maximum current [nA] | Km [mM] |
|---|---|---|
| Glucose | 914.4 | 19.55 |
| Xylose | ND | ND |
FIG. 8B
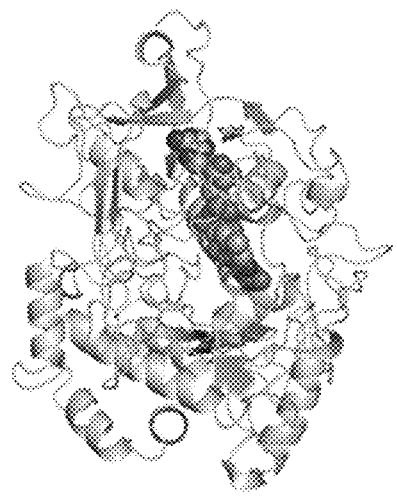
FIG. 8C

| Enzyme | Km (Glu) | Max current (nA)(Glu) | Yield (mg/L) | Linearity | | |
|---|---|---|---|---|---|---|
| | | | | R^ | a | b (nA) |
| FAD-GDHα Native mutant | 1.67 | 1341.9 | 10 | 0.4326 | NR | NR |
| FAD-GDHα Commercial | 24.7 | 3678 | NR | 0.971 | 65.44 | 210.07 |
| FAD-GDHα F406L | 19.55 | 914.4334 | 11.5 | 0.979 | 17.25 | 80.9 |
| FAD-GDHα S330G N474S | 10.87 | 1119.081167 | 15.6 | 0.9377 | 25.305 | 158.2 |
| FAD-GDHα T521A | 3.37 | 685.1705998 | 8.8 | 0.744 | 16.684 | 211 |

|  |  | Glucose |  |  | Xylose |  | Biochemistry Selectivity Kcat glu/Kcat | Electrochemistry Linearity Linearity | Current nA/mm |
|---|---|---|---|---|---|---|---|---|---|
| F406Q | 2.85 | 110.89 | 1.43 | 77.49 | 56.86 | 305.08 | 0.19 | 1.95 | 0.80 | 850.00 |
| F406R | 2.86 | 111.43 | 38.36 | 305.86 | 36.81 | 41.39 | 18.43 | 1.41 | 0.28 | 603.00 |
| F406H | 1.88 | 73.42 | 0.53 | 139.44 | 38.82 | 116.12 | 0.33 | 1.89 | 0.49 | 255.00 |
| F406M | 8.91 | 347.52 | 1.25 | 277.85 | 119.42 | 209.14 | 0.57 | 2.91 | 0.79 | 209.00 |
| F406N | 3.66 | 142.78 | 3.44 | 41.48 | 46.53 | 696.69 | 0.07 | 3.07 | 0.97 | 155.00 |
| F406G | 2.89 | 112.61 | 3.33 | 33.81 | 48.16 | 663.86 | 0.07 | 3.34 | 0.96 | 155.00 |
| F406L |  | 120.47 | 2.37 | 50.74 | 150.27 | 826.20 | 0.18 | 0.80 | 0.93 | 142.00 |
| F406I | 2.61 | 101.80 | 3.65 | 27.86 | 176.02 | 2948.50 | 0.06 | 0.58 | 0.96 | 125.00 |
| F406V | 7.96 | 310.29 | 5.47 | 56.76 | 112.39 | 1215.39 | 0.09 | 2.78 | 0.97 | 87.00 |
| F406W | 2.00 | 77.80 | 0.75 | 104.41 | 63.62 | 18.51 | 3.44 | 1.22 | 0.72 | 83.00 |
| F406C | 9.10 | 354.65 | 14.80 | 23.97 | 67.86 | 2096.37 | 0.03 | 5.23 | 0.99 | 58.00 |
| F406D | 3.52 | 82.98 | 4.23 | 19.61 | 59.18 | 423.76 | 0.14 | 1.40 | 0.99 | 56.00 |
| F406P | 4.26 | 130.68 | 4.12 | 31.71 | 37.40 | 461.81 | 0.08 | 3.49 | 1.00 | 46.00 |
| F406A | 2.81 | 109.70 | 14.75 | 7.44 | ND | ND | ND | 10000.00 | 1.00 | 34.00 |
| F406Y | 5.53 | 215.80 | 23.47 | 9.19 | ND | ND | ND | 10000.00 | 0.99 | 24.00 |
| F406T | 8.98 | 350.80 | 23.79 | 14.74 | ND | ND | ND | 10000.00 | 1.00 | 16.00 |
| F406S | 22.67 | 895.87 | 256.44 | 3.49 | ND | ND | ND | 10000.00 | 1.00 | 13.00 |
| F406E | 1.84 | 71.87 | 12.29 | 5.85 | 35.55 | 958.67 | 0.04 | 2.02 | 0.99 | 13.00 |
| Substitutions | S.A [umol/min/mg] | Kcat [min/1] | km [mM] | kcat/km | Kcat [1/min]2 | km [mM]2 | kcat/km ? |  |  |  |

FIG. 13A

|  | Biochemistry % | | | | | | |
|---|---|---|---|---|---|---|---|
|  |  | Glucose | | | Xylose | | |
| Substitutions | S.A. [umol/min/mg] | Kcat [1/min] | km [mM] | kcat/km | Kcat [1/min] | km [mM] | kcat/km |
| F406Q | 100.00 | 99.51 | 397.50 | 25.06 | 72.15 | 7128.11 | 1.03 |
| FADGDH (WT) | 100.00 | 100.00 | 100.00 | 100.00 | 100.00 | 100.00 | 100.00 |
| F406H | 65.96 | 65.89 | 146.26 | 45.09 | 49.26 | 2713.10 | 1.79 |
| F406M | 312.63 | 311.87 | 347.43 | 89.84 | 151.53 | 4886.45 | 3.10 |
| F406N | 128.42 | 128.14 | 956.23 | 13.41 | 59.04 | 16277.90 | 0.38 |
| F406G | 101.40 | 101.06 | 925.28 | 10.93 | 61.11 | 15510.72 | 0.38 |
| F406L | 0.00 | 108.11 | 659.49 | 16.41 | 190.67 | 19303.85 | 0.98 |
| F406I | 91.58 | 91.36 | 1015.10 | 9.01 | 223.34 | 68890.19 | 0.33 |
| F406V | 279.30 | 278.47 | 1518.53 | 18.35 | 142.61 | 28396.89 | 0.49 |
| F406W | 70.18 | 69.82 | 207.00 | 33.76 | 80.73 | 432.55 | 18.69 |
| F406C | 319.30 | 318.27 | 4111.11 | 7.75 | 86.11 | 48980.61 | 0.16 |
| F406D | 123.51 | 74.47 | 1175.00 | 6.34 | 75.09 | 9900.93 | 0.76 |
| F406P | 149.47 | 117.28 | 1144.74 | 10.25 | 47.45 | 10790.00 | 0.43 |
| F406A | 98.60 | 98.45 | 4097.22 | 2.41 | ND | ND | ND |
| F406Y | 194.04 | 193.66 | 6520.35 | 2.97 | ND | ND | ND |
| F406T | 315.09 | 314.82 | 6608.73 | 4.77 | ND | ND | ND |
| F406S | 795.44 | 803.97 | 71233.06 | 1.13 | ND | ND | ND |
| F406E | 64.56 | 64.50 | 3413.89 | 1.89 | 45.11 | 22398.83 | 0.22 |

FIG. 13B

|  | % | | |
| --- | --- | --- | --- |
|  | Biochemistry | Electrochemistry | |
|  | Selectivity | Linearity | Current |
| Substitutions | Kcat glu/Kcat xyl | Linearity | nA/mm2 |
| F406Q | 137.93 | 287.96 | 141.20 |
| FADGDH (WT) | 100.00 | 100.00 | 100.00 |
| F406H | 133.77 | 177.75 | 42.36 |
| F406M | 205.81 | 283.56 | 34.72 |
| F406N | 217.04 | 350.31 | 25.75 |
| F406G | 165.37 | 354.60 | 25.75 |
| F406L | 56.70 | 336.24 | 23.59 |
| F406I | 40.90 | 347.75 | 20.76 |
| F406V | 195.27 | 348.25 | 14.45 |
| F406W | 86.49 | 258.60 | 13.79 |
| F406C | 369.63 | 358.46 | 9.63 |
| F406D | 99.17 | 355.25 | 9.30 |
| F406P | 247.16 | 360.01 | 7.64 |
| F406A | 707260.16 | 359.21 | 5.65 |
| F406Y | 707260.16 | 357.92 | 3.99 |
| F406T | 707260.16 | 359.61 | 2.66 |
| F406S | 707260.16 | 359.79 | 2.16 |
| F406E | 142.98 | 358.28 | 2.16 |

FIG. 13C

| Substitutions | Glucose | | | | Xylose | | |
|---|---|---|---|---|---|---|---|
| | S.A umol/min/mg | Kcat [min/1] | km [mM] | kcat/km | Kcat [min/1] | km [mM] | kcat/km |
| FADGDH (WT) | 2.85 | 111.43 | 0.36 | 309.26 | 78.81 | 4.28 | 18.41 |
| N474A | 1.85 | 72.31 | 0.19 | 372.15 | 60.11 | 27.47 | 2.19 |
| N474G | 4.51 | 176.08 | 0.57 | 310.67 | 98.12 | 159.26 | 0.62 |
| N474H | 5.18 | 203.36 | 0.85 | 240.42 | 109.85 | 284.97 | 0.39 |
| N474L | 3.00 | 117.09 | 4.06 | 28.86 | ND | ND | ND |
| N474M | 2.37 | 92.90 | 0.24 | 381.51 | 69.02 | 25.91 | 2.66 |
| N474S | 2.18 | 85.34 | 0.42 | 205.04 | 65.49 | 134.24 | 0.49 |
| N474V | 7.23 | 282.61 | 1.95 | 144.59 | 80.81 | 399.25 | 0.20 |

FIG. 13D

| | Biochemistry % | | | | | | |
|---|---|---|---|---|---|---|---|
| | | Glucose | | | | Xylose | |
| | S.A. [umol/min/mg] | Kcat [1/Min] | km [mM] | kcat/km | Kcat [1/min]2 | km [mM]2 | kcat/km |
| FADGDH (WT) | 100.00 | 100.00 | 100.00 | 100.00 | 100.00 | 100.00 | 100.00 |
| N474A | 64.91 | 64.90 | 53.98 | 120.33 | 76.27 | 641.75 | 11.89 |
| N474G | 158.25 | 158.02 | 157.44 | 100.46 | 124.50 | 3721.11 | 3.35 |
| N474H | 181.75 | 182.50 | 234.96 | 77.74 | 139.38 | 6658.25 | 2.09 |
| N474L | 105.26 | 105.08 | 1126.87 | 9.33 | ND | ND | ND |
| N474M | 83.16 | 83.37 | 67.64 | 123.36 | 87.58 | 605.33 | 14.47 |
| N474S | 76.49 | 76.59 | 115.62 | 66.30 | 83.09 | 3136.41 | 2.65 |
| N474V | 253.68 | 253.62 | 542.94 | 46.75 | 102.54 | 9328.16 | 1.10 |

FIG. 13E

ND – Not detectable
Bold/italic marking – Negative example

| Substitutions | Linear fit ($R^2$) |
|---|---|
| F406S | 0.9977 |
| F406C | 0.994 |
| F406T | 0.9972 |
| F406V | 0.9657 |
| F406Y | 0.9925 |
| F406N | 0.9714 |
| F406P | 0.9983 |
| F406L | 0.9324 |
| F406G | 0.9833 |
| F406A | 0.9961 |
| F406I | 0.9643 |
| F406D | 0.9851 |
| F406E | 0.9935 |
| W.T | 0.2773 |

FIG. 40

|  |  | Glucose |  |  | Xylose |  |  |
|---|---|---|---|---|---|---|---|
| Substitutions | S.A. (μmol/min/mg) | Kcat [1/min] | km [mM] | kcat/km | Kcat [1/min]2 | km [mM]2 | kcat/km7 |
| F406S | 22.67 | 895.8656 | 256.439 | 3.49 | ND | ND | ND |
| F406C | 9.10 | 354.65 | 14.80 | 23.97 | 67.86 | 2096.37 | 0.03 |
| F406T | 8.98 | 350.8089 | 23.78141 | 14.74 | ND | ND | ND |
| F406M | 8.91 | 347.5189 | 1.250742 | 277.85 | 119.4309 | 209.1402 | 0.57 |
| F406V | 7.96 | 310.3943 | 5.466694 | 56.76 | 112.3889 | 1215.387 | 0.09 |
| F406Y | 5.53 | 215.8009 | 23.47327 | 9.19 | ND | ND | ND |
| F406N | 3.66 | 142.7834 | 3.442422 | 41.48 | 46.52752 | 696.6942 | 0.07 |
| F406P | 4.26 | 130.6831 | 4.121073 | 31.71 | 37.39547 | 461.812 | 0.08 |
| F406L |  | 120.4688 | 2.37416 | 50.74 | 150.2704 | 828.2048 | 0.18 |
| F406G | 2.89 | 112.6087 | 3.331009 | 33.81 | 48.15955 | 663.8588 | 0.07 |
| F406Q | 2.85 | 110.8854 | 1.430994 | 77.49 | 56.85793 | 305.0829 | 0.19 |
| F406A | 2.81 | 109.70 | 14.75 | 7.44 | ND | ND | ND |
| F406I | 2.61 | 101.7985 | 3.654363 | 27.86 | 176.0174 | 2948.5 | 0.06 |
| F406D | 3.52 | 82.98 | 4.23 | 19.61 | 59.18 | 423.76 | 0.14 |
| F406W | 2.00 | 77.80366 | 0.745194 | 104.41 | 63.62476 | 18.51327 | 3.44 |
| F406H | 1.88 | 73.42311 | 0.526541 | 139.44 | 38.81924 | 116.1207 | 0.33 |
| F406E | 1.84 | 71.87 | 12.29 | 5.85 | 35.55 | 958.67 | 0.04 |

ND – Not detectable

COMPOSITIONS AND METHODS FOR MEASURING BLOOD GLUCOSE LEVELS

RELATED APPLICATIONS

This application is a National Phase application of International Application No. PCT/IB2015/002431, filed Dec. 4, 2015, which claims the priority of U.S. provisional patent application U.S. Ser. No. 62/087,297, filed on Dec. 4, 2014; entitled "COMPOSITIONS AND METHODS OF MEASURING BLOOD GLUCOSE LEVELS," the entire contents of which are incorporated herein by reference in entirety for all purposes.

SEQUENCE LISTING

The instant application contains a Sequence Listing which has been filed electronically in ASCII format and is hereby incorporated by reference in its entirety. Said ASCII copy, created on Jan. 16, 2020, is named 151065-010605_SL.txt and is 580,318 bytes in size.

TECHNICAL FIELD

In some embodiments, the instant invention is related to compositions and methods for measuring blood glucose levels.

BACKGROUND

Blood glucose monitoring is a way of testing the concentration of glucose in the blood (glycemia). Particularly important in the care of diabetes mellitus, a blood glucose test is performed by piercing the skin (typically, on the finger) to draw blood, then applying the blood to a chemically active disposable 'test-strip'. The test is usually referred to as capillary blood glucose. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. This information should be available to the patient immediately.

A biosensor is a sensor which utilizes the molecule identifying abilities of biological materials such as microorganisms, enzymes, and antibodies to apply the biological materials as molecule recognition elements. To be specific, the biosensor utilizes a reaction which occurs when an immobilized biological material recognizes a target specific component, such as oxygen consumption by respiration of a micro-organism, an enzyme reaction, or luminescence. Among biosensors, enzyme sensors have been advanced in practical applications, and for example, enzyme sensors for glucose reduces an electron acceptor by an electron generated by a reaction between an enzyme and a substrate included in a sample solution as a specimen, and a measurement device electrochemically measures the oxidation-reduction quantity of the electron acceptor, thereby to perform quantitative analysis of the specimen. The first electrochemical glucose biosensor relied on a thin layer of glucose oxidase ($GO_x$) entrapped over an oxygen electrode via a semipermeable dialysis membrane. Measurements were made based on the monitoring of the oxygen consumed by the enzyme-catalyzed reaction (Wang 2008). Second and third generation biosensors also rely on the effects of enzyme-catalyzed reactions to determine glucose levels (Ferri et al. 2011).

SUMMARY OF INVENTION

In some embodiments, the present invention provides a protein comprising amino acids in the following sequence $L(X)_{n=14}X^3(X)_{n=1}X^1(X)_{n=1}E(X)_{n=4}P(X)_{n=1}NR(X)_{n=3}S(X)_{n=4}D(X)_{n=2}G(X)_{n=7}Y(X)_{n=4}Y(X)_{n=32-34}X^2$ (SEQ ID NO: 128), wherein each X independently represents any naturally occurring amino acid residue and n indicates the number of amino acid residues represented by the respective parenthetical at that position, wherein: a) $X^1$ is selected from the group consisting of S, C, T, M, V, Y, N, P, L, G, Q, A, I, D, W, H, or E, wherein if $X^1$ is L, H or V, then $X^3$ is D; and/or b) $X^2$ is selected from the group consisting of H, L, S or V.

In some embodiments, the present invention also provides a protein comprising amino acids in the sequence set forth by SEQ ID NO: 38 or SEQ ID NO: 39, except that: the amino acid at position 406 is an amino acid other than F; and/or the amino acid at position 474 is an amino acid other than N.

BRIEF DESCRIPTION OF DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

FIG. 6A shows some aspects of the embodiments of the present invention, illustrating a non-linear model FAD-GDHα (S330G and N474S) (from *B. cepacia*) and FIG. 6B is a table with quantified data relating to FIG. 6A. FIG. 6C is a homology model of FAD-GDH (S330G and N474S) alpha subunit based on Glucose oxidase determined structure.

FIG. 8A shows some aspects of some embodiments of the present invention, illustrating a non-linear fit FAD-GDHα F406L (from *B. cepacia*) and FIG. 8B is a table with quantified data relating to FIG. 8A. FIG. 8C is a homology model of FAD-GDH F406L alpha subunit based on Glucose oxidase determined structure.

FIGS. 13A-E show tables which show the collected data in connection with the compositions of the present invention. FIG. 13A describes biochemical and electrochemical parameters of the 406 mutants. FIG. 13B represents the biochemical kinetic characteristics of the 406 mutants as a percentage from the wild type (100%). FIG. 13C describes the biochemical selectivity and electrochemical linearity and current for the 406 mutants represented as a percentage from the wild type (100%). FIG. 13D describes biochemical rate of activity towards glucose and xylose of the 474 mutants. FIG. 13E describes biochemical rate of activity towards glucose and xylose of the 474 mutants, represented as a percentage from the wild type (100%). As used herein, "selectivity" can refer to an affinity of a protein, where the protein chooses to bind and/or catalyze one substrate instead of a second substrate—by way of illustration, but not limited to, FAD-GDHα binding and/or catalyzing glucose at a higher rate than xylose. As used herein, "biochemical activity" can refer to any function mediated by the protein, e.g., but not limited to, the catalytic activity of an enzyme.

FIG. 14 shows the biochemical response of FAD-GDHα N474L to varying concentrations of glucose (rhombus), and xylose (rectangle). FIG. 15 shows the biochemical response of N474L to glucose and the non-linear fit through which Km (k) and Vmax have been obtained.

FIG. 16A shows the biochemical response of FAD-GDHα N474V to varying concentrations of glucose (rhombus), and xylose (rectangle). FIG. 16B shows the biochemical response of FAD-GDHα N474V to glucose and the non-linear fit through which Km (k) and Vmax have been obtained.

FIG. 17A shows a biochemical response of FAD-GDHα N474H to varying concentrations of glucose (rhombus), and xylose (rectangle). FIG. 17B shows a biochemical response of FAD-GDHα N474H to glucose and the non-linear fit through which Km (k) and Vmax have been obtained.

FIG. 18A shows the biochemical response of FAD-GDHα N474S to varying concentrations of glucose (rhombus), and xylose (rectangle). FIG. 18B shows the biochemical response of FAD-GDHα N474S to glucose and the non-linear fit through which Km (k) and Vmax have been obtained.

FIG. 18A shows the biochemical response of FAD-GDHα N474A to glucose and the non-linear fit through which Km (k) and Vmax have been obtained.

FIG. 21B shows the biochemical response of FAD-GDHα F406L to varying concentrations of glucose (rhombus), and xylose (rectangle). FIG. 21B shows the biochemical response of F406L to glucose and the non-linear fit through which Km (k) and Vmax have been obtained.

FIGS. 23A-24C show some aspects of some embodiments of the present invention. FIG. 23A shows the biochemical response of FAD-GDHα F406A to varying concentrations of glucose (rhombus), and xylose (rectangle).

FIGS. 24A-C show some aspects of some embodiments of the present invention. FIG. 24A shows the biochemical response of FAD-GDHα F406C to varying concentrations of glucose (rhombus), and xylose (rectangle). FIG. 24B shows the iochemical response of F406C to glucose and the non-linear fit through which Km (k) and Vmax have been obtained. F406C enzyme activity was determined via monitoring decrease of Dichlorophenolindophenol (DCIP) signal at $OD_{600}$. FIG. 24C shows the electrochemical data representing the current response of the biosensor to various glucose concentrations (shown as a rhombus) and the linear fit across the data range is represented by the $R^2$ value.

FIG. 25A shows the biochemical response of FAD-GDHα F406E to varying concentrations of glucose (rhombus), and xylose (rectangle). FIG. 25B shows the biochemical response of F406E to glucose and the non-linear fit through which Km (k) and Vmax have been obtained. F406E enzyme activity was determined via monitoring decrease of Dichlorophenolindophenol (DCIP) signal at $OD_{600}$. FIG. 25C shows electrochemical data representing the current response of the biosensor to various glucose concentrations (shown as a rhombus) and the linear fit across the data range is represented by the $R^2$ value.

FIG. 26A shows the biochemical response of FAD-GDHα F406D to varying concentrations of glucose (rhombus), and xylose (rectangle). FIG. 26B shows the biochemical response of F406D to glucose and the non-linear fit through which Km (k) and Vmax have been obtained. F406D enzyme activity was determined via monitoring decrease of Dichlorophenolindophenol (DCIP) signal at $OD_{600}$. FIG. 26C shows the electrochemical data representing the current response of the biosensor to various glucose concentrations (shown as a rhombus) and the linear fit across the data range is represented by the $R^2$ value.

FIG. 27A shows the biochemical response of FAD-GDHα F406G to varying concentrations of glucose (rhombus), and xylose (rectangle). FIG. 27B shows the biochemical response of F406G to glucose and the non-linear fit through which Km (k) and Vmax have been obtained. F406G enzyme activity was determined via monitoring decrease of Dichlorophenolindophenol (DCIP) signal at $OD_{600}$. FIG. 27C shows electrochemical data representing the current response of the biosensor to various glucose concentrations (shown as a rhombus) and the linear fit across the data range is represented by the $R^2$ value.

FIG. 28A shows the biochemical response of FAD-GDHα F406H to varying concentrations of glucose (rhombus), and xylose (rectangle). FIG. 28B shows the biochemical response of F406H to glucose and the non-linear fit through which Km (k) and Vmax have been obtained.

FIG. 29A shows the biochemical response of FAD-GDHα F406I to varying concentrations of glucose (rhombus), and xylose (rectangle). FIG. 29B shows the biochemical response of F406I to glucose and the non-linear fit through which Km (k) and Vmax have been obtained. F406I enzyme activity was determined via monitoring decrease of Dichlorophenolindophenol (DCIP) signal at $OD_{600}$. FIG. 29C shows electrochemical data representing the current response of the biosensor to various glucose concentrations (shown as a rhombus) and the linear fit across the data range is represented by the $R^2$ value.

FIG. 30A shows the biochemical response of FAD-GDHα F406M to varying concentrations of glucose (rhombus), and xylose (rectangle). FIG. 30B shows the biochemical response of F406M to glucose and the non-linear fit through which Km (k) and Vmax have been obtained. F406M enzyme activity was determined via monitoring decrease of Dichlorophenolindophenol (DCIP) signal at $OD_{600}$.

FIG. 31A shows the biochemical response of FAD-GDHα F406N to varying concentrations of glucose (rhombus), and xylose (rectangle). FIG. 31B shows the biochemical response of F406N to glucose and the non-linear fit through which Km (k) and Vmax have been obtained. F406N enzyme activity was determined via monitoring decrease of Dichlorophenolindophenol (DCIP) signal at $OD_{600}$. FIG. 31C shows electrochemical data representing the current response of the biosensor to various glucose concentrations (shown as a rhombus) and the linear fit across the data range is represented by the $R^2$ value.

FIG. 32A shows the biochemical response of FAD-GDHα F406Q to varying concentrations of glucose (rhombus), and xylose (rectangle). FIG. 32B shows the biochemical response of F406Q to glucose and the non-linear fit through which Km (k) and Vmax have been obtained.

FIG. 33A shows biochemical response of FAD-GDHα F406S to varying concentrations of glucose (rhombus), and xylose (rectangle). FIG. 33 shows biochemical response of F406S to glucose and the non-linear fit through which Km (k) and Vmax have been obtained. F406S enzyme activity was determined via monitoring decrease of Dichlorophenolindophenol (DCIP) signal at $OD_{600}$. FIG. 33C shows electrochemical data representing the current response of the biosensor to various glucose concentrations (shown as a rhombus) and the linear fit across the data range is represented by the $R^2$ value.

FIG. 34A shows the biochemical response of FAD-GDHα F406T to varying concentrations of glucose (rhombus), and xylose (rectangle). FIG. 34B shows biochemical response of F406T to glucose and the non-linear fit through which Km (k) and Vmax have been obtained. F406T enzyme activity was determined via monitoring decrease of Dichlorophenolindophenol (DCIP) signal at $OD_{600}$. FIG. 34C shows electrochemical data representing the current response of the biosensor to various glucose concentrations (shown as a rhombus) and the linear fit across the data range is represented by the $R^2$ value.

FIG. 35A shows a biochemical response of FAD-GDHα F406W to varying concentrations of glucose (rhombus), and xylose (rectangle). FIG. 35B shows a biochemical response of F406W to glucose and the non-linear fit through which Km (k) and Vmax have been obtained.

FIG. 36A shows the biochemical response of FAD-GDHα F406Y to varying concentrations of glucose (rhombus), and xylose (rectangle). FIG. 36B shows the biochemical response of F406Y to glucose and the non-linear fit through which Km (k) and Vmax have been obtained. F406Y enzyme activity was determined via monitoring decrease of Dichlorophenolindophenol (DCIP) signal at $OD_{600}$. FIG. 36C shows electrochemical data representing the current response of the biosensor to various glucose concentrations (shown as a rhombus) and the linear fit across the data range is represented by the $R^2$ value.

FIG. 37A shows the biochemical response of FAD-GDHα F406V to varying concentrations of glucose (rhombus), and xylose (rectangle). FIG. 37B shows the biochemical response of F406V to glucose and the non-linear fit through which Km (k) and Vmax have been obtained. F406V enzyme activity was determined via monitoring decrease of Dichlorophenolindophenol (DCIP) signal at $OD_{600}$. FIG. 37C shows electrochemical data representing the current response of the biosensor to various glucose concentrations (shown as a rhombus) and the linear fit across the data range is represented by the $R^2$ value.

FIG. 38A shows the biochemical response of FAD-GDHα F406P to varying concentrations of glucose (rhombus), and xylose (rectangle). FIG. 38B shows the biochemical response of F406P to glucose and the non-linear fit through which Km (k) and Vmax have been obtained. F406P enzyme activity was determined via monitoring decrease of Dichlorophenolindophenol (DCIP) signal at $OD_{600}$. FIG. 38C shows electrochemical data representing the current response of the biosensor to various glucose concentrations (shown as a rhombus) and the linear fit across the data range is represented by the $R^2$ value.

FIG. 40 shows a table of electrochemistry data of the embodiments of the composition of the present invention. Mutations in position 406 provide improved linearity over the entire range of physiological range: F406-S/C/T/V/Y/N/P/L/G/A/I/D/E.

FIG. 41 shows some aspects of some embodiments of the present invention. Mutations in position 406 that provide improved selectivity of glucose: F406-S/C/T/M/V/Y/N/P/L/G/Q/A/I/D/H/E. F406W provides an example of a substitution that reduces the enzyme selectivity towards glucose.

Figure 42A:
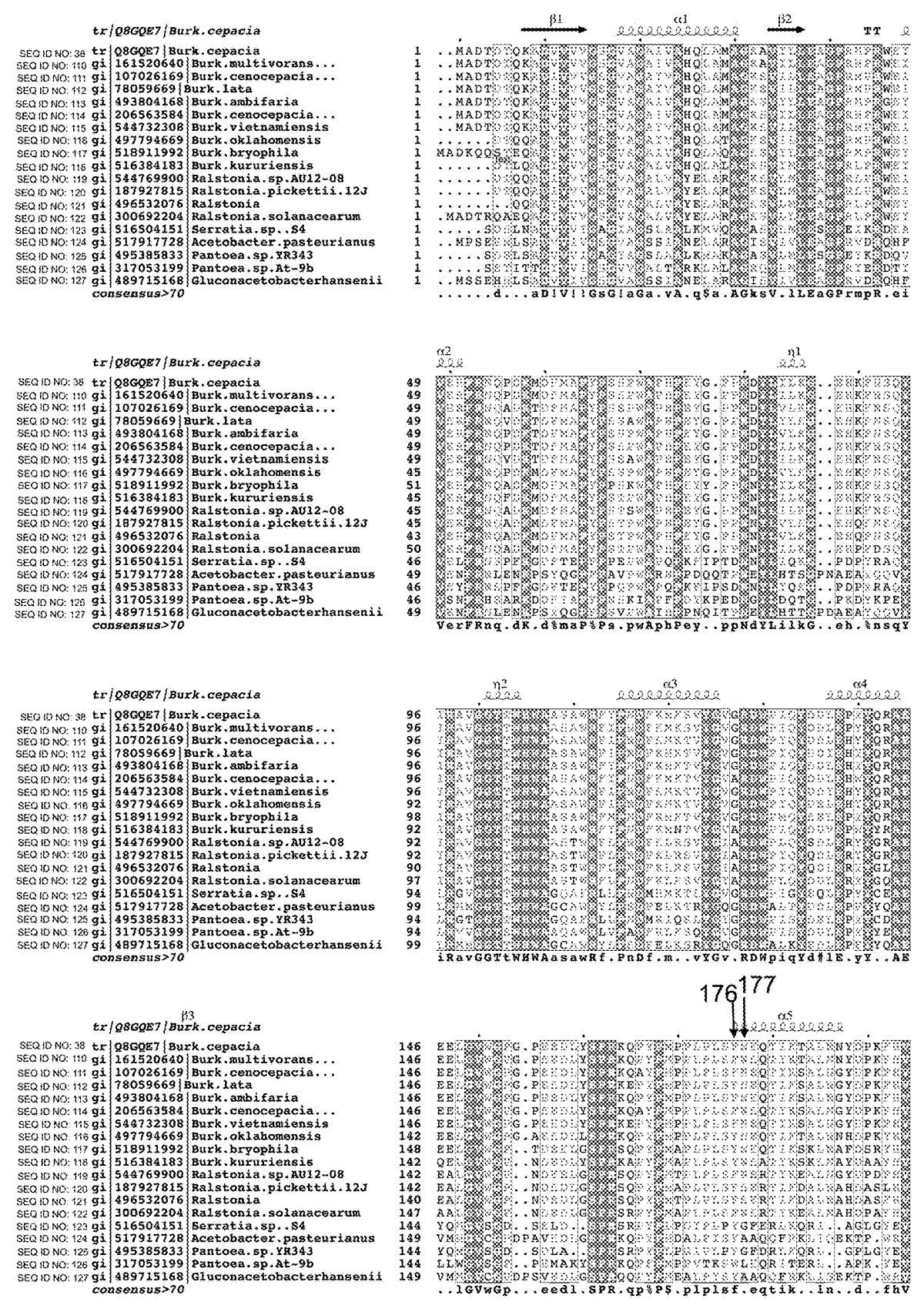
Figure 42B:
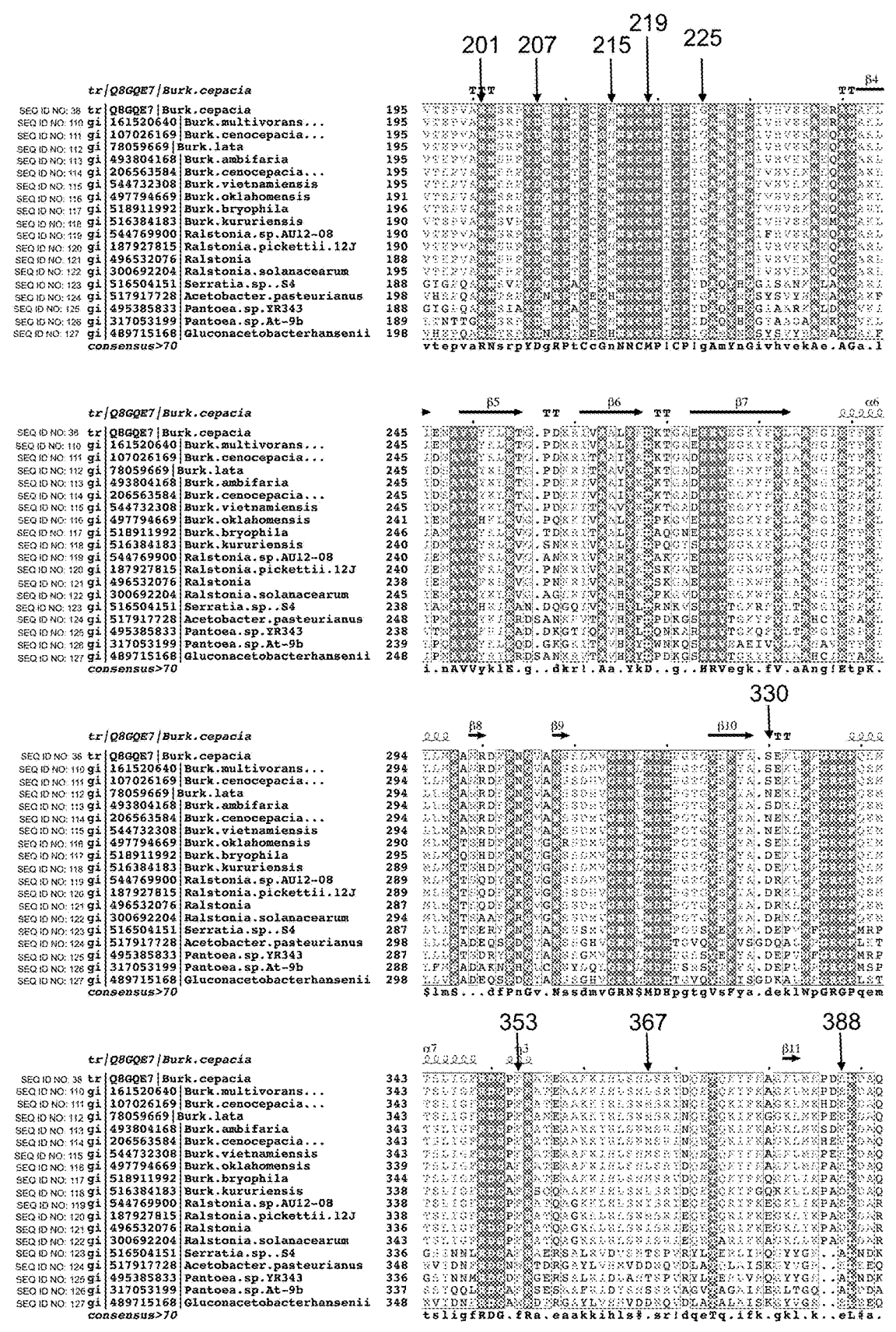
Figure 42C:
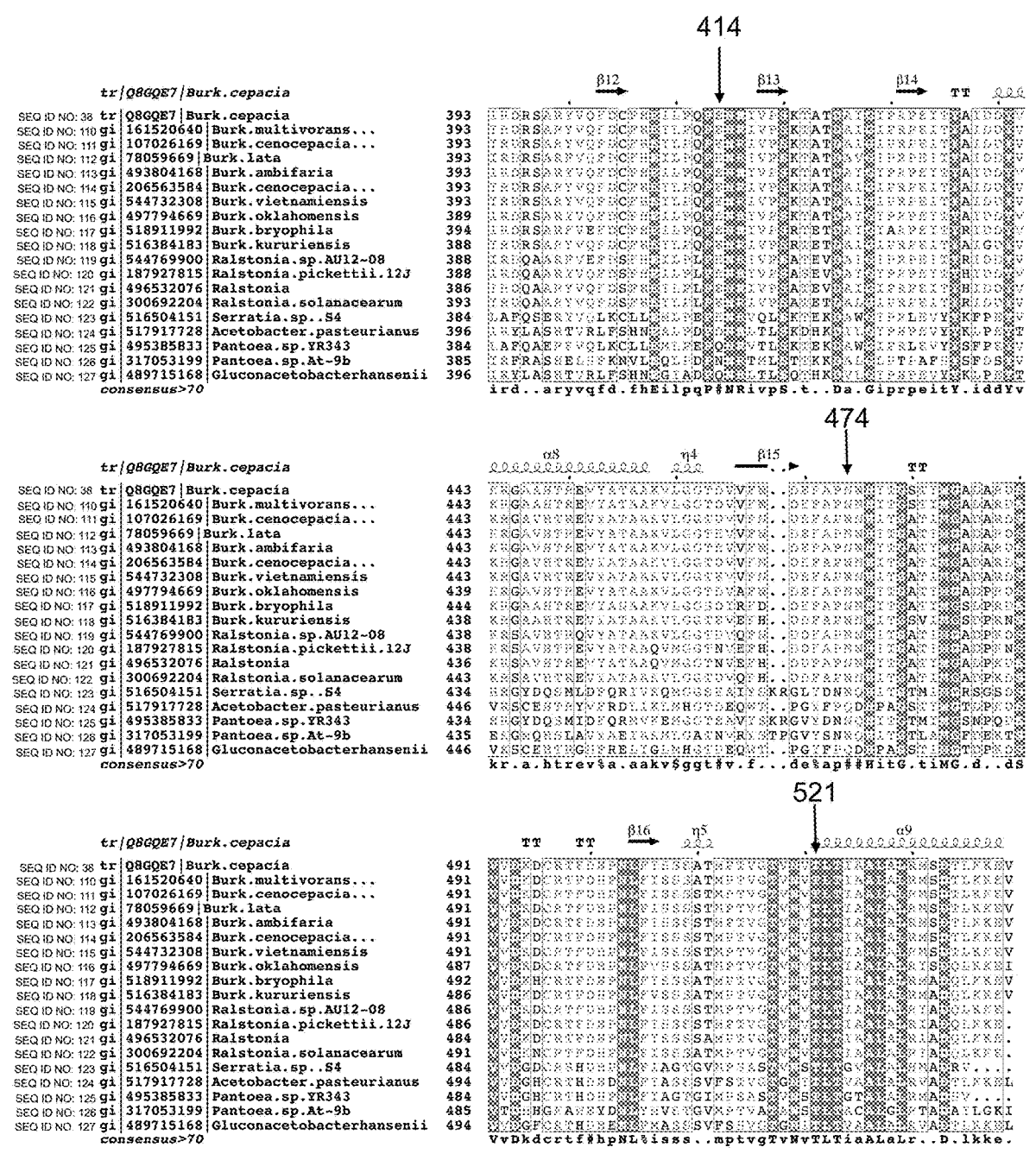

FIGS. 42A to 42C shows a sequence alignment for multiple different FAD-GDHα proteins (SEQ ID NOs: 110-127). For the consensus sequence, uppercase indicates identity, lowercase indicates consensus level of greaters than 0.5, ! is any one of I or V, $ is an one of L or M, % is any one of F or Y, # is any one of NDQEBZ.

Figure 1A:
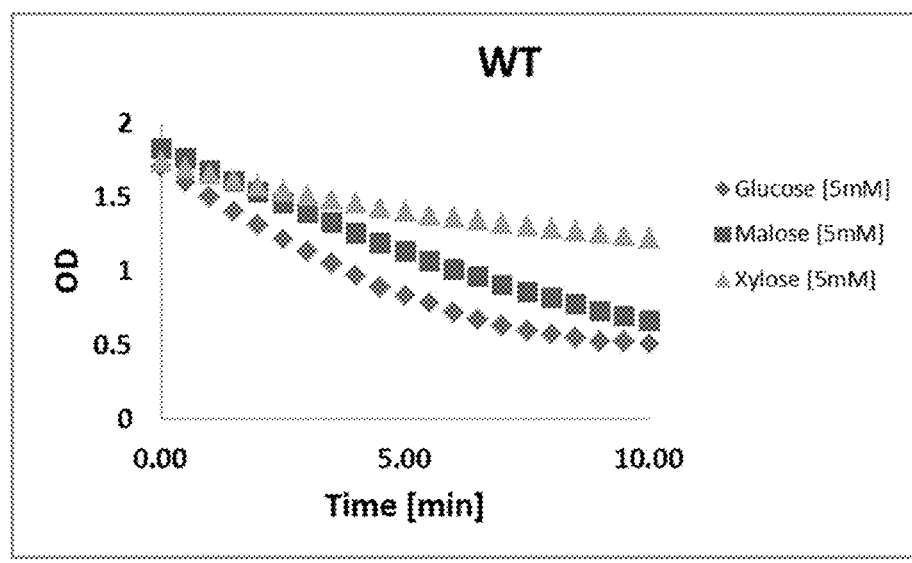
FIG. 1A shows some aspects of the embodiments of the present invention, showing the activity of wild type FAD-GDHα (SEQ ID NO: 1) by plotting absorbance of glucose, maltose, and xylose against reaction time.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

DESCRIPTION OF EXEMPLARY EMBODIMENTS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, throughout the specification, the meaning of "a," "an," and "the" include plural references. The meaning of "in" includes "in" and "on."

As used herein, "linearity" refers to the $R^2$ value of a linear fit which is calculated for the plot of the relation between substrate concentration and the measured current. In some embodiments, good linearity is considered as an $R^2$ value equal or above 0.85 across the entire range of physiological glucose level (0-600 mg/dL). In some embodiments, good linearity is considered to be an $R^2$ value that is equal or above 0.9 across the entire range of physiological glucose level. In some embodiments, good linearity is considered as an $R^2$ value equal or above 0.95 across the entire range of physiological glucose level. Glucose sensing devices transform the measured current to glucose level using a linear based algorithm. Thus the linear range of the glucose sensing enzyme improves the accuracy of measurement of the blood glucose concentration.

The flavoprotein Glucose dehydrogenase (FAD-GDH, EC 1.1.5.9) is quite recently utilized as a glucose sensing enzyme in glucose test strips. The FAD-GDH catalyzes the oxidation of glucose through the use various electron acceptors (such as Dichlorophenolindophenol).

To date FAD-GDH has been isolated from gram negative bacteria (*Burkholderia cepacia*), fungi (*Aspergillus* sp., *A. oryzae*, *A. niger*, *A. terreus*) and from insects (*Drosophila melanogaster*, *Anopheles gambiae*, *Apis mellifera*, *Tribolium castaneum*).

The protein is composed of three subunits: a catalytic subunit harboring FAD at its redox center (alpha, 67 kDa), a multiheme electron-transfer subunit (beta, 43 kDa) and a chaperon subunit (gamma, 20 kDa). The alpha subunit can be recombinantly expressed and purified in *E. Coli* independently of the other subunits, as well as with the beta and the gamma subunits while maintaining catalytic activity in either cases. FAD-GDH is an enzyme that catalyses the oxidation of glucose in the presence of an electron acceptor, such as 2,6-dichlorophenolindophenol or potassium ferricyanide. FAD-GDH can be used in analyte detection assays. FAD-GDH is comprised of multiple subunits, including the catalytic subunit alpha.

In some embodiments the FAD-GDH of the present invention, including all mutants described in the present invention, can be expressed with a beta (β) subunit (a cytochrome domain) in tandem or on a different plasmid, expressed and purified to generate a protein which can deliver improved electron transfer to various biosensor applications. In some embodiments, the FAD-GDH of the present invention can be expressed and purified without a beta (β) subunit, as further detailed below.

In some embodiments, analyte detection assays, e.g., glucose detection assays, can be based on the production of hydrogen peroxide and the subsequent detection thereof. For example, glucose is quantitated using assays by first oxidizing glucose with glucose oxidase to produce gluconic acid and hydrogen peroxide. The resultant hydrogen peroxide, in conjunction with a peroxidase, causes the conversion of one or more organic substrates, i.e. an indicator, into a chromogenic product, which product is then detected and related to the glucose concentration in the initial sample.

In the present invention, the inventors have mutated the alpha subunit and co-expressed it with a native gamma subunit. The artificially mutated FAD-GDH alpha subunit of the present invention can be co-expressed with either a native or a mutated gamma subunit, beta subunit, or both.

In some embodiments, the present invention provides a protein comprising amino acids in the following sequence $L(X)_{n=14}X^3(X)_{n=1}X^1(X)_{n=1}E(X)_{n=4}P(X)_{n=1}NR(X)_{n=3}S(X)_{n=4}D(X)_{n=2}G(X)_{n=7}Y(X)_{n=4}Y(X)_{n=32-34}X^2$ (SEQ ID NO: 128), wherein each X independently represents any naturally occurring amino acid residue and n indicates the number of amino acid residues represented by the respective parenthetical at that position, wherein: a) $X^1$ is selected from the group consisting of S, C, T, M, V, Y, N, P, L, G, Q, A, I, D, W, H, or E, wherein if $X^1$ is L, H or V, then $X^3$ is D; and/or b) $X^2$ is selected from the group consisting of H, L, S or V. In one embodiment, the protein comprises the sequence: $(X)_{n=3-11}D(X)_{n=1}V(X)_{n=2}G(X)_{n=1}G(X)_{n=2}G(X)_{n=3}A(X)_{n=5}AG(X)_{n=2}V(X)_{n=2}LE(X)_{n=1}GP(X)_{n=3}R(X)_{n=3}V(X)_{n=2}FR(X)_{n=4}K(X)_{n=5}P(X)_{n=1}P(X)_{n=4}A(X)_{n=2}P(X)_{n=5-6}N(X)_{n=1}YL(X)_{n=3}G(X)_{n=7-9}Y(X)_{n=1}R(X)_{n=2}GGT(X)_{n=1}WHWA(X)_{n=4}R(X)_{n=2}P$ $(X)_{n=1}D(X)_{n=6}YG(X)_{n=2}RDW(X)_{n=3}Y(X)_{n=3}E(X)_{n=2}Y(X)_{n=2}AE(X)_{n=3}GV(X)_{n=1}G(X)_{n=5-9}SP\ R(X)_{n=4}P(X)_{n=23-25}V(X)_{n=6}RN(X)_{n=3}YD(X)_{n=1}RP(X)_{n=1}C(X)_{n=1}G(X)_{n=1}$ NNCMP $(X)_{n=1}CP(X)_{n=2}A(X)_{n=1}Y(X)_{n=1}G(X)_{n=6}A(X)_{n=2}AG(X)_{n=6}AVV(X)_{n=3}E(X)_{n=8-9}A$ $(X)_{n=2}Y(X)_{n=1}D(X)_{n=5}HRV(X)_{n=5}V(X)_{n=2}A(X)_{n=3}E(X)_{n=2}K(X)_{n=4}S(X)_{n=5}P(X)_{n=1}G(X)_{n=2}N$ $(X)_{n=5}GRN(X)_{n=1}MDH(X)_{n=4}V(X)_{n=1}F(X)_{n=6-7}W(X)_{n=1}GRGP(X)_{n=9}RDG(X)_{n=2}R\ (X)_{n=19}T(X)_{n=12-14}L(X)_{n=14}X^3(X)_{n=1}X^1(X)_{n=1}E(X)_{n=4}P(X)_{n=1}NR(X)_{n=3}$ $S(X)_{n=4}D(X)_{n=2}G(X)_{n=7}Y(X)_{n=4}Y(X)_{n=32-34}X^2(X)_{n=2}H(X)_{n=2}G(X)_{n=3}MG(X)_{n=5}SV(X)_{n=1}D$ $(X)_{n=9}NL(X)_{n=12}T(X)_{n=1}N(X)_{n=1}TLT(X)_{n=2}AL(X)_{n=1}L(X)_{n=3}D(X)_{n=2-6}$ (SEQ ID NO: 129). A person of ordinary skill in the art would understand that to create a protein with Flavin Adenine Dinucleotide Glucose Dehydrogenase alpha subunit (FAD-GDHα) activity according to the instant invention, one would select amino acid residues for such a protein based on the amino acid sequence of a naturally-occurring FAD-GDHα protein. The amino acid residues specified in the above sequences (i.e. those residues not identified by "X") represent residues that are conserved among FAD-GDHα proteins. Such residues serve as a reference point to better specify for the person of ordinary skill in the art the location of amino acid residues in naturally-occurring FAD-GDHα (i.e. those identified herein as "$X^1$" and "$X^2$") which can be mutated to create a non naturally-occurring FAD-GDHα protein with improved properties.

In some embodiments, the FAD-GDHα proteins of the instant invention includes at least one mutation (e.g., a point mutation) in the amino acid sequence, e.g., SEQ ID NOs: 3-8, e.g., as shown in Table 2. In some embodiments, the the mutation is located at methionine 43 of FAD-GDHα. In some embodiments, the mutation is located at isoleucine 346 of FAD-GDHα. In some embodiments, the mutation is located at serine 420 of FAD-GDHα. In some embodiments, the mutation is located at serine 365 of FAD-GDHα. In some embodiments, the mutation is located at glycine 208 of FAD-GDHα. In some embodiments, the mutation is located at threonine 521 of FAD-GDHα. In some embodiments, the mutation is located at valine 306 of FAD-GDHα. In some embodiments, the mutation is located at glutamine 412 of FAD-GDHα. In some embodiments, the mutation is located at arginine 416 of FAD-GDHα. In some embodiments, the mutation is located at asparagine 215 of FAD-GDHα. In some embodiments, the mutation is located at alanine 487 of FAD-GDHα. In some embodiments, the mutation is located at asparagine 116 of FAD-GDHα. In some embodiments, the mutation is located at methionine 219 of FAD-GDHα. In some embodiments, the mutation is located at aspartic acid 440 of FAD-GDHα. In some embodiments, the mutation is located at serine 330 of FAD-GDHα. In some embodiments, the mutation is located at proline 257 of FAD-GDHα. In some embodiments, the mutation is located at asparagine 474 of FAD-GDHα. In some embodiments, the mutation is located at threonine 521 of FAD-GDHα. In some embodiments, the mutation is located at serine 420 of FAD-GDHα. In some embodiments, the mutation is located at serine 365 of FAD-GDHα. In some embodiments, the mutation is located at isoleucine 261 of FAD-GDHα. In some embodiments, the mutation is located at threonine 521 of FAD-GDHα. In some embodiments, the mutation is located at proline 173 of FAD-GDHα. In some embodiments, the mutation is located at methionine 219 of FAD-GDHα. In some embodiments, the mutation is located at aspartic acid 301 of FAD-GDHα. In some embodiments, the mutation is located at phenylalanine 353 of FAD-GDHα. In some embodiments, the mutation is located threonine 521 of FAD-GDHα. In some embodiments, the mutation is located phenylalanine 406 of FAD-GDHα. In some embodiments, FAD-GDHα has at least one mutation (e.g., 1 mutation, 2 mutations, 3 mutations, 4 mutations, 5 mutations, 6 mutations, 7 mutations, 8 mutations, 9 mutations, 10 mutations, 11 mutations, 12 mutations, 13 mutations, 14 mutations, 15 mutations, etc.). In some embodiments, FAD-GDHα has at least two mutations (e.g., 2 mutations, 3 mutations, 4 mutations, 5 mutations, 6 mutations, 7 mutations, 8 mutations, 9 mutations, 10 mutations, 11 mutations, 12 mutations, 13 mutations, 14 mutations, 15 mutations, etc.). In some embodiments, the mutations are point mutations. In some embodiments, asparagine 475 of FAD-GDHα is not mutated.

Artificially mutated FAD-GDHα protein is meant to refer to a FAD-GDHα protein which has at least one amino acid difference from a naturally-occurring FAD-GDHα protein. In some embodiments, the present invention is a protein, including: an artificially mutated FAD-GDHα protein including at least one mutation, where the at least one mutation (e.g., but not limited to, 1 mutation, 2 mutations, 3 mutations, 4 mutations, 5 mutations, 6 mutations, 7 mutations, 8 mutations, 9 mutations, 10 mutations, 11 mutations, 12 mutations, 13 mutations, 14 mutations, 15 mutations, etc.) is at position 406 of SEQ ID NO: 38 or SEQ ID NO: 39. In some embodiments, the at least one mutation is selected from the group including: F406S, F406C, F406T, F406M, F406V, F406Y, F406N, F406P, F406L, F406G, F406Q, F406A, F406I, F406D, F406W, F406H, and F406E. In some embodiments, the artificially mutated FAD-GDHα protein exhibits at least a 10% increase (e.g., but not limited to, 10%, 20%, 30%, 40%, 50%, 60%, 70%, 80%, 90%, 100%, etc.) in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-350% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-300% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-250% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-200% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-150% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-100% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 10%-50% increase in biochemical activity compared to a FAD-GDHα wild-type protein comprising an amino acid sequence of SEQ ID NO: 38 or SEQ ID NO: 39.

In some embodiments, the artificially mutated FAD-GDHα protein exhibits between a 50%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 100%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 200%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 250%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 300%-400% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 350%-400% increase in biochemical activity compared to a FAD-GDHα wild-type protein comprising an amino acid sequence of SEQ ID NO: 38 or SEQ ID NO: 39.

In some embodiments, the artificially mutated FAD-GDHα protein exhibits between a 50%-350% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 100%-300% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-250% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 200%-250% increase in biochemical activity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-200% increase in biochemical activity compared to a FAD-GDHα wild-type protein comprising an amino acid sequence of SEQ ID NO: 38 or SEQ ID NO: 39.

In some embodiments, the artificially mutated FAD-GDHα protein exhibits at least a 40% increase (e.g., but not limited to, 40%, 50%, 60%, 70%, 80%, 90%, 100%, etc.) in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 40% and 400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 100% and 400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 150% and 400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 200% and 400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 250% and 400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 300% and 400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 350% and 400% increase in selectivity compared to a FAD-GDHα wild-type protein comprising an amino acid sequence of SEQ ID NO: 38 or SEQ ID NO: 39.

In some embodiments, the artificially mutated FAD-GDHα protein exhibits between a 40% and 350% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 40% and 300% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 40% and 250% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 40% and 200% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 40% and 150% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 40% and 100% increase in selectivity compared to a FAD-GDHα wild-type protein comprising an amino acid sequence of SEQ ID NO: 38 or SEQ ID NO: 39.

In some embodiments, the artificially mutated FAD-GDHα protein exhibits between a 100% and 350% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 150% and 300% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 200% and 250% increase in selectivity compared to a FAD-GDHα wild-type protein comprising an amino acid sequence of SEQ ID NO: 38 or SEQ ID NO: 39.

In some embodiments, the artificially mutated FAD-GDHα protein exhibits at least a 20% increase (e.g., but not limited to, 20%, 30%, 40%, 50%, 60%, 70%, 80%, 90%, 100%, etc.) in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 50% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 100% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 150% and 500% increase in linearity compared to a FAD-GDHα wild-type protein comprising an amino acid sequence of SEQ ID NO: 38 or SEQ ID NO: 39. In some embodiments, the artificially FAD-GDHα protein exhibits between a 200% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 250% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 300% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 350% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 400% and 500% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 450% and 500% increase in linearity compared to a FAD-GDHα wild-type protein comprising an amino acid sequence of SEQ ID NO: 38 or SEQ ID NO: 39.

In some embodiments, the artificially mutated FAD-GDHα protein exhibits between a 20% and 450% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 400% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 350% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 300% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 250% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 200% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 150% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 100% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 20% and 50% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 50% and 450% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 100% and 400% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 150% and 350% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 200% and 300% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 200% and 250% increase in linearity compared to a FAD-GDHα wild-type protein comprising an amino acid sequence of SEQ ID NO: 38 or SEQ ID NO: 39. In some embodiments, the artificially mutated FAD-GDHα protein exhibits between a 250% and 300% increase in linearity compared to a FAD-GDHα wild-type protein comprising an amino acid sequence of SEQ ID NO: 38 or SEQ ID NO: 39.

The present invention is a protein, including: an artificially mutated FAD-GDHα protein including at least one mutation (e.g., but not limited to, 1 mutation, 2 mutations, 3 mutations, 4 mutations, 5 mutations, 6 mutations, 7 mutations, 8 mutations, 9 mutations, 10 mutations, 11 mutations, 12 mutations, 13 mutations, 14 mutations, 15 mutations, etc.), wherein the at least one mutation is at position 474 of SEQ ID NO: 1. In some embodiments, the at least one mutation is selected from the group consisting of: N474H, N474L, N474S and N474V. In some embodiments, the artificially mutated FAD-GDHα protein exhibits at least a 20% increase (e.g., but not limited to, 20%, 30%, 40%, 50%, 60%, 70%, 80%, 90%, 100%, etc.) in activity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 50%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 100%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 200%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 250%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 300%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 350%-400% increase in activity compared to a FAD-GDHα wild-type protein comprising an amino acid sequence of SEQ ID NO: 38 or SEQ ID NO: 39.

In some embodiments, the artificially mutated FAD-GDHα protein exhibits between a 20%-350% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-300% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-250% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-200% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-100% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-50% increase in activity compared to a FAD-GDHα wild-type protein comprising an amino acid sequence of SEQ ID NO: 38 or SEQ ID NO: 39.

In some embodiments, the artificially mutated FAD-GDHα protein exhibits between a 50%-400% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 100%-350% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-300% increase in activity compared to a FAD-GDHα wild-type protein comprising an amino acid sequence of SEQ ID NO: 38 or SEQ ID NO: 39. In some embodiments, the artificially mutated FAD-GDHα protein exhibits between a 200%-250% increase in activity compared to a FAD-GDHα wild-type protein comprising an amino acid sequence of SEQ ID NO: 38 or SEQ ID NO: 39.

In some embodiments, the artificially mutated FAD-GDHα protein exhibits at least a 20% increase (e.g., but not limited to, 20%, 30%, 40%, 50%, 60%, 70%, 80%, 90%, 100%, etc.) in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 50%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 100%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 200%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 250%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 300%-400% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 350%-400% increase in selectivity compared to a FAD-GDHα wild-type protein comprising an amino acid sequence of SEQ ID NO: 38 or SEQ ID NO: 39.

In some embodiments, the artificially mutated FAD-GDHα protein exhibits between a 20%-350% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-300% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-250% increase in selectivity compared to a FAD-GDHα wild-type protein comprising an amino acid sequence of SEQ ID NO:

38 or SEQ ID NO: 39. In some embodiments, the artificially mutated FAD-GDHα protein exhibits between a 20%-200% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-150% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-100% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 20%-50% increase in selectivity compared to a FAD-GDHα wild-type protein comprising an amino acid sequence of SEQ ID NO: 38 or SEQ ID NO: 39.

In some embodiments, the artificially mutated FAD-GDHα protein exhibits between a 50%-350% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 100%-300% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-250% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 200%-250% increase in selectivity compared to a FAD-GDHα wild-type protein comprising an amino acid sequence of SEQ ID NO: 38 or SEQ ID NO: 39. In some embodiments, the artificially mutated FAD-GDHα protein exhibits between a 150%-200% increase in selectivity compared to a FAD-GDHα wild-type protein comprising an amino acid sequence of SEQ ID NO: 38 or SEQ ID NO: 39.

In some embodiments, the protein of the present invention includes at least one mutation at position 406 of SEQ ID NO: 38 or SEQ ID NO: 39, where a phenylalanine at the position 406 of SEQ ID NO: 38 or SEQ ID NO: 39 is replaced with any amino acid other than K or R.

In some embodiments, a mutated FAD-GDHα protein, having at least one amino acid mutation, has at least 95% sequence identity (e.g., but not limited to, 95%, 96%, 97%, 98%, etc.) to SEQ ID NO: 38 or SEQ ID NO: 39. In some embodiments, a phenylalanine at the position 406 of SEQ ID NO: 38 or SEQ ID NO: 39 is replaced with any amino acid other than K or R.

In some embodiments, a mutated FAD-GDHα protein, having at least one amino acid mutation, has at least 96% sequence identity (e.g., but not limited to, 96%, 97%, 98%, etc.) to SEQ ID NO: 38 or SEQ ID NO: 39. In some embodiments, a phenylalanine at the position 406 of SEQ ID NO: 38 or SEQ ID NO: 39 is replaced with any amino acid other than K or R.

In some embodiments, a mutated FAD-GDHα protein, having at least one amino acid mutation, has at least 97% sequence identity (e.g., but not limited to, 97%, 97.5%, 98%, etc.) to SEQ ID NO: 38 or SEQ ID NO: 39. In some embodiments, a phenylalanine at the position 406 of SEQ ID NO: 38 or SEQ ID NO: 39 is replaced with any amino acid other than K or R.

In some embodiments, a mutated FAD-GDHα protein, having at least one amino acid mutation, has at least 98% sequence identity (e.g., but not limited to, 98%, 98.1%, 98.2%, etc.) to SEQ ID NO: 38 or SEQ ID NO: 39. In some embodiments, a phenylalanine at the position 406 of SEQ ID NO: 38 or SEQ ID NO: 39 is replaced with any amino acid other than K or R.

In some embodiments, a mutated FAD-GDHα protein, having at least one amino acid mutation, has at least 99% sequence identity (e.g., but not limited to, 99%, 99.1%, 99.2%, etc.) to SEQ ID NO: 38 or SEQ ID NO: 39. In some embodiments, a phenylalanine at the position 406 of SEQ ID NO: 38 or SEQ ID NO: 39 is replaced with any amino acid other than K or R.

In some embodiments, a mutated FAD-GDHα protein, having at least one amino acid mutation, has at least 95% sequence identity (e.g., but not limited to, 95%, 96%, 97%, 98%, etc.) to SEQ ID NO: 38 or SEQ ID NO: 39, where the asparagine residue at position 474 is substituted with valine, histidine, leucine, or serine.

In some embodiments, a mutated FAD-GDHα protein, having at least one amino acid mutation, has at least 96% sequence identity (e.g., but not limited to, 96%, 97%, 98%, etc.) to SEQ ID NO: 38 or SEQ ID NO: 39, where the asparagine residue at position 474 is substituted with valine, histidine, leucine, or serine.

In some embodiments, a mutated FAD-GDHα protein, having at least one amino acid mutation, has at least 97% sequence identity (e.g., but not limited to, 97%, 97.5%, 98%, etc.) to SEQ ID NO: 38 or SEQ ID NO: 39, where the asparagine residue at position 474 is substituted with valine, histidine, leucine, or serine.

In some embodiments, a mutated FAD-GDHα protein, having at least one amino acid mutation, has at least 98% sequence identity (e.g., but not limited to, 98%, 98.1%, 98.2%, etc.) to SEQ ID NO: 38 or SEQ ID NO: 39, where the asparagine residue at position 474 is substituted with valine, histidine, leucine, or serine.

In some embodiments, a mutated FAD-GDHα protein, having at least one amino acid mutation, has at least 99% sequence identity (e.g., but not limited to, 99%, 99.1%, 99.2%, etc.) to SEQ ID NO: 38 or SEQ ID NO: 39, where the asparagine residue at position 474 is substituted with valine, histidine, leucine, or serine.

In some embodiments, the present invention is a FAD-GDHα protein having at least 95% sequence identity to any of SEQ IDS: 9-29, 40-66, or 86-104. In some embodiments, the present invention is a FAD-GDHα protein having at least 96% sequence identity to any of SEQ IDS: 9-29, 40-66, or 86-104. In some embodiments, the present invention is a FAD-GDHα protein having at least 97% sequence identity to any of SEQ IDS: 9-29, 40-66, or 86-104. In some embodiments, the present invention is a FAD-GDHα protein having at least 98% sequence identity to any of SEQ IDS: 9-29, 40-66, or 86-104. In some embodiments, the present invention is a FAD-GDHα protein having at least 99% sequence identity to any of SEQ IDS: 9-29, 40-66, or 86-104.

In some embodiments, the present invention is a FAD-GDHα protein of any one of SEQ IDs: 9-29, 40-66, or 86-104 having between 1-5 amino acid mutations. In some embodiments, the present invention is a FAD-GDHα protein of any one of SEQ IDs: 9-29, 40-66, or 86-104 having between 1-10 amino acid mutations. In some embodiments, the present invention is a FAD-GDHα protein of any one of SEQ IDs: 9-29, 40-66, or 86-104 having between 1-15 amino acid mutations. Proteins of the instant invention are understood to comprise the full length of the amino acid sequence described in such SEQ ID NOs and not a subset.

In some embodiments, the present invention is a FAD-GDHα protein (SEQ ID NO:38 or SEQ ID NO: 39) wherein the FAD-GDHα protein includes between 1-15 amino acid substitutions, where at least one amino acid substitution includes a substitution of the phenylalanine at position 406 to another other amino acid other than lysine or arginine.

In some embodiments, the present invention is a FAD-GDHα protein (SEQ ID:1) wherein the FAD-GDHα protein includes between 1-15 amino acid substitutions, where at least one amino acid substitution includes a substitution of the arginine at position 474 to a histidine, leucine, serine, or valine.

In some embodiments, the present invention is a method for measuring the glucose level of a subject, the method including: contacting a body fluid obtained from the subject with a mutant FAD-GDHα protein, measuring the current generated by the mutant FAD-GDHα protein, calculating the measured current to a glucose level, or any combination thereof. In some embodiments, the mutant FAD-GDHα protein includes between 1-15 amino acid substitutions including, e.g., but not limited to, a position of 406 or 474 of SEQ ID NO: 38 or SEQ ID NO: 39.

Amino acids of the present invention include, but are not limited to the 20 commonly occurring amino acids. Also included are naturally occurring and synthetic derivatives, for example, selenocysteine. Amino acids further include amino acid analogs. An amino acid "analog" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a polypeptide.

The phrases "amino acid" and "amino acid sequence" as defined here and in the claims can include one or more components which are amino acid derivatives and/or amino acid analogs comprising part or the entirety of the residues for any one or more of the 20 naturally occurring amino acids indicated by that sequence. For example, in an amino acid sequence having one or more tyrosine residues, a portion of one or more of those residues can be substituted with homotyrosine.

The one letter and three letter amino acid codes (and the amino acid that each represents) are as follows: A means ala (alanine); C means cys (cysteine); D means asp (aspartic acid); E means glu (glutamic acid); F means phe (phenylalanine); G means gly (glycine); H means his (histidine); I means ile (isoleucine); K means lys (lysine); L means leu (leucine); M means met (methionine); N means asn (asparagine); P means pro (proline); Q means gln (glutamine); R means arg (arginine); S means ser (serine); T means thr (threonine); V means val (valine); W means trp (tryptophan); and Y means tyr (tyrosine).

Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; (6) aromatic: trp, tyr, phe. A person skilled in the art would understand that certain conservative substitution may be made in the amino acid sequence of a protein. Conservative substitutions of interest are shown in Table 1

TABLE 1

Exemplary and Preferred Amino acid substitutions.

| Original | Exemplary | Preferred |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

In some embodiments, the present invention also provides a glucose sensor comprising any of the FAD-GDHα proteins of the instant invention. Glucose sensors employing FAD-GDH are known in the art and have been described, for example, in U.S. Pat. No. 8,658,011, which is hereby incorporated by reference. The proteins of the instant invention may be employed in any biosensor know in the art that is designed to employ FAD-GDH.

In some embodiments, the present invention also provides a composition comprising the FAD-GDHα of the instant invention and a solid support. Such support may be in the form of a reagent layer or a reagent test strip. In some embodiments the composition is in a dry or solid state. Reagent layers for glucose sensors are known in the art, and have been described, for example, in U.S. Pat. No. 8,658,011. A person skilled in the art would understand that any reagent layer known in the art designed for use with FAD-GDH can be made to comprise the FAD-GDHα proteins of the instant invention. Reagent test strips are used in the determination of the concentration of an analyte, e.g. glucose, in a physiological sample, e.g. blood. The test strips can include a porous matrix, one or more members of an analyte oxidation signal producing system and at least one hemolyzing agent. In using the subject test strips for analyte concentration determination, a physiological sample is applied to the test strip. Next, the appearance of a chromogenic product of the signal producing system is detected and related to the concentration of the analyte in the sample.

Typically, a user inserts a test strip into a meter and lances a finger or alternate body site to obtain a blood sample. The drawn sample is applied to the test strip and the meter reads the strip and determines analyte concentration, which is then conveyed to the user. For example, the blood glucose meter converts a current generated by the enzymatic reaction in the test strip to a corresponding blood glucose value which is displayed or otherwise provided to the patient to show the level of glucose at the time of testing.

In some embodiments, the present invention also provides the FAD-GDHα proteins of the instant invention immobilized to the conductive component of an electrode of a glucose sensor. Electrodes for glucose sensors are known in the art, and have been described, for example, in U.S. Pat. No. 7,497,940, the contents of which are hereby incorporated by reference. A person skilled in the art would understand that any electrode known in the art designed for use with FAD-GDH can be made to comprise the FAD-GDHα proteins of the instant invention.

In some embodiments, the present invention also provides a DNA sequence encoding any of the proteins of the instant invention. Such DNA sequence may be expressed according to any technique known in the art. By way of non-limiting example, such sequence may be incorporated into a vector for expression in a cell. The term "vector" refers to a polynucleotide molecule capable of carrying and transferring another polynucleotide fragment or sequence to which it has been linked from one location (e.g., a host, a system) to another. The term includes vectors for in vivo or in vitro expression systems. As a non-limiting example, vectors can be in the form of "plasmids" which refer to circular double stranded DNA loops which are typically maintained episomally but may also be integrated into the host genome. In some embodiments, the present invention accordingly provides a host cell comprising the DNA encoding the protein and a process of producing the protein comprising culturing the host cell under conditions conducive to the production of the protein, and recovering the protein.

An exemplary embodiment of the activity of wild type FAD-GDHα (SEQ ID NO: 38) is shown by plotting absorbance of glucose, maltose, and xylose against reaction time, as shown in FIG. 1A.

Figure 1B:
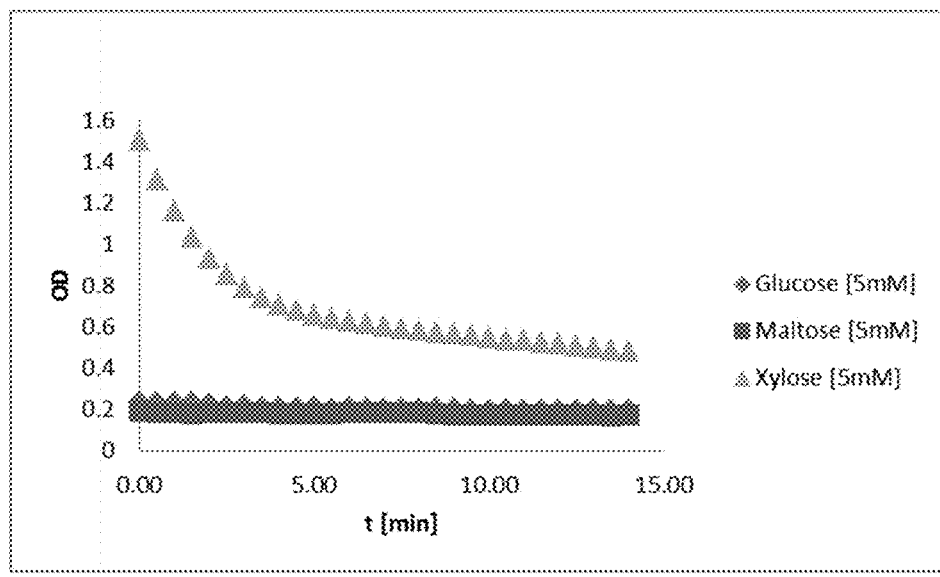
FIG. 1B shows the activity of mutated of FAD-GDHα (SEQ ID NO: 8) by plotting absorbance of glucose, maltose, and xylose against reaction time.

An exemplary embodiment of the activity of mutated GAD-GDHα is shown by plotting absorbance of glucose, maltose, and xylose against reaction time, as shown in FIG. 1B.

Figure 2:
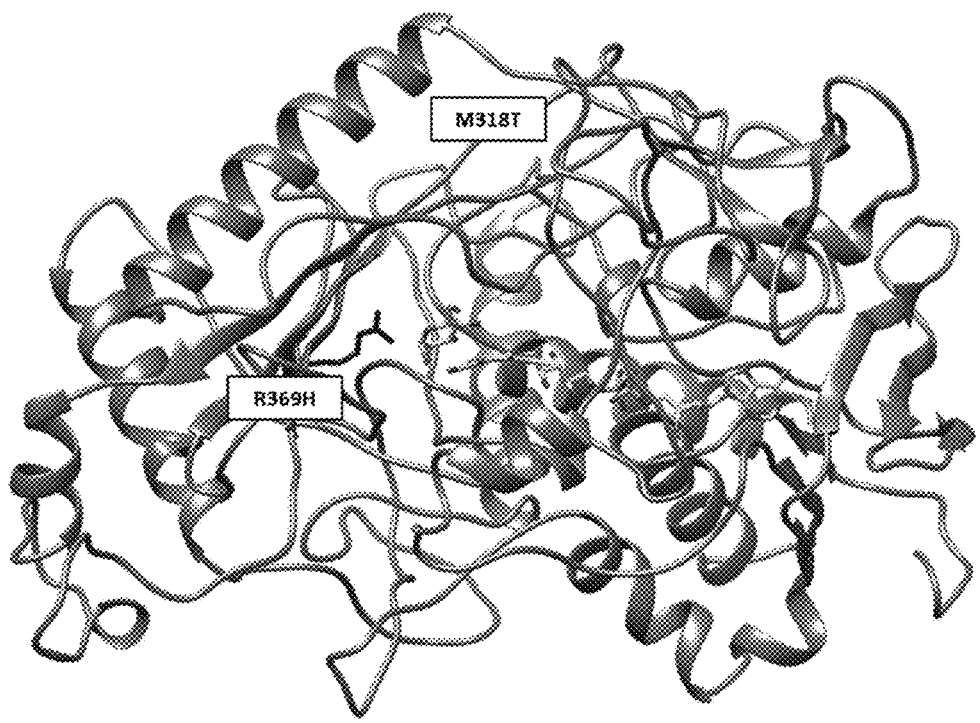
FIGS. 2 and 3 show some aspects of the embodiments of the present invention protein models of FAD-GDHα and the point mutations as described in SEQ ID NO: 8 (e.g., M318T and R369H).
Figure 3:
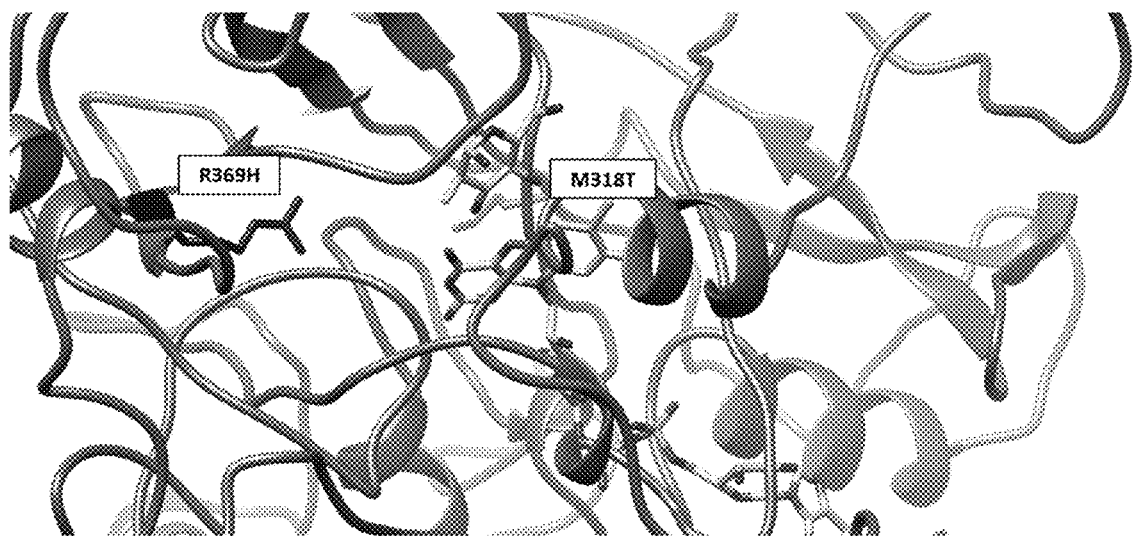

Exemplary embodiments of protein models of FAD-GDHα and the point mutations as described in SEQ8 (e.g., M318T and R369H) are shown in FIGS. 2 and 3.

Figures 4A, 4B:
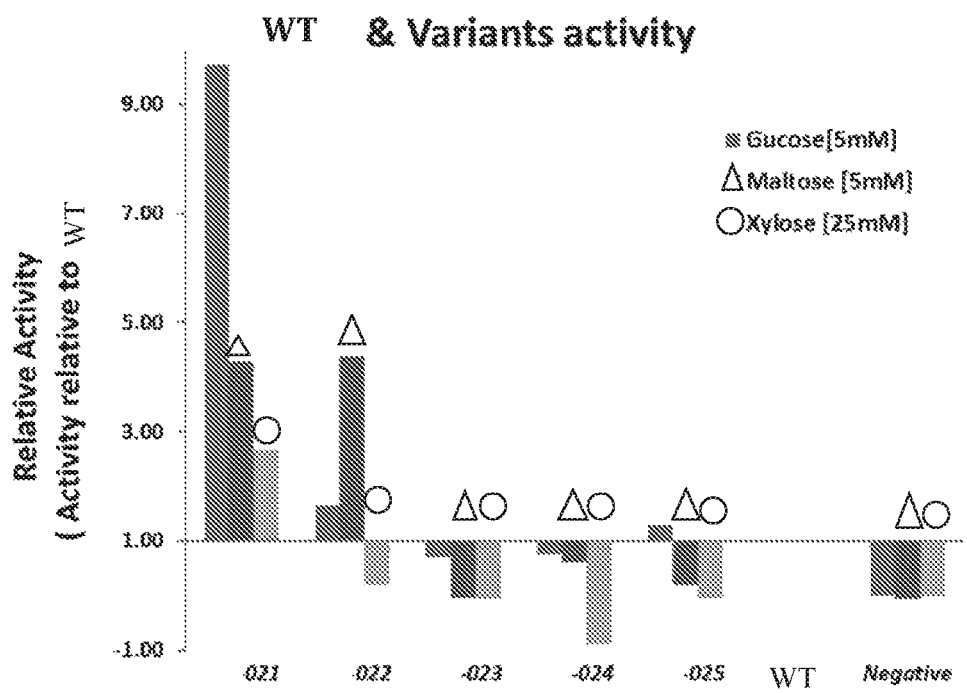
FIGS. 4A and 4B show some aspects of the embodiments of the present invention, showing a FIG. 4A) and table (4B) depicting the relative activity of several FAD-GDHα (from *B. cepacia*) proteins.

Exemplary embodiments of relative activity of several FAD-GDHα (from B. cepacia) mutants (e.g., 021, 022, 023, 024, 025), wild-type enzyme (B. cepacia FAD-GDHα) and negative control (bacterial lysate without FAD-GDHα (B. cepacia)) are shown in FIGS. 4A and 4B.

Exemplary embodiments of several curves indicating improved sensitivity of the enzyme (FIG. 5A), and improved specificity (FIG. 5B) are shown herein.

An exemplary embodiment of a non-linear model FAD-GDHα (S330G and N474S) (from B. cepacia) is shown in FIG. 6A. Exemplary embodiments of quantified data, as relating to FIG. 6A, are shown in the table of FIG. 6B. An exemplary embodiment of a homology model of the FAD-GDHα (S330G and N474S) alpha subunit based on the Glucose oxidase determined structure is shown in FIG. 6C.

Figures 7A, 7B:
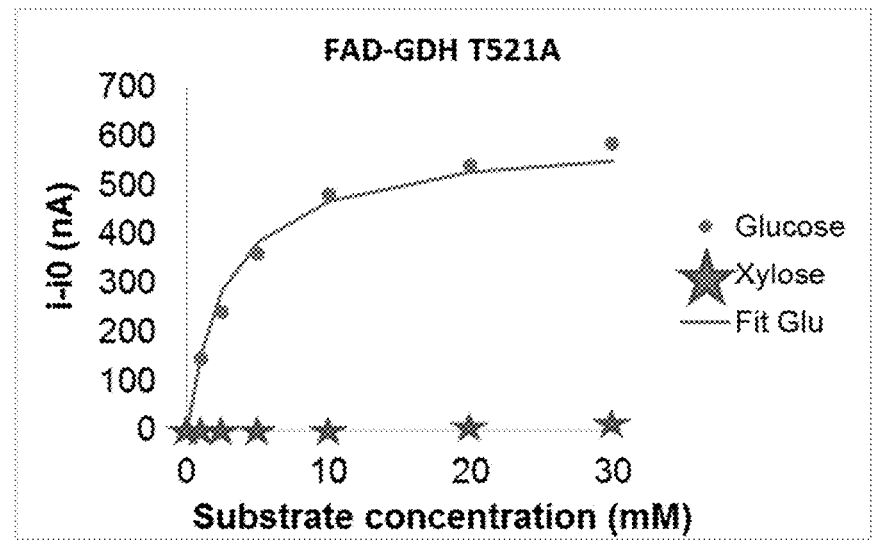
FIG. 7A shows some aspects of the embodiments of the present invention, illustrating a non-linear model FAD-GDHα T521A (from *B. cepacia*)
FIG. 7B is a table with quantified data relating to FIG. 7A.
Figure 7C:
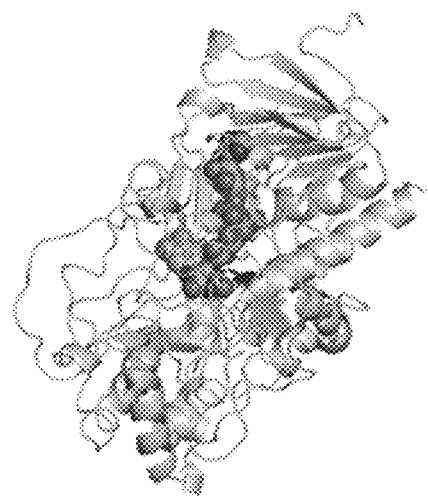
FIG. 7C is a homology model of FAD-GDH T521A alpha subunit based on Glucose oxidase determined structure.

An exemplary embodiment of a non-linear model FAD-GDHα T521A (from B. cepacia) is shown in FIG. 7A. Exemplary embodiments of quantified data, as relating to FIG. 7A, are shown in the table of FIG. 7B. An exemplary embodiment of a homology model of the FAD-GDHα T521A alpha subunit based on Glucose oxidase determined structure is shown in FIG. 7C.

An exemplary embodiment of a non-linear model FAD-GDHα F406L (from B. cepacia) is shown in FIG. 8A. An exemplary embodiment of quantified data, as relating to FIG. 8A, is shown in the table of FIG. 8B. An exemplary embodiment of a homology model of FAD-GDHα F406L alpha subunit based on Glucose oxidase determined structure of is shown in FIG. 8C.

Figure 9:
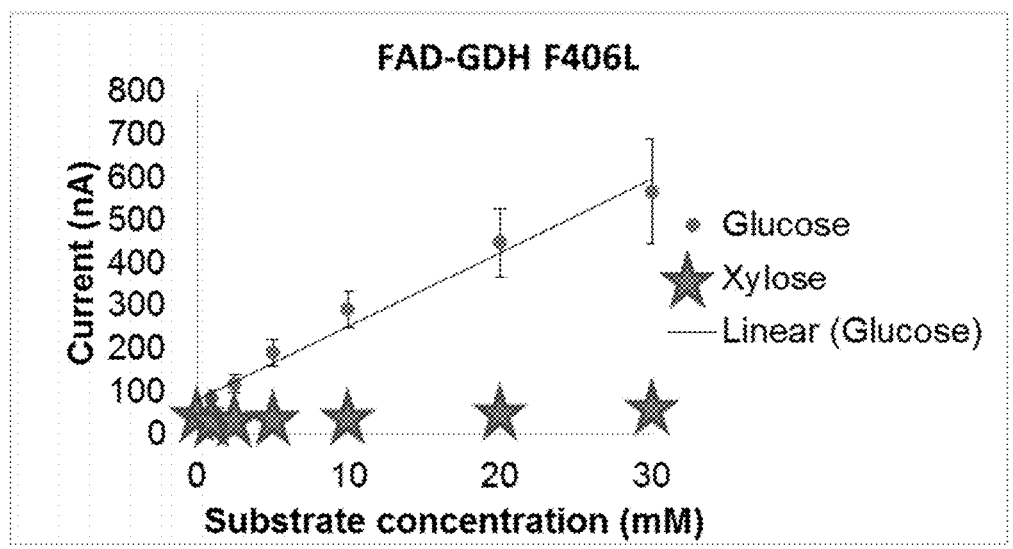
FIG. 9 shows some aspects of some embodiments of the present invention, illustrating an assessment of linearity of mutant enzymatic dynamic range by linear fitting the whole range of measured points and extraction of both the quality of the fit (R-square), the slope (a) and intersection with the Y axis (b). The $R^2$ value=0.979, a=17.25, and b=80.9 nA.

An exemplary embodiment showing an assessment of linearity of mutant enzymatic dynamic range by linear fitting the whole range of measured points and extraction of both the quality of the fit (R-square), the slope (a) and intersection with the Y axis (b) is shown in FIG. 9.

Figure 10:
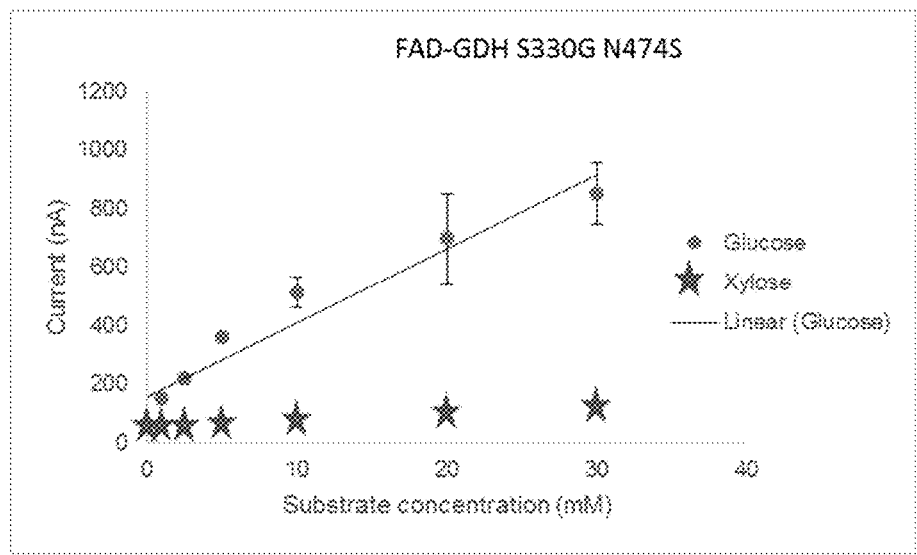
FIG. 10 shows some aspects of some embodiments of mutant 24 of the present invention, illustrating an assessment of linearity of mutant enzymatic dynamic range by linear fitting the whole range of measured points and extraction of both the quality of the fit (R-square), the slope (a) and intersection with the Y axis (b). The $R^2$ value=0.938, a=25.3, and b=158.23 nA.

An exemplary embodiment showing an assessment of linearity of mutant enzymatic dynamic range by linear fitting the whole range of measured points and extraction of both the quality of the fit (R-square), the slope (a) and intersection with the Y axis (b) is shown in FIG. 10 (Mutant 24). The $R^2$ value=0.938, a=25.3, and b=158.23 nA.

Figures 11, 12:
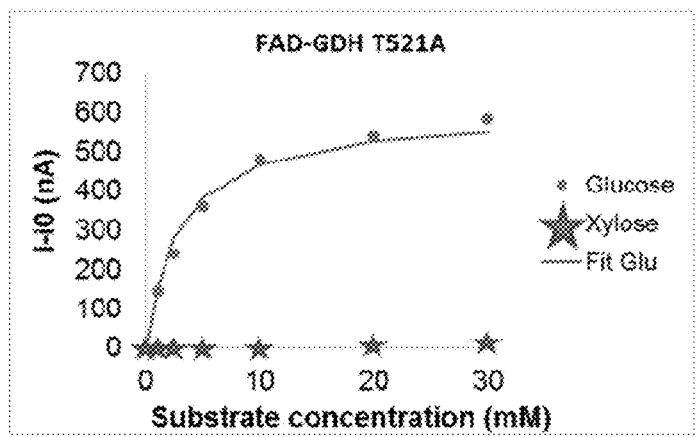
FIG. 11 shows some aspects of some embodiments of the present invention, illustrating an assessment of linearity of mutant enzymatic dynamic range by linear fitting the whole range of measured points and extraction of both the quality of the fit (R-square), the slope (a) and intersection with the Y axis (b). The $R^2$ value=0.744, a=16.68, and b=211 nA.
FIG. 12 is a table of some aspects of some embodiments of the present invention, summarizing the mutation positions and enzymatic and bio-electrochemical properties (X100Y means residue "X" at position 100 is mutated to residue "Y").

An exemplary embodiment showing an assessment of linearity of mutant enzymatic dynamic range by linear fitting the whole range of measured points and extraction of both the quality of the fit (R-square), the slope (a) and intersection with the Y axis (b) is shown in FIG. 11.

Exemplary embodiments of the mutation positions and enzymatic and bio-electrochemical properties (X100Y means residue "X" at position 100 is mutated to residue "Y") are shown in the table of FIG. 12.

Exemplary embodiments of the collected data in connection with the compositions of the present invention are shown in the tables of FIGS. 13A-E. FIG. 13A describes biochemical and electrochemical parameters of the 406 mutants. FIG. 13B represents the biochemical kinetic characteristics of the 406 mutants as a percentage from the wild type (100%). FIG. 13C describes the biochemical selectivity and electrochemical linearity and current for the 406 mutants represented as a percentage from the wild type (100%). FIG. 13D describes biochemical rate of activity towards glucose and xylose of the 474 mutants. FIG. 13E describes biochemical rate of activity towards glucose and xylose of the 474 mutants, represented as a percentage from the wild type (100%).

Figure 14:
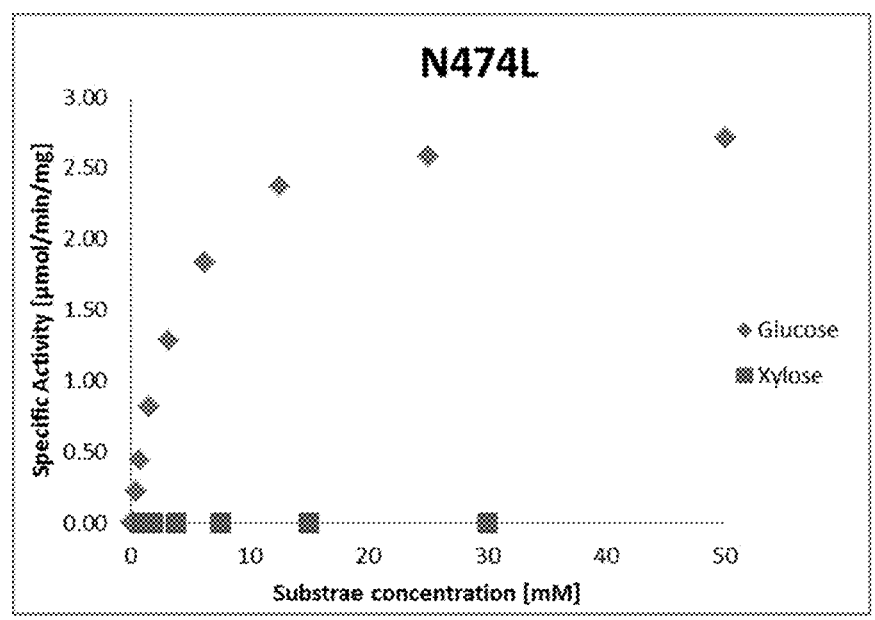
FIGS. 14 and 15 show some aspects of some embodiments of the present invention.
Figure 15:
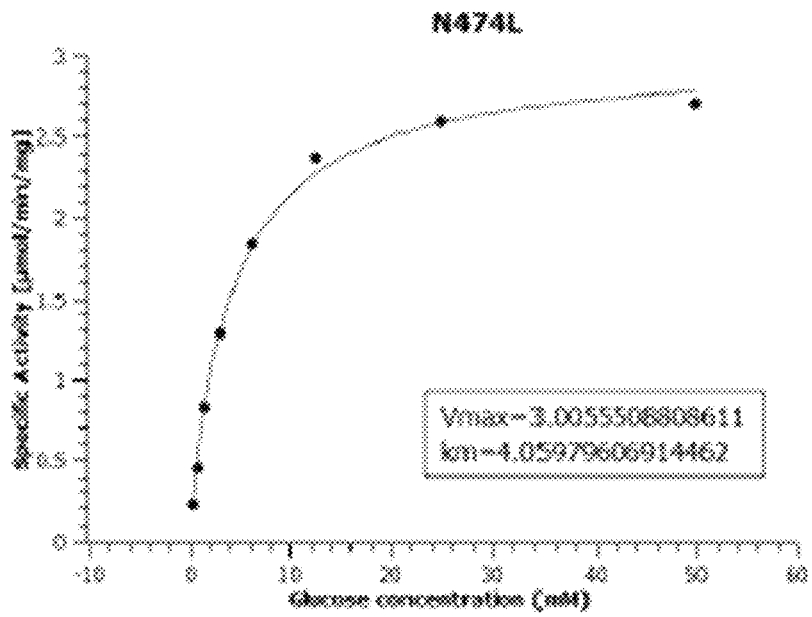

Exemplary embodiments of the composition of the present invention are shown in FIGS. 14 and 15. FIG. 14 shows the biochemical response of FAD-GDHα N474L to varying concentrations of glucose (rhombus), and xylose (rectangle). FIG. 15 shows the biochemical response of N474L to glucose and the non-linear fit through which Km (k) and Vmax have been obtained. N474L enzyme activity was determined via monitoring decrease of Dichlorophenolindophenol (DCIP) signal at $OD_{600}$.

Figure 16A:
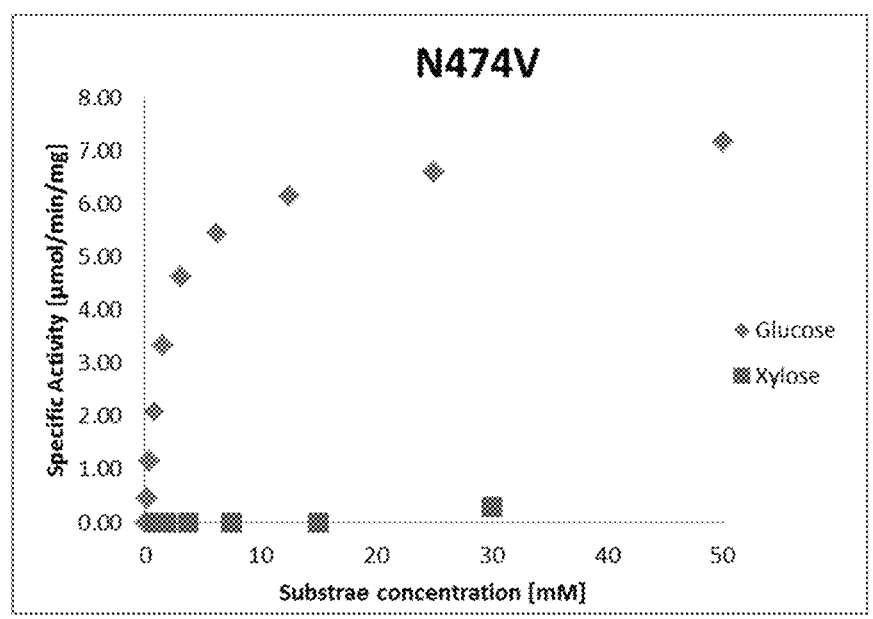
FIGS. 16A and 16B show aspects of some embodiments of the present invention.
Figure 16B:
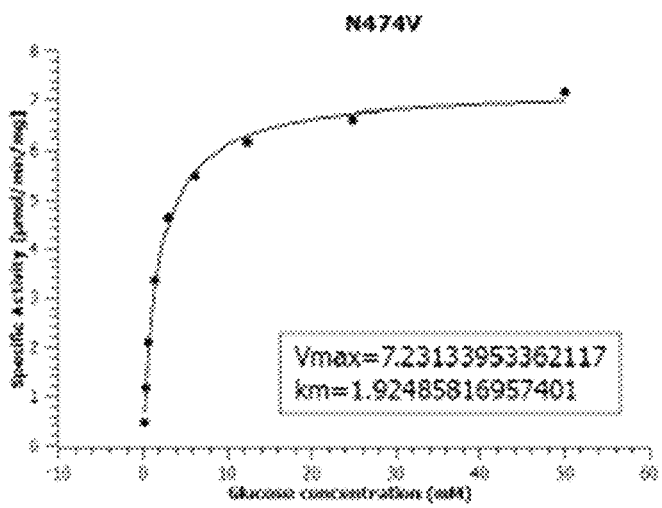

Exemplary embodiments of the composition of the present invention are shown in FIGS. 16A and 16B. FIG. 16A shows the biochemical response of FAD-GDHα N474V to varying concentrations of glucose (rhombus), and xylose (rectangle). FIG. 16B shows the biochemical response of FAD-GDHα N474V to glucose and the non-linear fit through which Km (k) and Vmax have been obtained. N474V enzyme activity was determined via monitoring decrease of Dichlorophenolindophenol (DCIP) signal at $OD_{600}$.

Figure 17A:
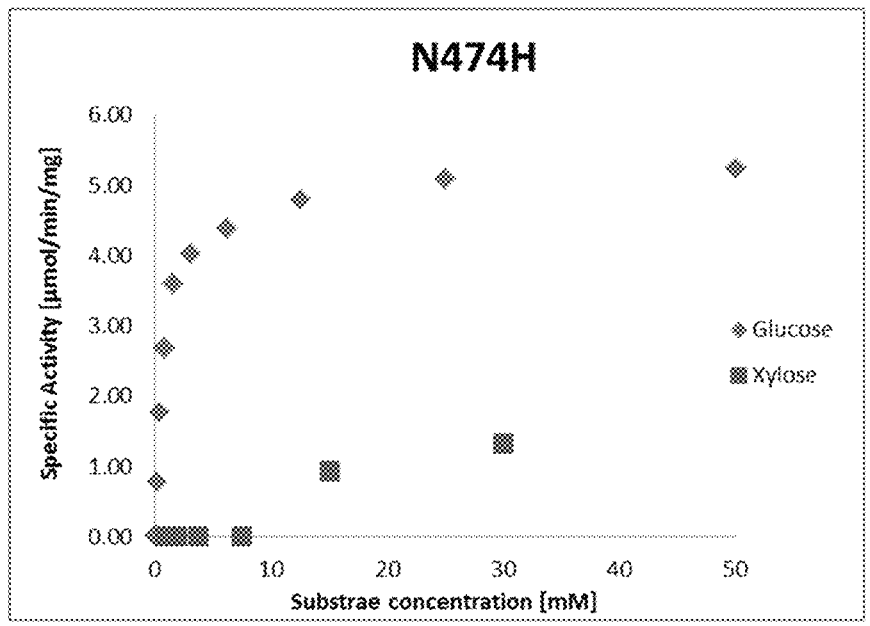
FIGS. 17A and 17B show some aspects of some embodiments of the present invention.
Figure 17B:
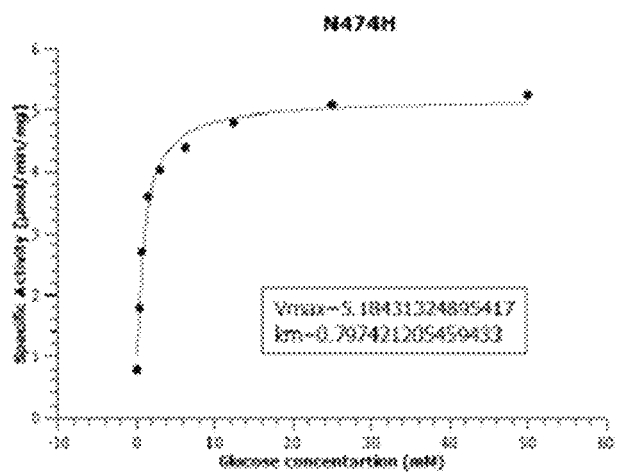

Exemplary embodiments of the composition of the present invention are shown in FIGS. 17A and 17B. FIG. 17A shows a biochemical response of FAD-GDHα N474H to varying concentrations of glucose (rhombus), and xylose (rectangle). FIG. 17B shows a biochemical response of FAD-GDHα N474H to glucose and the non-linear fit through which Km (k) and Vmax have been obtained. FAD-GDHα N474H enzyme activity was determined via monitoring decrease of Dichlorophenolindophenol (DCIP) signal at $OD_{600}$.

Figure 18A:
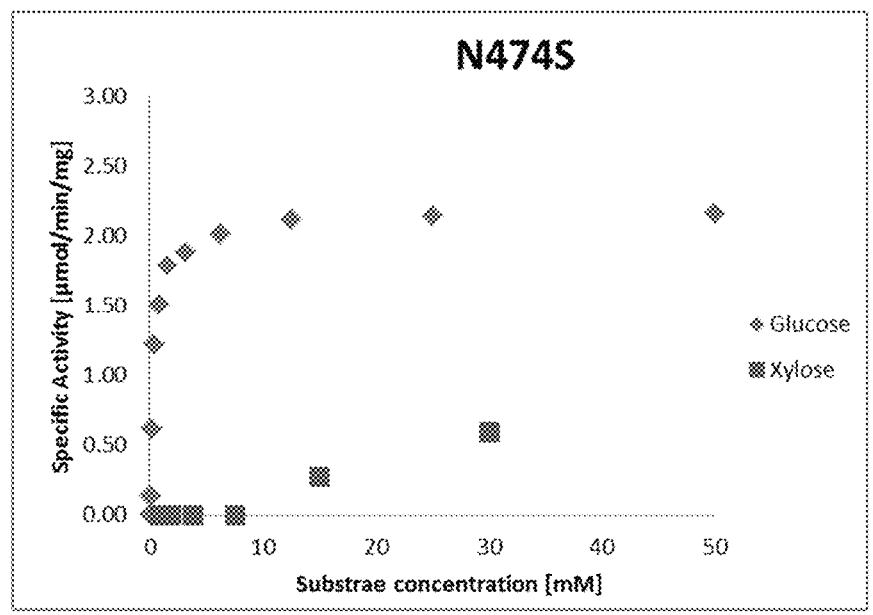
FIGS. 18A and 18B show some aspects of some embodiments of the present invention.
Figure 18B:
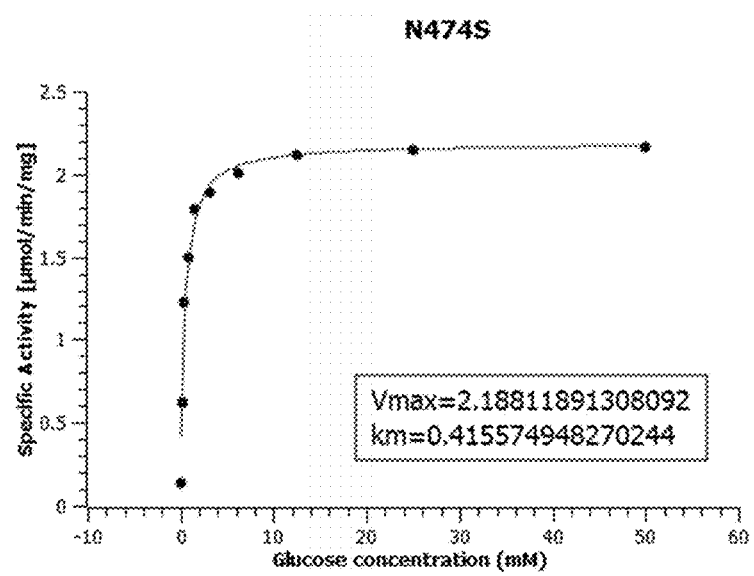

Exemplary embodiments of the composition of the present invention are shown in FIGS. 18A and 18B. FIG. 18A shows the biochemical response of FAD-GDHα N474S to varying concentrations of glucose (rhombus), and xylose (rectangle). FIG. 18B shows the biochemical response of FAD-GDHα N474S to glucose and the non-linear fit through which Km (k) and Vmax have been obtained. N474S enzyme activity was determined via monitoring decrease of Dichlorophenolindophenol (DCIP) signal at $OD_{600}$.

Figure 19A:
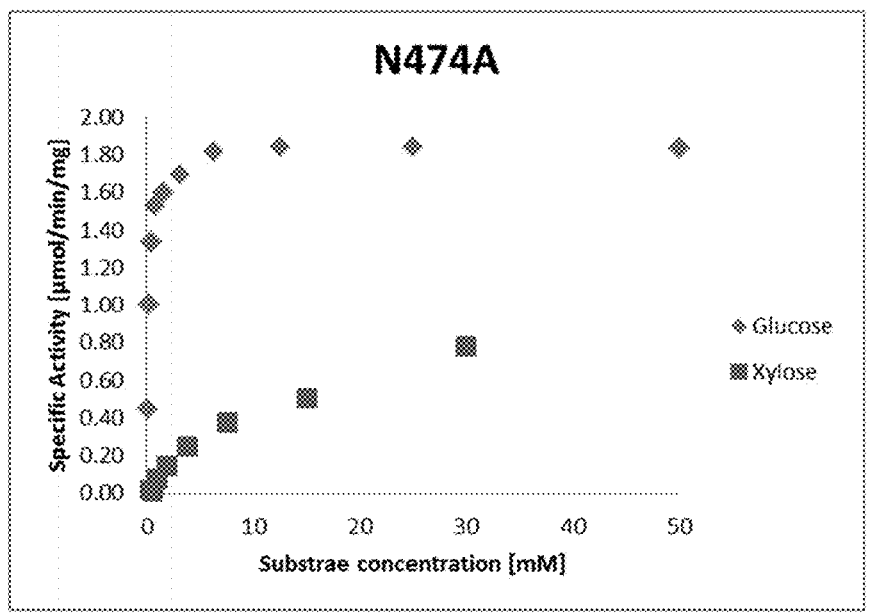
FIGS. 19A and 19B show some aspects of some embodiments of the present invention.
Figures 19B, 20:
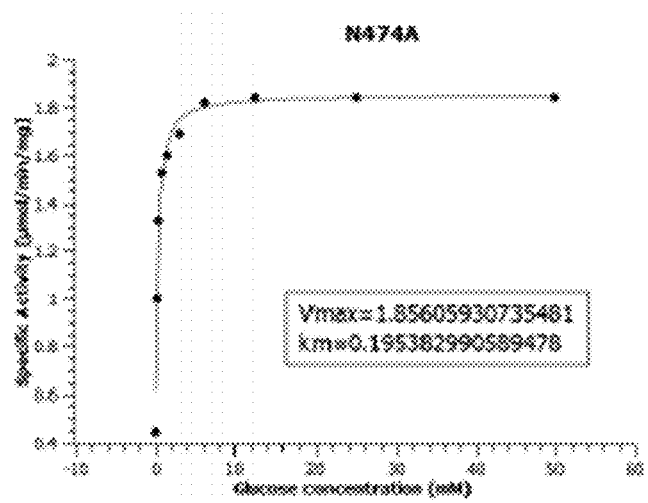
FIG. 20 shows a table summarizing some embodiments of the composition of the present invention.

Exemplary embodiments of the composition of the present invention are shown in FIGS. 19A and 19B. FIG. 18A shows the biochemical response of FAD-GDHα N474A to glucose and the non-linear fit through which Km (k) and Vmax have been obtained. N474A enzyme activity was determined via monitoring decrease of Dichlorophenolindophenol (DCIP) signal at $OD_{600}$.

Exemplary embodiments of the composition of the present invention are shown in the table summary of FIG. 20.

Figure 21A:
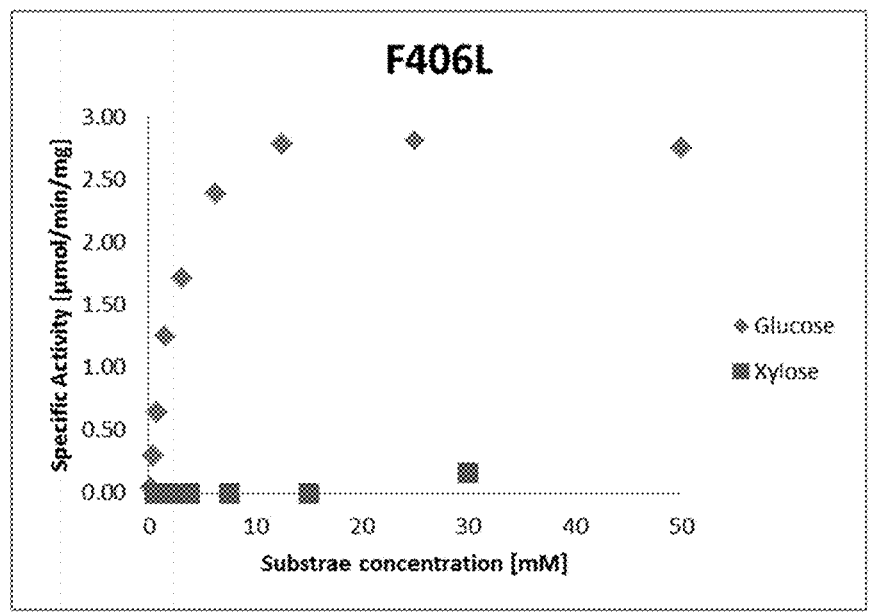
FIGS. 21A and 21B show some aspects of some embodiments of the present invention.
Figure 21B:
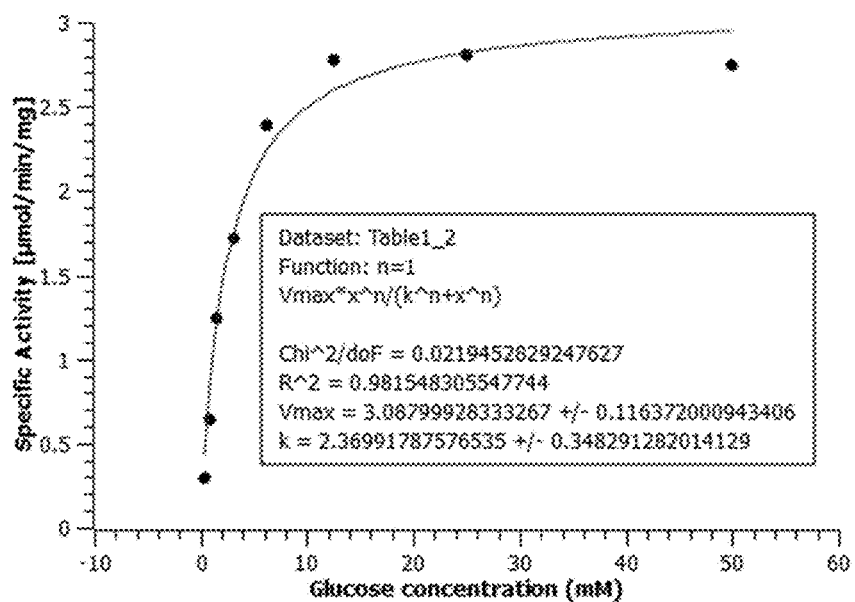

Exemplary embodiments of the composition of the present invention are shown in FIGS. 21A and 21B. FIG. 21B shows the biochemical response of FAD-GDHα F406L to varying concentrations of glucose (rhombus), and xylose (rectangle). FIG. 21B shows the biochemical response of F406L to glucose and the non-linear fit through which Km (k) and Vmax have been obtained. F406L enzyme activity was determined via monitoring decrease of Dichlorophenolindophenol (DCIP) signal at $OD_{600}$.

Figure 22:
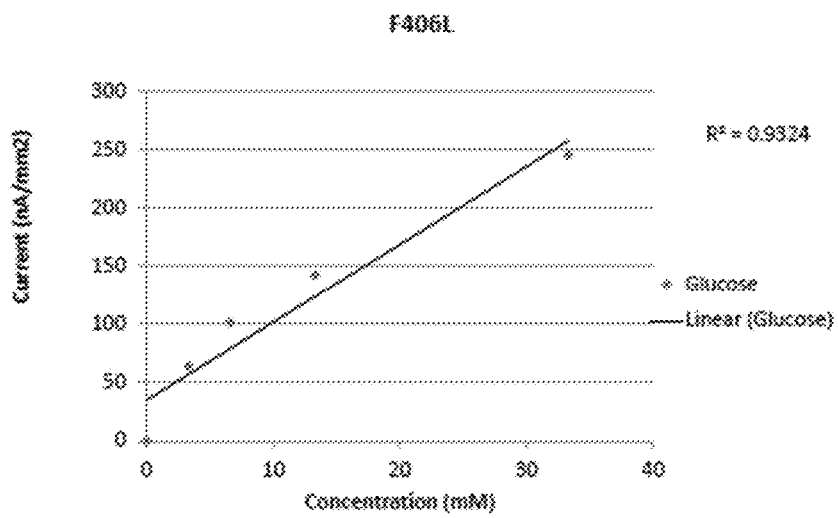
FIG. 22 shows some aspects of an embodiment of the composition of the present invention, showing the electrochemical data in connection with FAD-GDHα F406L.

An exemplary embodiment of the composition of the present invention, showing the electrochemical data in connection with FAD-GDHα F406L, is shown in FIG. 22.

Figure 23A:
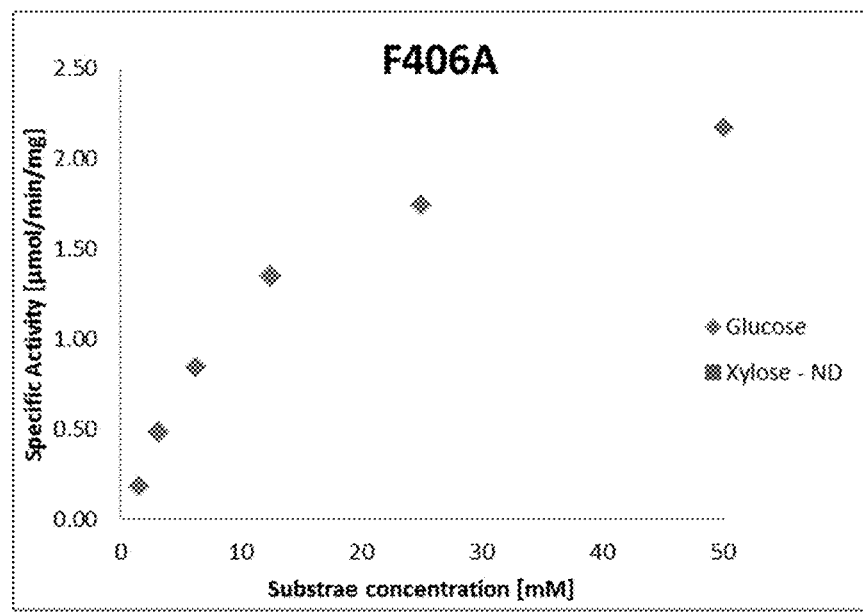
Figure 23B:
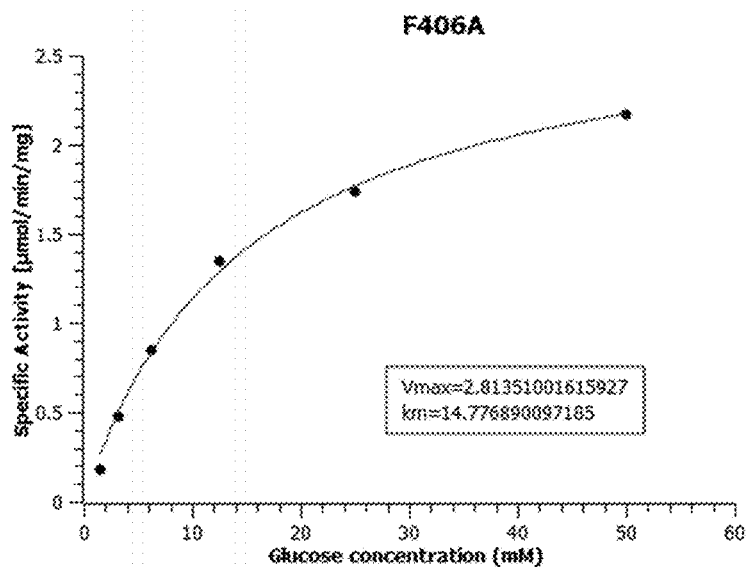
FIG. 23B shows the biochemical response of F406A to glucose and the non-linear fit through which Km (k) and Vmax have been obtained. F406A enzyme activity was determined via monitoring decrease of Dichlorophenolindophenol (DCIP) signal at $OD_{600}$.
Figure 23C:
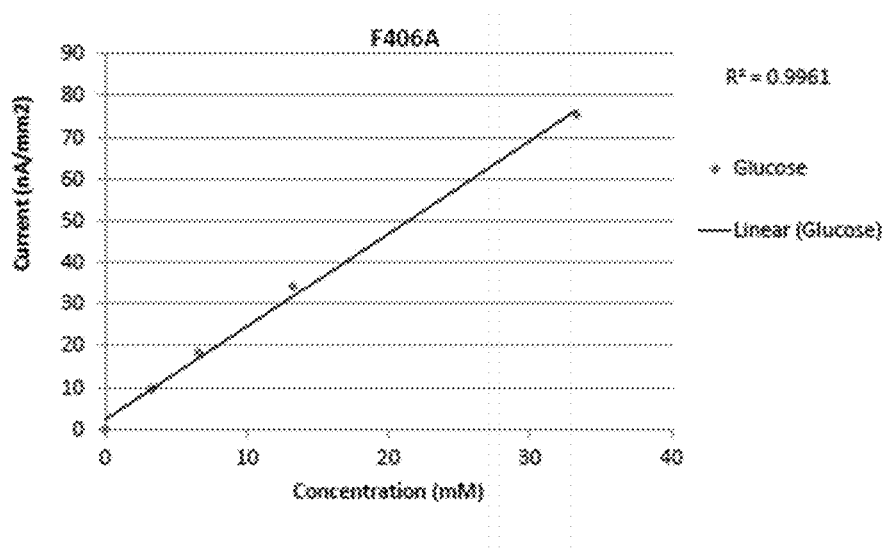
FIG. 23C shows electrochemical data representing the current response of the biosensor to various glucose concentrations (shown as a rhombus) and the linear fit across the data range is represented by the $R^2$ value.

Exemplary embodiments of the composition of the present invention are shown in FIGS. 23A-24C. FIG. 23A shows the biochemical response of FAD-GDHα F406A to varying concentrations of glucose (rhombus), and xylose (rectangle). FIG. 23B shows the biochemical response of F406A to glucose and the non-linear fit through which Km (k) and Vmax have been obtained. F406A enzyme activity was determined via monitoring decrease of Dichlorophenolindophenol (DCIP) signal at $OD_{600}$. FIG. 23C shows electrochemical data representing the current response of the biosensor to various glucose concentrations (shown as a rhombus) and the linear fit across the data range is represented by the $R^2$ value.

Figure 24A:
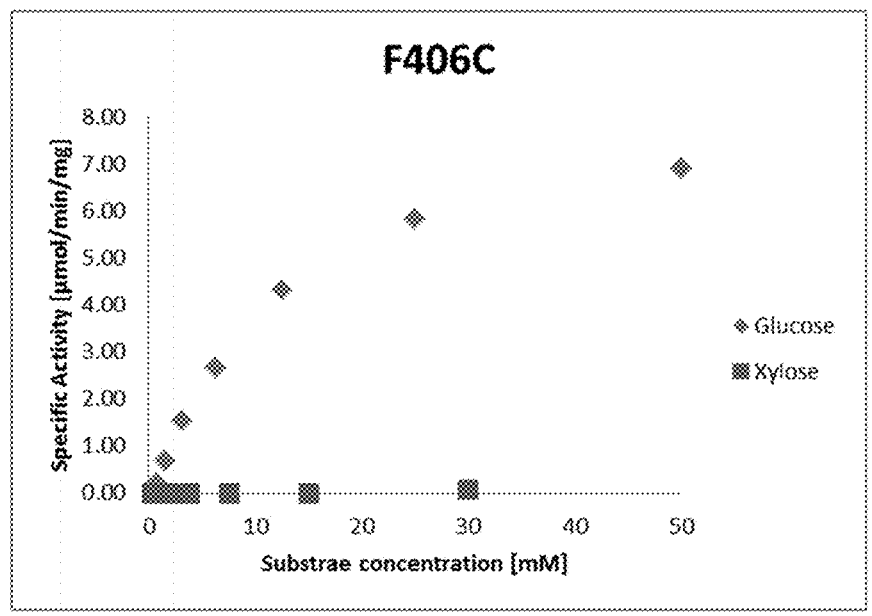
Figure 24B:
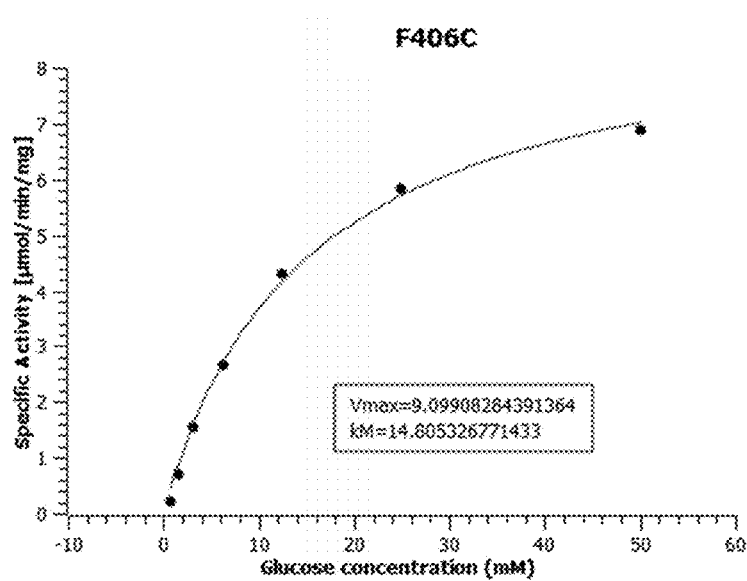
Figure 24C:
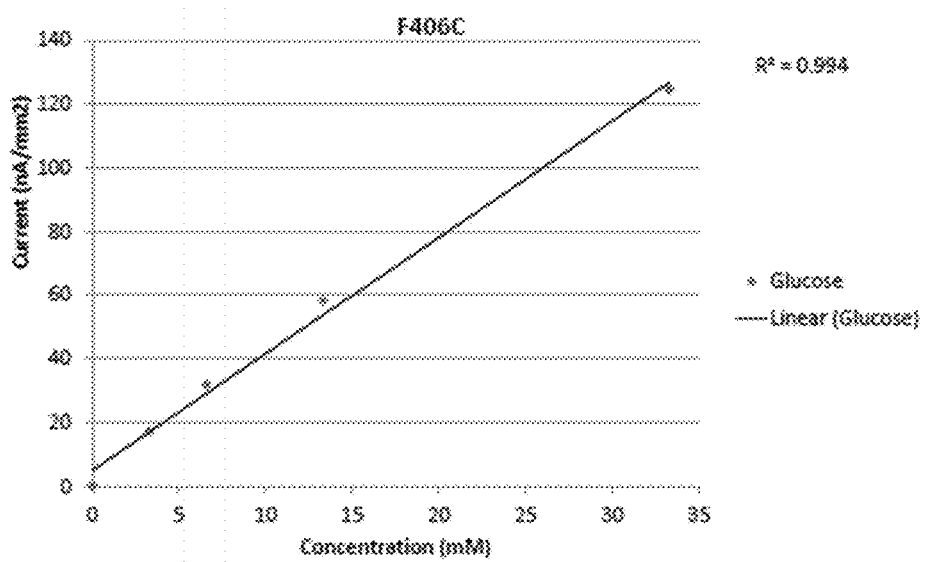

Exemplary embodiments of the compositions of the present invention are shown in FIGS. 24A-C. FIG. 24A shows the biochemical response of FAD-GDHα F406C to varying concentrations of glucose (rhombus), and xylose (rectangle). FIG. 24B shows the iochemical response of F406C to glucose and the non-linear fit through which Km (k) and Vmax have been obtained. F406C enzyme activity was determined via monitoring decrease of Dichlorophenolindophenol (DCIP) signal at $OD_{600}$. FIG. 24C shows the electrochemical data representing the current response of the biosensor to various glucose concentrations (shown as a rhombus) and the linear fit across the data range is represented by the $R^2$ value.

Figure 25A:
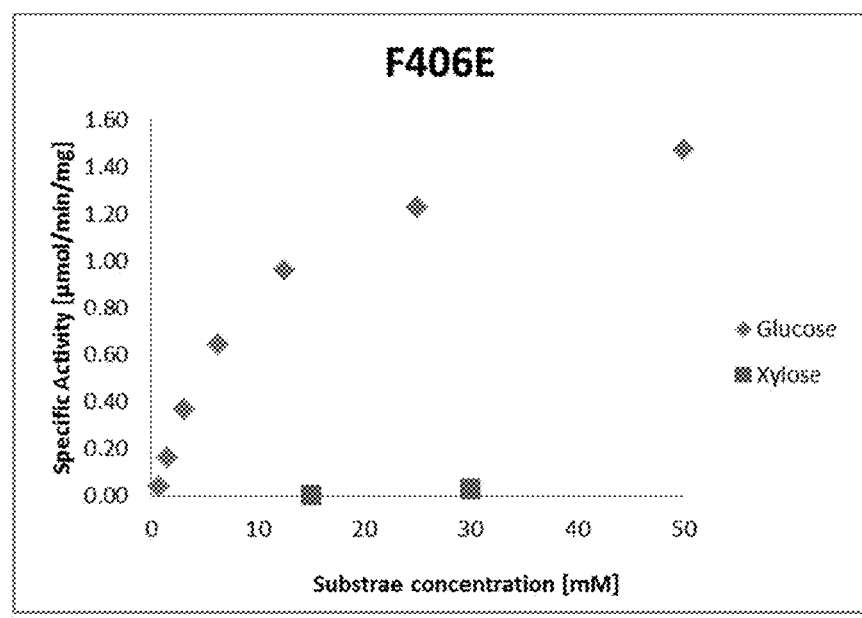
FIGS. 25A-C shows aspects of some embodiments of the present invention.
Figure 25B:
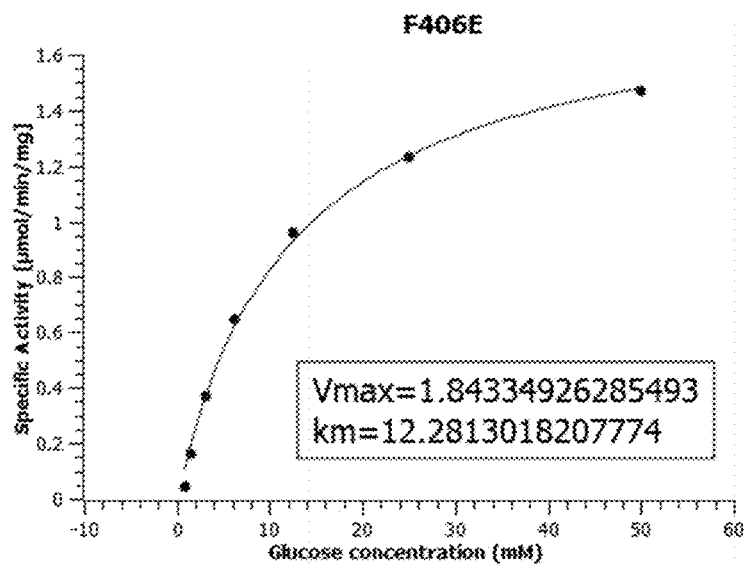
Figure 25C:
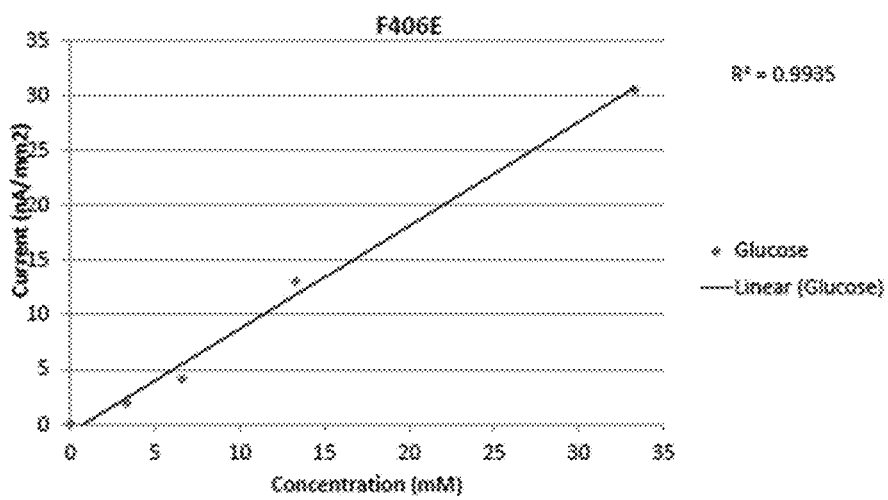

Exemplary embodiments of the compositions of the present invention are shown in FIGS. 25A-C. FIG. 25A shows the biochemical response of FAD-GDHα F406E to varying concentrations of glucose (rhombus), and xylose (rectangle). FIG. 25B shows the biochemical response of F406E to glucose and the non-linear fit through which Km (k) and Vmax have been obtained. F406E enzyme activity was determined via monitoring decrease of Dichlorophenolindophenol (DCIP) signal at $OD_{600}$. FIG. 25C shows electrochemical data representing the current response of the biosensor to various glucose concentrations (shown as a rhombus) and the linear fit across the data range is represented by the $R^2$ value.

Figure 26A:
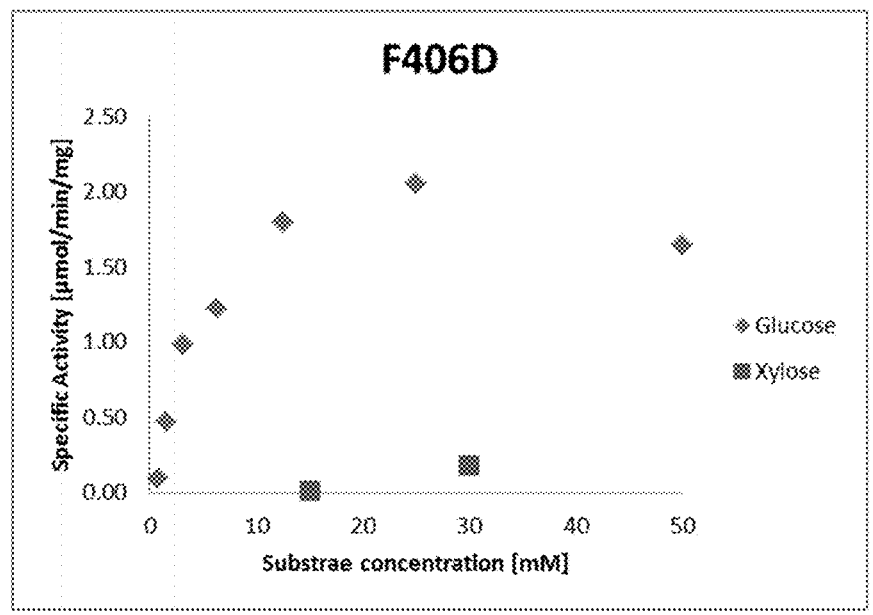
FIGS. 26A-C show some aspects of some embodiments of the present invention.
Figure 26B:
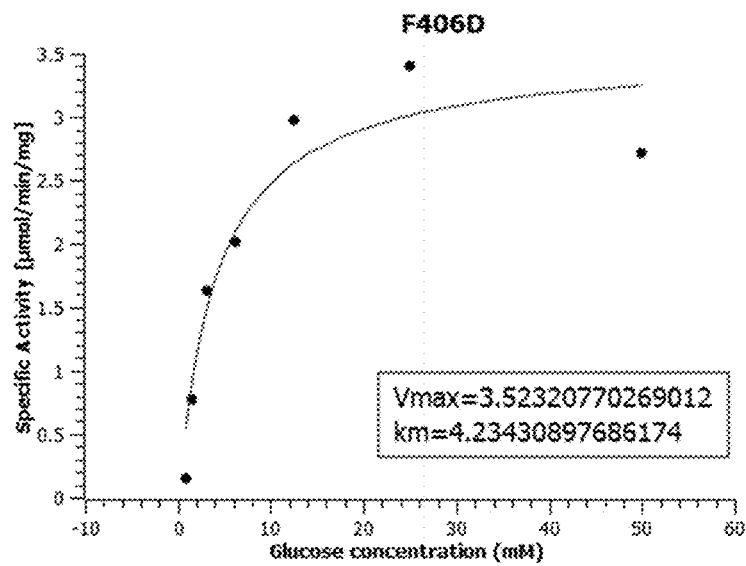
Figure 26C:
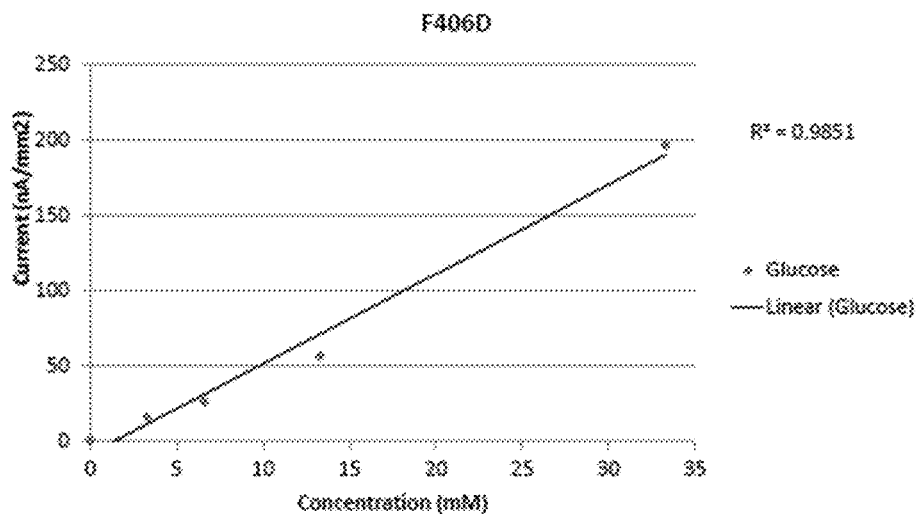

Exemplary embodiments of the compositions of the present invention are shown in FIGS. 26A-C. FIG. 26A shows the biochemical response of FAD-GDHα F406D to varying concentrations of glucose (rhombus), and xylose (rectangle). FIG. 26B shows the biochemical response of F406D to glucose and the non-linear fit through which Km (k) and Vmax have been obtained. F406D enzyme activity was determined via monitoring decrease of Dichlorophenolindophenol (DCIP) signal at $OD_{600}$. FIG. 26C shows the electrochemical data representing the current response of the biosensor to various glucose concentrations (shown as a rhombus) and the linear fit across the data range is represented by the $R^2$ value.

Figure 27A:
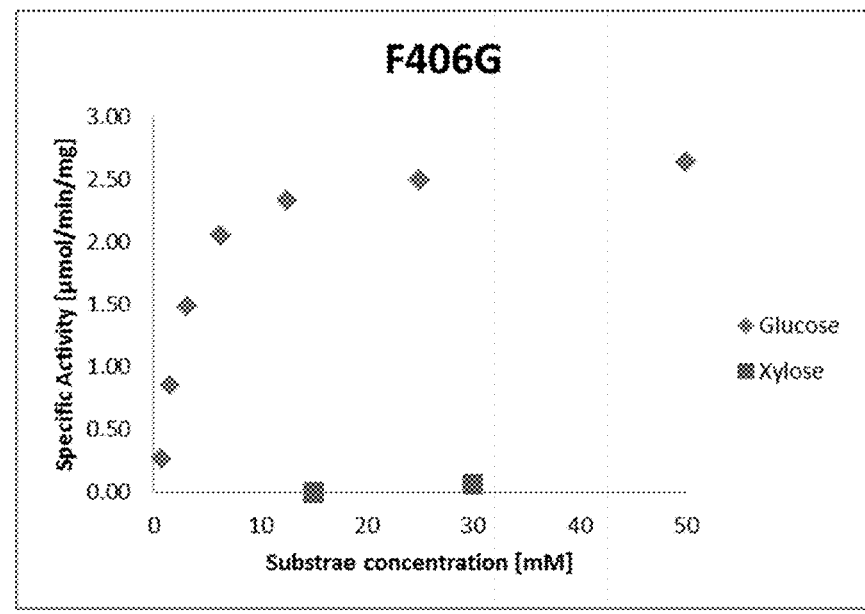
FIGS. 27A-C show some aspects of some embodiments of the present invention.
Figure 27B:
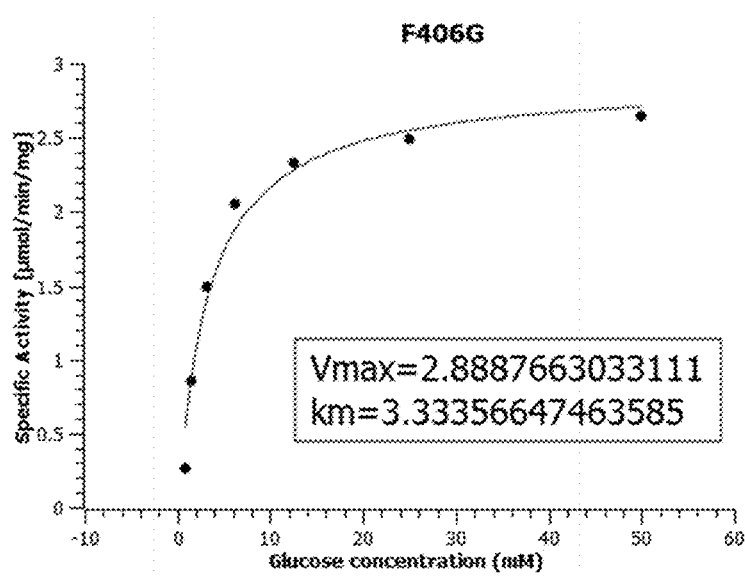
Figure 27C:
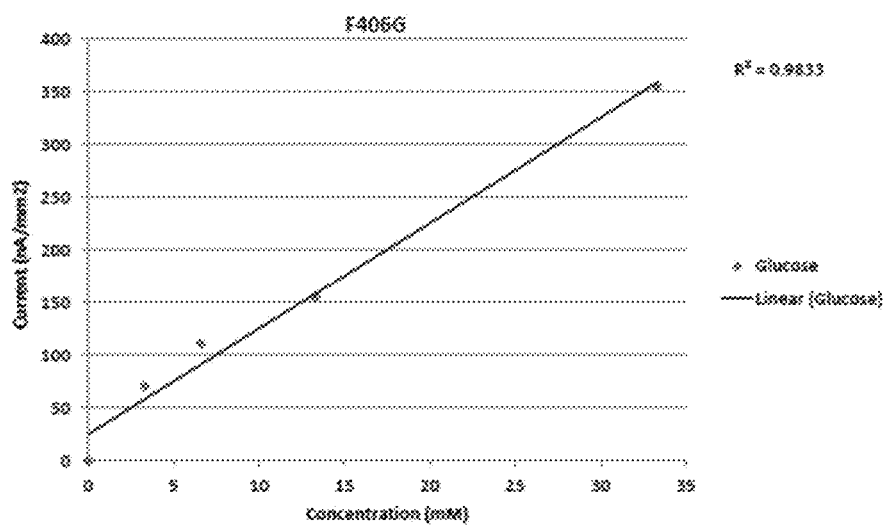

Exemplary embodiments of the compositions of the present invention are shown in FIGS. 27A-C. FIG. 27A shows the biochemical response of FAD-GDHα F406G to varying concentrations of glucose (rhombus), and xylose (rectangle). FIG. 27B shows the biochemical response of F406G to glucose and the non-linear fit through which Km (k) and Vmax have been obtained. F406G enzyme activity was determined via monitoring decrease of Dichlorophenolindophenol (DCIP) signal at $OD_{600}$. FIG. 27C shows electrochemical data representing the current response of the biosensor to various glucose concentrations (shown as a rhombus) and the linear fit across the data range is represented by the $R^2$ value.

Figure 28A:
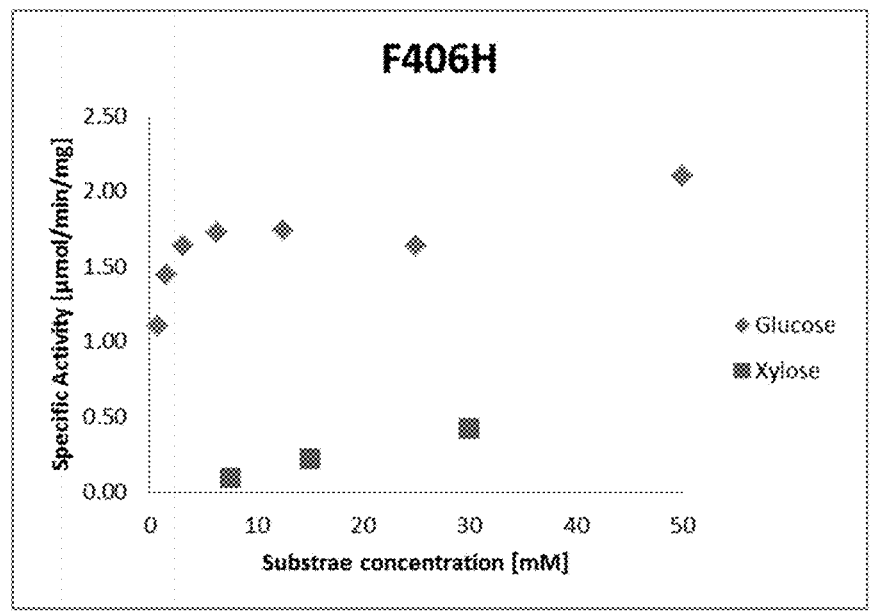
FIGS. 28A and 28B show aspects of some embodiments of the present invention.
Figure 28B:
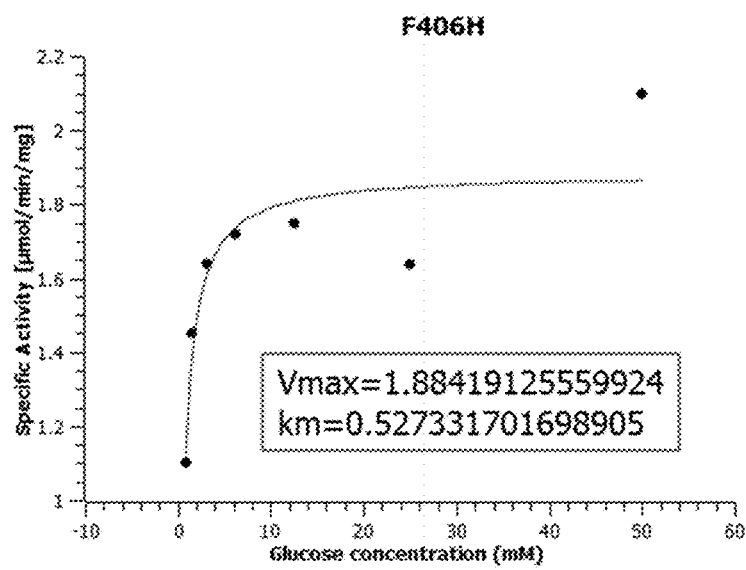

Exemplary embodiments of the compositions of the present invention are shown in FIGS. 28A and 28B. FIG. 28A shows the biochemical response of FAD-GDHα F406H to varying concentrations of glucose (rhombus), and xylose (rectangle). FIG. 28B shows the biochemical response of F406H to glucose and the non-linear fit through which Km (k) and Vmax have been obtained. F406H enzyme activity was determined via monitoring decrease of Dichlorophenolindophenol (DCIP) signal at $OD_{600}$.

Figure 29A:
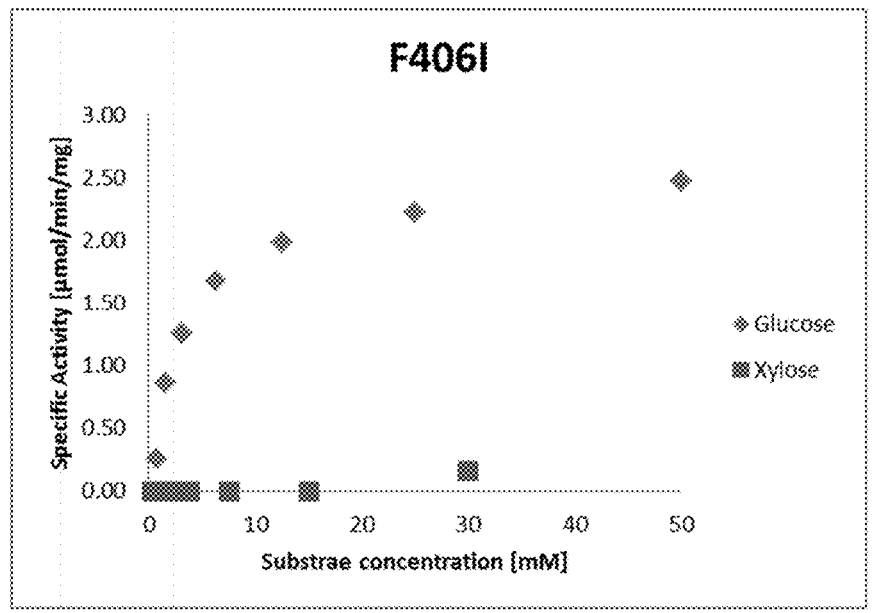
FIGS. 29A-C show some aspects of some embodiments of the present invention.
Figure 29B:
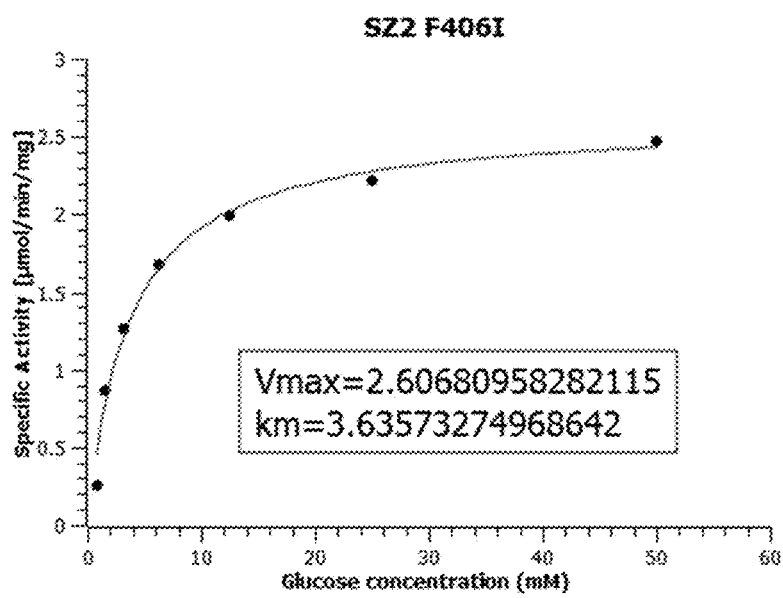
Figure 29C:
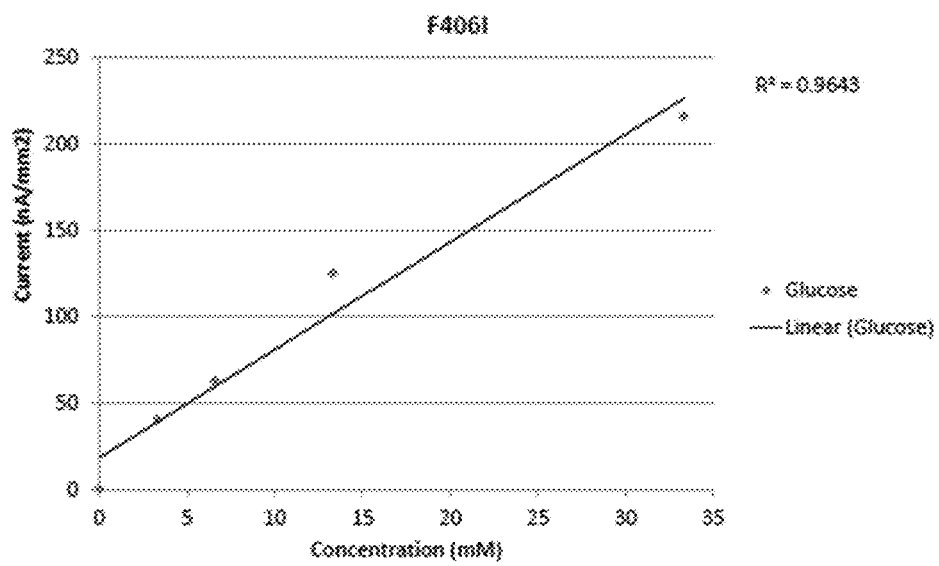

Exemplary embodiments of the compositions of the present invention are shown in FIGS. 29A-C. FIG. 29A shows the biochemical response of FAD-GDHα F406I to varying concentrations of glucose (rhombus), and xylose (rectangle). FIG. 29B shows the biochemical response of F406I to glucose and the non-linear fit through which Km (k) and Vmax have been obtained. F406I enzyme activity was determined via monitoring decrease of Dichlorophenolindophenol (DCIP) signal at $OD_{600}$. FIG. 29C shows electrochemical data representing the current response of the biosensor to various glucose concentrations (shown as a rhombus) and the linear fit across the data range is represented by the $R^2$ value.

Figure 30A:
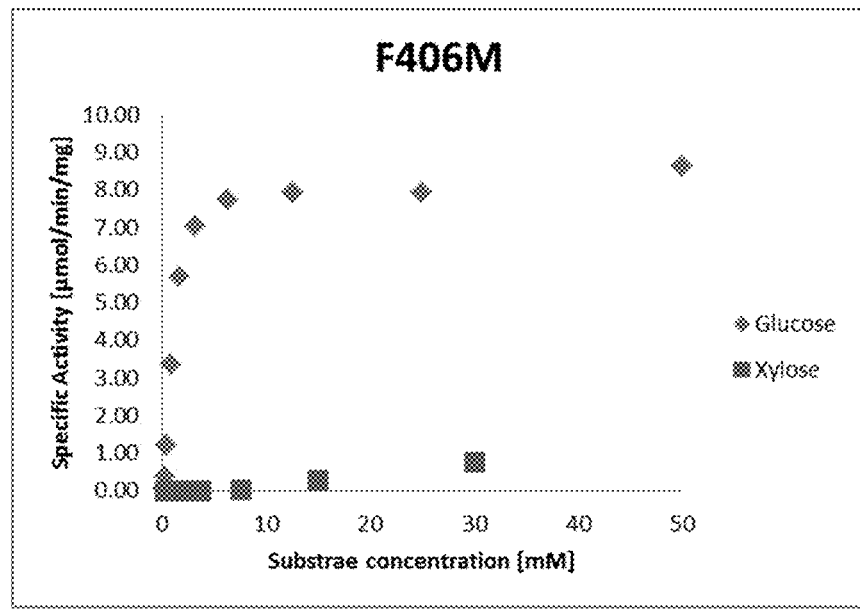
FIGS. 30A and 30B show some aspects of some embodiments of the present invention.
Figure 30B:
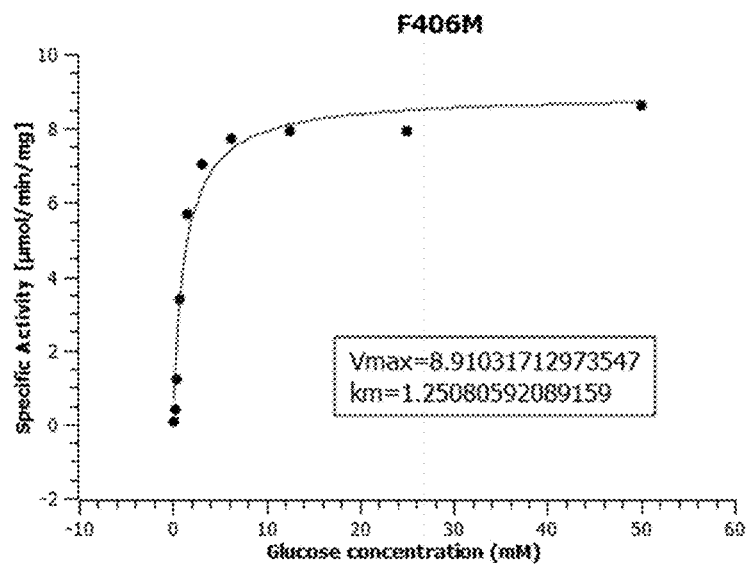

Exemplary embodiments of the compositions of the present invention are shown in FIGS. 30A and 30B. FIG. 30A shows the biochemical response of FAD-GDHα F406M to varying concentrations of glucose (rhombus), and xylose (rectangle). FIG. 30B shows the biochemical response of F406M to glucose and the non-linear fit through which Km (k) and Vmax have been obtained. F406M enzyme activity was determined via monitoring decrease of Dichlorophenolindophenol (DCIP) signal at $OD_{600}$.

Figure 31A:
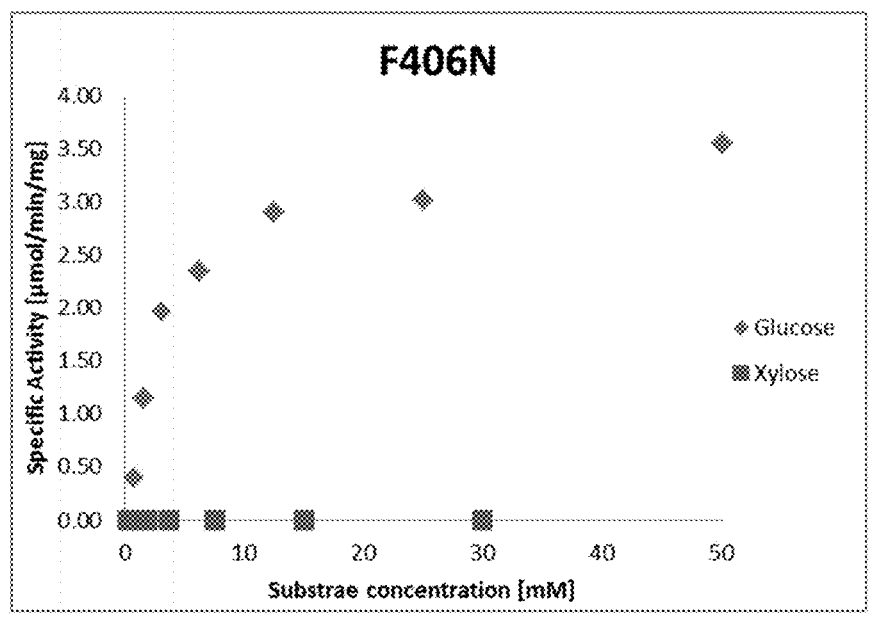
FIGS. 31A-C show some aspects of some embodiments of the present invention.
Figure 31B:
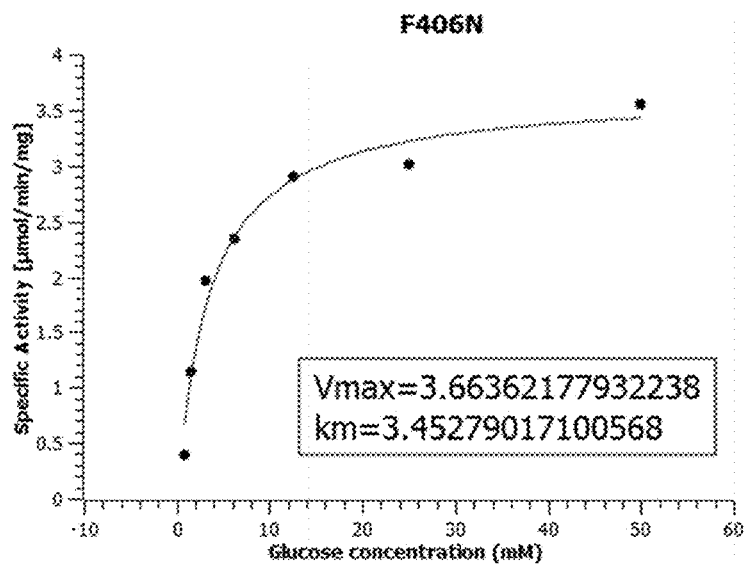
Figure 31C:
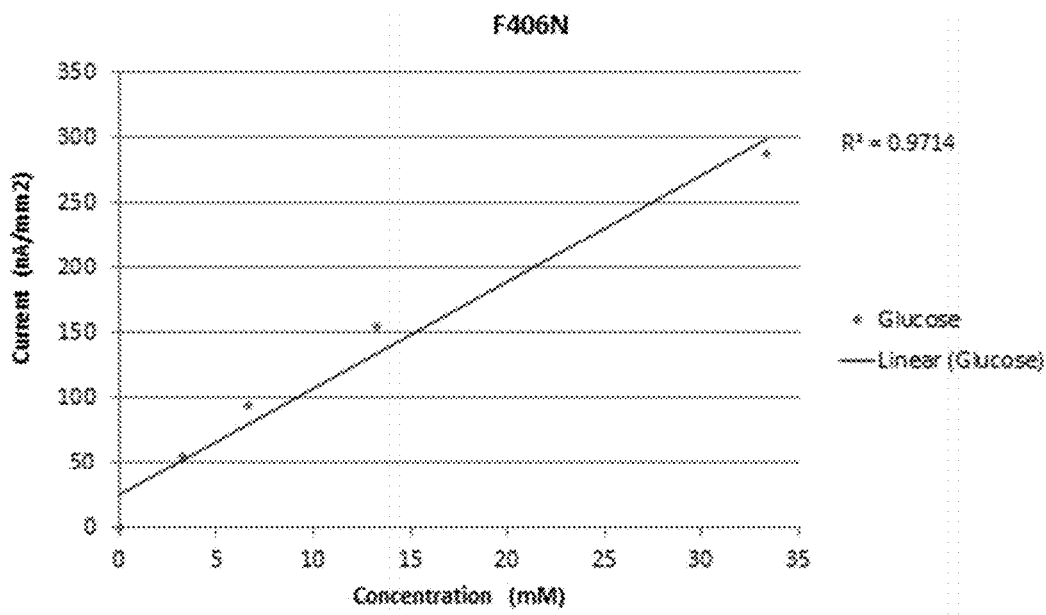

Exemplary embodiments of the compositions of the present invention are shown in FIGS. 31A-C. FIG. 31A shows the biochemical response of FAD-GDHα F406N to varying concentrations of glucose (rhombus), and xylose (rectangle). FIG. 31B shows the biochemical response of F406N to glucose and the non-linear fit through which Km (k) and Vmax have been obtained. F406N enzyme activity was determined via monitoring decrease of Dichlorophenolindophenol (DCIP) signal at $OD_{600}$. FIG. 31C shows electrochemical data representing the current response of the biosensor to various glucose concentrations (shown as a rhombus) and the linear fit across the data range is represented by the $R^2$ value.

Figure 32A:
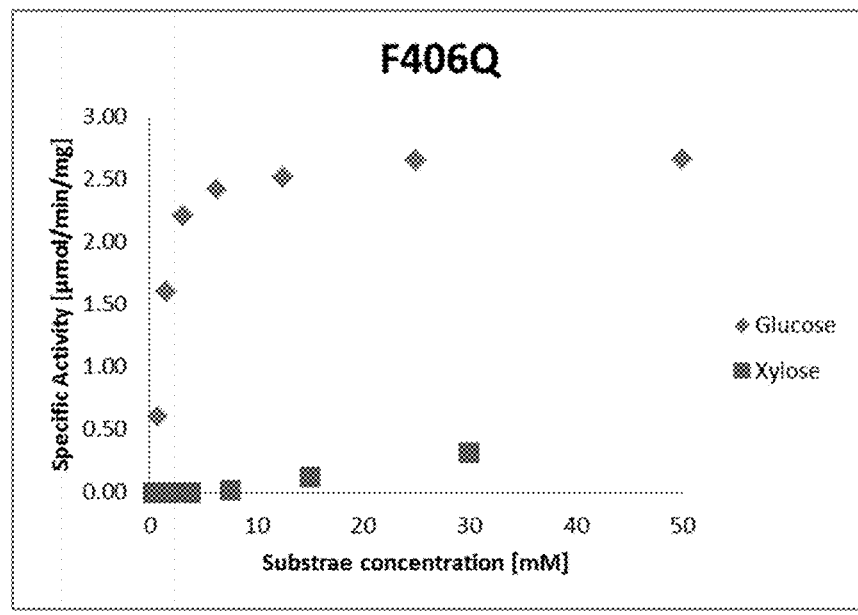
FIGS. 32A and 32B show some aspects of some embodiments of the present invention.
Figure 32B:
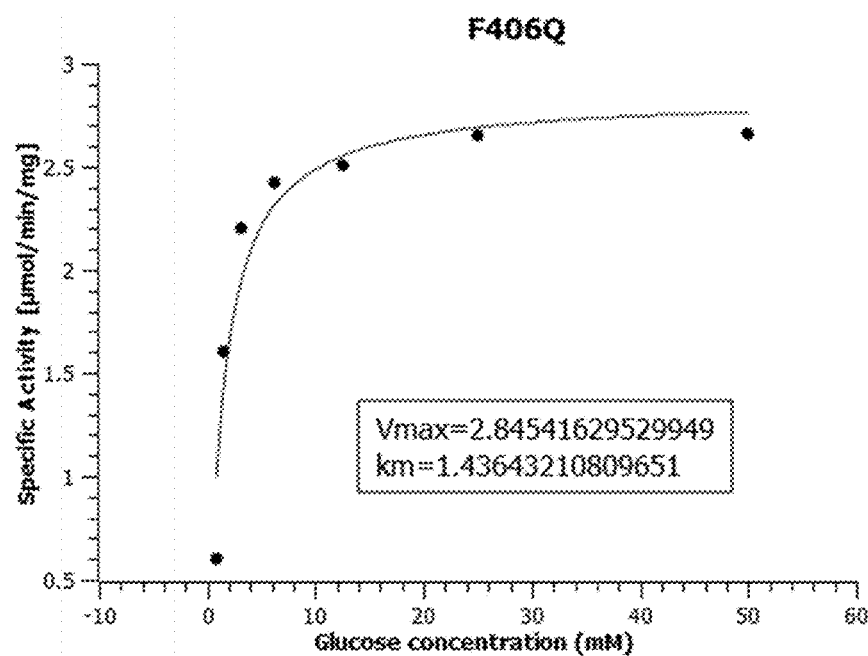

Exemplary embodiments of the compositions of the present invention are shown in FIGS. 32A and 32B. FIG. 32A shows the biochemical response of FAD-GDHα F406Q to varying concentrations of glucose (rhombus), and xylose (rectangle). FIG. 32B shows the biochemical response of F406Q to glucose and the non-linear fit through which Km (k) and Vmax have been obtained. F406Q enzyme activity was determined via monitoring decrease of Dichlorophenolindophenol (DCIP) signal at $OD_{600}$.

Figure 33A:
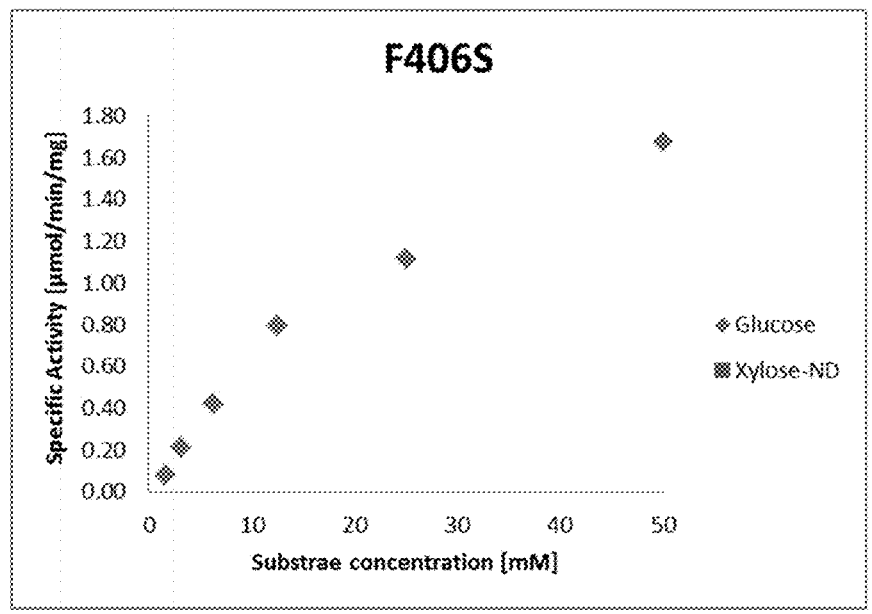
FIGS. 33A-C show some aspects of some embodiments of the present invention.
Figure 33B:
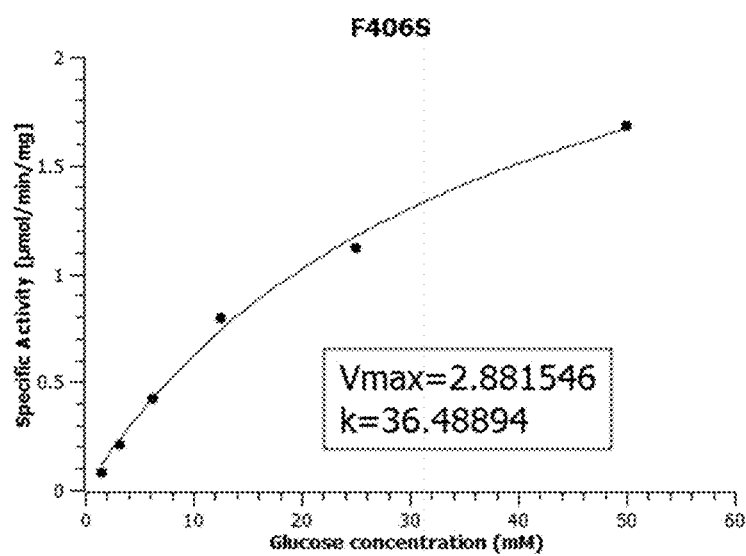
Figure 33C:
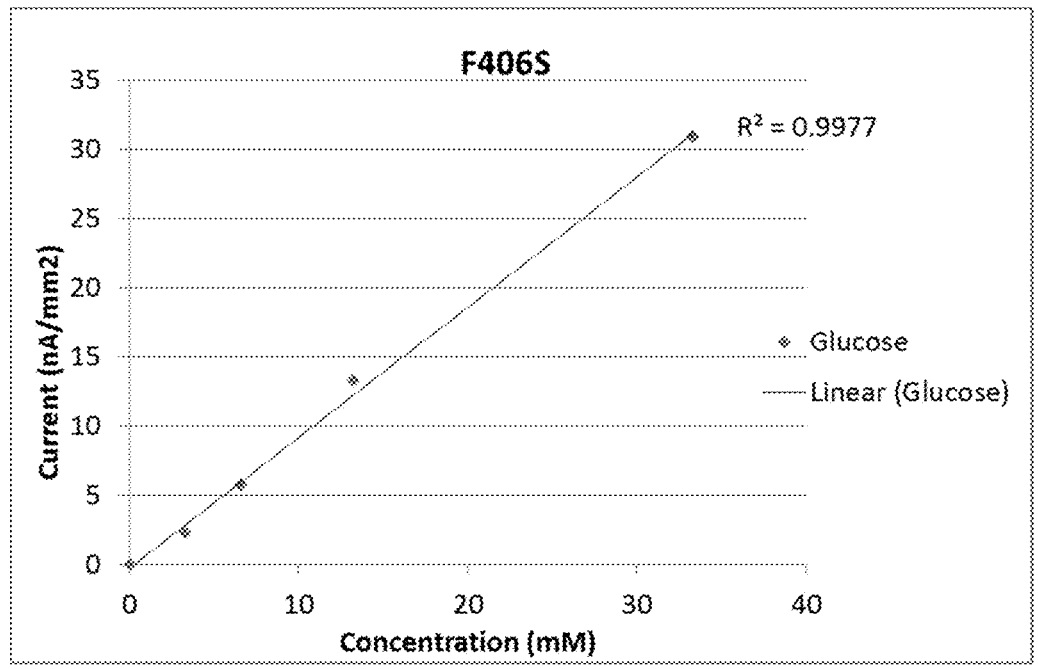

Exemplary embodiments of the compositions of the present invention are shown in FIGS. 33A-C. FIG. 33A shows biochemical response of FAD-GDHα F406S to varying concentrations of glucose (rhombus), and xylose (rectangle). FIG. 33 Biochemical response of F406S to glucose and the non-linear fit through which Km (k) and Vmax have been obtained. F406S enzyme activity was determined via monitoring decrease of Dichlorophenolindophenol (DCIP) signal at $OD_{600}$. FIG. 33C shows electrochemical data representing the current response of the biosensor to various glucose concentrations (shown as a rhombus) and the linear fit across the data range is represented by the $R^2$ value.

Figure 34A:
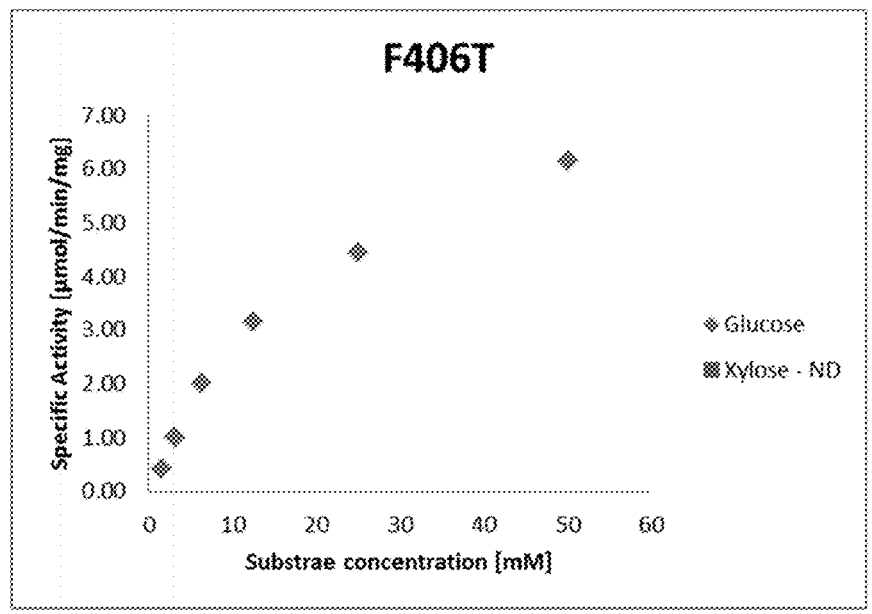
FIGS. 34A-C show some aspects of some embodiments of the present invention.
Figure 34B:
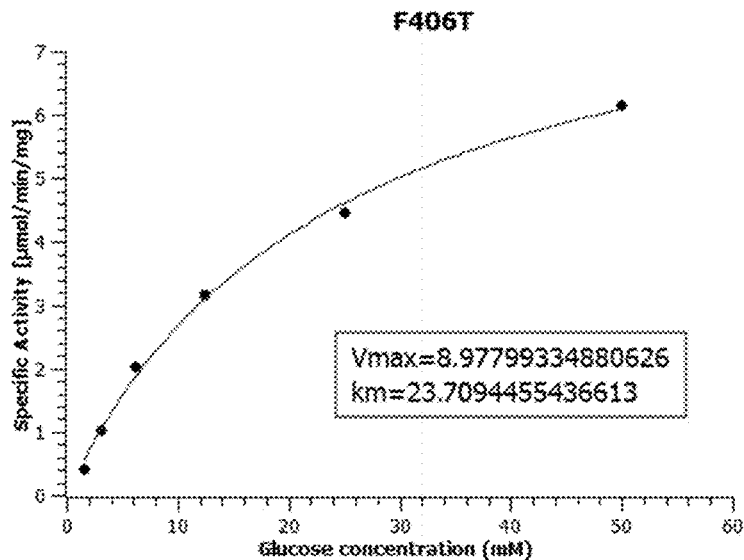
Figure 34C:
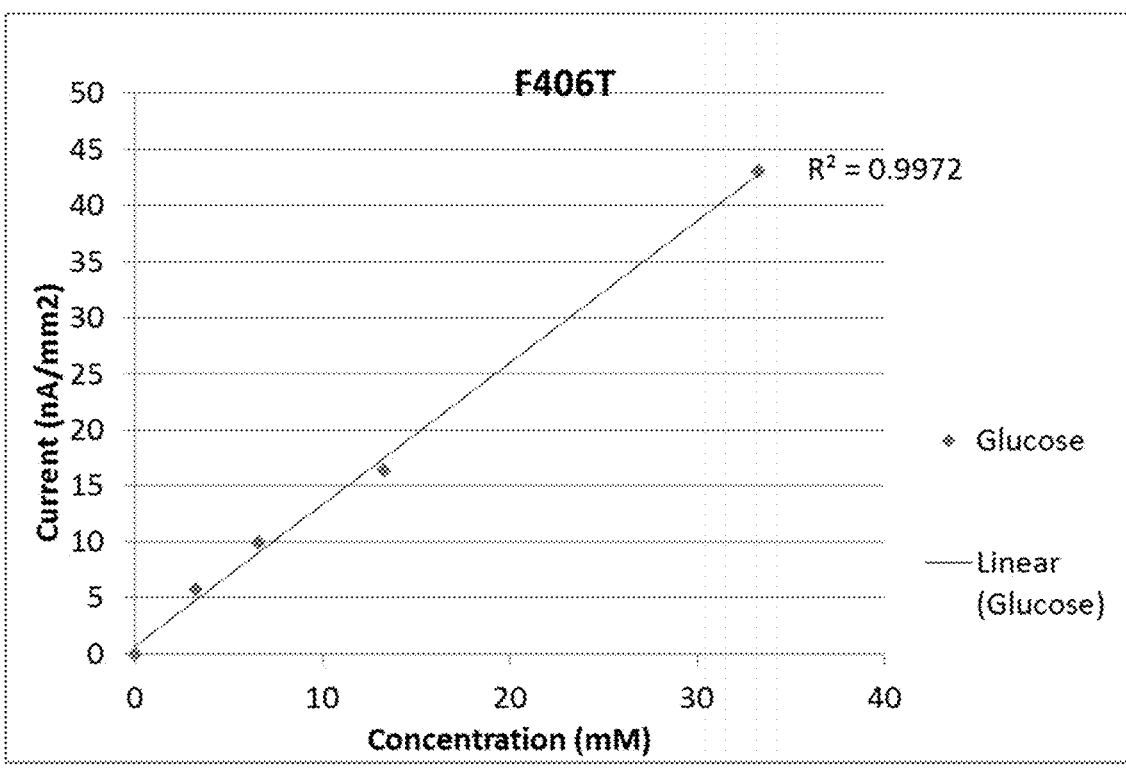

Exemplary embodiments of the compositions of the present invention are shown in FIGS. 34A-C. FIG. 34A shows the biochemical response of FAD-GDHα F406T to varying concentrations of glucose (rhombus), and xylose (rectangle). FIG. 34B shows biochemical response of F406T to glucose and the non-linear fit through which Km (k) and Vmax have been obtained. F406T enzyme activity was determined via monitoring decrease of Dichlorophenolindophenol (DCIP) signal at $OD_{600}$. FIG. 34C shows electrochemical data representing the current response of the biosensor to various glucose concentrations (shown as a rhombus) and the linear fit across the data range is represented by the $R^2$ value.

Figure 35A:
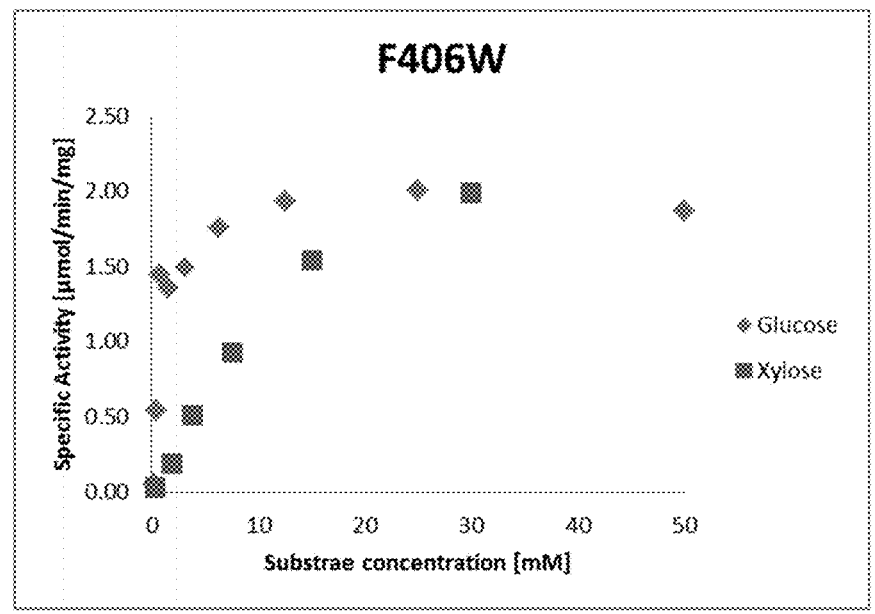
FIGS. 35A-B show negative results.
Figure 35B:
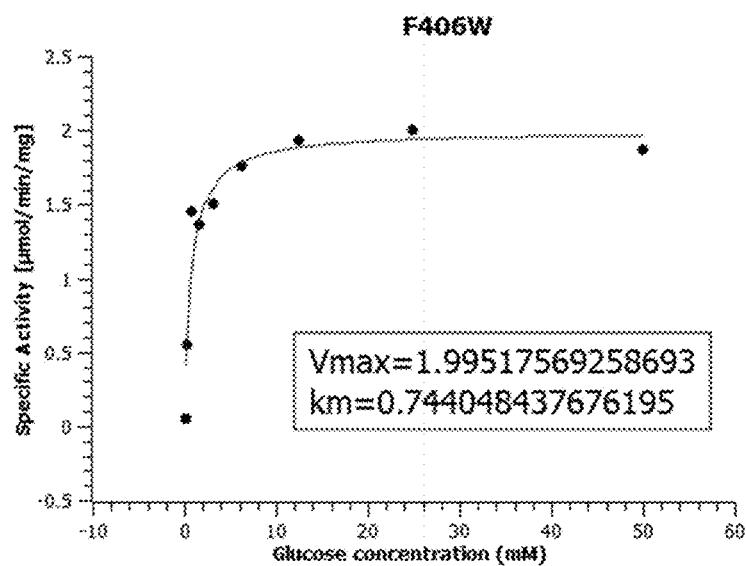

Exemplary embodiments of the compositions of the present invention are shown in FIGS. 35A-B. FIG. 35A shows a biochemical response of FAD-GDHα F406W to varying concentrations of glucose (rhombus), and xylose (rectangle). FIG. 35B shows a biochemical response of F406W to glucose and the non-linear fit through which Km (k) and Vmax have been obtained. F406W enzyme activity was determined via monitoring decrease of Dichlorophenolindophenol (DCIP) signal at $OD_{600}$.

Figure 36A:
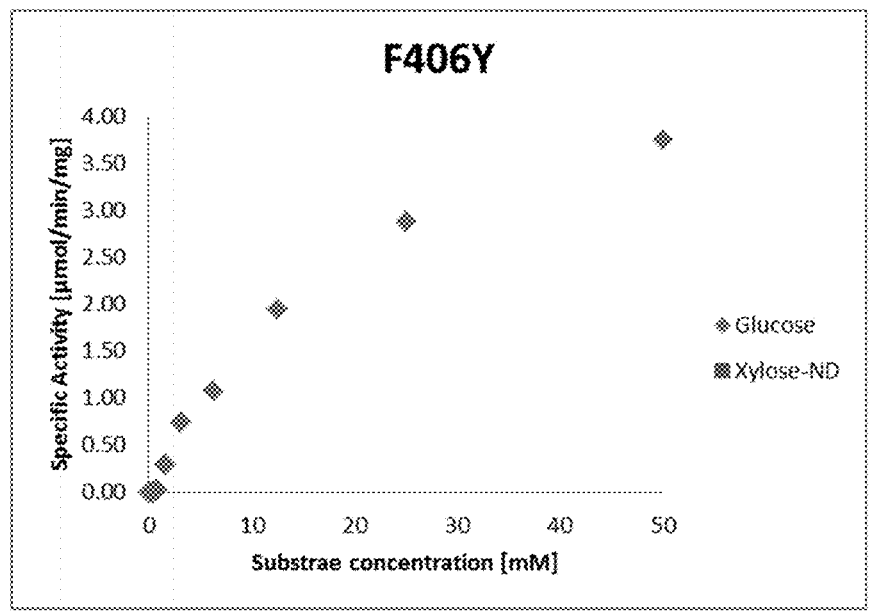
FIGS. 36A-C show some aspects of some embodiments of the present invention.
Figure 36B:
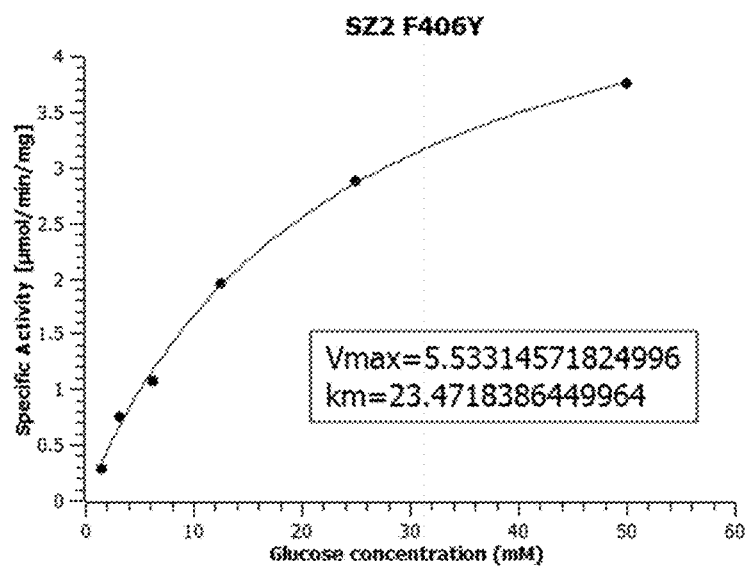
Figure 36C:
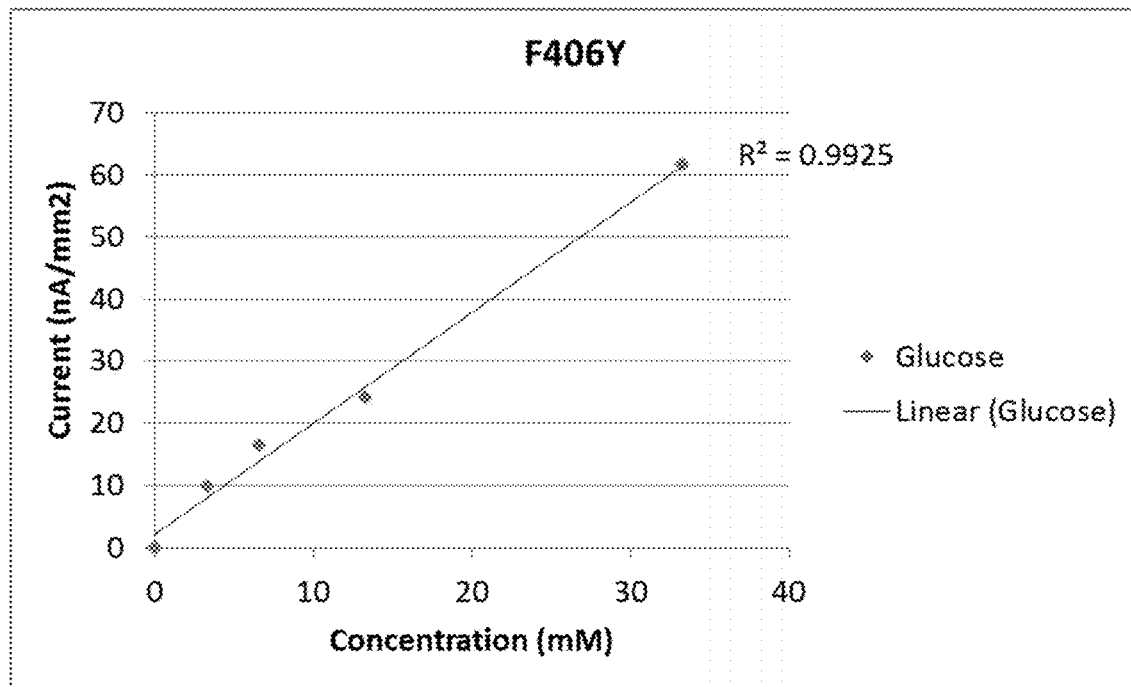

Exemplary embodiments of the compositions of the present invention are shown in FIGS. 36A-C. FIG. 36A shows the biochemical response of FAD-GDHα F406Y to varying concentrations of glucose (rhombus), and xylose (rectangle). FIG. 36B shows the biochemical response of F406Y to glucose and the non-linear fit through which Km (k) and Vmax have been obtained. F406Y enzyme activity was determined via monitoring decrease of Dichlorophenolindophenol (DCIP) signal at $OD_{600}$. FIG. 36C shows electrochemical data representing the current response of the biosensor to various glucose concentrations (shown as a rhombus) and the linear fit across the data range is represented by the $R^2$ value.

Figure 37A:
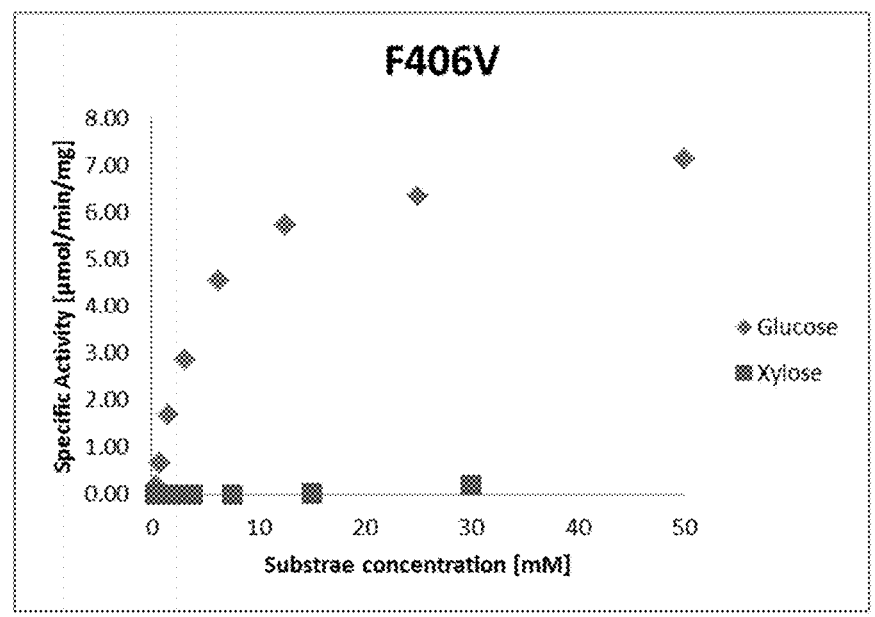
FIGS. 37A-C show some aspects of some embodiments of the present invention.
Figure 37B:
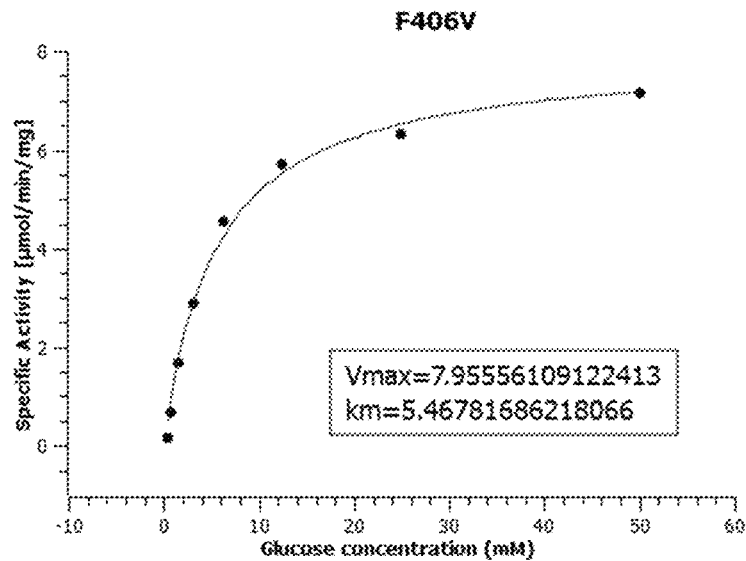
Figure 37C:
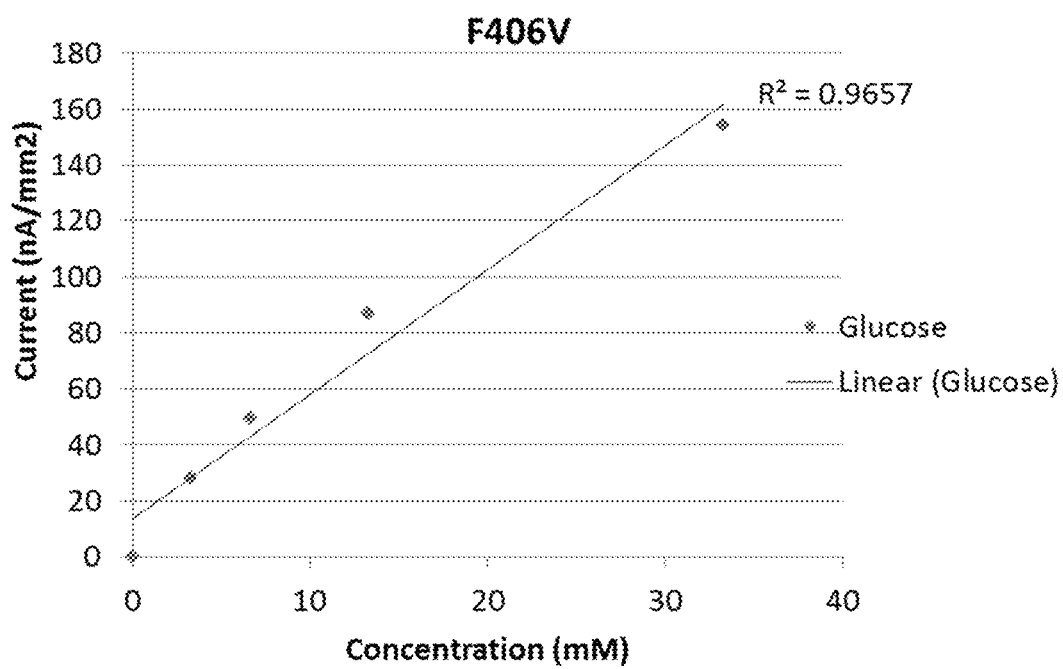

Exemplary embodiments of the compositions of the present invention are shown in FIGS. 37A-C. FIG. 37A shows the biochemical response of FAD-GDHα F406V to varying concentrations of glucose (rhombus), and xylose (rectangle). FIG. 37B shows the biochemical response of F406V to glucose and the non-linear fit through which Km (k) and Vmax have been obtained. F406V enzyme activity was determined via monitoring decrease of Dichlorophenolindophenol (DCIP) signal at $OD_{600}$. FIG. 37C shows electrochemical data representing the current response of the biosensor to various glucose concentrations (shown as a rhombus) and the linear fit across the data range is represented by the $R^2$ value.

Figure 38A:
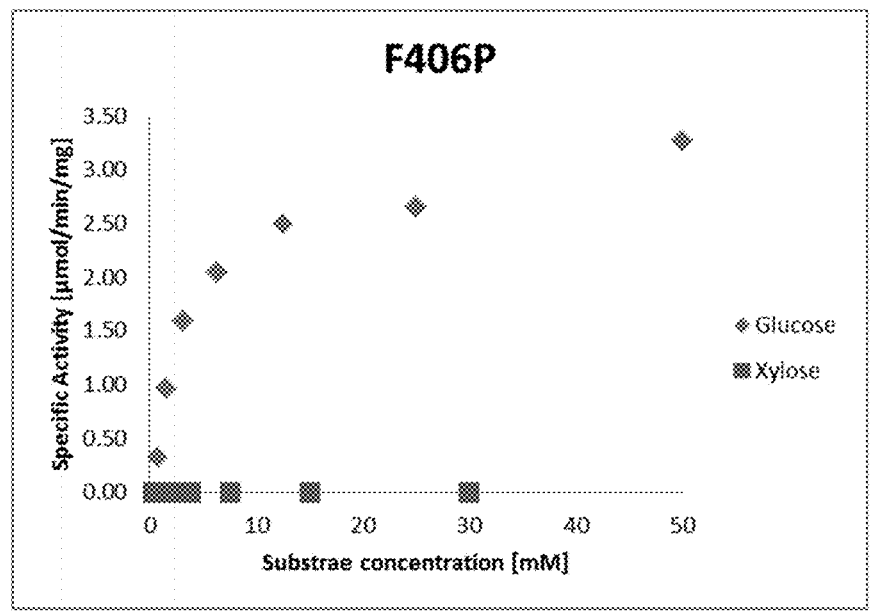
FIGS. 38A-C show some aspects of some embodiments of the present invention.
Figure 38B:
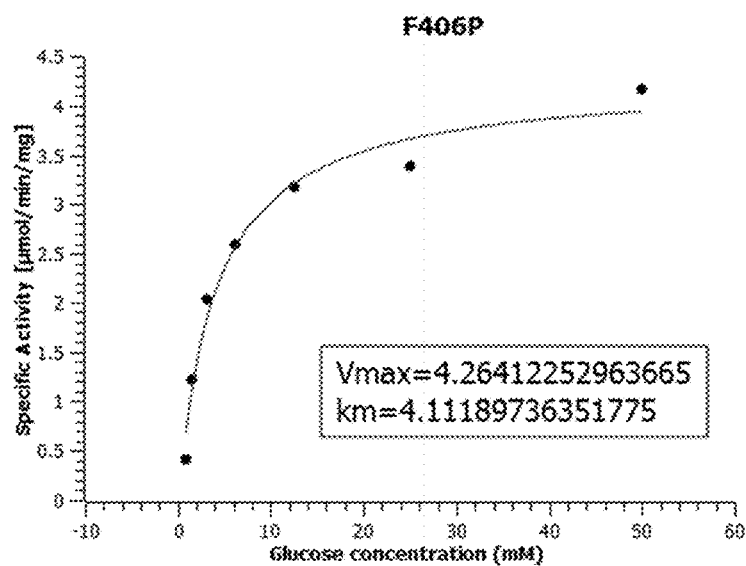
Figure 38C:
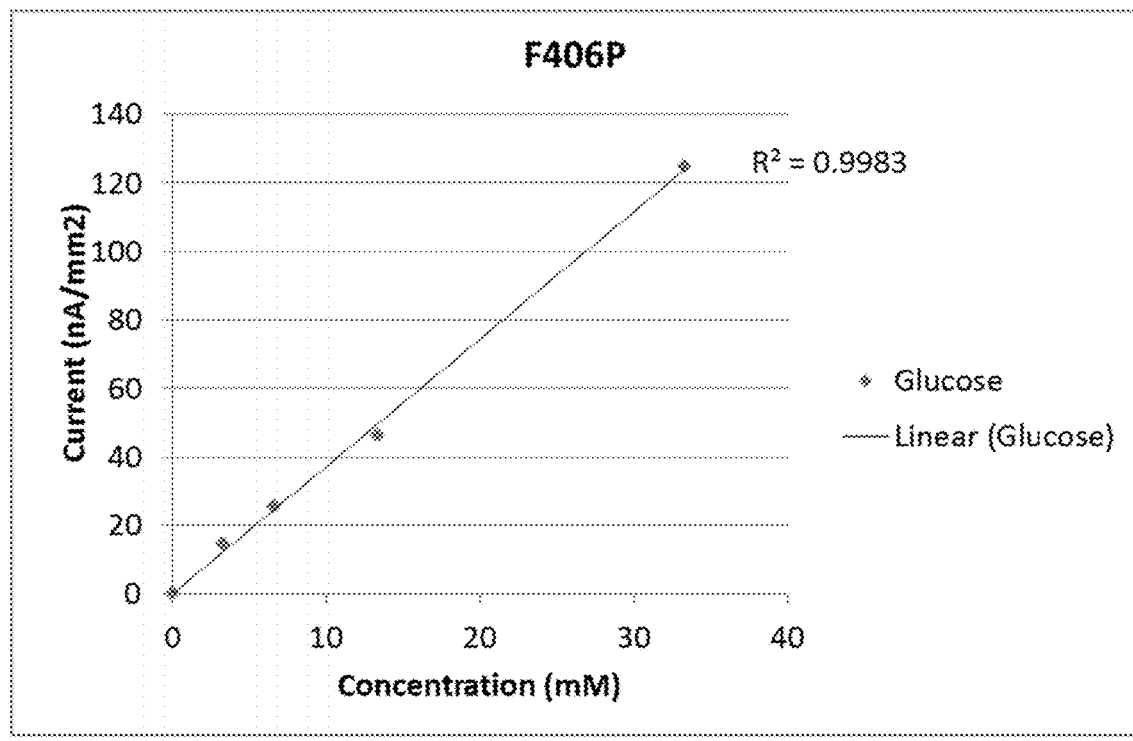

Exemplary embodiments of the compositions of the present invention are shown in FIGS. 38A-C. FIG. 38A shows the biochemical response of FAD-GDHα F406P to varying concentrations of glucose (rhombus), and xylose (rectangle). FIG. 38B shows the biochemical response of F406P to glucose and the non-linear fit through which Km (k) and Vmax have been obtained. F406P enzyme activity was determined via monitoring decrease of Dichlorophenolindophenol (DCIP) signal at $OD_{600}$. FIG. 38C shows electrochemical data representing the current response of the biosensor to various glucose concentrations (shown as a rhombus) and the linear fit across the data range is represented by the $R^2$ value.

Figure 39:
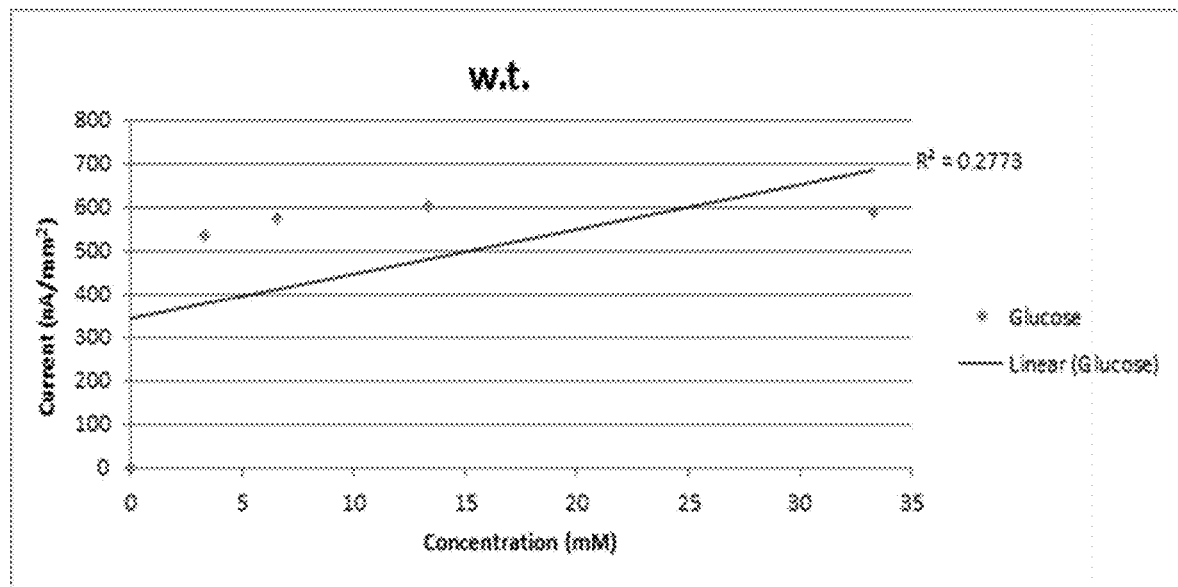
FIG. 39 shows electrochemistry data in connection with the wild type FAD-GDHα protein.

Exemplary embodiments showing electrochemistry data in connection with the wild type FAD-GDHα protein are shown in FIG. 39.

Exemplary embodiments are shown in a table listing electrochemistry data of the composition of the present invention in FIG. 40. Mutations in position 406 provide improved linearity over the entire range of physiological range: F406-S/C/T/V/Y/N/P/L/G/A/I/D/E.

Exemplary embodiments of the composition of the present invention are shown in FIG. 41. Mutations in position 406 that provide improved selectivity of glucose: F406-S/C/T/M/V/Y/N/P/L/G/Q/A/I/D/H/E. F406W provides an example of a substitution that reduces the enzyme selectivity towards glucose.

In some embodiments, the protein of the present invention can be linked to an epitope tag, e.g., but not limited to, a HIS tag, a 6×HIS tag, a maltose binding protein tag, a green fluorescent protein tag, a glutathione-s-transferase tag, a streptavidin tag, etc. The epitope tag can be separated from the protein by using a linker having, e.g., 1-n amino acids in length.

EXAMPLES: MUTATED FAD-GDH, ALPHA SUBUNIT (A), STRAIN B. CEPACIA

Example 1

FAD-GDHα was mutated to include the following point mutations: M43T and I346V, as shown in SEQ ID NO: 3.

Example 2

FAD-GDHα was mutated to include the following point mutations: S420N, S365F, as shown in SEQ ID NO: 4.

Example 3

FAD-GDHα was mutated to include the following point mutation: G208D, as shown in SEQ ID NO: 5.

Example 4

FAD-GDHα was mutated to include the following point mutation: T521A, as shown in SEQ ID NO: 6.

Example 5

FAD-GDHα was mutated to include the following point mutation: V306A, Q412R, and R416C as shown in SEQ ID NO: 7.

Example 6

FAD-GDHα was mutated to include the following point mutation: M318T and R369H as shown in SEQ ID NO: 8.

Example: Generating Recombinant Enzyme

Random point mutations of FAD-GDHα subunit (FADα) are generated using error prone PCR methods, e.g, GeneMorph II Random Mutagenesis Kit (Agilent) with primers listed in SEQ ID NOs: 30-33.

The DNA sequences of FADα and FADγ are based on either accession#AF430844.1 (*B. cepacia*) or accession #CP000152.1 (*B. lata*) and its protein sequences are detailed as SEQ ID NO: 1 (*B. cepacia*) and SEQ ID NO: 2 (*B. lata*), respectively (for FADα).

The FADα was cloned via ligation-dependent cloning into the plasmid vector, pTrcHis2A, which was linearized via digestion with NcoI and HindIII restriction endonucleases. The ligation position was in tandem and 3' to the FAD-GDH gamma (FADγ) subunit in such a manner that the last nucleotide of the FADγ stop codon (Adenine) is the first nucleotide of the FADα start codon (Adenine). The ligation was conducted overnight at 16° C. by mixing varying molar ratios of NcoI- and HindIII-digested FADα and pTrcHis2A. Ligation products were transformed into DH5a competent cells and the resulting colonies were used to isolate DNA and analyze the resulting plasmid DNA for positive ligation. Aside from pTrcHis2A, the fusion protein can be expressed in pET system plasmids (such as pET14, pET15, pET16, pET19-pET30, pET30 EK/LIC, pET30 Xa/LIC, pET32-pET42) although the specific restriction endonuclease sites might vary according to the relevant sites available in the plasmid vector.

The pTrcHis2A-FADγ-FADα (pFADα) was tested for protein expression and GDH activity in for example, but not limited to, the following bacterial strains: DH5a, BL21, BL21(DE3), BL21-Codon-plus/RIL, BL21(DE3)-Codon-plus/RIL, BL21(DE3)-Rosetta2, although it can be tested in BL21(DE3)-Rosetta, BL21(DE3)-pLysS, BL21-SI, BLI21-AI, BL21-Tuner, BL21-Tuner-pLysS, BL21-Rosetta-Gami, B L21-Rosetta-Gami-pLysS, Lemo21 (DE3). Protein expression was induced at semi-log phase culture density (OD of ~0.6 at 600 nm) by addition 0.1 mM-0.5 mM Isopropyl 3-D-1-thiogalactopyranoside (IPTG) to the bacterial culture at varying temperature settings (20° C., 30° C., 37° C. and can also be tested at 18° C., 27° C. temperature settings) with Luria-Bertani (LB), Terrific Broth (TB) or Autoinduction media (LB or TB based). Protein expression levels were tested at the protein level after performing cell lysis through the use of sonication and/or use of cell lysis solution and/or homogenization and observation of protein profile via Sodium-Dodecyl-Sulfate polyacrylamide gel electrophoresis (SDS-PAGE) analysis at 10-15% percent acrylamide. Protein expression levels were also tested through monitoring GDH activity levels by mixing cell lysate with reaction buffered solution (e.g., pH 7 or pH 6.5) containing 0.3-0.8 mM of 2,6-dichlorophenolindophenol (DCIP) and 0.3-0.8 mM phenazine methosulfate (PMS) incubated at e.g., 37° C. or 30° C. in the presence of varying glucose concentrations. GDH activity was monitored via spectrophotometer at 600 nm band width.

Medium and large scale protein expression was initiated in 600 ml cultures of TB at 37° C. At mid-log phase, IPTG was added to the media while temperature setting was switched to 20° C. for an overnight growth protein expression induction. The cells were collected by centrifugation at 6000 rpm for 15 minutes at 4° C. The cell pellet was resuspended in protein buffer (buffered solution (pH 7 or preferably pH 6.5) and 150-500 mM NaCl) supplemented with 10 mM Imidazole, protease inhibitor cocktail tablet and 10 μg DNAse I (lysis buffer). Lysis was conducted via three passes of French press at 15,000 PSI cell pressure or 5 sonication sessions (each session consists of 30 seconds on, 30 seconds rest) and followed by a centrifugation at 20,000 g for 60 minutes. The soluble fraction was loaded on gravity-flow column packed with 5 ml of 50% Ni-NTA slurry pre-quilibrated with lysis buffer. The binding step was followed by three washing steps with increasing imidazole concentration (20, 30 and 40 mM) and accompanying varying salt concentrations (150, 500 and 150 mM) while keeping the solution buffered (pH 7 or preferably pH 6.5). The elution step was conducted by elevating the imidazole concentration to 300 mM in the presence of 150 mM NaCl while keeping the solution buffered (pH 7 or preferably pH 6.5). The eluted protein was evaluated for protein purification and GDH activity level via SDS-PAGE analysis and spectrophotometer analysis at 600 nm as described before and selected fractions were pooled, dialyzed against PBS pH 7.4 and concentrated to 1-5 mg/ml before flash frozen in liquid nitrogen or freeze dried.

TABLE 2

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
| --- | --- |
| SEQ ID NO: 1 | Protein sequence ORF2 (FADα)-*B. cepacia* Wild type<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIALALRMSDT<br>LKKEVGSGSGHHHHHH* |
| SEQ ID NO: 2 | Protein sequence ORF2 (FADα)-*B. lata* Wild type<br>MADTDTQKADVVVVGSGVAGAIVAHQLAMAGKSVILLEAGPRMPRWE<br>IVERFRNQPDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET |

TABLE 2-continued

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
|---|---|
|  | PKILLMSANRDFPNGVANSSDMVGRNLMDHPGTGVSFYASEKLWPGR<br>GPQEMTSLIGFRDGPFRANEAAKKIHLSNLSRINQETQKIFKAGGKLMKP<br>EELDAQIRDRSARFVQFDCFHEILPQPENRIVPSKTATDAIGIPRPEITYAI<br>DDYVKRGAVHTREVYATAAKVLGGTDVVFNDEFAPNNHITGATIMGA<br>DARDSVVDKDCRTFDHPNLFISSSSTMPTVGTVNVTLTIAALALRMSDT<br>LKKEVGSGSGHHHHHH |
| SEQ ID NO: 3 | Protein sequence ORF2 (FADα)-*B. cepacia* mutant<br>MADTDTQKADVVVVGSGVAGAIVAHQLAMAGKSVILLEAGPRMPRWE<br>IVERFRNQPDKTDFMAPYPSSAWAPHPEYGPPNDYLILKGEHKFNSQYIR<br>AVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKF<br>HVVTEPVARNSRPYDGRPTCCGNNNCMPICPIGAMYNGIVHVEKAERA<br>GAKLIENAVVYKLETGPDKRITAAVYKDKTGADHRVEGKYFVIAANGI<br>ETPKILLMSANRDFPNGVANSSDMVGRNLMDHPGTGVSFYASEKLWPG<br>RGPQEMTSLIGFRDGPFRANEAAKKIHLSNLSRINQETQKIFKAGGKLMK<br>PDELDAQIRDRSARFVQFDCFHEILPQPENRIVPSKTATDAIGIPRPEITYA<br>IDDYVKRGAVHTREVYATAAKVLGGTDVVFNDEFAPNNHITGATIMGA<br>DARDSVVDKDCRTFDHPNLFISSSSTMPTVGTVNVTLTIAALALRMSDT<br>LKKEVGSGSGHHHHHH |
| SEQ ID NO: 4 | Protein sequence ORF2 (FADα)-*B. cepacia* mutant<br>MADTDTQKADVVVVGSGVAGAIVAHQLAMAGKSVILLEAGPRMPRWE<br>IVERFRNQPDKTDFMAPYPSSAWAPHPEYGPPNDYLILKGEHKFNSQYIR<br>AVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKF<br>HVVTEPVARNSRPYDGRPTCCGNNNCMPICPIGAMYNGIVHVEKAERA<br>GAKLIENAVVYKLETGPDKRITAAVYKDKTGADHRVEGKYFVIAANGI<br>ETPKILLMSANRDFPNGVANSSDMVGRNLMDHPGTGVSFYASEKLWPG<br>RGPQEMTSLIGFRDGPFRANEAAKKIHLSNLSRINQETQKIFKAGGKLMK<br>PDELDAQIRDRSARFVQFDCFHEILPQPENRIVPSKTATDAIGIPRPEITYA<br>IDDYVKRGAVHTREVYATAAKVLGGTDVVFNDEFAPNNHITGATIMGA<br>DARDSVVDKDCRTFDHPNLFISSSSTMPTVGTVNVTLTIAALALRMSDT<br>LKKEVGSGSGHHHHHH |
| SEQ ID NO: 5 | Protein sequence ORF2 (FADα)-*B. cepacia* mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 6 | Protein sequence ORF2 (FADα)-*B. cepacia* mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVALTIAALALRMSDT<br>LKKEVGSGSGHHHHHH |
| SEQ ID NO: 7 | Protein sequence ORF2 (FADα)-*B. cepacia* mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGAANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPRPENCIVPSKTATDAIGIPRPEITYA |

TABLE 2-continued

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
|---|---|
| | IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 8 | Protein sequence ORF2 (FADα)-*B. cepacia* mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLTDHPGTGVSFYASEKLWPG<br>RGPQEMTSLIGFRDGPFRATEAAKKIHLSNLSHIDQETQKIFKAGKLMKP<br>DELDAQIRDRSARYVQFDCFHEILPQPENRIVPSKTATDAIGIPRPEITYAI<br>DDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 9 | Protein sequence ORF2 (FADα)-*B. cepacia* F406L mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCLHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 10 | Protein sequence ORF2 (FADα)-*B. cepacia* F406D mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCDHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 11 | Protein sequence ORF2 (FADα)-*B. cepacia* F406H mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCHHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 12 | Protein sequence ORF2 (FADα)-*B. cepacia* F406M mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCMHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |

TABLE 2-continued

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
|---|---|
| SEQ ID NO: 13 | Protein sequence ORF2 (FADα)-*B. cepacia* F406E mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCEHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 14 | Protein sequence ORF2 (FADα)-*B. cepacia* F406S mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCSHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 15 | Protein sequence ORF2 (FADα)-*B. cepacia* F406T mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCTHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 16 | Protein sequence ORF2 (FAD) - *B. cepacia* F406Y mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCYHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 17 | Protein sequence ORF2 (FADα)-*B. cepacia* F406N mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCNHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |

TABLE 2-continued

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
| --- | --- |
| SEQ ID NO: 18 | Protein sequence ORF2 (FADα)-*B. cepacia* F406Q mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCQHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 19 | Protein sequence ORF2 (FADα)-*B. cepacia* F406C mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCCHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 20 | Protein sequence OM (FADα)-*B. cepacia* F406G mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCGHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 21 | Protein sequence ORF2 (FADα)-*B. cepacia* F406P mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCPHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 22 | Protein sequence ORF2 (FADα)-*B. cepacia* F406A mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCAHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 23 | Protein sequence ORF2 (FADα)-*B. cepacia* F406V mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY |

TABLE 2-continued

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
| --- | --- |
| | IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCVHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 24 | Protein sequence ORF2 (FADα)-*B. cepacia* F406I mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCIHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEVGSGSGHHHHHH |
| SEQ ID NO: 25 | Protein sequence ORF2 (FADα)-*B. cepacia* F406W mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCWHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEVGSGSGHHHHHH |
| SEQ ID NO: 26 | Protein sequence ORF2 (FADα)-*B. cepacia* N474H mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPHNHITGSTIMGA<br>DARDSVVDKDCRTFDHPNLFISSSATMPTVGTVNVTLTIAALALRMSDT<br>LKKEVGSGSGHHHHHH |
| SEQ ID NO: 27 | Protein sequence ORF2 (FADα)-*B. cepacia* N474L mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPLNHITGSTIMGA<br>DARDSVVDKDCRTFDHPNLFISSSATMPTVGTVNVTLTIAALALRMSDT<br>LKKEVGSGSGHHHHHH |
| SEQ ID NO: 28 | Protein sequence ORF2 (FADα)-*B. cepacia* N474S mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER |

TABLE 2-continued

Protein sequences of FAD-GDHγα from *B. cepacia* (SEQ ID NO: 1, 3-29) and *B. lata* (SEQ ID NO: 2) and DNA sequences of primers used for random mutagenesis via error prone PCR. Each protein sequence ends in a removable 6x-His tag.

| SEQ ID | Sequence |
|---|---|
| | AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPSNHITGSTIMGA<br>DARDSVVDKDCRTFDHPNLFISSSATMPTVGTVNVTLTIAALALRMSDT<br>LKKEVGSGSGHHHHHH |
| SEQ ID NO: 29 | Protein sequence ORF2 (FADα)-*B. cepacia* N474V mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPVNHITGSTIMGA<br>DARDSVVDKDCRTFDHPNLFISSSATMPTVGTVNVTLTIAALALRMSDT<br>LKKEVGSGSGHHHHHH |
| SEQ ID NO: 30 | Primer used for random mutagenesis via error prone PCR method<br>CCAGGCAAATTCTGTTTTATCAGACC |
| SEQ ID NO: 31 | Primer used for random mutagenesis via error prone PCR method<br>CAAGCTGGAGACCGTTTAAACTC |
| SEQ ID NO: 32 | Primer used for random mutagenesis via error prone PCR method<br>CGCTATTCAGATCCTCTTCTGAGATG |
| SEQ ID NO: 33 | Primer used for random mutagenesis via error prone PCR method<br>GCTTCTGCGTTCTGATTTAATCTG |
| SEQ ID NO: 34 | Primer used for random mutagenesis via error prone PCR method<br>GGTCGTGGTCGGATCCGGTGTGGCAGGTGCTATTGTG |
| SEQ ID NO: 35 | Primer used for random mutagenesis via error prone PCR method<br>CGTTCTTATTGCCCGAATAAACC |
| SEQ ID NO: 36 | Primer used for random mutagenesis via error prone PCR method<br>CGAAGAAGCCCTGATGTTTGG |
| SEQ ID NO: 37 | Primer used for random mutagenesis via error prone PCR method<br>GAAGCATGGTATCTGGGCATTGTTG |

Bold text indicates mutations relative to wild-type within the amino acid sequence

TABLE 3

Protein sequences of FAD-GDHγα from *B. cepacia* (SEQ ID NO: 38, SEQ ID NOs: 40-66) and *B. lata* (SEQ ID NO: 39).

| SEQ ID NO: 38 | Protein sequence ORF2 (FADα)-*B. cepacia* Wild type<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEV |
|---|---|
| SEQ ID NO: 39 | Protein sequence ORF2 (FADα)-*B. lata* Wild type<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK |

TABLE 3-continued

Protein sequences of FAD-GDHγα from B. cepacia (SEQ ID NO: 38, SEQ ID NOs: 40-66) and B. lata (SEQ ID NO: 39).

FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV

SEQ ID NO: 40    Protein sequence ORF2 (FADα)-B. cepacia mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV SEQ ID NO: 41    Protein sequence ORF2 (FADα)-B. cepacia mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV SEQ ID NO: 42    Protein sequence ORF2 (FADα)-B. cepacia mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV SEQ ID NO: 43    Protein sequence ORF2 (FADα)-B. cepacia mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVALTIAALALRMSDT
LKKEV SEQ ID NO: 44    Protein sequence ORF2 (FADα)-B. cepacia mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG TABLE 3-continued Protein sequences of FAD-GDHγ from *B. cepacia* (SEQ ID NO: 38, SEQ ID NOs: 40-66) and *B. lata* (SEQ ID NO: 39).

IETPKILLMSANRDFPNGAANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPRPENCIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV

SEQ ID NO: 45   Protein sequence ORF2 (FADα)-*B. cepacia* mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLTDHPGTGVSFYASEKLWPG
RGPQEMTSLIGFRDGPFRATEAAKKIHLSNLSHIDQETQKIFKAGKLMKP
DELDAQIRDRSARYVQFDCFHEILPQPENRIVPSKTATDAIGIPRPEITYAI
DDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV SEQ ID NO: 46   Protein sequence ORF2 (FADα)-*B. cepacia* F406L mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCLHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV SEQ ID NO: 47   Protein sequence ORF2 (FADα)-*I. cepacia* F406D mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCDHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV SEQ ID NO: 48   Protein sequence ORF2 (FADα)-*B. cepacia* F406H mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCHHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV SEQ ID NO: 49   Protein sequence ORF2 (FADα)-*B. cepacia* F406M mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCMHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV

TABLE 3-continued

Protein sequences of FAD-GDHγα from *B. cepacia* (SEQ ID NO: 38, SEQ ID NOs: 40-66) and *B. lata* (SEQ ID NO: 39).

| | |
|---|---|
| SEQ ID NO: 50 | Protein sequence ORF2 (FADα)-*B. cepacia* F406E mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCEHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEV |
| SEQ ID NO: 51 | Protein sequence ORF2 (FADα)-*B. cepacia* F406S mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCSHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEV |
| SEQ ID NO: 52 | Protein sequence ORF2 (FADα)-*B. cepacia* F406T mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCTHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEV |
| SEQ ID NO: 53 | Protein sequence ORF2 (FADα)-*B. cepacia* F406Y mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCYHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEV |
| SEQ ID NO: 54 | Protein sequence ORF2 (FADα)-*B. cepacia* F406N mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCNHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEV |
| SEQ ID NO: 55 | Protein sequence ORF2 (FADα)-*B. cepacia* F406Q mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG |

TABLE 3-continued

Protein sequences of FAD-GDHα from *B. cepacia* (SEQ ID NO: 38, SEQ ID NOs: 40-66) and *B. lata* (SEQ ID NO: 39).

IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCQHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV

SEQ ID NO: 56    Protein sequence ORF2 (FADα)-*B. cepacia* F406C mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCCHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV SEQ ID NO: 57    Protein sequence ORF2 (FADα)-*B. cepacia* F406G mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCGHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV SEQ ID NO: 58    Protein sequence ORF2 (FADα)-*B. cepacia* F406P mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCPHEILPQPENRIVPSKTATDAIGIPRPEITYA
IDDYVKRGAAHTREVYATAAKVLGGTDVVFNDEFAPNNHITGSTIMGA
DARDSVVDKDCRTFDHPNLFISSSATMPTVGTVNVTLTIAALALRMSDT
LKKEV SEQ ID NO: 59    Protein sequence ORF2 (FADα)-*B. cepacia* F406A mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCAHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV SEQ ID NO: 60    Protein sequence ORF2 (FADα)-*B. cepacia* F406V mutant
MADTDTQKADVVVVGSGVAGAIVAHQLAMAGKAVILLEAGPRMPRW
EIVERFRNQPDKMDFMAPYPSSPWAPHPEYGPPNDYLILKGEHKFNSQY
IRAVGGTTWHWAASAWRFIPNDFKMKSVYGVGRDWPIQYDDLEPYYQ
RAEEELGVWGPGPEEDLYSPRKQPYPMPPLPLSFNEQTIKTALNNYDPK
FHVVTEPVARNSRPYDGRPTCCGNNNCMPICPIGAMYNGIVHVEKAER
AGAKLIENAVVYKLETGPDKRIVAALYKDKTGAEHRVEGKYFVLAANG
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCVHEILPQPENRIVPSKTATDAIGIPRPEITY
AIDDYVKRGAAHTREVYATAAKVLGGTDVVFNDEFAPNNHITGSTIMG
ADARDSVVDKDCRTFDHPNLFISSSATMPTVGTVNVTLTIAALALRMSD
TLKKEV TABLE 3-continued Protein sequences of FAD-GDHγα from *B. cepacia* (SEQ ID NO: 38, SEQ ID NOs: 40-66) and *B. lata* (SEQ ID NO: 39).

| | |
|---|---|
| SEQ ID NO: 61 | Protein sequence ORF2 (FADα)-*B. cepacia* F406I mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCIHEILPQPENRIVPSKTATDAIGIPRPEITYA<br>IDDYVKRGAAHTREVYATAAKVLGGTDVVFNDEFAPNNHITGSTIMGA<br>DARDSVVDKDCRTFDHPNLFISSSATMPTVGTVNVTLTIAALALRMSDT<br>LKKEV |
| SEQ ID NO: 62 | Protein sequence ORF2 (FADα)-*B. cepacia* F406W mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCWHEILPQPENRIVPSKTATDAIGIPRPEITY<br>AIDDYVKRGAAHTREVYATAAKVLGGTDVVFNDEFAPNNHITGSTIMG<br>ADARDSVVDKDCRTFDHPNLFISSSATMPTVGTVNVTLTIAALALRMSD<br>TLKKEV |
| SEQ ID NO: 63 | Protein sequence ORF2 (FADα)-*B. cepacia* N474H mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPHNHITGSTIMGA<br>DARDSVVDKDCRTFDHPNLFISSSATMPTVGTVNVTLTIAALALRMSDT<br>LKKEV |
| SEQ ID NO: 64 | Protein sequence ORF2 (FADα)-*B. cepacia* N474L mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPLNHITGSTIMGA<br>DARDSVVDKDCRTFDHPNLFISSSATMPTVGTVNVTLTIAALALRMSDT<br>LKKEV |
| SEQ ID NO: 65 | Protein sequence ORF2 (FADα)-*B. cepacia* N474S mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG<br>IETPKILLMSANRDFPNGVANSSDMVGRNLMDHPGTGVSFYASEKLWP<br>GRGPQEMTSLIGFRDGPFRATEAAKKIHLSNLSRIDQETQKIFKAGKLMK<br>PDELDAQIRDRSARYVQFDCFHEILPQPENRIVPSKTATDAIGIPRPEITYA<br>IDDYVKRGAAHTREVYATAAKVLGGTDVVFNDEFAPSNHITGSTIMGA<br>DARDSVVDKDCRTFDHPNLFISSSATMPTVGTVNVTLTIAALALRMSDT<br>LKKEV |
| SEQ ID NO: 66 | Protein sequence ORF2 (FADα)-*B. cepacia* N474V mutant<br>MADTDTQKADVVVVGSGVAGAIVAHQLAMAGKAVILLEAGPRMPRW<br>EIVERFRNQPDKMDFMAPYPSSPWAPHPEYGPPNDYLILKGEHKFNSQY<br>IRAVGGTTWHWAASAWRFIPNDFKMKSVYGVGRDWPIQYDDLEPYYQ<br>RAEEELGVWGPGPEEDLYSPRKQPYPMPPLPLSFNEQTIKTALNNYDPK<br>FHVVTEPVARNSRPYDGRPTCCGNNNCMPICPIGAMYNGIVHVEKAER<br>AGAKLIENAVVYKLETGPDKRIVAALYKDKTGAEHRVEGKYFVLAANG |

TABLE 3-continued

Protein sequences of FAD-GDHγ from *B. cepacia* (SEQ ID NO: 38, SEQ ID NOs: 40-66) and *B. lata* (SEQ ID NO: 39).

```
IETPKILLMSANRDFPNGVANSSDMVGRNLMDHPGTGVSFYASEKLWP
GRGPQEMTSLIGFRDGPFRATEAAKKIHLSNLSRIDQETQKIFKAGKLMK
PDELDAQIRDRSARYVQFDCFHEILPQPENRIVPSKTATDAIGIPRPEITYA
IDDYVKRGAAHTREVYATAAKVLGGTDVVFNDEFAPVNHITGSTIMGA
DARDSVVDKDCRTFDHPNLFISSSATMPTVGTVNVTLTIAALALRMSDT
LKKEV
```

TABLE 4

Protein sequences of FAD-GDHγ for *B. lata* mutants with removable 6x-His tag.

| SEQ ID | Sequence |
| --- | --- |
| SEQ ID NO: 67 | Protein sequence ORF2 (FADα)-*B. lata* F406A mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCAHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH |
| SEQ ID NO: 68 | Protein sequence ORF2 (FADα)-*B. lata* F406C mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCCHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 69 | Protein sequence ORF2 (FADα)-*B. lata* F406D mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCDHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 70 | Protein sequence ORF2 (FADα)-*B. lata* F406E mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCEHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 71 | Protein sequence ORF2 (FADα)-*B. lata* F406G mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR |

TABLE 4-continued

Protein sequences of FAD-GDHγα for *B. lata* mutants with removable 6x-His tag.

| SEQ ID | Sequence |
|---|---|
| | AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDSRARFVQFDCGHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 72 | Protein sequence ORF2 (FADα)-*B. lata* F406H mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDSRARFVQFDCHHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 73 | Protein sequence ORF2 (FADα)-*B. lata* F406I mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDSRARFVQFDCIHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 74 | Protein sequence ORF2 (FADα)-*B. lata* F406K mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDSRARFVQFDCKHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 75 | Protein sequence ORF2 (FADα)-*B. lata* F406L mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDSRARFVQFDCLHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 76 | Protein sequence ORF2 (FADα)-*B. lata* F406M mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP |

TABLE 4-continued

Protein sequences of FAD-GDHγα for *B. lata* mutants with removable 6x-His tag.

| SEQ ID | Sequence |
| --- | --- |
|  | EELDAQIRDRSARFVQFDCMHEILPQPENRIVPSKTATDAVGIPRPEITYA<br>IDDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 77 | Protein sequence ORF2 (FADα)-*B. lata* F406N mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCNHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 78 | Protein sequence ORF2 (FADα)-*B. lata* F406Q mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCQHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 79 | Protein sequence ORF2 (FADα)-*B. lata* F406S mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLID SAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCSHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 80 | Protein sequence ORF2 (FADα)-*B. lata* F406P mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCPHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 81 | Protein sequence ORF2 (FADα)-*B. lata* F406V mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCVHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |

TABLE 4-continued

Protein sequences of FAD-GDHγα for B. lata mutants with removable 6x-His tag.

| SEQ ID | Sequence |
| --- | --- |
| SEQ ID NO: 82 | Protein sequence ORF2 (FADα)-B. lata F406R mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCRHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 83 | Protein sequence ORF2 (FADα)-B. lata F406T mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCTHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 84 | Protein sequence ORF2 (FADα)-B. lata F406W mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCWHEILPQPENRIVPSKTATDAVGIPRPEITYA<br>IDDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |
| SEQ ID NO: 85 | Protein sequence ORF2 (FADα)-B. lata F406Y mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCYHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSGHHHHHH* |

TABLE 4

Protein sequences of FAD-GDHγα for B. lata mutants.

| SEQ ID | Sequence |
| --- | --- |
| SEQ ID NO: 86 | Protein sequence ORF2 (FADα)-B. lata F406A mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCAHEILPQPENRIVPSKTATDAVGIPRPEITYAI |

TABLE 4-continued

Protein sequences of FAD-GDHγ for *B. lata* mutants.

| SEQ ID | Sequαence |
|---|---|
| | DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 87 | Protein sequence ORF2 (FADα)-*B. lata* F406C mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCCHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 88 | Protein sequence ORF2 (FADα)-*B. lata* F406D mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCDHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 89 | Protein sequence ORF2 (FADα)-*B. lata* F406E mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCEHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 90 | Protein sequence ORF2 (FADα)-*B. lata* F406G mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCGHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 91 | Protein sequence ORF2 (FADα)-*B. lata* F406H mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCHHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |

TABLE 4-continued

Protein sequences of FAD-GDHγ for *B. lata* mutants.

| SEQ ID | Sequence |
| --- | --- |
| SEQ ID NO: 92 | Protein sequence ORF2 (FADα)-*B. lata* F406I mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCIHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 93 | Protein sequence ORF2 (FADα)-*B. lata* F406K mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCKHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 94 | Protein sequence ORF2 (FADα)-*B. lata* F406L mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCLHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 95 | Protein sequence ORF2 (FADα)-*B. lata* F406M mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCMHEILPQPENRIVPSKTATDAVGIPRPEITYA<br>IDDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 96 | Protein sequence ORF2 (FADα)-*B. lata* F406N mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCNHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 97 | Protein sequence ORF2 (FADα)-*B. lata* F406Q mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG |

TABLE 4-continued

Protein sequences of FAD-GDHγ for *B. lata* mutants.

| SEQ ID | Sequence |
|---|---|
|  | AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCQHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 98 | Protein sequence ORF2 (FADα)-*B. lata* F406S mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCSHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 99 | Protein sequence ORF2 (FADα)-*B. lata* F406P mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCPHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEV |
| SEQ ID NO: 100 | Protein sequence ORF2 (FADα)-*B. lata* F406V mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCVHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSG |
| SEQ ID NO: 101 | Protein sequence ORF2 (FADα)-*B. lata* F406R mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCRHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSG |
| SEQ ID NO: 102 | Protein sequence ORF2 (FADα)-*B. lata* F406T mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCTHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSG |

TABLE 4-continued

Protein sequences of FAD-GDHγα for B. lata mutants.

| SEQ ID | Sequaence |
|---|---|
| SEQ ID NO: 103 | Protein sequence ORF2 (FADα)-B. lata F406W mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCWHEILPQPENRIVPSKTATDAVGIPRPEITYA<br>IDDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSG |
| SEQ ID NO: 104 | Protein sequence ORF2 (FADα)-B. lata F406Y mutant<br>MADTDTQKADVVVVGSGVAGAIVAHQLAMAGKSVILLEAGPRMPRWE<br>IVERFRNQVDKTDFMAPYPSSAWAPHPEYGPPNDYLILKGEHKFNSQYI<br>RAVGGTTWHWAASAWRFIPNDFKMKTVYGVGRDWPIQYDDIEHYYQR<br>AEEELGVWGPGPEEDLYSPRKEPYPMPPLPLSFNEQTIKSALNGYDPKFH<br>VVTEPVARNSRPYDGRPTCCGNNNCMPICPIGAMYNGIVHVEKAEQAG<br>AKLIDSAVVYKLETGPDKRITAAVYKDKTGADHRVEGKYFVIAANGIET<br>PKILLMSANRDFPNGVANSSDMVGRNLMDHPGTGVSFYANEKLWPGR<br>GPQEMTSLIGFRDGPFRANEAAKKIHLSNMSRINQETQKIFKGGKLMKP<br>EELDAQIRDRSARFVQFDCYHEILPQPENRIVPSKTATDAVGIPRPEITYAI<br>DDYVKRGAVHTREVYATAAKVLGGTEVVFNDEFAPNNHITGATIMGA<br>DARDSVVDKDCRAFDHPNLFISSSSTMPTVGTVNVTLTIAALALRMSDT<br>LKKEVGSGSG |

FIGS. 4A and 4B show a FIG. 4A) and table (4B) depicting the relative activity of several mutants (e.g., 021, 022, 023, 024, 025), wild-type enzyme (B. cepacia FAD-GDHα) and negative control (bacterial lysate without FAD-GDHα (B. cepacia)). The activity assay was conducted using mutant enzymes, wild type bacterial FAD-GDHα enzyme, and control cells following an overnight protein expression, cell breakage by lysis solution and clarification of soluble fraction. For example, E. coli was transformed with plasmid containing DNA encoding FAD-GDHα enzyme (or a negative control, transformed with only plasmid without an FAD-GDHα DNA insert). The transformed E. coli samples were incubated overnight and induced to generate the FAD-GDHα enzyme as described in the example above. The soluble fraction was then used to test activity, as illustrated in FIG. 4A. FIG. 4B illustrates the point mutations generated within the FAD-GDHα enzyme.

Figure 5A:
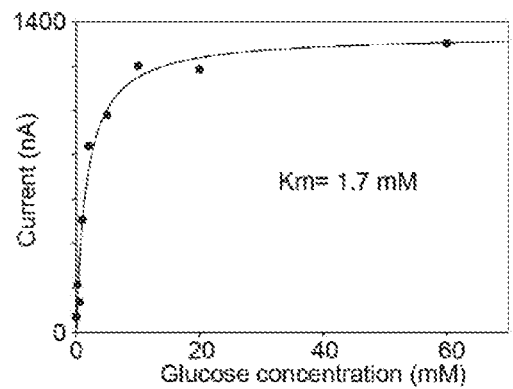
FIGS. 5A-5B show some aspects of the embodiments of the present invention, showing several curves of some embodiments of the present invention, indicating improved sensitivity of the enzyme (FIG. 5A), and improved specificity (FIG. 5B).
Figure 5B:
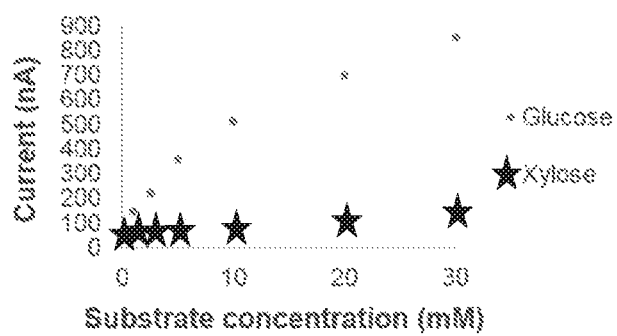

FIGS. 5A-5B show several curves indicating improved sensitivity of the FAD-GDHα (B. cepacia) (FIG. 5A), and improved specificity of the FAD-GDHα B. cepacia) (FIG. 5B). Notably, current applications of FAD-GDHα on test strips for glucometers display substantial non-specific activity towards xylose. For example: the upper limit of FAD-GDHα activity when in the presence of xylose is 58 mg/dL (concentration tested was 100 mg/dL); the bias (mg/dL) was 103.7, and thus the % bias was 36.3.

FIG. 6A shows a non-linear model FAD-GDHα (S330G and N474S) and FIG. 6B is a table with quantified data relating to FIG. 6A. 2 ug of FAD-GDHα (S330G and N474S) were immobilized to a carbon-based screen printed electrodes. The graph represents the current measured following a glucose challenge with indicated glucose concentrations. Fitting was performed through the hill algorithm assuming a single binding site (n=1). Fitting (FIG. 6B) was performed through the hill algorithm assuming a single binding site (n=1). The maximum current and Michaelis constant (Km) was derived from the fitting of the graph scatter plot. ND, not determined. FIG. 6C is a homology model of FAD-GDHα (S330G and N474S) alpha subunit based on Glucose oxidase determined structure. The molecule of FAD-GDHα (space filling representation) was derived from the superposition ofGOx structure (PDB code 1CF3) on the model of FAD-GDHα alpha subunit.

FIG. 7A shows a non-linear fit FAD-GDHα T521A and FIG. 7B is a table with quantified data relating to FIG. 7A. 2 μg of FAD-GDHα T521A were immobilized to a carbon-based screen printed electrodes. The graph represents the current measured following a glucose challenge with indicated glucose concentrations. Fitting was performed through the hill algorithm assuming a single binding site (n=1). Fitting (FIG. 7B) was performed through the hill algorithm assuming a single binding site (n=1). The maximum current and Michaelis constant (Km) was derived from the fitting of the graph scatter plot. ND, not determined. FIG. 7C is a homology model of FAD-GDH T521A alpha subunit based on Glucose oxidase determined structure. The molecule of FAD-GDHα (space filling representation) was derived from the superposition ofGOx structure (PDB code 1CF3) on the model of FAD-GDH alpha subunit.

FIG. 8A is a graph showing results derived from an FAD-GDHα F406L mutant. 2 ug of FAD-GDHα F406L were immobilized to a carbon-based screen printed electrodes. The graph represents the current measured following a glucose challenge with indicated glucose concentrations. Fitting (FIG. 8B) was performed through the hill algorithm assuming a single binding site (n=1). The maximum current and Michaelis constant (Km) was derived from the fitting of the graph scatter plot. ND, not determined. FIG. 8C is a homology model of FAD-GDH F406L alpha subunit based on Glucose oxidase determined structure. The molecule of FAD-GDHα (space filling representation) was derived from the superposition ofGOx structure (PDB code 1CF3) on the model of FAD-GDH alpha subunit.

FIG. 9 shows an assessment of linearity of mutant enzymatic dynamic range by linear fitting the whole range of measured points and extraction of both the quality of the fit (R-square), the slope (a) and intersection with the Y axis (b). The $R^2$ value=0.979, a=17.25, and b=80.9 nA.

FIG. 10 shows an assessment of mutant 24's linearity of mutant enzymatic dynamic range by linear fitting the whole range of measured points and extraction of both the quality of the fit (R-square), the slope (a) and intersection with the Y axis (b). The $R^2$ value=0.938, a=25.3, and b=158.23 nA.

FIG. 11 shows an assessment of linearity of mutant enzymatic dynamic range by linear fitting the whole range of measured points and extraction of both the quality of the fit (R-square), the slope (a) and intersection with the Y axis (b). The $R^2$ value=0.744, a=16.68, and b=211 nA.

FIG. 12 is a table summarizing the mutation positions and enzymatic and bio-electrochemical properties (X100Y means residue "X" at position 100 is mutated to residue "Y"). Linearity is measured by linear fitting the data plot from glucose concentration 0 to 30 mM.

FIGS. 13A-E show tables which show the collected data in connection with the compositions of the present invention. FIG. 13A describes biochemical and electrochemical parameters of the 406 mutants. FIG. 13B represents the biochemical kinetic characteristics of the 406 mutants as a percentage from the wild type (100%). FIG. 13C describes the biochemical selectivity and electrochemical linearity and current for the 406 mutants represented as a percentage from the wild type (100%). FIG. 13D describes biochemical rate of activity towards glucose and xylose of the 474 mutants. FIG. 13E describes biochemical rate of activity towards glucose and xylose of the 474 mutants, represented as a percentage from the wild type (100%).

FIGS. 14 and 15 show some embodiments of the composition of the present invention. FIG. 14 shows the biochemical response of FAD-GDHα N474L to varying concentrations of glucose (rhombus), and xylose (rectangle). FIG. 15 shows the biochemical response of N474L to glucose and the non-linear fit through which Km (k) and Vmax have been obtained. N474L enzyme activity was determined via monitoring decrease of Dichlorophenolindophenol (DCIP) signal at $OD_{600}$.

FIGS. 16A and 16B show some embodiments of the composition of the present invention. FIG. 16A shows the biochemical response of FAD-GDHα N474V to varying concentrations of glucose (rhombus), and xylose (rectangle). FIG. 16B shows the biochemical response of FAD-GDHα N474V to glucose and the non-linear fit through which Km (k) and Vmax have been obtained. N474V enzyme activity was determined via monitoring decrease of Dichlorophenolindophenol (DCIP) signal at $OD_{600}$.

FIGS. 17A and 17B show some embodiments of the composition of the present invention. FIG. 17A shows a biochemical response of FAD-GDHα N474H to varying concentrations of glucose (rhombus), and xylose (rectangle). FIG. 17B shows a biochemical response of FAD-GDHα N474H to glucose and the non-linear fit through which Km (k) and Vmax have been obtained. N474H enzyme activity was determined via monitoring decrease of Dichlorophenolindophenol (DCIP) signal at $OD_{600}$.

FIGS. 18A and 18B show some embodiments of the composition of the present invention. FIG. 18A shows the biochemical response of FAD-GDHα N474S to varying concentrations of glucose (rhombus), and xylose (rectangle). FIG. 18B shows the biochemical response of FAD-GDHα N474S to glucose and the non-linear fit through which Km (k) and Vmax have been obtained. N474S enzyme activity was determined via monitoring decrease of Dichlorophenolindophenol (DCIP) signal at $OD_{600}$.

FIGS. 19A and 19B show some embodiments of the composition of the present invention. FIG. 18A shows the biochemical response of FAD-GDHα N474A to glucose and the non-linear fit through which Km (k) and Vmax have been obtained. N474A enzyme activity was determined via monitoring decrease of Dichlorophenolindophenol (DCIP) signal at $OD_{600}$.

FIG. 20 shows a table summarizing some some embodiments of the composition of the present invention.

FIGS. 21A and 21B show some embodiments of the composition of the present invention. FIG. 21B shows the biochemical response of FAD-GDHα F406L to varying concentrations of glucose (rhombus), and xylose (rectangle). FIG. 21B shows the biochemical response of F406L to glucose and the non-linear fit through which Km (k) and Vmax have been obtained. F406L enzyme activity was determined via monitoring decrease of Dichlorophenolindophenol (DCIP) signal at $OD_{600}$.

FIG. 22 shows an embodiment of the composition of the present invention, showing the electrochemical data in connection with FAD-GDHα F406L.

FIGS. 23A-24C show some embodiments of the composition of the present invention. FIG. 23A shows the biochemical response of FAD-GDHα F406A to varying concentrations of glucose (rhombus), and xylose (rectangle). FIG. 23B shows the biochemical response of F406A to glucose and the non-linear fit through which Km (k) and Vmax have been obtained. F406A enzyme activity was determined via monitoring decrease of Dichlorophenolindophenol (DCIP) signal at $OD_{600}$. FIG. 23C shows electrochemical data representing the current response of the biosensor to various glucose concentrations (shown as a rhombus) and the linear fit across the data range is represented by the $R^2$ value.

FIGS. 24A-C show some embodiments of the composition of the present invention. FIG. 24A shows the biochemical response of FAD-GDHα F406C to varying concentrations of glucose (rhombus), and xylose (rectangle). FIG. 24B shows the iochemical response of F406C to glucose and the non-linear fit through which Km (k) and Vmax have been obtained. F406C enzyme activity was determined via monitoring decrease of Dichlorophenolindophenol (DCIP) signal at $OD_{600}$. FIG. 24C shows the electrochemical data representing the current response of the biosensor to various glucose concentrations (shown as a rhombus) and the linear fit across the data range is represented by the $R^2$ value.

FIGS. 25A-C shows embodiments of the composition of the present invention. FIG. 25A shows the biochemical response of FAD-GDHα F406E to varying concentrations of glucose (rhombus), and xylose (rectangle). FIG. 25B shows the biochemical response of F406E to glucose and the non-linear fit through which Km (k) and Vmax have been obtained. F406E enzyme activity was determined via monitoring decrease of Dichlorophenolindophenol (DCIP) signal at $OD_{600}$. FIG. 25C shows electrochemical data representing the current response of the biosensor to various glucose concentrations (shown as a rhombus) and the linear fit across the data range is represented by the $R^2$ value.

FIGS. 26A-C show some embodiments of the composition of the present invention. FIG. 26A shows the biochemical response of FAD-GDHα F406D to varying concentrations of glucose (rhombus), and xylose (rectangle). FIG. 26B shows the biochemical response of F406D to glucose and the non-linear fit through which Km (k) and Vmax have been obtained. F406D enzyme activity was determined via monitoring decrease of Dichlorophenolindophenol (DCIP) signal at $OD_{600}$. FIG. 26C shows the electrochemical data representing the current response of the biosensor to various glucose concentrations (shown as a rhombus) and the linear fit across the data range is represented by the $R^2$ value.

FIGS. 27A-C show some embodiments of the composition of the present invention. FIG. 27A shows the biochemical response of FAD-GDHα F406G to varying concentrations of glucose (rhombus), and xylose (rectangle). FIG. 27B shows the biochemical response of F406G to glucose and the non-linear fit through which Km (k) and Vmax have been obtained. F406G enzyme activity was determined via monitoring decrease of Dichlorophenolindophenol (DCIP) signal at $OD_{600}$. FIG. 27C shows electrochemical data representing the current response of the biosensor to various glucose concentrations (shown as a rhombus) and the linear fit across the data range is represented by the $R^2$ value.

FIGS. 28A and 28B show some embodiments of the composition of the present invention. FIG. 28A shows the biochemical response of FAD-GDHα F406H to varying concentrations of glucose (rhombus), and xylose (rectangle). FIG. 28B shows the biochemical response of F406H to glucose and the non-linear fit through which Km (k) and Vmax have been obtained. F406H enzyme activity was determined via monitoring decrease of Dichlorophenolindophenol (DCIP) signal at $OD_{600}$.

FIGS. 29A-C show some embodiments of the composition of the present invention. FIG. 29A shows the biochemical response of FAD-GDHα F406I to varying concentrations of glucose (rhombus), and xylose (rectangle). FIG. 29B shows the biochemical response of F406I to glucose and the non-linear fit through which Km (k) and Vmax have been obtained. F406I enzyme activity was determined via monitoring decrease of Dichlorophenolindophenol (DCIP) signal at $OD_{600}$. FIG. 29C shows electrochemical data representing the current response of the biosensor to various glucose concentrations (shown as a rhombus) and the linear fit across the data range is represented by the $R^2$ value.

FIGS. 30A and 30B show some embodiments of the composition of the present invention. FIG. 30A shows the biochemical response of FAD-GDHα F406M to varying concentrations of glucose (rhombus), and xylose (rectangle). FIG. 30B shows the biochemical response of F406M to glucose and the non-linear fit through which Km (k) and Vmax have been obtained. F406M enzyme activity was determined via monitoring decrease of Dichlorophenolindophenol (DCIP) signal at $OD_{600}$.

FIGS. 31A-C show some embodiments of the composition of the present invention. FIG. 31A shows the biochemical response of FAD-GDHα F406N to varying concentrations of glucose (rhombus), and xylose (rectangle). FIG. 31B shows the biochemical response of F406N to glucose and the non-linear fit through which Km (k) and Vmax have been obtained. F406N enzyme activity was determined via monitoring decrease of Dichlorophenolindophenol (DCIP) signal at $OD_{600}$. FIG. 31C shows electrochemical data representing the current response of the biosensor to various glucose concentrations (shown as a rhombus) and the linear fit across the data range is represented by the $R^2$ value.

FIGS. 32A and 32B show some embodiments of the composition of the present invention. FIG. 32A shows the biochemical response of FAD-GDHα F406Q to varying concentrations of glucose (rhombus), and xylose (rectangle). FIG. 32B shows the biochemical response of F406Q to glucose and the non-linear fit through which Km (k) and Vmax have been obtained. F406Q enzyme activity was determined via monitoring decrease of Dichlorophenolindophenol (DCIP) signal at $OD_{600}$.

FIGS. 33A-C show some embodiments of the compositions of the present invention. FIG. 33A shows biochemical response of FAD-GDHα F406S to varying concentrations of glucose (rhombus), and xylose (rectangle). FIG. 33 shows biochemical response of F406S to glucose and the non-linear fit through which Km (k) and Vmax have been obtained. F406S enzyme activity was determined via monitoring decrease of Dichlorophenolindophenol (DCIP) signal at $OD_{600}$. FIG. 33C shows electrochemical data representing the current response of the biosensor to various glucose concentrations (shown as a rhombus) and the linear fit across the data range is represented by the $R^2$ value.

FIGS. 34A-C show some embodiments of the composition of the present invention. FIG. 34A shows the biochemical response of FAD-GDHα F406T to varying concentrations of glucose (rhombus), and xylose (rectangle). FIG. 34B shows biochemical response of F406T to glucose and the non-linear fit through which Km (k) and Vmax have been obtained. F406T enzyme activity was determined via monitoring decrease of Dichlorophenolindophenol (DCIP) signal at $OD_{600}$. FIG. 34C shows electrochemical data representing the current response of the biosensor to various glucose concentrations (shown as a rhombus) and the linear fit across the data range is represented by the $R^2$ value.

FIGS. 35A-B show a negative results. FIG. 35A shows a biochemical response of FAD-GDHα F406W to varying concentrations of glucose (rhombus), and xylose (rectangle). FIG. 35B shows a biochemical response of F406W to glucose and the non-linear fit through which Km (k) and Vmax have been obtained. F406W enzyme activity was determined via monitoring decrease of Dichlorophenolindophenol (DCIP) signal at $OD_{600}$.

FIGS. 36A-C show some embodiments of the composition of the present invention. FIG. 36A shows the biochemical response of FAD-GDHα F406Y to varying concentrations of glucose (rhombus), and xylose (rectangle). FIG. 36B shows the biochemical response of F406Y to glucose and the non-linear fit through which Km (k) and Vmax have been obtained. F406Y enzyme activity was determined via monitoring decrease of Dichlorophenolindophenol (DCIP) signal at $OD_{600}$. FIG. 36C shows electrochemical data representing the current response of the biosensor to various glucose concentrations (shown as a rhombus) and the linear fit across the data range is represented by the $R^2$ value.

FIGS. 37A-C show some embodiments of the composition of the present invention. FIG. 37A shows the biochemical response of FAD-GDHα F406V to varying concentrations of glucose (rhombus), and xylose (rectangle). FIG. 37B shows the biochemical response of F406V to glucose and the non-linear fit through which Km (k) and Vmax have been obtained. F406V enzyme activity was determined via monitoring decrease of Dichlorophenolindophenol (DCIP) signal at $OD_{600}$. FIG. 37C shows electrochemical data representing the current response of the biosensor to various glucose concentrations (shown as a rhombus) and the linear fit across the data range is represented by the $R^2$ value.

FIGS. 38A-C show some embodiments of the composition of the present invention. FIG. 38A shows the biochemical response of FAD-GDHα F406P to varying concentrations of glucose (rhombus), and xylose (rectangle). FIG. 38B shows the biochemical response of F406P to glucose and the non-linear fit through which Km (k) and Vmax have been obtained. F406P enzyme activity was determined via monitoring decrease of Dichlorophenolindophenol (DCIP) signal at $OD_{600}$. FIG. 38C shows electrochemical data representing the current response of the biosensor to various glucose concentrations (shown as a rhombus) and the linear fit across the data range is represented by the $R^2$ value.

FIG. 39 shows electrochemistry data in connection with the wild type FAD-GDHα protein.

FIG. 40 shows a table of electrochemistry data of the embodiments of the composition of the present invention. Mutations in position 406 provide improved linearity over the entire range of physiological range: F406-S/C/T/V/Y/N/P/L/G/A/I/D/E.

FIG. 41 shows embodiments of the composition of the present invention. Mutations in position 406 that provide improved selectivity of glucose: F406-S/C/T/M/V/Y/N/P/L/G/Q/A/I/D/H/E. F406W provides an example of a substitution that reduces the enzyme selectivity towards glucose.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated). All publications and other references mentioned herein are incorporated by reference in their entirety, as if each individual publication or reference were specifically and individually indicated to be incorporated by reference. Publications and references cited herein are not admitted to be prior art.

REFERENCES

Wang, Joseph (2008). *Electrochemical Glucose Biosensors*. Chem. Rev. 2008, 108, 814-825.

Ferri, Stefano et al. (2011) *Review of Glucose Oxidases and Glucose Dehydrogenases: A Bird's Eye View of Glucose Sensing Enzymes*. Journal of Diabetes Science and Technology. Volume 5, Issue 5, September 2011

What is claimed is:

1. A mutated Flavoprotein Glucose Dehydrogenase subunit alpha (FAD-GDHα) protein, wherein the mutated FAD-GDHα protein has glucose dehydrogenase activity, and comprises an amino acid sequence having at least 99% sequence identity to the amino acid sequence set forth in SEQ ID NO: 38 and wherein the amino acid of the mutated FAD-GDHα protein at the position corresponding to residue 406 of the amino acid sequence of SEQ ID NO: 38 is an amino acid other than F or W.

2. The mutated FAD-GDHα protein of claim 1, wherein the amino acid at the position corresponding to residue 406 of the SEQ ID NO: 38 is selected from the group consisting of S, C, T, M, V, Y, N, P, L, G, Q, A, I, D, H, and E.

3. The mutated FAD-GDHα protein of claim 1, comprising the amino acid sequence of any one of SEQ ID NO: 46-61.

4. A glucose sensor comprising the mutated FAD-GDHα protein of claim 1.

5. The mutated FAD-GDHα protein of claim 1, wherein the protein exhibits at least a 10% increase in glucose dehydrogenase activity compared to a FAD-GDHα wild-type protein comprising the amino acid sequence of SEQ ID NO: 38.

6. The mutated FAD-GDHα protein of claim 1, wherein the protein exhibits at least a 40% increase in selectivity towards glucose compared to a FAD-GDHα wild-type protein comprising the amino acid sequence of SEQ ID NO: 38.

7. The mutated FAD-GDHα protein of claim 1, wherein the protein exhibits at least a 20% increase in linearity over physiological glucose levels ranging from 0 to 600 mg/dL compared to a FAD-GDHα wild-type protein comprising an amino acid sequence of SEQ ID NO: 38.

* * * * *

SEQUENCE LISTING

<160> NUMBER OF SEQ ID NOS: 129

<210> SEQ ID NO 1
<211> LENGTH: 550
<212> TYPE: PRT
<213> ORGANISM: Artificial Sequence
<220> FEATURE:
<223> OTHER INFORMATION: Recombinant sequence

<400> SEQUENCE: 1

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

```
Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His
545                 550

<210> SEQ ID NO 2
<211> LENGTH: 550
<212> TYPE: PRT
<213> ORGANISM: Artificial Sequence
<220> FEATURE:
<223> OTHER INFORMATION: Recombinant sequence

<400> SEQUENCE: 2

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45
```

Val Glu Arg Phe Arg Asn Gln Val Asp Lys Thr Asp Phe Met Ala Pro
 50                  55                  60

Tyr Pro Ser Ser Ala Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

-continued

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
            530                 535                 540

His His His His His His
545                 550

<210> SEQ ID NO 3
<211> LENGTH: 549
<212> TYPE: PRT
<213> ORGANISM: Artificial Sequence
<220> FEATURE:
<223> OTHER INFORMATION: Recombinant sequence

<400> SEQUENCE: 3

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Thr Pro Arg Trp Glu Ile
            35                  40                  45

Val Glu Arg Phe Arg Asn Gln Pro Asp Lys Met Asp Phe Met Ala Pro
    50                  55                  60

Tyr Pro Ser Ser Trp Ala Pro His Pro Glu Tyr Gly Pro Pro Asn Asp
65                  70                  75                  80

Tyr Leu Ile Leu Lys Gly Glu His Lys Phe Asn Ser Gln Tyr Ile Arg
                85                  90                  95

Ala Val Gly Gly Thr Thr Trp His Trp Ala Ala Ser Ala Trp Arg Phe
            100                 105                 110

Ile Pro Asn Asp Phe Lys Met Lys Ser Val Tyr Gly Val Gly Arg Asp
            115                 120                 125

Trp Pro Ile Gln Tyr Asp Asp Leu Glu Pro Tyr Tyr Gln Arg Ala Glu
    130                 135                 140

Glu Glu Leu Gly Val Trp Gly Pro Gly Pro Glu Glu Asp Leu Tyr Ser
145                 150                 155                 160

Pro Arg Lys Gln Pro Tyr Pro Met Pro Pro Leu Pro Leu Ser Phe Asn
                165                 170                 175

Glu Gln Thr Ile Lys Thr Ala Leu Asn Asn Tyr Asp Pro Lys Phe His
            180                 185                 190

Val Val Thr Glu Pro Val Ala Arg Asn Ser Arg Pro Tyr Asp Gly Arg
            195                 200                 205

Pro Thr Cys Cys Gly Asn Asn Asn Cys Met Pro Ile Cys Pro Ile Gly
    210                 215                 220

Ala Met Tyr Asn Gly Ile Val His Val Glu Lys Ala Glu Arg Ala Gly
225                 230                 235                 240

Ala Lys Leu Ile Glu Asn Ala Val Val Tyr Lys Leu Glu Thr Gly Pro
                245                 250                 255

Asp Lys Arg Ile Val Ala Ala Leu Tyr Lys Asp Lys Thr Gly Ala Glu
            260                 265                 270

His Arg Val Glu Gly Lys Tyr Phe Val Leu Ala Ala Asn Gly Ile Glu
            275                 280                 285

Thr Pro Lys Ile Leu Leu Met Ser Ala Asn Arg Asp Phe Pro Asn Gly
        290                 295                 300

Val Ala Asn Ser Ser Asp Met Val Gly Arg Asn Leu Met Asp His Pro
305                 310                 315                 320

Gly Thr Gly Val Ser Phe Tyr Ala Ser Glu Lys Leu Trp Pro Gly Arg
                325                 330                 335

Gly Pro Gln Glu Met Thr Ser Leu Val Gly Phe Arg Asp Gly Pro Phe
            340                 345                 350

Arg Ala Thr Glu Ala Ala Lys Lys Ile His Leu Ser Asn Leu Ser Arg
        355                 360                 365

Ile Asp Gln Glu Thr Gln Lys Ile Phe Lys Ala Gly Lys Leu Met Lys
        370                 375                 380

Pro Asp Glu Leu Asp Ala Gln Ile Arg Asp Arg Ser Ala Arg Tyr Val
385                 390                 395                 400

Gln Phe Asp Cys Phe His Glu Ile Leu Pro Gln Pro Glu Asn Arg Ile
                405                 410                 415

Val Pro Ser Lys Thr Ala Thr Asp Ala Ile Gly Ile Pro Arg Pro Glu
            420                 425                 430

Ile Thr Tyr Ala Ile Asp Asp Tyr Val Lys Arg Gly Ala Ala His Thr
        435                 440                 445

Arg Glu Val Tyr Ala Thr Ala Ala Lys Val Leu Gly Gly Thr Asp Val
        450                 455                 460

Val Phe Asn Asp Glu Phe Ala Pro Asn Asn His Ile Thr Gly Ser Thr
465                 470                 475                 480

Ile Met Gly Ala Asp Ala Arg Asp Ser Val Val Asp Lys Asp Cys Arg
                485                 490                 495

Thr Phe Asp His Pro Asn Leu Phe Ile Ser Ser Ala Thr Met Pro
            500                 505                 510

Thr Val Gly Thr Val Asn Val Thr Leu Thr Ile Ala Ala Leu Ala Leu
        515                 520                 525

Arg Met Ser Asp Thr Leu Lys Lys Glu Val Gly Ser Gly Ser Gly His
530                 535                 540

His His His His His
545

<210> SEQ ID NO 4
<211> LENGTH: 550
<212> TYPE: PRT
<213> ORGANISM: Artificial Sequence
<220> FEATURE:
<223> OTHER INFORMATION: Recombinant sequence

<400> SEQUENCE: 4

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

-continued

```
Asp Tyr Leu Ile Leu Lys Gly Glu His Lys Phe Asn Ser Gln Tyr Ile
            85                  90                  95

Arg Ala Val Gly Gly Thr Thr Trp His Trp Ala Ala Ser Ala Trp Arg
        100                 105                 110

Phe Ile Pro Asn Asp Phe Lys Met Lys Ser Val Tyr Gly Val Gly Arg
    115                 120                 125

Asp Trp Pro Ile Gln Tyr Asp Asp Leu Glu Pro Tyr Tyr Gln Arg Ala
130                 135                 140

Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Phe Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Asn Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
```

```
                    500                 505                 510
Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
        530                 535                 540

His His His His His His
545                 550

<210> SEQ ID NO 5
<211> LENGTH: 550
<212> TYPE: PRT
<213> ORGANISM: Artificial Sequence
<220> FEATURE:
<223> OTHER INFORMATION: Recombinant sequence

<400> SEQUENCE: 5

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
```

```
              305                 310                 315                 320
Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Ile His Leu Ser Asn Leu Ser
                355                 360                 365

Arg Ile Asp Gln Glu Thr Gln Lys Ile Phe Lys Ala Gly Lys Leu Met
                370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                    405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Gly Ser Gly Ser Gly
                530                 535                 540

His His His His His His
545                 550

<210> SEQ ID NO 6
<211> LENGTH: 550
<212> TYPE: PRT
<213> ORGANISM: Artificial Sequence
<220> FEATURE:
<223> OTHER INFORMATION: Recombinant sequence

<400> SEQUENCE: 6

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
```

```
                115                 120                 125
Asp Trp Pro Ile Gln Tyr Asp Asp Leu Glu Pro Tyr Tyr Gln Arg Ala
130                 135                 140
Glu Glu Glu Leu Gly Val Trp Gly Pro Gly Glu Glu Asp Leu Tyr
145                 150                 155                 160
Ser Pro Arg Lys Gln Pro Tyr Pro Met Pro Pro Leu Pro Leu Ser Phe
                165                 170                 175
Asn Glu Gln Thr Ile Lys Thr Ala Leu Asn Asn Tyr Asp Pro Lys Phe
                180                 185                 190
His Val Val Thr Glu Pro Val Ala Arg Asn Ser Arg Pro Tyr Asp Gly
                195                 200                 205
Arg Pro Thr Cys Cys Gly Asn Asn Asn Cys Met Pro Ile Cys Pro Ile
210                 215                 220
Gly Ala Met Tyr Asn Gly Ile Val His Val Glu Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
                260                 265                 270
Glu His Arg Val Glu Gly Lys Tyr Phe Val Leu Ala Ala Asn Gly Ile
                275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Ser Glu Lys Leu Trp Pro Gly
                325                 330                 335
Arg Gly Pro Gln Glu Met Thr Ser Leu Ile Gly Phe Arg Asp Gly Pro
                340                 345                 350
Phe Arg Ala Thr Glu Ala Ala Lys Lys Ile His Leu Ser Asn Leu Ser
                355                 360                 365
Arg Ile Asp Gln Glu Thr Gln Lys Ile Phe Lys Ala Gly Lys Leu Met
370                 375                 380
Lys Pro Asp Glu Leu Asp Ala Gln Ile Arg Asp Arg Ser Ala Arg Tyr
385                 390                 395                 400
Val Gln Phe Asp Cys Phe His Glu Ile Leu Pro Gln Pro Glu Asn Arg
                405                 410                 415
Ile Val Pro Ser Lys Thr Ala Thr Asp Ala Ile Gly Ile Pro Arg Pro
                420                 425                 430
Glu Ile Thr Tyr Ala Ile Asp Asp Tyr Val Lys Arg Gly Ala Ala His
                435                 440                 445
Thr Arg Glu Val Tyr Ala Thr Ala Ala Lys Val Leu Gly Gly Thr Asp
                450                 455                 460
Val Val Phe Asn Asp Glu Phe Ala Pro Asn Asn His Ile Thr Gly Ser
465                 470                 475                 480
Thr Ile Met Gly Ala Asp Ala Arg Asp Ser Val Val Asp Lys Asp Cys
                485                 490                 495
Arg Thr Phe Asp His Pro Asn Leu Phe Ile Ser Ser Ala Thr Met
                500                 505                 510
Pro Thr Val Gly Thr Val Asn Val Ala Leu Thr Ile Ala Ala Leu Ala
                515                 520                 525
Leu Arg Met Ser Asp Thr Leu Lys Lys Glu Val Gly Ser Gly Ser Gly
530                 535                 540
```

-continued

His His His His His His
545         550

<210> SEQ ID NO 7
<211> LENGTH: 550
<212> TYPE: PRT
<213> ORGANISM: Artificial Sequence
<220> FEATURE:
<223> OTHER INFORMATION: Recombinant sequence

<400> SEQUENCE: 7

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Ala Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

```
Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Arg Pro Glu Asn Cys
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
    530                 535                 540

His His His His His His
545                 550

<210> SEQ ID NO 8
<211> LENGTH: 550
<212> TYPE: PRT
<213> ORGANISM: Artificial Sequence
<220> FEATURE:
<223> OTHER INFORMATION: Recombinant sequence

<400> SEQUENCE: 8

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160
```

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Thr Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

His Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
530                 535                 540

His His His His His His
545                 550

<210> SEQ ID NO 9
<211> LENGTH: 550

<212> TYPE: PRT
<213> ORGANISM: Artificial Sequence
<220> FEATURE:
<223> OTHER INFORMATION: Recombinant sequence

<400> SEQUENCE: 9

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

```
Lys Pro Asp Glu Leu Asp Ala Gln Ile Arg Asp Arg Ser Ala Arg Tyr
385                 390                 395                 400

Val Gln Phe Asp Cys Leu His Glu Ile Leu Pro Gln Pro Glu Asn Arg
            405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
    530                 535                 540

His His His His His His
545                 550

<210> SEQ ID NO 10
<211> LENGTH: 550
<212> TYPE: PRT
<213> ORGANISM: Artificial Sequence
<220> FEATURE:
<223> OTHER INFORMATION: Recombinant sequence

<400> SEQUENCE: 10

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190
```

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
            245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys Asp His Glu Ile Leu Pro Gln Pro Glu Asn Arg
            405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 11
<211> LENGTH: 550
<212> TYPE: PRT
<213> ORGANISM: Artificial Sequence
<220> FEATURE:
<223> OTHER INFORMATION: Recombinant sequence

<400> SEQUENCE: 11

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
50              55                  60

Tyr Pro Ser Ser Pro Trp Ala Pro His Pro Glu Tyr Gly Pro Pro Asn
65              70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
            130                 135                 140

Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
            210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys His His Glu Ile Leu Pro Gln Pro Glu Asn Arg
                405                 410                 415

Ile Val Pro Ser Lys Thr Ala Thr Asp Ala Ile Gly Ile Pro Arg Pro
```

-continued

```
                420                 425                 430
Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
            530                 535                 540

His His His His His His
545                 550

<210> SEQ ID NO 12
<211> LENGTH: 550
<212> TYPE: PRT
<213> ORGANISM: Artificial Sequence
<220> FEATURE:
<223> OTHER INFORMATION: Recombinant sequence

<400> SEQUENCE: 12

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Leu Pro Leu Ser Phe
            165                 170                 175

Asn Glu Gln Thr Ile Lys Thr Ala Leu Asn Asn Tyr Asp Pro Lys Phe
        180                 185                 190

His Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Arg Ala
```

```
                225                 230                 235                 240
Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
                355                 360                 365

Arg Ile Asp Gln Glu Thr Gln Lys Ile Phe Lys Ala Gly Lys Leu Met
                370                 375                 380

Lys Pro Asp Glu Leu Asp Ala Gln Ile Arg Asp Ser Ala Arg Tyr
385                 390                 395                 400

Val Gln Phe Asp Cys Met His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Ala Lys Val Leu Gly Gly Thr Asp
                450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Gly Ser Gly Ser Gly
530                 535                 540

His His His His His His
545                 550

<210> SEQ ID NO 13
<211> LENGTH: 550
<212> TYPE: PRT
<213> ORGANISM: Artificial Sequence
<220> FEATURE:
<223> OTHER INFORMATION: Recombinant sequence

<400> SEQUENCE: 13

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
```

```
                35                  40                  45
Val Glu Arg Phe Arg Asn Gln Pro Asp Lys Met Asp Phe Met Ala Pro
 50                  55                  60

Tyr Pro Ser Ser Pro Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
            115                 120                 125

Asp Trp Pro Ile Gln Tyr Asp Leu Glu Pro Tyr Tyr Gln Arg Ala
            130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys Glu His Glu Ile Leu Pro Gln Pro Glu Asn Arg
                405                 410                 415

Ile Val Pro Ser Lys Thr Ala Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
450                 455                 460
```

```
Val Val Phe Asn Asp Glu Phe Ala Pro Asn His Ile Thr Gly Ser
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ala Thr Met
        500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
        530                 535                 540

His His His His His His
545                 550

<210> SEQ ID NO 14
<211> LENGTH: 550
<212> TYPE: PRT
<213> ORGANISM: Artificial Sequence
<220> FEATURE:
<223> OTHER INFORMATION: Recombinant sequence

<400> SEQUENCE: 14

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
            85                  90                  95

Arg Ala Val Gly Gly Thr Thr Trp His Trp Ala Ala Ser Ala Trp Arg
        100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270
```

```
Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Ser His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His His
545                 550

<210> SEQ ID NO 15
<211> LENGTH: 550
<212> TYPE: PRT
<213> ORGANISM: Artificial Sequence
<220> FEATURE:
<223> OTHER INFORMATION: Recombinant sequence

<400> SEQUENCE: 15

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80
```

```
Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Ser Ala Arg Tyr
385                 390                 395                 400

Val Gln Phe Asp Cys Thr His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495
```

```
Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
            530                 535                 540

His His His His His His
545                 550

<210> SEQ ID NO 16
<211> LENGTH: 550
<212> TYPE: PRT
<213> ORGANISM: Artificial Sequence
<220> FEATURE:
<223> OTHER INFORMATION: Recombinant sequence

<400> SEQUENCE: 16

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
290                 295                 300
```

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys Tyr His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 17
<211> LENGTH: 550
<212> TYPE: PRT
<213> ORGANISM: Artificial Sequence
<220> FEATURE:
<223> OTHER INFORMATION: Recombinant sequence

<400> SEQUENCE: 17

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

-continued

```
Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Asn His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
```

His His His His His His
545                 550

<210> SEQ ID NO 18
<211> LENGTH: 550
<212> TYPE: PRT
<213> ORGANISM: Artificial Sequence
<220> FEATURE:
<223> OTHER INFORMATION: Recombinant sequence

<400> SEQUENCE: 18

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
                35                  40                  45

Val Glu Arg Phe Arg Asn Gln Pro Asp Lys Met Asp Phe Met Ala Pro
            50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
            210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro

```
                 340                 345                 350
Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
        370                 375                 380

Lys Pro Asp Glu Leu Asp Ala Gln Ile Arg Asp Arg Ser Ala Arg Tyr
385                 390                 395                 400

Val Gln Phe Asp Cys Gln His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His His
545                 550

<210> SEQ ID NO 19
<211> LENGTH: 550
<212> TYPE: PRT
<213> ORGANISM: Artificial Sequence
<220> FEATURE:
<223> OTHER INFORMATION: Recombinant sequence

<400> SEQUENCE: 19

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
```

```
                145                 150                 155                 160
Ser Pro Arg Lys Gln Pro Tyr Pro Met Pro Pro Leu Pro Leu Ser Phe
                    165                 170                 175
Asn Glu Gln Thr Ile Lys Thr Ala Leu Asn Asn Tyr Asp Pro Lys Phe
                180                 185                 190
His Val Thr Glu Pro Val Ala Arg Asn Ser Arg Pro Tyr Asp Gly
                195                 200                 205
Arg Pro Thr Cys Cys Gly Asn Asn Cys Met Pro Ile Cys Pro Ile
210                 215                 220
Gly Ala Met Tyr Asn Gly Ile Val His Val Glu Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
                260                 265                 270
Glu His Arg Val Glu Gly Lys Tyr Phe Val Leu Ala Ala Asn Gly Ile
                275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Ser Glu Lys Leu Trp Pro Gly
                    325                 330                 335
Arg Gly Pro Gln Glu Met Thr Ser Leu Ile Gly Phe Arg Asp Gly Pro
                340                 345                 350
Phe Arg Ala Thr Glu Ala Ala Lys Lys Ile His Leu Ser Asn Leu Ser
            355                 360                 365
Arg Ile Asp Gln Glu Thr Gln Lys Ile Phe Lys Ala Gly Lys Leu Met
        370                 375                 380
Lys Pro Asp Glu Leu Asp Ala Gln Ile Arg Asp Arg Ser Ala Arg Tyr
385                 390                 395                 400
Val Gln Phe Asp Cys Cys His Glu Ile Leu Pro Gln Pro Glu Asn Arg
                405                 410                 415
Ile Val Pro Ser Lys Thr Ala Thr Asp Ala Ile Gly Ile Pro Arg Pro
                420                 425                 430
Glu Ile Thr Tyr Ala Ile Asp Asp Tyr Val Lys Arg Gly Ala Ala His
                435                 440                 445
Thr Arg Glu Val Tyr Ala Thr Ala Ala Lys Val Leu Gly Gly Thr Asp
        450                 455                 460
Val Val Phe Asn Asp Glu Phe Ala Pro Asn Asn His Ile Thr Gly Ser
465                 470                 475                 480
Thr Ile Met Gly Ala Asp Ala Arg Asp Ser Val Val Asp Lys Asp Cys
                    485                 490                 495
Arg Thr Phe Asp His Pro Asn Leu Phe Ile Ser Ser Ala Thr Met
                500                 505                 510
Pro Thr Val Gly Thr Val Asn Val Thr Leu Thr Ile Ala Ala Leu Ala
            515                 520                 525
Leu Arg Met Ser Asp Thr Leu Lys Lys Glu Val Gly Ser Gly Ser Gly
        530                 535                 540
His His His His His His
545                 550

<210> SEQ ID NO 20
```

<211> LENGTH: 550
<212> TYPE: PRT
<213> ORGANISM: Artificial Sequence
<220> FEATURE:
<223> OTHER INFORMATION: Recombinant sequence

<400> SEQUENCE: 20

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

```
Lys Pro Asp Glu Leu Asp Ala Gln Ile Arg Asp Arg Ser Ala Arg Tyr
385                 390                 395                 400

Val Gln Phe Asp Cys Gly His Glu Ile Leu Pro Gln Pro Glu Asn Arg
            405                 410                 415

Ile Val Pro Ser Lys Thr Ala Thr Asp Ala Ile Gly Ile Pro Arg Pro
        420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 21
<211> LENGTH: 550
<212> TYPE: PRT
<213> ORGANISM: Artificial Sequence
<220> FEATURE:
<223> OTHER INFORMATION: Recombinant sequence

<400> SEQUENCE: 21

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190
```

His Val Thr Glu Pro Val Ala Arg Asn Ser Arg Pro Tyr Asp Gly
         195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
                275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
                355                 360                 365

Arg Ile Asp Gln Glu Thr Gln Lys Ile Phe Lys Ala Gly Lys Leu Met
                370                 375                 380

Lys Pro Asp Glu Leu Asp Ala Gln Ile Arg Asp Arg Ser Ala Arg Tyr
385                 390                 395                 400

Val Gln Phe Asp Cys Pro His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Ala Lys Val Leu Gly Gly Thr Asp
                450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Gly Ser Gly Ser Gly
530                 535                 540

His His His His His
545                 550

<210> SEQ ID NO 22
<211> LENGTH: 550
<212> TYPE: PRT
<213> ORGANISM: Artificial Sequence
<220> FEATURE:
<223> OTHER INFORMATION: Recombinant sequence

<400> SEQUENCE: 22

-continued

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
                35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
                115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Ile His Leu Ser Asn Leu Ser
            355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Ala His Glu Ile Leu Pro Gln Pro Glu Asn Arg
                405                 410                 415
```

```
Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His His
545                 550

<210> SEQ ID NO 23
<211> LENGTH: 550
<212> TYPE: PRT
<213> ORGANISM: Artificial Sequence
<220> FEATURE:
<223> OTHER INFORMATION: Recombinant sequence

<400> SEQUENCE: 23

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220
```

```
Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
            245                 250                 255

Pro Asp Lys Arg Ile Val Ala Ala Leu Tyr Lys Asp Lys Thr Gly Ala
        260                 265                 270

Glu His Arg Val Glu Gly Lys Tyr Phe Val Leu Ala Ala Asn Gly Ile
    275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
            325                 330                 335

Arg Gly Pro Gln Glu Met Thr Ser Leu Ile Gly Phe Arg Asp Gly Pro
        340                 345                 350

Phe Arg Ala Thr Glu Ala Ala Lys Lys Ile His Leu Ser Asn Leu Ser
    355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Val His Glu Ile Leu Pro Gln Pro Glu Asn Arg
            405                 410                 415

Ile Val Pro Ser Lys Thr Ala Thr Asp Ala Ile Gly Ile Pro Arg Pro
        420                 425                 430

Glu Ile Thr Tyr Ala Ile Asp Asp Tyr Val Lys Arg Gly Ala Ala His
    435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ala Thr Met
        500                 505                 510

Pro Thr Val Gly Thr Val Asn Val Thr Leu Thr Ile Ala Ala Leu Ala
    515                 520                 525

Leu Arg Met Ser Asp Thr Leu Lys Lys Glu Val Gly Ser Gly Ser Gly
530                 535                 540

His His His His His His
545                 550

<210> SEQ ID NO 24
<211> LENGTH: 550
<212> TYPE: PRT
<213> ORGANISM: Artificial Sequence
<220> FEATURE:
<223> OTHER INFORMATION: Recombinant sequence

<400> SEQUENCE: 24

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30
```

-continued

```
Ala Val Ile Leu Leu Glu Ala Gly Pro Arg Met Pro Arg Trp Glu Ile
             35                  40                  45
Val Glu Arg Phe Arg Asn Gln Pro Asp Lys Met Asp Phe Met Ala Pro
 50                  55                  60
Tyr Pro Ser Ser Pro Trp Ala Pro His Pro Glu Tyr Gly Pro Pro Asn
 65                  70                  75                  80
Asp Tyr Leu Ile Leu Lys Gly Glu His Lys Phe Asn Ser Gln Tyr Ile
             85                  90                  95
Arg Ala Val Gly Gly Thr Thr Trp His Trp Ala Ala Ser Ala Trp Arg
            100                 105                 110
Phe Ile Pro Asn Asp Phe Lys Met Lys Ser Val Tyr Gly Val Gly Arg
            115                 120                 125
Asp Trp Pro Ile Gln Tyr Asp Asp Leu Glu Pro Tyr Tyr Gln Arg Ala
            130                 135                 140
Glu Glu Glu Leu Gly Val Trp Gly Pro Gly Pro Glu Glu Asp Leu Tyr
145                 150                 155                 160
Ser Pro Arg Lys Gln Pro Tyr Pro Met Pro Pro Leu Pro Leu Ser Phe
                165                 170                 175
Asn Glu Gln Thr Ile Lys Thr Ala Leu Asn Asn Tyr Asp Pro Lys Phe
            180                 185                 190
His Val Val Thr Glu Pro Val Ala Arg Asn Ser Arg Pro Tyr Asp Gly
            195                 200                 205
Arg Pro Thr Cys Cys Gly Asn Asn Cys Met Pro Ile Cys Pro Ile
            210                 215                 220
Gly Ala Met Tyr Asn Gly Ile Val His Val Glu Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
                260                 265                 270
Glu His Arg Val Glu Gly Lys Tyr Phe Val Leu Ala Ala Asn Gly Ile
            275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Ser Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Thr Glu Ala Ala Lys Lys Ile His Leu Ser Asn Leu Ser
            355                 360                 365
Arg Ile Asp Gln Glu Thr Gln Lys Ile Phe Lys Ala Gly Lys Leu Met
            370                 375                 380
Lys Pro Asp Glu Leu Asp Ala Gln Ile Arg Asp Arg Ser Ala Arg Tyr
385                 390                 395                 400
Val Gln Phe Asp Cys Ile His Glu Ile Leu Pro Gln Pro Glu Asn Arg
                405                 410                 415
Ile Val Pro Ser Lys Thr Ala Thr Asp Ala Ile Gly Ile Pro Arg Pro
                420                 425                 430
Glu Ile Thr Tyr Ala Ile Asp Asp Tyr Val Lys Arg Gly Ala Ala His
            435                 440                 445
Thr Arg Glu Val Tyr Ala Thr Ala Ala Lys Val Leu Gly Gly Thr Asp
```

```
                450            455             460
Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Gly Ser Gly Ser Gly
            530                 535                 540

His His His His His His
545                 550

<210> SEQ ID NO 25
<211> LENGTH: 550
<212> TYPE: PRT
<213> ORGANISM: Artificial Sequence
<220> FEATURE:
<223> OTHER INFORMATION: Recombinant sequence

<400> SEQUENCE: 25

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
```

-continued

Glu His Arg Val Glu Gly Lys Tyr Phe Val Leu Ala Ala Asn Gly Ile
            260                 265                 270
        275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                    325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
        370                 375                 380

Lys Pro Asp Glu Leu Asp Ala Gln Ile Arg Asp Arg Ser Ala Arg Tyr
385                 390                 395                 400

Val Gln Phe Asp Cys Trp His Glu Ile Leu Pro Gln Pro Glu Asn Arg
                    405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
        450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                    485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
        530                 535                 540

His His His His His His
545                 550

<210> SEQ ID NO 26
<211> LENGTH: 550
<212> TYPE: PRT
<213> ORGANISM: Artificial Sequence
<220> FEATURE:
<223> OTHER INFORMATION: Recombinant sequence

<400> SEQUENCE: 26

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn

-continued

```
                65                  70                  75                  80
Asp Tyr Leu Ile Leu Lys Gly Glu His Lys Phe Asn Ser Gln Tyr Ile
                        85                  90                  95
Arg Ala Val Gly Gly Thr Thr Trp His Trp Ala Ala Ser Ala Trp Arg
                    100                 105                 110
Phe Ile Pro Asn Asp Phe Lys Met Lys Ser Val Tyr Gly Val Gly Arg
                115                 120                 125
Asp Trp Pro Ile Gln Tyr Asp Asp Leu Glu Pro Tyr Tyr Gln Arg Ala
            130                 135                 140
Glu Glu Glu Leu Gly Val Trp Gly Pro Gly Glu Glu Asp Leu Tyr
145                 150                 155                 160
Ser Pro Arg Lys Gln Pro Tyr Pro Met Pro Pro Leu Pro Leu Ser Phe
                165                 170                 175
Asn Glu Gln Thr Ile Lys Thr Ala Leu Asn Asn Tyr Asp Pro Lys Phe
                180                 185                 190
His Val Val Thr Glu Pro Val Ala Arg Asn Ser Arg Pro Tyr Asp Gly
            195                 200                 205
Arg Pro Thr Cys Cys Gly Asn Asn Asn Cys Met Pro Ile Cys Pro Ile
        210                 215                 220
Gly Ala Met Tyr Asn Gly Ile Val His Val Glu Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
            260                 265                 270
Glu His Arg Val Glu Gly Lys Tyr Phe Val Leu Ala Ala Asn Gly Ile
        275                 280                 285
Glu Thr Pro Lys Ile Leu Leu Met Ser Ala Asn Arg Asp Phe Pro Asn
        290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Ser Glu Lys Leu Trp Pro Gly
                325                 330                 335
Arg Gly Pro Gln Glu Met Thr Ser Leu Ile Gly Phe Arg Asp Gly Pro
                340                 345                 350
Phe Arg Ala Thr Glu Ala Ala Lys Lys Ile His Leu Ser Asn Leu Ser
            355                 360                 365
Arg Ile Asp Gln Glu Thr Gln Lys Ile Phe Lys Ala Gly Lys Leu Met
        370                 375                 380
Lys Pro Asp Glu Leu Asp Ala Gln Ile Arg Asp Arg Ser Ala Arg Tyr
385                 390                 395                 400
Val Gln Phe Asp Cys Phe His Glu Ile Leu Pro Gln Pro Glu Asn Arg
                405                 410                 415
Ile Val Pro Ser Lys Thr Ala Thr Asp Ala Ile Gly Ile Pro Arg Pro
                420                 425                 430
Glu Ile Thr Tyr Ala Ile Asp Asp Tyr Val Lys Arg Gly Ala Ala His
            435                 440                 445
Thr Arg Glu Val Tyr Ala Thr Ala Ala Lys Val Leu Gly Gly Thr Asp
        450                 455                 460
Val Val Phe Asn Asp Glu Phe Ala Pro His Asn His Ile Thr Gly Ser
465                 470                 475                 480
Thr Ile Met Gly Ala Asp Ala Arg Asp Ser Val Val Asp Lys Asp Cys
                485                 490                 495
```

```
Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
            530                 535                 540

His His His His His His
545             550

<210> SEQ ID NO 27
<211> LENGTH: 550
<212> TYPE: PRT
<213> ORGANISM: Artificial Sequence
<220> FEATURE:
<223> OTHER INFORMATION: Recombinant sequence

<400> SEQUENCE: 27

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
290                 295                 300
```

-continued

```
Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
            325                 330                 335

Arg Gly Pro Gln Glu Met Thr Ser Leu Ile Gly Phe Arg Asp Gly Pro
        340                 345                 350

Phe Arg Ala Thr Glu Ala Ala Lys Lys Ile His Leu Ser Asn Leu Ser
    355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Leu Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
530                 535                 540

His His His His His His
545                 550
```

<210> SEQ ID NO 28
<211> LENGTH: 550
<212> TYPE: PRT
<213> ORGANISM: Artificial Sequence
<220> FEATURE:
<223> OTHER INFORMATION: Recombinant sequence

<400> SEQUENCE: 28

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110
```

```
Phe Ile Pro Asn Asp Phe Lys Met Lys Ser Val Tyr Gly Val Gly Arg
        115                 120                 125

Asp Trp Pro Ile Gln Tyr Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
        260                 265                 270

Glu His Arg Val Glu Gly Lys Tyr Phe Val Leu Ala Ala Asn Gly Ile
    275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
    355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
    450                 455                 460

Val Val Phe Asn Asp Glu Phe Ala Pro Ser Asn His Ile Thr Gly Ser
465                 470                 475                 480

Thr Ile Met Gly Ala Asp Ala Arg Asp Ser Val Asp Lys Asp Cys
                485                 490                 495

Arg Thr Phe Asp His Pro Asn Leu Phe Ile Ser Ser Ser Ala Thr Met
                500                 505                 510

Pro Thr Val Gly Thr Val Asn Val Thr Leu Thr Ile Ala Ala Leu Ala
                515                 520                 525
```

```
Leu Arg Met Ser Asp Thr Leu Lys Lys Glu Val Gly Ser Gly Ser Gly
        530                 535                 540

His His His His His His
545                 550

<210> SEQ ID NO 29
<211> LENGTH: 550
<212> TYPE: PRT
<213> ORGANISM: Artificial Sequence
<220> FEATURE:
<223> OTHER INFORMATION: Recombinant sequence

<400> SEQUENCE: 29

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
                35                  40                  45

Val Glu Arg Phe Arg Asn Gln Pro Asp Lys Met Asp Phe Met Ala Pro
            50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
        130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335
```

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
        370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Val Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His His
545                 550

<210> SEQ ID NO 30
<211> LENGTH: 26
<212> TYPE: DNA
<213> ORGANISM: Artificial Sequence
<220> FEATURE:
<223> OTHER INFORMATION: Recombinant sequence

<400> SEQUENCE: 30
ccaggcaaat tctgttttat cagacc                                          26

<210> SEQ ID NO 31
<211> LENGTH: 23
<212> TYPE: DNA
<213> ORGANISM: Artificial Sequence
<220> FEATURE:
<223> OTHER INFORMATION: Recombinant sequence

<400> SEQUENCE: 31
caagctggag accgttaaa ctc                                              23

<210> SEQ ID NO 32
<211> LENGTH: 26
<212> TYPE: DNA
<213> ORGANISM: Artificial Sequence
<220> FEATURE:
<223> OTHER INFORMATION: Recombinant sequence

<400> SEQUENCE: 32
cgctattcag atcctcttct gagatg                                          26

```
<210> SEQ ID NO 33
<211> LENGTH: 24
<212> TYPE: DNA
<213> ORGANISM: Artificial Sequence
<220> FEATURE:
<223> OTHER INFORMATION: Recombinant sequence

<400> SEQUENCE: 33
gcttctgcgt tctgatttaa tctg                                            24

<210> SEQ ID NO 34
<211> LENGTH: 37
<212> TYPE: DNA
<213> ORGANISM: Artificial Sequence
<220> FEATURE:
<223> OTHER INFORMATION: Recombinant sequence

<400> SEQUENCE: 34
ggtcgtggtc ggatccggtg tggcaggtgc tattgtg                              37

<210> SEQ ID NO 35
<211> LENGTH: 23
<212> TYPE: DNA
<213> ORGANISM: Artificial Sequence
<220> FEATURE:
<223> OTHER INFORMATION: Recombinant sequence

<400> SEQUENCE: 35
cgttcttatt gcccgaataa acc                                             23

<210> SEQ ID NO 36
<211> LENGTH: 21
<212> TYPE: DNA
<213> ORGANISM: Artificial Sequence
<220> FEATURE:
<223> OTHER INFORMATION: Recombinant sequence

<400> SEQUENCE: 36
cgaagaagcc ctgatgtttg g                                               21

<210> SEQ ID NO 37
<211> LENGTH: 25
<212> TYPE: DNA
<213> ORGANISM: Artificial Sequence
<220> FEATURE:
<223> OTHER INFORMATION: Recombinant sequence

<400> SEQUENCE: 37
gaagcatggt atctgggcat tgttg                                           25

<210> SEQ ID NO 38
<211> LENGTH: 539
<212> TYPE: PRT
<213> ORGANISM: Artificial Sequence
<220> FEATURE:
<223> OTHER INFORMATION: Recombinant sequence

<400> SEQUENCE: 38

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
```

-continued

```
                50                  55                  60
Tyr Pro Ser Ser Pro Trp Ala Pro His Pro Glu Tyr Gly Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
                115                 120                 125

Asp Trp Pro Ile Gln Tyr Asp Asp Leu Glu Pro Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
450                 455                 460

Val Val Phe Asn Asp Glu Phe Ala Pro Asn Asn His Ile Thr Gly Ser
465                 470                 475                 480
```

```
Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
        500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
        530                 535

<210> SEQ ID NO 39
<211> LENGTH: 539
<212> TYPE: PRT
<213> ORGANISM: Artificial Sequence
<220> FEATURE:
<223> OTHER INFORMATION: Recombinant sequence

<400> SEQUENCE: 39

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300
```

```
Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535

<210> SEQ ID NO 40
<211> LENGTH: 538
<212> TYPE: PRT
<213> ORGANISM: Artificial Sequence
<220> FEATURE:
<223> OTHER INFORMATION: Recombinant sequence

<400> SEQUENCE: 40

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Thr Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Trp Ala Pro His Pro Glu Tyr Gly Pro Pro Asn Asp
65                  70                  75                  80

Tyr Leu Ile Leu Lys Gly Glu His Lys Phe Asn Ser Gln Tyr Ile Arg
                85                  90                  95

Ala Val Gly Gly Thr Thr Trp His Trp Ala Ala Ser Ala Trp Arg Phe
            100                 105                 110

Ile Pro Asn Asp Phe Lys Met Lys Ser Val Tyr Gly Val Gly Arg Asp
        115                 120                 125
```

```
Trp Pro Ile Gln Tyr Asp Asp Leu Glu Pro Tyr Tyr Gln Arg Ala Glu
    130                 135                 140

Glu Glu Leu Gly Val Trp Gly Pro Gly Pro Glu Asp Leu Tyr Ser
145                 150                 155                 160

Pro Arg Lys Gln Pro Tyr Pro Met Pro Pro Leu Pro Leu Ser Phe Asn
                165                 170                 175

Glu Gln Thr Ile Lys Thr Ala Leu Asn Asn Tyr Asp Pro Lys Phe His
                180                 185                 190

Val Val Thr Glu Pro Val Ala Arg Asn Ser Arg Pro Tyr Asp Gly Arg
            195                 200                 205

Pro Thr Cys Cys Gly Asn Asn Cys Met Pro Ile Cys Pro Ile Gly
    210                 215                 220

Ala Met Tyr Asn Gly Ile Val His Val Glu Lys Ala Glu Arg Ala Gly
225                 230                 235                 240

Ala Lys Leu Ile Glu Asn Ala Val Val Tyr Lys Leu Glu Thr Gly Pro
                245                 250                 255

Asp Lys Arg Ile Val Ala Ala Leu Tyr Lys Asp Lys Thr Gly Ala Glu
                260                 265                 270

His Arg Val Glu Gly Lys Tyr Phe Val Leu Ala Ala Asn Gly Ile Glu
            275                 280                 285

Thr Pro Lys Ile Leu Leu Met Ser Ala Asn Arg Asp Phe Pro Asn Gly
    290                 295                 300

Val Ala Asn Ser Ser Asp Met Val Gly Arg Asn Leu Met Asp His Pro
305                 310                 315                 320

Gly Thr Gly Val Ser Phe Tyr Ala Ser Glu Lys Leu Trp Pro Gly Arg
                325                 330                 335

Gly Pro Gln Glu Met Thr Ser Leu Val Gly Phe Arg Asp Gly Pro Phe
            340                 345                 350

Arg Ala Thr Glu Ala Ala Lys Lys Ile His Leu Ser Asn Leu Ser Arg
        355                 360                 365

Ile Asp Gln Glu Thr Gln Lys Ile Phe Lys Ala Gly Lys Leu Met Lys
    370                 375                 380

Pro Asp Glu Leu Asp Ala Gln Ile Arg Asp Arg Ser Ala Arg Tyr Val
385                 390                 395                 400

Gln Phe Asp Cys Phe His Glu Ile Leu Pro Gln Pro Glu Asn Arg Ile
                405                 410                 415

Val Pro Ser Lys Thr Ala Thr Asp Ala Ile Gly Ile Pro Arg Pro Glu
            420                 425                 430

Ile Thr Tyr Ala Ile Asp Asp Tyr Val Lys Arg Gly Ala Ala His Thr
    435                 440                 445

Arg Glu Val Tyr Ala Thr Ala Lys Val Leu Gly Gly Thr Asp Val
450                 455                 460

Val Phe Asn Asp Glu Phe Ala Pro Asn Asn His Ile Thr Gly Ser Thr
465                 470                 475                 480

Ile Met Gly Ala Asp Ala Arg Asp Ser Val Asp Lys Asp Cys Arg
                485                 490                 495

Thr Phe Asp His Pro Asn Leu Phe Ile Ser Ser Ser Ala Thr Met Pro
            500                 505                 510

Thr Val Gly Thr Val Asn Val Thr Leu Thr Ile Ala Ala Leu Ala Leu
        515                 520                 525

Arg Met Ser Asp Thr Leu Lys Lys Glu Val
    530                 535
```

```
<210> SEQ ID NO 41
<211> LENGTH: 539
<212> TYPE: PRT
<213> ORGANISM: Artificial Sequence
<220> FEATURE:
<223> OTHER INFORMATION: Recombinant sequence

<400> SEQUENCE: 41

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Phe Asn Leu Ser
        355                 360                 365
```

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
            405                 410                 415

Ile Val Pro Asn Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ala Thr Met
        500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535

<210> SEQ ID NO 42
<211> LENGTH: 539
<212> TYPE: PRT
<213> ORGANISM: Artificial Sequence
<220> FEATURE:
<223> OTHER INFORMATION: Recombinant sequence

<400> SEQUENCE: 42

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
            245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
            530                 535

<210> SEQ ID NO 43
<211> LENGTH: 539
<212> TYPE: PRT
<213> ORGANISM: Artificial Sequence
<220> FEATURE:
<223> OTHER INFORMATION: Recombinant sequence

<400> SEQUENCE: 43

Met Ala Asp Thr Asp Thr Gln Lys Ala Asp Val Val Val Val Gly Ser
1               5                   10                  15

-continued

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His

```
                435                 440                 445
Thr Arg Glu Val Tyr Ala Thr Ala Ala Lys Val Leu Gly Gly Thr Asp
        450                 455                 460
Val Val Phe Asn Asp Glu Phe Ala Pro Asn Asn His Ile Thr Gly Ser
465                 470                 475                 480
Thr Ile Met Gly Ala Asp Ala Arg Asp Ser Val Val Asp Lys Asp Cys
                485                 490                 495
Arg Thr Phe Asp His Pro Asn Leu Phe Ile Ser Ser Ala Thr Met
                500                 505                 510
Pro Thr Val Gly Thr Val Asn Val Ala Leu Thr Ile Ala Ala Leu Ala
        515                 520                 525
Leu Arg Met Ser Asp Thr Leu Lys Lys Glu Val
        530                 535

<210> SEQ ID NO 44
<211> LENGTH: 539
<212> TYPE: PRT
<213> ORGANISM: Artificial Sequence
<220> FEATURE:
<223> OTHER INFORMATION: Recombinant sequence

<400> SEQUENCE: 44

Met Ala Asp Thr Asp Thr Gln Lys Ala Asp Val Val Val Val Gly Ser
1               5                   10                  15
Gly Val Ala Gly Ala Ile Val Ala His Gln Leu Ala Met Ala Gly Lys
            20                  25                  30
Ala Val Ile Leu Leu Glu Ala Gly Pro Arg Met Pro Arg Trp Glu Ile
        35                  40                  45
Val Glu Arg Phe Arg Asn Gln Pro Asp Lys Met Asp Phe Met Ala Pro
    50                  55                  60
Tyr Pro Ser Ser Pro Trp Ala Pro His Pro Glu Tyr Gly Pro Pro Asn
65                  70                  75                  80
Asp Tyr Leu Ile Leu Lys Gly Glu His Lys Phe Asn Ser Gln Tyr Ile
                85                  90                  95
Arg Ala Val Gly Gly Thr Thr Trp His Trp Ala Ala Ser Ala Trp Arg
            100                 105                 110
Phe Ile Pro Asn Asp Phe Lys Met Lys Ser Val Tyr Gly Val Gly Arg
        115                 120                 125
Asp Trp Pro Ile Gln Tyr Asp Asp Leu Glu Pro Tyr Tyr Gln Arg Ala
    130                 135                 140
Glu Glu Glu Leu Gly Val Trp Gly Pro Gly Glu Glu Asp Leu Tyr
145                 150                 155                 160
Ser Pro Arg Lys Gln Pro Tyr Pro Met Pro Pro Leu Pro Leu Ser Phe
                165                 170                 175
Asn Glu Gln Thr Ile Lys Thr Ala Leu Asn Asn Tyr Asp Pro Lys Phe
            180                 185                 190
His Val Val Thr Glu Pro Val Ala Arg Asn Ser Arg Pro Tyr Asp Gly
        195                 200                 205
Arg Pro Thr Cys Cys Gly Asn Asn Cys Met Pro Ile Cys Pro Ile
    210                 215                 220
Gly Ala Met Tyr Asn Gly Ile Val His Val Glu Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
```

```
                260             265             270
Glu His Arg Val Glu Gly Lys Tyr Phe Val Leu Ala Ala Asn Gly Ile
            275             280             285

Glu Thr Pro Lys Ile Leu Leu Met Ser Ala Asn Arg Asp Phe Pro Asn
        290             295             300

Gly Ala Ala Asn Ser Ser Asp Met Val Gly Arg Asn Leu Met Asp His
305             310             315             320

Pro Gly Thr Gly Val Ser Phe Tyr Ala Ser Glu Lys Leu Trp Pro Gly
                325             330             335

Arg Gly Pro Gln Glu Met Thr Ser Leu Ile Gly Phe Arg Asp Gly Pro
            340             345             350

Phe Arg Ala Thr Glu Ala Ala Lys Lys Ile His Leu Ser Asn Leu Ser
        355             360             365

Arg Ile Asp Gln Glu Thr Gln Lys Ile Phe Lys Ala Gly Lys Leu Met
    370             375             380

Lys Pro Asp Glu Leu Asp Ala Gln Ile Arg Asp Arg Ser Ala Arg Tyr
385             390             395             400

Val Gln Phe Asp Cys Phe His Glu Ile Leu Pro Arg Pro Glu Asn Cys
                405             410             415

Ile Val Pro Ser Lys Thr Ala Thr Asp Ala Ile Gly Ile Pro Arg Pro
            420             425             430

Glu Ile Thr Tyr Ala Ile Asp Asp Tyr Val Lys Arg Gly Ala Ala His
        435             440             445

Thr Arg Glu Val Tyr Ala Thr Ala Lys Val Leu Gly Gly Thr Asp
    450             455             460

Val Val Phe Asn Asp Glu Phe Ala Pro Asn Asn His Ile Thr Gly Ser
465             470             475             480

Thr Ile Met Gly Ala Asp Ala Arg Asp Ser Val Val Asp Lys Asp Cys
                485             490             495

Arg Thr Phe Asp His Pro Asn Leu Phe Ile Ser Ser Ala Thr Met
            500             505             510

Pro Thr Val Gly Thr Val Asn Val Thr Leu Thr Ile Ala Ala Leu Ala
        515             520             525

Leu Arg Met Ser Asp Thr Leu Lys Lys Glu Val
    530             535
```

<210> SEQ ID NO 45
<211> LENGTH: 539
<212> TYPE: PRT
<213> ORGANISM: Artificial Sequence
<220> FEATURE:
<223> OTHER INFORMATION: Recombinant sequence
<400> SEQUENCE: 45

```
Met Ala Asp Thr Asp Thr Gln Lys Ala Asp Val Val Val Val Gly Ser
1               5               10              15

Gly Val Ala Gly Ala Ile Val Ala His Gln Leu Ala Met Ala Gly Lys
            20              25              30

Ala Val Ile Leu Leu Glu Ala Gly Pro Arg Met Pro Arg Trp Glu Ile
        35              40              45

Val Glu Arg Phe Arg Asn Gln Pro Asp Lys Met Asp Phe Met Ala Pro
    50              55              60

Tyr Pro Ser Ser Pro Trp Ala Pro His Pro Glu Tyr Gly Pro Pro Asn
65              70              75              80

Asp Tyr Leu Ile Leu Lys Gly Glu His Lys Phe Asn Ser Gln Tyr Ile
```

```
                        85                  90                  95
Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
                115                 120                 125

Asp Trp Pro Ile Gln Tyr Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Thr Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
                355                 360                 365

His Ile Asp Gln Glu Thr Gln Lys Ile Phe Lys Ala Gly Lys Leu Met
                370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510
```

-continued

Pro Thr Val Gly Thr Val Asn Val Thr Leu Thr Ile Ala Ala Leu Ala
        515                 520                 525

Leu Arg Met Ser Asp Thr Leu Lys Lys Glu Val
        530                 535

<210> SEQ ID NO 46
<211> LENGTH: 539
<212> TYPE: PRT
<213> ORGANISM: Artificial Sequence
<220> FEATURE:
<223> OTHER INFORMATION: Recombinant sequence

<400> SEQUENCE: 46

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
        130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
        210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

-continued

Arg Gly Pro Gln Glu Met Thr Ser Leu Ile Gly Phe Arg Asp Gly Pro
            340                 345                 350

Phe Arg Ala Thr Glu Ala Ala Lys Ile His Leu Ser Asn Leu Ser
            355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Leu His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535

<210> SEQ ID NO 47
<211> LENGTH: 539
<212> TYPE: PRT
<213> ORGANISM: Artificial Sequence
<220> FEATURE:
<223> OTHER INFORMATION: Recombinant sequence

<400> SEQUENCE: 47

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
            130                 135                 140

Glu Glu Glu Leu Gly Val Trp Gly Pro Gly Pro Glu Glu Asp Leu Tyr
145                 150                 155                 160

```
Ser Pro Arg Lys Gln Pro Tyr Pro Met Pro Pro Leu Pro Leu Ser Phe
            165                 170                 175

Asn Glu Gln Thr Ile Lys Thr Ala Leu Asn Asn Tyr Asp Pro Lys Phe
        180                 185                 190

His Val Val Thr Glu Pro Val Ala Arg Asn Ser Arg Pro Tyr Asp Gly
    195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
            245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
        370                 375                 380

Lys Pro Asp Glu Leu Asp Ala Gln Ile Arg Arg Ser Ala Arg Tyr
385                 390                 395                 400

Val Gln Phe Asp Cys Asp His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Asp Lys Asp Cys
            485                 490                 495

Arg Thr Phe Asp His Pro Asn Leu Phe Ile Ser Ser Ser Ala Thr Met
                500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535
```

<210> SEQ ID NO 48
<211> LENGTH: 539
<212> TYPE: PRT
<213> ORGANISM: Artificial Sequence
<220> FEATURE:

<223> OTHER INFORMATION: Recombinant sequence

<400> SEQUENCE: 48

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400
```

```
Val Gln Phe Asp Cys His His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
        450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
        530                 535

<210> SEQ ID NO 49
<211> LENGTH: 539
<212> TYPE: PRT
<213> ORGANISM: Artificial Sequence
<220> FEATURE:
<223> OTHER INFORMATION: Recombinant sequence

<400> SEQUENCE: 49

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220
```

```
Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
            245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Met His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535

<210> SEQ ID NO 50
<211> LENGTH: 539
<212> TYPE: PRT
<213> ORGANISM: Artificial Sequence
<220> FEATURE:
<223> OTHER INFORMATION: Recombinant sequence

<400> SEQUENCE: 50

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45
```

-continued

```
Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Glu His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
```

```
                465                 470                 475                 480
        Thr Ile Met Gly Ala Asp Ala Arg Asp Ser Val Val Asp Lys Asp Cys
                        485                 490                 495

Arg Thr Phe Asp His Pro Asn Leu Phe Ile Ser Ser Ala Thr Met
                        500                 505                 510

Pro Thr Val Gly Thr Val Asn Val Thr Leu Thr Ile Ala Ala Leu Ala
                        515                 520                 525

Leu Arg Met Ser Asp Thr Leu Lys Lys Glu Val
                        530                 535

<210> SEQ ID NO 51
<211> LENGTH: 539
<212> TYPE: PRT
<213> ORGANISM: Artificial Sequence
<220> FEATURE:
<223> OTHER INFORMATION: Recombinant sequence

<400> SEQUENCE: 51

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
```

```
            290                 295                 300
Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Ser His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 52
<211> LENGTH: 539
<212> TYPE: PRT
<213> ORGANISM: Artificial Sequence
<220> FEATURE:
<223> OTHER INFORMATION: Recombinant sequence

<400> SEQUENCE: 52

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
```

```
            115                 120                 125
Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
        370                 375                 380

Lys Pro Asp Glu Leu Asp Ala Gln Ile Arg Asp Arg Ser Ala Arg Tyr
385                 390                 395                 400

Val Gln Phe Asp Cys Thr His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535
```

```
<210> SEQ ID NO 53
<211> LENGTH: 539
<212> TYPE: PRT
<213> ORGANISM: Artificial Sequence
<220> FEATURE:
<223> OTHER INFORMATION: Recombinant sequence

<400> SEQUENCE: 53
```

| | | | | | | | | | | | | | | | |
|---|---|---|---|---|---|---|---|---|---|---|---|---|---|---|---|
| Met | Ala | Asp | Thr | Asp | Thr | Gln | Lys | Ala | Asp | Val | Val | Val | Gly | Ser | |
| 1 | | | | 5 | | | | | 10 | | | | | 15 | |
| Gly | Val | Ala | Gly | Ala | Ile | Val | Ala | His | Gln | Leu | Ala | Met | Ala | Gly | Lys |
| | | | 20 | | | | | 25 | | | | | 30 | | |
| Ala | Val | Ile | Leu | Leu | Glu | Ala | Gly | Pro | Arg | Met | Pro | Arg | Trp | Glu | Ile |
| | | | 35 | | | | | 40 | | | | | 45 | | |
| Val | Glu | Arg | Phe | Arg | Asn | Gln | Pro | Asp | Lys | Met | Asp | Phe | Met | Ala | Pro |
| | 50 | | | | | 55 | | | | | 60 | | | | |
| Tyr | Pro | Ser | Ser | Pro | Trp | Ala | Pro | His | Pro | Glu | Tyr | Gly | Pro | Pro | Asn |
| 65 | | | | | 70 | | | | | 75 | | | | | 80 |
| Asp | Tyr | Leu | Ile | Leu | Lys | Gly | Glu | His | Lys | Phe | Asn | Ser | Gln | Tyr | Ile |
| | | | | 85 | | | | | 90 | | | | | 95 | |
| Arg | Ala | Val | Gly | Gly | Thr | Thr | Trp | His | Trp | Ala | Ala | Ser | Ala | Trp | Arg |
| | | | 100 | | | | | 105 | | | | | 110 | | |
| Phe | Ile | Pro | Asn | Asp | Phe | Lys | Met | Lys | Ser | Val | Tyr | Gly | Val | Gly | Arg |
| | | | 115 | | | | | 120 | | | | | 125 | | |
| Asp | Trp | Pro | Ile | Gln | Tyr | Asp | Asp | Leu | Glu | Pro | Tyr | Tyr | Gln | Arg | Ala |
| | 130 | | | | | 135 | | | | | 140 | | | | |
| Glu | Glu | Glu | Leu | Gly | Val | Trp | Gly | Pro | Gly | Pro | Glu | Glu | Asp | Leu | Tyr |
| 145 | | | | | 150 | | | | | 155 | | | | | 160 |
| Ser | Pro | Arg | Lys | Gln | Pro | Tyr | Pro | Met | Pro | Pro | Leu | Pro | Leu | Ser | Phe |
| | | | | 165 | | | | | 170 | | | | | 175 | |
| Asn | Glu | Gln | Thr | Ile | Lys | Thr | Ala | Leu | Asn | Asn | Tyr | Asp | Pro | Lys | Phe |
| | | | 180 | | | | | 185 | | | | | 190 | | |
| His | Val | Val | Thr | Glu | Pro | Val | Ala | Arg | Asn | Ser | Arg | Pro | Tyr | Asp | Gly |
| | | | 195 | | | | | 200 | | | | | 205 | | |
| Arg | Pro | Thr | Cys | Cys | Gly | Asn | Asn | Cys | Met | Pro | Ile | Cys | Pro | Ile | |
| | 210 | | | | | 215 | | | | | 220 | | | | |
| Gly | Ala | Met | Tyr | Asn | Gly | Ile | Val | His | Val | Glu | Lys | Ala | Glu | Arg | Ala |
| 225 | | | | | 230 | | | | | 235 | | | | | 240 |
| Gly | Ala | Lys | Leu | Ile | Glu | Asn | Ala | Val | Val | Tyr | Lys | Leu | Glu | Thr | Gly |
| | | | | 245 | | | | | 250 | | | | | 255 | |
| Pro | Asp | Lys | Arg | Ile | Val | Ala | Ala | Leu | Tyr | Lys | Asp | Lys | Thr | Gly | Ala |
| | | | 260 | | | | | 265 | | | | | 270 | | |
| Glu | His | Arg | Val | Glu | Gly | Lys | Tyr | Phe | Val | Leu | Ala | Ala | Asn | Gly | Ile |
| | | | 275 | | | | | 280 | | | | | 285 | | |
| Glu | Thr | Pro | Lys | Ile | Leu | Leu | Met | Ser | Ala | Asn | Arg | Asp | Phe | Pro | Asn |
| | 290 | | | | | 295 | | | | | 300 | | | | |
| Gly | Val | Ala | Asn | Ser | Ser | Asp | Met | Val | Gly | Arg | Asn | Leu | Met | Asp | His |
| 305 | | | | | 310 | | | | | 315 | | | | | 320 |
| Pro | Gly | Thr | Gly | Val | Ser | Phe | Tyr | Ala | Ser | Glu | Lys | Leu | Trp | Pro | Gly |
| | | | | 325 | | | | | 330 | | | | | 335 | |
| Arg | Gly | Pro | Gln | Glu | Met | Thr | Ser | Leu | Ile | Gly | Phe | Arg | Asp | Gly | Pro |
| | | | 340 | | | | | 345 | | | | | 350 | | |
| Phe | Arg | Ala | Thr | Glu | Ala | Ala | Lys | Lys | Ile | His | Leu | Ser | Asn | Leu | Ser |
| | | | 355 | | | | | 360 | | | | | 365 | | |

```
Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys Tyr His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Ala Lys Val Leu Gly Gly Thr Asp
            450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
            530                 535

<210> SEQ ID NO 54
<211> LENGTH: 539
<212> TYPE: PRT
<213> ORGANISM: Artificial Sequence
<220> FEATURE:
<223> OTHER INFORMATION: Recombinant sequence

<400> SEQUENCE: 54

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190
```

His Val Thr Glu Pro Val Ala Arg Asn Ser Arg Pro Tyr Asp Gly
    195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Asn His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
            450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
            530                 535

<210> SEQ ID NO 55
<211> LENGTH: 539
<212> TYPE: PRT
<213> ORGANISM: Artificial Sequence
<220> FEATURE:
<223> OTHER INFORMATION: Recombinant sequence

<400> SEQUENCE: 55

Met Ala Asp Thr Asp Thr Gln Lys Ala Asp Val Val Val Val Gly Ser
1               5                   10                  15

```
Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Gln His Glu Ile Leu Pro Gln Pro Glu Asn Arg
                405                 410                 415

Ile Val Pro Ser Lys Thr Ala Asp Ala Ile Gly Ile Pro Arg Pro
            420                 425                 430
```

```
Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465             470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
    530                 535

<210> SEQ ID NO 56
<211> LENGTH: 539
<212> TYPE: PRT
<213> ORGANISM: Artificial Sequence
<220> FEATURE:
<223> OTHER INFORMATION: Recombinant sequence

<400> SEQUENCE: 56

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
    115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
    195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255
```

```
Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Cys His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 57
<211> LENGTH: 539
<212> TYPE: PRT
<213> ORGANISM: Artificial Sequence
<220> FEATURE:
<223> OTHER INFORMATION: Recombinant sequence

<400> SEQUENCE: 57

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80
```

-continued

```
Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Gly His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
```

```
                500             505             510
Pro Thr Val Gly Thr Val Asn Val Thr Leu Thr Ile Ala Ala Leu Ala
            515                 520                 525

Leu Arg Met Ser Asp Thr Leu Lys Lys Glu Val
            530                 535

<210> SEQ ID NO 58
<211> LENGTH: 539
<212> TYPE: PRT
<213> ORGANISM: Artificial Sequence
<220> FEATURE:
<223> OTHER INFORMATION: Recombinant sequence

<400> SEQUENCE: 58

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
```

```
                   325                 330                 335
Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
        370                 375                 380

Lys Pro Asp Glu Leu Asp Ala Gln Ile Arg Asp Arg Ser Ala Arg Tyr
385                 390                 395                 400

Val Gln Phe Asp Cys Pro His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 59
<211> LENGTH: 539
<212> TYPE: PRT
<213> ORGANISM: Artificial Sequence
<220> FEATURE:
<223> OTHER INFORMATION: Recombinant sequence

<400> SEQUENCE: 59

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
```

```
            145                 150                 155                 160
Ser Pro Arg Lys Gln Pro Tyr Pro Met Pro Pro Leu Pro Leu Ser Phe
                    165                 170                 175

Asn Glu Gln Thr Ile Lys Thr Ala Leu Asn Asn Tyr Asp Pro Lys Phe
                    180                 185                 190

His Val Thr Glu Pro Val Ala Arg Asn Ser Arg Pro Tyr Asp Gly
                195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                    245                 250                 255

Pro Asp Lys Arg Ile Val Ala Ala Leu Tyr Lys Asp Lys Thr Gly Ala
                    260                 265                 270

Glu His Arg Val Glu Gly Lys Tyr Phe Val Leu Ala Ala Asn Gly Ile
                275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                    325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Ala His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
    530                 535

<210> SEQ ID NO 60
<211> LENGTH: 539
<212> TYPE: PRT
<213> ORGANISM: Artificial Sequence
```

<220> FEATURE:
<223> OTHER INFORMATION: Recombinant sequence

<400> SEQUENCE: 60

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
                115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
                210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
                260                 265                 270

Glu His Arg Val Glu Gly Lys Tyr Phe Val Leu Ala Ala Asn Gly Ile
                275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Leu Ser
                355                 360                 365

Arg Ile Asp Gln Glu Thr Gln Lys Ile Phe Lys Ala Gly Lys Leu Met
                370                 375                 380

Lys Pro Asp Glu Leu Asp Ala Gln Ile Arg Asp Arg Ser Ala Arg Tyr
385                 390                 395                 400
```

```
Val Gln Phe Asp Cys Val His Glu Ile Leu Pro Gln Pro Glu Asn Arg
            405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
        450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
            530                 535

<210> SEQ ID NO 61
<211> LENGTH: 539
<212> TYPE: PRT
<213> ORGANISM: Artificial Sequence
<220> FEATURE:
<223> OTHER INFORMATION: Recombinant sequence

<400> SEQUENCE: 61

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
            85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
            165                 170                 175

Asn Glu Gln Thr Ile Lys Thr Ala Leu Asn Asn Tyr Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220
```

-continued

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
            245                 250                 255

Pro Asp Lys Arg Ile Val Ala Ala Leu Tyr Lys Asp Lys Thr Gly Ala
        260                 265                 270

Glu His Arg Val Glu Gly Lys Tyr Phe Val Leu Ala Ala Asn Gly Ile
    275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
            325                 330                 335

Arg Gly Pro Gln Glu Met Thr Ser Leu Ile Gly Phe Arg Asp Gly Pro
        340                 345                 350

Phe Arg Ala Thr Glu Ala Ala Lys Lys Ile His Leu Ser Asn Leu Ser
    355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Ile His Glu Ile Leu Pro Gln Pro Glu Asn Arg
            405                 410                 415

Ile Val Pro Ser Lys Thr Ala Thr Asp Ala Ile Gly Ile Pro Arg Pro
        420                 425                 430

Glu Ile Thr Tyr Ala Ile Asp Asp Tyr Val Lys Arg Gly Ala Ala His
    435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ser Ala Thr Met
        500                 505                 510

Pro Thr Val Gly Thr Val Asn Val Thr Leu Thr Ile Ala Ala Leu Ala
    515                 520                 525

Leu Arg Met Ser Asp Thr Leu Lys Lys Glu Val
530                 535

<210> SEQ ID NO 62
<211> LENGTH: 539
<212> TYPE: PRT
<213> ORGANISM: Artificial Sequence
<220> FEATURE:
<223> OTHER INFORMATION: Recombinant sequence

<400> SEQUENCE: 62

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

```
Val Glu Arg Phe Arg Asn Gln Pro Asp Lys Met Asp Phe Met Ala Pro
 50                  55                  60

Tyr Pro Ser Ser Pro Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Trp His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Ala Lys Val Leu Gly Gly Thr Asp
    450                 455                 460
```

```
Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535
```

<210> SEQ ID NO 63
<211> LENGTH: 539
<212> TYPE: PRT
<213> ORGANISM: Artificial Sequence
<220> FEATURE:
<223> OTHER INFORMATION: Recombinant sequence

<400> SEQUENCE: 63

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285
```

```
Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
450                 455                 460

Val Val Phe Asn Asp Glu Phe Ala Pro His Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
530                 535
```

<210> SEQ ID NO 64
<211> LENGTH: 539
<212> TYPE: PRT
<213> ORGANISM: Artificial Sequence
<220> FEATURE:
<223> OTHER INFORMATION: Recombinant sequence

<400> SEQUENCE: 64

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110
```

Phe Ile Pro Asn Asp Phe Lys Met Lys Ser Val Tyr Gly Val Gly Arg
            115                 120                 125

Asp Trp Pro Ile Gln Tyr Asp Leu Glu Pro Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Lys Val Leu Gly Gly Thr Asp
    450                 455                 460

Val Val Phe Asn Asp Glu Phe Ala Pro Leu Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val

<210> SEQ ID NO 65
<211> LENGTH: 539
<212> TYPE: PRT
<213> ORGANISM: Artificial Sequence
<220> FEATURE:
<223> OTHER INFORMATION: Recombinant sequence

<400> SEQUENCE: 65

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser

```
                355                 360                 365
Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Ala His
                435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Ser Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
    530                 535

<210> SEQ ID NO 66
<211> LENGTH: 539
<212> TYPE: PRT
<213> ORGANISM: Artificial Sequence
<220> FEATURE:
<223> OTHER INFORMATION: Recombinant sequence

<400> SEQUENCE: 66

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ala Val Ile Leu Leu Glu Ala Gly Pro Arg Met Pro Arg Trp Glu Ile
            35                  40                  45

Val Glu Arg Phe Arg Asn Gln Pro Asp Lys Met Asp Phe Met Ala Pro
        50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
        130                 135                 140

Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
```

|   |   | 180 |   |   |   | 185 |   |   |   | 190 |   |
|---|---|---|---|---|---|---|---|---|---|---|---|

His Val Val Thr Glu Pro Val Ala Arg Asn Ser Arg Pro Tyr Asp Gly
            195                200                205

Arg Pro Thr Cys Cys Gly Asn Asn Cys Met Pro Ile Cys Pro Ile
210                215                220

Gly Ala Met Tyr Asn Gly Ile Val His Val Glu Lys Ala Glu Arg Ala
225                230                235                240

Gly Ala Lys Leu Ile Glu Asn Ala Val Val Tyr Lys Leu Glu Thr Gly
            245                250                255

Pro Asp Lys Arg Ile Val Ala Ala Leu Tyr Lys Asp Lys Thr Gly Ala
            260                265                270

Glu His Arg Val Glu Gly Lys Tyr Phe Val Leu Ala Ala Asn Gly Ile
            275                280                285

Glu Thr Pro Lys Ile Leu Leu Met Ser Ala Asn Arg Asp Phe Pro Asn
            290                295                300

Gly Val Ala Asn Ser Ser Asp Met Val Gly Arg Asn Leu Met Asp His
305                310                315                320

Pro Gly Thr Gly Val Ser Phe Tyr Ala Ser Glu Lys Leu Trp Pro Gly
            325                330                335

Arg Gly Pro Gln Glu Met Thr Ser Leu Ile Gly Phe Arg Asp Gly Pro
            340                345                350

Phe Arg Ala Thr Glu Ala Ala Lys Lys Ile His Leu Ser Asn Leu Ser
            355                360                365

Arg Ile Asp Gln Glu Thr Gln Lys Ile Phe Lys Ala Gly Lys Leu Met
            370                375                380

Lys Pro Asp Glu Leu Asp Ala Gln Ile Arg Asp Arg Ser Ala Arg Tyr
385                390                395                400

Val Gln Phe Asp Cys Phe His Glu Ile Leu Pro Gln Pro Glu Asn Arg
            405                410                415

Ile Val Pro Ser Lys Thr Ala Thr Asp Ala Ile Gly Ile Pro Arg Pro
            420                425                430

Glu Ile Thr Tyr Ala Ile Asp Asp Tyr Val Lys Arg Gly Ala Ala His
            435                440                445

Thr Arg Glu Val Tyr Ala Thr Ala Ala Lys Val Leu Gly Gly Thr Asp
            450                455                460

Val Val Phe Asn Asp Glu Phe Ala Pro Val Asn His Ile Thr Gly Ser
465                470                475                480

Thr Ile Met Gly Ala Asp Ala Arg Asp Ser Val Val Asp Lys Asp Cys
            485                490                495

Arg Thr Phe Asp His Pro Asn Leu Phe Ile Ser Ser Ala Thr Met
            500                505              510

Pro Thr Val Gly Thr Val Asn Val Thr Leu Thr Ile Ala Ala Leu Ala
            515                520                525

Leu Arg Met Ser Asp Thr Leu Lys Lys Glu Val
530                535

<210> SEQ ID NO 67
<211> LENGTH: 550
<212> TYPE: PRT
<213> ORGANISM: Artificial Sequence
<220> FEATURE:
<223> OTHER INFORMATION: Recombinant sequence

<400> SEQUENCE: 67

Met Ala Asp Thr Asp Thr Gln Lys Ala Asp Val Val Val Val Gly Ser

-continued

```
1               5                   10                  15
Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
                130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
                355                 360                 365

Arg Ile Asn Gln Glu Thr Gln Lys Ile Phe Lys Gly Gly Lys Leu Met
                370                 375                 380

Lys Pro Glu Glu Leu Asp Ala Gln Ile Arg Asp Arg Ser Ala Arg Phe
385                 390                 395                 400

Val Gln Phe Asp Cys Ala His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430
```

```
Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Gly Ser Gly Ser Gly
530                 535                 540

His His His His His His
545                 550
```

```
<210> SEQ ID NO 68
<211> LENGTH: 550
<212> TYPE: PRT
<213> ORGANISM: Artificial Sequence
<220> FEATURE:
<223> OTHER INFORMATION: Recombinant sequence

<400> SEQUENCE: 68

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240
```

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
        260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Cys His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His His
545                 550

<210> SEQ ID NO 69
<211> LENGTH: 550
<212> TYPE: PRT
<213> ORGANISM: Artificial Sequence
<220> FEATURE:
<223> OTHER INFORMATION: Recombinant sequence

<400> SEQUENCE: 69

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
 50                  55                  60

Tyr Pro Ser Ser Ala Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Ile Glu His Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Asp His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

```
Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
    530                 535                 540

His His His His His His
545                 550

<210> SEQ ID NO 70
<211> LENGTH: 550
<212> TYPE: PRT
<213> ORGANISM: Artificial Sequence
<220> FEATURE:
<223> OTHER INFORMATION: Recombinant sequence

<400> SEQUENCE: 70

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270
```

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Glu His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
530                 535                 540

His His His His His His
545                 550

<210> SEQ ID NO 71
<211> LENGTH: 550
<212> TYPE: PRT
<213> ORGANISM: Artificial Sequence
<220> FEATURE:
<223> OTHER INFORMATION: Recombinant sequence

<400> SEQUENCE: 71

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

```
Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
            165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Gly His Glu Ile Leu Pro Gln Pro Glu Asn Arg
            405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Ser Thr Met
```

```
                500               505               510
Pro Thr Val Gly Thr Val Asn Val Thr Leu Thr Ile Ala Ala Leu Ala
            515               520               525

Leu Arg Met Ser Asp Thr Leu Lys Lys Glu Val Gly Ser Gly Ser Gly
530             535               540

His His His His His His
545             550

<210> SEQ ID NO 72
<211> LENGTH: 550
<212> TYPE: PRT
<213> ORGANISM: Artificial Sequence
<220> FEATURE:
<223> OTHER INFORMATION: Recombinant sequence

<400> SEQUENCE: 72

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
```

Pro Gly Thr Gly Val Ser Phe Tyr Ala Asn Glu Lys Leu Trp Pro Gly
305                 310                 315                 320

Arg Gly Pro Gln Glu Met Thr Ser Leu Ile Gly Phe Arg Asp Gly Pro
            325                 330                 335

Phe Arg Ala Asn Glu Ala Ala Lys Ile His Leu Ser Asn Met Ser
            340                 345                 350

Arg Ile Asn Gln Glu Thr Gln Lys Ile Phe Lys Gly Gly Lys Leu Met
            355                 360                 365

Lys Pro Glu Glu Leu Asp Ala Gln Ile Arg Asp Arg Ser Ala Arg Phe
370                 375                 380

Val Gln Phe Asp Cys His His Glu Ile Leu Pro Gln Pro Glu Asn Arg
385                 390                 395                 400

Ile Val Pro Ser Lys Thr Ala Thr Asp Ala Val Gly Ile Pro Arg Pro
            405                 410                 415

Glu Ile Thr Tyr Ala Ile Asp Asp Tyr Val Lys Arg Gly Ala Val His
            420                 425                 430

Thr Arg Glu Val Tyr Ala Thr Ala Lys Val Leu Gly Gly Thr Glu
            435                 440                 445

Val Val Phe Asn Asp Glu Phe Ala Pro Asn Asn His Ile Thr Gly Ala
450                 455                 460

Thr Ile Met Gly Ala Asp Ala Arg Asp Ser Val Val Asp Lys Asp Cys
465                 470                 475                 480

Arg Ala Phe Asp His Pro Asn Leu Phe Ile Ser Ser Ser Thr Met
            485                 490                 495

Pro Thr Val Gly Thr Val Asn Val Thr Leu Thr Ile Ala Ala Leu Ala
            500                 505                 510

Leu Arg Met Ser Asp Thr Leu Lys Lys Glu Val Gly Ser Gly Ser Gly
            515                 520                 525

His His His His His His
545                 550
            530                 535                 540

<210> SEQ ID NO 73
<211> LENGTH: 550
<212> TYPE: PRT
<213> ORGANISM: Artificial Sequence
<220> FEATURE:
<223> OTHER INFORMATION: Recombinant sequence

<400> SEQUENCE: 73

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
            85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg

```
            115                 120                 125
Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Ile His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540
```

```
His His His His His His
545                 550

<210> SEQ ID NO 74
<211> LENGTH: 550
<212> TYPE: PRT
<213> ORGANISM: Artificial Sequence
<220> FEATURE:
<223> OTHER INFORMATION: Recombinant sequence

<400> SEQUENCE: 74

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350
```

```
Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Lys His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
        530                 535                 540

His His His His His His
545                 550

<210> SEQ ID NO 75
<211> LENGTH: 550
<212> TYPE: PRT
<213> ORGANISM: Artificial Sequence
<220> FEATURE:
<223> OTHER INFORMATION: Recombinant sequence

<400> SEQUENCE: 75

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
        130                 135                 140

Glu Glu Glu Leu Gly Val Trp Gly Pro Gly Pro Glu Glu Asp Leu Tyr
145                 150                 155                 160
```

Ser Pro Arg Lys Glu Pro Tyr Pro Met Pro Pro Leu Pro Leu Ser Phe
            165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Arg Ser Ala Arg Phe
385                 390                 395                 400

Val Gln Phe Asp Cys Leu His Glu Ile Leu Pro Gln Pro Glu Asn Arg
            405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 76
<211> LENGTH: 550

<212> TYPE: PRT
<213> ORGANISM: Artificial Sequence
<220> FEATURE:
<223> OTHER INFORMATION: Recombinant sequence

<400> SEQUENCE: 76

```
Met Ala Asp Thr Asp Thr Gln Lys Ala Asp Val Val Val Gly Ser
1               5                  10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
        210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
    370                 375                 380
```

```
Lys Pro Glu Glu Leu Asp Ala Gln Ile Arg Asp Ser Ala Arg Phe
385                 390                 395                 400

Val Gln Phe Asp Cys Met His Glu Ile Leu Pro Gln Pro Glu Asn Arg
            405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 77
<211> LENGTH: 550
<212> TYPE: PRT
<213> ORGANISM: Artificial Sequence
<220> FEATURE:
<223> OTHER INFORMATION: Recombinant sequence

<400> SEQUENCE: 77

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190
```

-continued

```
His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Asn His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 78
<211> LENGTH: 550
<212> TYPE: PRT
<213> ORGANISM: Artificial Sequence
<220> FEATURE:
<223> OTHER INFORMATION: Recombinant sequence

<400> SEQUENCE: 78
```

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Gln His Glu Ile Leu Pro Gln Pro Glu Asn Arg
            405                 410                 415

Ile Val Pro Ser Lys Thr Ala Thr Asp Ala Val Gly Ile Pro Arg Pro
```

```
                420           425           430
Glu Ile Thr Tyr Ala Ile Asp Asp Tyr Val Lys Arg Gly Ala Val His
            435                 440                 445
Thr Arg Glu Val Tyr Ala Thr Ala Ala Lys Val Leu Gly Gly Thr Glu
    450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
            500                 505                 510
Pro Thr Val Gly Thr Val Asn Val Thr Leu Thr Ile Ala Ala Leu Ala
            515                 520                 525
Leu Arg Met Ser Asp Thr Leu Lys Lys Glu Val Gly Ser Gly Ser Gly
            530                 535                 540
His His His His His His
545                 550
```

<210> SEQ ID NO 79
<211> LENGTH: 550
<212> TYPE: PRT
<213> ORGANISM: Artificial Sequence
<220> FEATURE:
<223> OTHER INFORMATION: Recombinant sequence

<400> SEQUENCE: 79

```
Met Ala Asp Thr Asp Thr Gln Lys Ala Asp Val Val Val Gly Ser
1               5                  10                  15
Gly Val Ala Gly Ala Ile Val Ala His Gln Leu Ala Met Ala Gly Lys
            20                  25                  30
Ser Val Ile Leu Leu Glu Ala Gly Pro Arg Met Pro Arg Trp Glu Ile
        35                  40                  45
Val Glu Arg Phe Arg Asn Gln Val Asp Lys Thr Asp Phe Met Ala Pro
    50                  55                  60
Tyr Pro Ser Ser Ala Trp Ala Pro His Pro Glu Tyr Gly Pro Pro Asn
65                  70                  75                  80
Asp Tyr Leu Ile Leu Lys Gly Glu His Lys Phe Asn Ser Gln Tyr Ile
                85                  90                  95
Arg Ala Val Gly Gly Thr Thr Trp His Trp Ala Ala Ser Ala Trp Arg
            100                 105                 110
Phe Ile Pro Asn Asp Phe Lys Met Lys Thr Val Tyr Gly Val Gly Arg
        115                 120                 125
Asp Trp Pro Ile Gln Tyr Asp Asp Ile Glu His Tyr Tyr Gln Arg Ala
    130                 135                 140
Glu Glu Glu Leu Gly Val Trp Gly Pro Gly Pro Glu Glu Asp Leu Tyr
145                 150                 155                 160
Ser Pro Arg Lys Glu Pro Tyr Pro Met Pro Leu Pro Leu Ser Phe
            165                 170                 175
Asn Glu Gln Thr Ile Lys Ser Ala Leu Asn Gly Tyr Asp Pro Lys Phe
        180                 185                 190
His Val Thr Glu Pro Val Ala Arg Asn Ser Arg Pro Tyr Asp Gly
            195                 200                 205
Arg Pro Thr Cys Cys Gly Asn Asn Asn Cys Met Pro Ile Cys Pro Ile
    210                 215                 220
Gly Ala Met Tyr Asn Gly Ile Val His Val Glu Lys Ala Glu Gln Ala
```

```
            225                 230                 235                 240
    Gly Ala Lys Leu Ile Asp Ser Ala Val Val Tyr Lys Leu Glu Thr Gly
                    245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
    305                 310                 315                 320

Pro Gly Thr Gly Val Ser Phe Tyr Ala Asn Glu Lys Leu Trp Pro Gly
                    325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
    385                 390                 395                 400

Val Gln Phe Asp Cys Ser His Glu Ile Leu Pro Gln Pro Glu Asn Arg
                    405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
    465                 470                 475                 480

Thr Ile Met Gly Ala Asp Ala Arg Asp Ser Val Val Asp Lys Asp Cys
                    485                 490                 495

Arg Ala Phe Asp His Pro Asn Leu Phe Ile Ser Ser Ser Ser Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
        530                 535                 540

His His His His His His
    545                 550

<210> SEQ ID NO 80
<211> LENGTH: 550
<212> TYPE: PRT
<213> ORGANISM: Artificial Sequence
<220> FEATURE:
<223> OTHER INFORMATION: Recombinant sequence

<400> SEQUENCE: 80

Met Ala Asp Thr Asp Thr Gln Lys Ala Asp Val Val Val Val Gly Ser
    1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
```

```
            35                  40                  45
Val Glu Arg Phe Arg Asn Gln Val Asp Lys Thr Asp Phe Met Ala Pro
 50                  55                  60
Tyr Pro Ser Ser Ala Trp Ala Pro His Pro Glu Tyr Gly Pro Pro Asn
 65                  70                  75                  80
Asp Tyr Leu Ile Leu Lys Gly Glu His Lys Phe Asn Ser Gln Tyr Ile
                     85                  90                  95
Arg Ala Val Gly Gly Thr Thr Trp His Trp Ala Ala Ser Ala Trp Arg
                    100                 105                 110
Phe Ile Pro Asn Asp Phe Lys Met Lys Thr Val Tyr Gly Val Gly Arg
            115                 120                 125
Asp Trp Pro Ile Gln Tyr Asp Asp Ile Glu His Tyr Tyr Gln Arg Ala
            130                 135                 140
Glu Glu Glu Leu Gly Val Trp Gly Pro Gly Glu Glu Asp Leu Tyr
145                 150                 155                 160
Ser Pro Arg Lys Glu Pro Tyr Pro Met Pro Pro Leu Pro Leu Ser Phe
                    165                 170                 175
Asn Glu Gln Thr Ile Lys Ser Ala Leu Asn Gly Tyr Asp Pro Lys Phe
                    180                 185                 190
His Val Val Thr Glu Pro Val Ala Arg Asn Ser Arg Pro Tyr Asp Gly
                    195                 200                 205
Arg Pro Thr Cys Cys Gly Asn Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                    245                 250                 255
Pro Asp Lys Arg Ile Thr Ala Ala Val Tyr Lys Asp Lys Thr Gly Ala
                    260                 265                 270
Asp His Arg Val Glu Gly Lys Tyr Phe Val Ile Ala Ala Asn Gly Ile
                    275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                    325                 330                 335
Arg Gly Pro Gln Glu Met Thr Ser Leu Ile Gly Phe Arg Asp Gly Pro
                    340                 345                 350
Phe Arg Ala Asn Glu Ala Ala Lys Lys Ile His Leu Ser Asn Met Ser
            355                 360                 365
Arg Ile Asn Gln Glu Thr Gln Lys Ile Phe Lys Gly Gly Lys Leu Met
            370                 375                 380
Lys Pro Glu Glu Leu Asp Ala Gln Ile Arg Asp Arg Ser Ala Arg Phe
385                 390                 395                 400
Val Gln Phe Asp Cys Pro His Glu Ile Leu Pro Gln Pro Glu Asn Arg
                    405                 410                 415
Ile Val Pro Ser Lys Thr Ala Asp Ala Val Gly Ile Pro Arg Pro
                    420                 425                 430
Glu Ile Thr Tyr Ala Ile Asp Asp Tyr Val Lys Arg Gly Ala Val His
            435                 440                 445
Thr Arg Glu Val Tyr Ala Thr Ala Ala Lys Val Leu Gly Gly Thr Glu
450                 455                 460
```

```
Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
            530                 535                 540

His His His His His His
545                 550

<210> SEQ ID NO 81
<211> LENGTH: 550
<212> TYPE: PRT
<213> ORGANISM: Artificial Sequence
<220> FEATURE:
<223> OTHER INFORMATION: Recombinant sequence

<400> SEQUENCE: 81

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
            85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
            165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270
```

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Val His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
        530                 535                 540

His His His His His His
545                 550

<210> SEQ ID NO 82
<211> LENGTH: 550
<212> TYPE: PRT
<213> ORGANISM: Artificial Sequence
<220> FEATURE:
<223> OTHER INFORMATION: Recombinant sequence

<400> SEQUENCE: 82

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

```
Asp Tyr Leu Ile Leu Lys Gly Glu His Lys Phe Asn Ser Gln Tyr Ile
            85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Asp Leu Tyr
145                 150                 155                 160

Ser Pro Arg Lys Glu Pro Tyr Pro Met Pro Pro Leu Pro Leu Ser Phe
            165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Arg His Gly Ile Leu Pro Gln Pro Glu Asn Arg
            405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
            450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495
```

```
Arg Ala Phe Asp His Pro Asn Leu Phe Ile Ser Ser Ser Ser Thr Met
                500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

His His His His His His
545                 550

<210> SEQ ID NO 83
<211> LENGTH: 550
<212> TYPE: PRT
<213> ORGANISM: Artificial Sequence
<220> FEATURE:
<223> OTHER INFORMATION: Recombinant sequence

<400> SEQUENCE: 83

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
    115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
    195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
    290                 295                 300
```

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Thr His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540

His His His His His His
545                 550

<210> SEQ ID NO 84
<211> LENGTH: 550
<212> TYPE: PRT
<213> ORGANISM: Artificial Sequence
<220> FEATURE:
<223> OTHER INFORMATION: Recombinant sequence

<400> SEQUENCE: 84

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

```
Phe Ile Pro Asn Asp Phe Lys Met Lys Thr Val Tyr Gly Val Gly Arg
            115                 120                 125
Asp Trp Pro Ile Gln Tyr Asp Asp Ile Glu His Tyr Tyr Gln Arg Ala
        130                 135                 140
Glu Glu Glu Leu Gly Val Trp Gly Pro Gly Glu Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
            180                 185                 190
His Val Val Thr Glu Pro Val Ala Arg Asn Ser Arg Pro Tyr Asp Gly
        195                 200                 205
Arg Pro Thr Cys Cys Gly Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
        275                 280                 285
Glu Thr Pro Lys Ile Leu Leu Met Ser Ala Asn Arg Asp Phe Pro Asn
        290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
        355                 360                 365
Arg Ile Asn Gln Glu Thr Gln Lys Ile Phe Lys Gly Gly Lys Leu Met
        370                 375                 380
Lys Pro Glu Glu Leu Asp Ala Gln Ile Arg Asp Arg Ser Ala Arg Phe
385                 390                 395                 400
Val Gln Phe Asp Cys Trp His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
        435                 440                 445
Thr Arg Glu Val Tyr Ala Thr Ala Lys Val Leu Gly Gly Thr Glu
        450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
            500                 505                 510
Pro Thr Val Gly Thr Val Asn Val Thr Leu Thr Ile Ala Ala Leu Ala
        515                 520                 525
Leu Arg Met Ser Asp Thr Leu Lys Lys Glu Val Gly Ser Gly Ser Gly
```

His His His His His His
545             550

<210> SEQ ID NO 85
<211> LENGTH: 550
<212> TYPE: PRT
<213> ORGANISM: Artificial Sequence
<220> FEATURE:
<223> OTHER INFORMATION: Recombinant sequence

<400> SEQUENCE: 85

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
                130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Cys Met Pro Ile Cys Pro Ile
                210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro

```
                340                 345                 350
        Phe Arg Ala Asn Glu Ala Ala Lys Lys Ile His Leu Ser Asn Met Ser
                    355                 360                 365

Arg Ile Asn Gln Glu Thr Gln Lys Ile Phe Lys Gly Gly Lys Leu Met
                370                 375                 380

Lys Pro Glu Glu Leu Asp Ala Gln Ile Arg Asp Arg Ser Ala Arg Phe
        385                 390                 395                 400

Val Gln Phe Asp Cys Tyr His Glu Ile Leu Pro Gln Pro Glu Asn Arg
                            405                 410                 415

Ile Val Pro Ser Lys Thr Ala Thr Asp Ala Val Gly Ile Pro Arg Pro
                        420                 425                 430

Glu Ile Thr Tyr Ala Ile Asp Asp Tyr Val Lys Arg Gly Ala Val His
                    435                 440                 445

Thr Arg Glu Val Tyr Ala Thr Ala Ala Lys Val Leu Gly Gly Thr Glu
                450                 455                 460

Val Val Phe Asn Asp Glu Phe Ala Pro Asn Asn His Ile Thr Gly Ala
        465                 470                 475                 480

Thr Ile Met Gly Ala Asp Ala Arg Asp Ser Val Val Asp Lys Asp Cys
                            485                 490                 495

Arg Ala Phe Asp His Pro Asn Leu Phe Ile Ser Ser Ser Thr Met
                        500                 505                 510

Pro Thr Val Gly Thr Val Asn Val Thr Leu Thr Ile Ala Ala Leu Ala
                    515                 520                 525

Leu Arg Met Ser Asp Thr Leu Lys Lys Glu Val Gly Ser Gly Ser Gly
                530                 535                 540

His His His His His His
        545                 550

<210> SEQ ID NO 86
<211> LENGTH: 539
<212> TYPE: PRT
<213> ORGANISM: Artificial Sequence
<220> FEATURE:
<223> OTHER INFORMATION: Recombinant sequence

<400> SEQUENCE: 86

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
```

```
           145                 150                 155                 160
Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
        210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Ala His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
        530                 535

<210> SEQ ID NO 87
<211> LENGTH: 539
<212> TYPE: PRT
<213> ORGANISM: Artificial Sequence
```

<220> FEATURE:
<223> OTHER INFORMATION: Recombinant sequence

<400> SEQUENCE: 87

```
Met Ala Asp Thr Asp Thr Gln Lys Ala Asp Val Val Val Gly Ser
 1               5                  10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
        130                 135                 140

Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400
```

-continued

```
Val Gln Phe Asp Cys Cys His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535
```

<210> SEQ ID NO 88
<211> LENGTH: 539
<212> TYPE: PRT
<213> ORGANISM: Artificial Sequence
<220> FEATURE:
<223> OTHER INFORMATION: Recombinant sequence

<400> SEQUENCE: 88

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220
```

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
        260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
        340                 345                 350

Phe Arg Ala Asn Glu Ala Ala Lys Lys Ile His Leu Ser Asn Met Ser
    355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Asp His Glu Ile Leu Pro Gln Pro Glu Asn Arg
            405                 410                 415

Ile Val Pro Ser Lys Thr Ala Thr Asp Ala Val Gly Ile Pro Arg Pro
        420                 425                 430

Glu Ile Thr Tyr Ala Ile Asp Asp Tyr Val Lys Arg Gly Ala Val His
    435                 440                 445

Thr Arg Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Ser Thr Met
        500                 505                 510

Pro Thr Val Gly Thr Val Asn Val Thr Leu Thr Ile Ala Ala Leu Ala
    515                 520                 525

Leu Arg Met Ser Asp Thr Leu Lys Lys Glu Val
530                 535

<210> SEQ ID NO 89
<211> LENGTH: 539
<212> TYPE: PRT
<213> ORGANISM: Artificial Sequence
<220> FEATURE:
<223> OTHER INFORMATION: Recombinant sequence

<400> SEQUENCE: 89

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

```
Val Glu Arg Phe Arg Asn Gln Val Asp Lys Thr Asp Phe Met Ala Pro
     50                  55                  60

Tyr Pro Ser Ser Ala Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
        210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Glu His Glu Ile Leu Pro Gln Pro Glu Asn Arg
            405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
450                 455                 460
```

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Ala Phe Asp His Pro Asn Leu Phe Ile Ser Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535

<210> SEQ ID NO 90
<211> LENGTH: 539
<212> TYPE: PRT
<213> ORGANISM: Artificial Sequence
<220> FEATURE:
<223> OTHER INFORMATION: Recombinant sequence

<400> SEQUENCE: 90

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Gly His Glu Ile Leu Pro Gln Pro Glu Asn Arg
                405                 410                 415

Ile Val Pro Ser Lys Thr Ala Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
530                 535

<210> SEQ ID NO 91
<211> LENGTH: 539
<212> TYPE: PRT
<213> ORGANISM: Artificial Sequence
<220> FEATURE:
<223> OTHER INFORMATION: Recombinant sequence

<400> SEQUENCE: 91

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ser Ala Trp Arg
            100                 105                 110

-continued

```
Phe Ile Pro Asn Asp Phe Lys Met Lys Thr Val Tyr Gly Val Gly Arg
            115                 120                 125
Asp Trp Pro Ile Gln Tyr Asp Asp Ile Glu His Tyr Tyr Gln Arg Ala
130                 135                 140
Glu Glu Glu Leu Gly Val Trp Gly Pro Gly Glu Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
            180                 185                 190
His Val Val Thr Glu Pro Val Ala Arg Asn Ser Arg Pro Tyr Asp Gly
            195                 200                 205
Arg Pro Thr Cys Cys Gly Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
            275                 280                 285
Glu Thr Pro Lys Ile Leu Leu Met Ser Ala Asn Arg Asp Phe Pro Asn
            290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
            355                 360                 365
Arg Ile Asn Gln Glu Thr Gln Lys Ile Phe Lys Gly Gly Lys Leu Met
370                 375                 380
Lys Pro Glu Glu Leu Asp Ala Gln Ile Arg Asp Arg Ser Ala Arg Phe
385                 390                 395                 400
Val Gln Phe Asp Cys His His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
            435                 440                 445
Thr Arg Glu Val Tyr Ala Thr Ala Lys Val Leu Gly Gly Thr Glu
450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
            500                 505                 510
Pro Thr Val Gly Thr Val Asn Val Thr Leu Thr Ile Ala Ala Leu Ala
            515                 520                 525
Leu Arg Met Ser Asp Thr Leu Lys Lys Glu Val
```

```
           530             535
```

<210> SEQ ID NO 92
<211> LENGTH: 591
<212> TYPE: PRT
<213> ORGANISM: Artificial Sequence
<220> FEATURE:
<223> OTHER INFORMATION: Recombinant sequence

<400> SEQUENCE: 92

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Met Ala Asp Thr Asp Thr Gln Lys Ala Asp Val Val
        50                  55                  60

Val Val Gly Ser Gly Val Ala Gly Ala Ile Val Ala His Gln Leu Ala
65                  70                  75                  80

Met Ala Gly Lys Ser Val Ile Leu Leu Glu Ala Gly Pro Arg Met Pro
                85                  90                  95

Arg Trp Glu Ile Val Glu Arg Phe Arg Asn Gln Val Asp Lys Thr Asp
            100                 105                 110

Phe Met Ala Pro Tyr Pro Ser Ser Ala Trp Ala Pro His Pro Glu Tyr
            115                 120                 125

Gly Pro Pro Asn Asp Tyr Leu Ile Leu Lys Gly Glu His Lys Phe Asn
        130                 135                 140

Ser Gln Tyr Ile Arg Ala Val Gly Gly Thr Thr Trp His Trp Ala Ala
145                 150                 155                 160

Ser Ala Trp Arg Phe Ile Pro Asn Asp Phe Lys Met Lys Thr Val Tyr
                165                 170                 175

Gly Val Gly Arg Asp Trp Pro Ile Gln Tyr Asp Asp Ile Glu His Tyr
            180                 185                 190

Tyr Gln Arg Ala Glu Glu Leu Gly Val Trp Gly Pro Gly Pro Glu
        195                 200                 205

Glu Asp Leu Tyr Ser Pro Arg Lys Glu Pro Tyr Pro Met Pro Pro Leu
    210                 215                 220

Pro Leu Ser Phe Asn Glu Gln Thr Ile Lys Ser Ala Leu Asn Gly Tyr
225                 230                 235                 240

Asp Pro Lys Phe His Val Val Thr Glu Pro Val Ala Arg Asn Ser Arg
                245                 250                 255

Pro Tyr Asp Gly Arg Pro Thr Cys Cys Gly Asn Asn Asn Cys Met Pro
            260                 265                 270

Ile Cys Pro Ile Gly Ala Met Tyr Asn Gly Ile Val His Val Glu Lys
        275                 280                 285

Ala Glu Gln Ala Gly Ala Lys Leu Ile Asp Ser Ala Val Val Tyr Lys
    290                 295                 300

Leu Glu Thr Gly Pro Asp Lys Arg Ile Thr Ala Ala Val Tyr Lys Asp
305                 310                 315                 320

Lys Thr Gly Ala Asp His Arg Val Glu Gly Lys Tyr Phe Val Ile Ala
                325                 330                 335

Ala Asn Gly Ile Glu Thr Pro Lys Ile Leu Leu Met Ser Ala Asn Arg
            340                 345                 350

Asp Phe Pro Asn Gly Val Ala Asn Ser Ser Asp Met Val Gly Arg Asn
```

```
                355                 360                 365
Leu Met Asp His Pro Gly Thr Gly Val Ser Phe Tyr Ala Asn Glu Lys
370                 375                 380

Leu Trp Pro Gly Arg Gly Pro Gln Glu Met Thr Ser Leu Ile Gly Phe
385                 390                 395                 400

Arg Asp Gly Pro Phe Arg Ala Asn Glu Ala Lys Lys Ile His Leu
                405                 410                 415

Ser Asn Met Ser Arg Ile Asn Gln Glu Thr Gln Lys Ile Phe Lys Gly
            420                 425                 430

Gly Lys Leu Met Lys Pro Glu Glu Leu Asp Ala Gln Ile Arg Asp Arg
        435                 440                 445

Ser Ala Arg Phe Val Gln Phe Asp Cys Ile His Glu Ile Leu Pro Gln
    450                 455                 460

Pro Glu Asn Arg Ile Val Pro Ser Lys Thr Ala Thr Asp Ala Val Gly
465                 470                 475                 480

Ile Pro Arg Pro Glu Ile Thr Tyr Ala Ile Asp Asp Tyr Val Lys Arg
                485                 490                 495

Gly Ala Val His Thr Arg Glu Val Tyr Ala Thr Ala Ala Lys Val Leu
            500                 505                 510

Gly Gly Thr Glu Val Val Phe Asn Asp Glu Phe Ala Pro Asn Asn His
        515                 520                 525

Ile Thr Gly Ala Thr Ile Met Gly Ala Asp Ala Arg Asp Ser Val Val
    530                 535                 540

Asp Lys Asp Cys Arg Ala Phe Asp His Pro Asn Leu Phe Ile Ser Ser
545                 550                 555                 560

Ser Ser Thr Met Pro Thr Val Gly Thr Val Asn Val Thr Leu Thr Ile
                565                 570                 575

Ala Ala Leu Ala Leu Arg Met Ser Asp Thr Leu Lys Lys Glu Val
            580                 585                 590

<210> SEQ ID NO 93
<211> LENGTH: 539
<212> TYPE: PRT
<213> ORGANISM: Artificial Sequence
<220> FEATURE:
<223> OTHER INFORMATION: Recombinant sequence

<400> SEQUENCE: 93

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
```

```
            130                 135                 140
Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Lys His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 94
```

```
<211> LENGTH: 539
<212> TYPE: PRT
<213> ORGANISM: Artificial Sequence
<220> FEATURE:
<223> OTHER INFORMATION: Recombinant sequence

<400> SEQUENCE: 94
```

| | | | | | | | | | | | | | | | |
|---|---|---|---|---|---|---|---|---|---|---|---|---|---|---|---|
| Met | Ala | Asp | Thr | Asp | Thr | Gln | Lys | Ala | Asp | Val | Val | Val | Gly | Ser | |
| 1 | | | | 5 | | | | | 10 | | | | | 15 | |
| Gly | Val | Ala | Gly | Ala | Ile | Val | Ala | His | Gln | Leu | Ala | Met | Ala | Gly | Lys |
| | | | 20 | | | | | 25 | | | | | 30 | | |
| Ser | Val | Ile | Leu | Leu | Glu | Ala | Gly | Pro | Arg | Met | Pro | Arg | Trp | Glu | Ile |
| | | | 35 | | | | | 40 | | | | | 45 | | |
| Val | Glu | Arg | Phe | Arg | Asn | Gln | Val | Asp | Lys | Thr | Asp | Phe | Met | Ala | Pro |
| 50 | | | | | 55 | | | | | 60 | | | | | |
| Tyr | Pro | Ser | Ser | Ala | Trp | Ala | Pro | His | Pro | Tyr | Gly | Pro | Pro | Asn | |
| 65 | | | | | 70 | | | | | 75 | | | | | 80 |
| Asp | Tyr | Leu | Ile | Leu | Lys | Gly | Glu | His | Lys | Phe | Asn | Ser | Gln | Tyr | Ile |
| | | | | 85 | | | | | 90 | | | | | 95 | |
| Arg | Ala | Val | Gly | Gly | Thr | Thr | Trp | His | Trp | Ala | Ala | Ser | Ala | Trp | Arg |
| | | | 100 | | | | | 105 | | | | | 110 | | |
| Phe | Ile | Pro | Asn | Asp | Phe | Lys | Met | Lys | Thr | Val | Tyr | Gly | Val | Gly | Arg |
| | | | 115 | | | | | 120 | | | | | 125 | | |
| Asp | Trp | Pro | Ile | Gln | Tyr | Asp | Asp | Ile | Glu | His | Tyr | Tyr | Gln | Arg | Ala |
| | 130 | | | | | 135 | | | | | 140 | | | | |
| Glu | Glu | Glu | Leu | Gly | Val | Trp | Gly | Pro | Gly | Pro | Glu | Glu | Asp | Leu | Tyr |
| 145 | | | | | 150 | | | | | 155 | | | | | 160 |
| Ser | Pro | Arg | Lys | Glu | Pro | Tyr | Pro | Met | Pro | Pro | Leu | Pro | Leu | Ser | Phe |
| | | | | 165 | | | | | 170 | | | | | 175 | |
| Asn | Glu | Gln | Thr | Ile | Lys | Ser | Ala | Leu | Asn | Gly | Tyr | Asp | Pro | Lys | Phe |
| | | | | 180 | | | | | 185 | | | | | 190 | |
| His | Val | Val | Thr | Glu | Pro | Val | Ala | Arg | Asn | Ser | Arg | Pro | Tyr | Asp | Gly |
| | | | 195 | | | | | 200 | | | | | 205 | | |
| Arg | Pro | Thr | Cys | Cys | Gly | Asn | Asn | Asn | Cys | Met | Pro | Ile | Cys | Pro | Ile |
| | 210 | | | | | 215 | | | | | 220 | | | | |
| Gly | Ala | Met | Tyr | Asn | Gly | Ile | Val | His | Val | Glu | Lys | Ala | Glu | Gln | Ala |
| 225 | | | | | 230 | | | | | 235 | | | | | 240 |
| Gly | Ala | Lys | Leu | Ile | Asp | Ser | Ala | Val | Val | Tyr | Lys | Leu | Glu | Thr | Gly |
| | | | | 245 | | | | | 250 | | | | | 255 | |
| Pro | Asp | Lys | Arg | Ile | Thr | Ala | Ala | Val | Tyr | Lys | Asp | Lys | Thr | Gly | Ala |
| | | | | 260 | | | | | 265 | | | | | 270 | |
| Asp | His | Arg | Val | Glu | Gly | Lys | Tyr | Phe | Val | Ile | Ala | Ala | Asn | Gly | Ile |
| | | | 275 | | | | | 280 | | | | | 285 | | |
| Glu | Thr | Pro | Lys | Ile | Leu | Leu | Met | Ser | Ala | Asn | Arg | Asp | Phe | Pro | Asn |
| | 290 | | | | | 295 | | | | | 300 | | | | |
| Gly | Val | Ala | Asn | Ser | Ser | Asp | Met | Val | Gly | Arg | Asn | Leu | Met | Asp | His |
| 305 | | | | | 310 | | | | | 315 | | | | | 320 |
| Pro | Gly | Thr | Gly | Val | Ser | Phe | Tyr | Ala | Asn | Glu | Lys | Leu | Trp | Pro | Gly |
| | | | | 325 | | | | | 330 | | | | | 335 | |
| Arg | Gly | Pro | Gln | Glu | Met | Thr | Ser | Leu | Ile | Gly | Phe | Arg | Asp | Gly | Pro |
| | | | | 340 | | | | | 345 | | | | | 350 | |
| Phe | Arg | Ala | Asn | Glu | Ala | Ala | Lys | Lys | Ile | His | Leu | Ser | Asn | Met | Ser |
| | | | 355 | | | | | 360 | | | | | 365 | | |
| Arg | Ile | Asn | Gln | Glu | Thr | Gln | Lys | Ile | Phe | Lys | Gly | Gly | Lys | Leu | Met |
| | 370 | | | | | 375 | | | | | 380 | | | | |

```
Lys Pro Glu Glu Leu Asp Ala Gln Ile Arg Asp Arg Ser Ala Arg Phe
385                 390                 395                 400

Val Gln Phe Asp Cys Leu His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
                435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 95
<211> LENGTH: 539
<212> TYPE: PRT
<213> ORGANISM: Artificial Sequence
<220> FEATURE:
<223> OTHER INFORMATION: Recombinant sequence

<400> SEQUENCE: 95

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205
```

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Met His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 96
<211> LENGTH: 539
<212> TYPE: PRT
<213> ORGANISM: Artificial Sequence
<220> FEATURE:
<223> OTHER INFORMATION: Recombinant sequence

<400> SEQUENCE: 96

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

```
Ser Val Ile Leu Glu Ala Gly Pro Arg Met Pro Arg Trp Glu Ile
        35              40                  45

Val Glu Arg Phe Arg Asn Gln Val Asp Lys Thr Asp Phe Met Ala Pro
 50                  55                  60

Tyr Pro Ser Ser Ala Trp Ala Pro His Pro Glu Tyr Gly Pro Pro Asn
 65              70                  75                      80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
        130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Asn His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445
```

```
Thr Arg Glu Val Tyr Ala Thr Ala Ala Lys Val Leu Gly Gly Thr Glu
        450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
                500                 505                 510
Pro Thr Val Gly Thr Val Asn Val Thr Leu Thr Ile Ala Ala Leu Ala
                515                 520                 525
Leu Arg Met Ser Asp Thr Leu Lys Lys Glu Val
        530                 535
```

<210> SEQ ID NO 97
<211> LENGTH: 539
<212> TYPE: PRT
<213> ORGANISM: Artificial Sequence
<220> FEATURE:
<223> OTHER INFORMATION: Recombinant sequence

<400> SEQUENCE: 97

```
Met Ala Asp Thr Asp Thr Gln Lys Ala Asp Val Val Val Val Gly Ser
1               5                   10                  15
Gly Val Ala Gly Ala Ile Val Ala His Gln Leu Ala Met Ala Gly Lys
                20                  25                  30
Ser Val Ile Leu Leu Glu Ala Gly Pro Arg Met Pro Arg Trp Glu Ile
            35                  40                  45
Val Glu Arg Phe Arg Asn Gln Val Asp Lys Thr Asp Phe Met Ala Pro
50                  55                  60
Tyr Pro Ser Ser Ala Trp Ala Pro His Pro Glu Tyr Gly Pro Pro Asn
65                  70                  75                  80
Asp Tyr Leu Ile Leu Lys Gly Glu His Lys Phe Asn Ser Gln Tyr Ile
                85                  90                  95
Arg Ala Val Gly Gly Thr Thr Trp His Trp Ala Ala Ser Ala Trp Arg
                100                 105                 110
Phe Ile Pro Asn Asp Phe Lys Met Lys Thr Val Tyr Gly Val Gly Arg
                115                 120                 125
Asp Trp Pro Ile Gln Tyr Asp Asp Ile Glu His Tyr Tyr Gln Arg Ala
                130                 135                 140
Glu Glu Glu Leu Gly Val Trp Gly Pro Gly Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
                180                 185                 190
His Val Val Thr Glu Pro Val Ala Arg Asn Ser Arg Pro Tyr Asp Gly
                195                 200                 205
Arg Pro Thr Cys Cys Gly Asn Asn Cys Met Pro Ile Cys Pro Ile
            210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
                260                 265                 270
```

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Gln His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 98
<211> LENGTH: 539
<212> TYPE: PRT
<213> ORGANISM: Artificial Sequence
<220> FEATURE:
<223> OTHER INFORMATION: Recombinant sequence

<400> SEQUENCE: 98

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

-continued

```
Arg Ala Val Gly Gly Thr Thr Trp His Trp Ala Ser Ala Trp Arg
            100                 105                 110
Phe Ile Pro Asn Asp Phe Lys Met Lys Thr Val Tyr Gly Val Gly Arg
            115                 120                 125
Asp Trp Pro Ile Gln Tyr Asp Asp Ile Glu His Tyr Tyr Gln Arg Ala
        130                 135                 140
Glu Glu Glu Leu Gly Val Trp Gly Pro Gly Pro Glu Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
            180                 185                 190
His Val Val Thr Glu Pro Val Ala Arg Asn Ser Arg Pro Tyr Asp Gly
            195                 200                 205
Arg Pro Thr Cys Cys Gly Asn Asn Cys Met Pro Ile Cys Pro Ile
        210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
        275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
        355                 360                 365
Arg Ile Asn Gln Glu Thr Gln Lys Ile Phe Lys Gly Gly Lys Leu Met
    370                 375                 380
Lys Pro Glu Glu Leu Asp Ala Gln Ile Arg Asp Arg Ser Ala Arg Phe
385                 390                 395                 400
Val Gln Phe Asp Cys Ser His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
        435                 440                 445
Thr Arg Glu Val Tyr Ala Thr Ala Ala Lys Val Leu Gly Gly Thr Glu
    450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Ser Thr Met
            500                 505                 510
Pro Thr Val Gly Thr Val Asn Val Thr Leu Thr Ile Ala Ala Leu Ala
```

```
            515                 520                 525
Leu Arg Met Ser Asp Thr Leu Lys Lys Glu Val
    530                 535

<210> SEQ ID NO 99
<211> LENGTH: 539
<212> TYPE: PRT
<213> ORGANISM: Artificial Sequence
<220> FEATURE:
<223> OTHER INFORMATION: Recombinant sequence

<400> SEQUENCE: 99

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
    115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
    195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
```

-continued

```
                340                 345                 350
    Phe Arg Ala Asn Glu Ala Ala Lys Lys Ile His Leu Ser Asn Met Ser
                355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
    385                 390                 395                 400

Val Gln Phe Asp Cys Pro His Glu Ile Leu Pro Gln Pro Glu Asn Arg
                    405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
    465                 470                 475                 480

Thr Ile Met Gly Ala Asp Ala Arg Asp Ser Val Val Asp Lys Asp Cys
                    485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
        530                 535
```

<210> SEQ ID NO 100
<211> LENGTH: 544
<212> TYPE: PRT
<213> ORGANISM: Artificial Sequence
<220> FEATURE:
<223> OTHER INFORMATION: Recombinant sequence

<400> SEQUENCE: 100

```
    Met Ala Asp Thr Asp Thr Gln Lys Ala Asp Val Val Val Val Gly Ser
    1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
    65                  70                  75                  80

Asp Tyr Leu Ile Leu Lys Gly Glu His Lys Phe Asn Ser Gln Tyr Ile
                    85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
        130                 135                 140

Glu Glu Glu Leu Gly Val Trp Gly Pro Gly Pro Glu Glu Asp Leu Tyr
    145                 150                 155                 160

Ser Pro Arg Lys Glu Pro Tyr Pro Met Pro Pro Leu Pro Leu Ser Phe
```

```
                165                 170                 175
Asn Glu Gln Thr Ile Lys Ser Ala Leu Asn Gly Tyr Asp Pro Lys Phe
            180                 185                 190
His Val Thr Glu Pro Val Ala Arg Asn Ser Arg Pro Tyr Asp Gly
        195                 200                 205
Arg Pro Thr Cys Cys Gly Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
        275                 280                 285
Glu Thr Pro Lys Ile Leu Leu Met Ser Ala Asn Arg Asp Phe Pro Asn
    290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
        355                 360                 365
Arg Ile Asn Gln Glu Thr Gln Lys Ile Phe Lys Gly Gly Lys Leu Met
    370                 375                 380
Lys Pro Glu Glu Leu Asp Ala Gln Ile Arg Asp Arg Ser Ala Arg Phe
385                 390                 395                 400
Val Gln Phe Asp Cys Val His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
        435                 440                 445
Thr Arg Glu Val Tyr Ala Thr Ala Lys Val Leu Gly Gly Thr Glu
    450                 455                 460
Val Val Phe Asn Asp Glu Phe Ala Pro Asn Asn His Ile Thr Gly Ala
465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
            500                 505                 510
Pro Thr Val Gly Thr Val Asn Val Thr Leu Thr Ile Ala Ala Leu Ala
        515                 520                 525
Leu Arg Met Ser Asp Thr Leu Lys Lys Glu Val Gly Ser Gly Ser Gly
    530                 535                 540
```

<210> SEQ ID NO 101
<211> LENGTH: 544
<212> TYPE: PRT
<213> ORGANISM: Artificial Sequence
<220> FEATURE:
<223> OTHER INFORMATION: Recombinant sequence

<400> SEQUENCE: 101

```
Met Ala Asp Thr Asp Thr Gln Lys Ala Asp Val Val Val Gly Ser
 1               5                  10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
            50                  55                  60

Tyr Pro Ser Ser Ala Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Arg His Glu Ile Leu Pro Gln Pro Glu Asn Arg
                405                 410                 415
```

```
Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465             470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540
```

<210> SEQ ID NO 102
<211> LENGTH: 544
<212> TYPE: PRT
<213> ORGANISM: Artificial Sequence
<220> FEATURE:
<223> OTHER INFORMATION: Recombinant sequence

<400> SEQUENCE: 102

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240
```

```
Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Thr His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
    530                 535                 540

<210> SEQ ID NO 103
<211> LENGTH: 544
<212> TYPE: PRT
<213> ORGANISM: Artificial Sequence
<220> FEATURE:
<223> OTHER INFORMATION: Recombinant sequence

<400> SEQUENCE: 103

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60
```

-continued

```
Tyr Pro Ser Ser Ala Trp Ala Pro His Pro Glu Tyr Gly Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
                355                 360                 365

Arg Ile Asn Gln Glu Thr Gln Lys Ile Phe Lys Gly Gly Lys Leu Met
                370                 375                 380

Lys Pro Glu Glu Leu Asp Ala Gln Ile Arg Asp Arg Ser Ala Arg Phe
385                 390                 395                 400

Val Gln Phe Asp Cys Trp His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
                435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480
```

```
Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Gly Ser Gly Ser Gly
530                 535                 540
```

<210> SEQ ID NO 104
<211> LENGTH: 544
<212> TYPE: PRT
<213> ORGANISM: Artificial Sequence
<220> FEATURE:
<223> OTHER INFORMATION: Recombinant sequence

<400> SEQUENCE: 104

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300
```

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Tyr His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Gly Ser Gly Ser Gly
530                 535                 540

<210> SEQ ID NO 105
<211> LENGTH: 539
<212> TYPE: PRT
<213> ORGANISM: Artificial Sequence
<220> FEATURE:
<223> OTHER INFORMATION: Recombinant sequence

<400> SEQUENCE: 105

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

```
Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
                355                 360                 365

Arg Ile Asn Gln Glu Thr Gln Lys Ile Phe Lys Gly Gly Lys Leu Met
                370                 375                 380

Lys Pro Glu Glu Leu Asp Ala Gln Ile Arg Asp Arg Ser Ala Arg Phe
385                 390                 395                 400

Val Gln Phe Asp Cys Val His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
                435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
530                 535
```

```
<210> SEQ ID NO 106
<211> LENGTH: 539
<212> TYPE: PRT
<213> ORGANISM: Artificial Sequence
<220> FEATURE:
<223> OTHER INFORMATION: Recombinant sequence

<400> SEQUENCE: 106

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
```

```
                    370                 375                 380
Lys Pro Glu Glu Leu Asp Ala Gln Ile Arg Asp Arg Ser Ala Arg Phe
385                 390                 395                 400

Val Gln Phe Asp Cys Arg His Glu Ile Leu Pro Gln Pro Glu Asn Arg
                    405                 410                 415

Ile Val Pro Ser Lys Thr Ala Thr Asp Ala Val Gly Ile Pro Arg Pro
                    420                 425                 430

Glu Ile Thr Tyr Ala Ile Asp Asp Tyr Val Lys Arg Gly Ala Val His
                    435                 440                 445

Thr Arg Glu Val Tyr Ala Thr Ala Ala Lys Val Leu Gly Gly Thr Glu
                    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                    485                 490                 495

Arg Ala Phe Asp His Pro Asn Leu Phe Ile Ser Ser Ser Thr Met
                    500                 505                 510

Pro Thr Val Gly Thr Val Asn Val Thr Leu Thr Ile Ala Ala Leu Ala
                    515                 520                 525

Leu Arg Met Ser Asp Thr Leu Lys Lys Glu Val
                    530                 535
```

<210> SEQ ID NO 107
<211> LENGTH: 539
<212> TYPE: PRT
<213> ORGANISM: Artificial Sequence
<220> FEATURE:
<223> OTHER INFORMATION: Recombinant sequence

<400> SEQUENCE: 107

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
                35                  40                  45

Val Glu Arg Phe Arg Asn Gln Val Asp Lys Thr Asp Phe Met Ala Pro
            50                  55                  60

Tyr Pro Ser Ser Ala Trp Ala Pro His Pro Glu Tyr Gly Pro Pro Asn
65              70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
                130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
```

```
              195                 200                 205
Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Thr His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 108
<211> LENGTH: 539
<212> TYPE: PRT
<213> ORGANISM: Artificial Sequence
<220> FEATURE:
<223> OTHER INFORMATION: Recombinant sequence

<400> SEQUENCE: 108

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
```

```
            20              25              30
Ser Val Ile Leu Leu Glu Ala Gly Pro Arg Met Pro Arg Trp Glu Ile
         35              40              45
Val Glu Arg Phe Arg Asn Gln Val Asp Lys Thr Asp Phe Met Ala Pro
 50              55              60
Tyr Pro Ser Ser Ala Trp Ala Pro His Pro Glu Tyr Gly Pro Pro Asn
 65              70              75              80
Asp Tyr Leu Ile Leu Lys Gly Glu His Lys Phe Asn Ser Gln Tyr Ile
                 85              90              95
Arg Ala Val Gly Gly Thr Thr Trp His Trp Ala Ala Ser Ala Trp Arg
                100             105             110
Phe Ile Pro Asn Asp Phe Lys Met Lys Thr Val Tyr Gly Val Gly Arg
             115             120             125
Asp Trp Pro Ile Gln Tyr Asp Asp Ile Glu His Tyr Tyr Gln Arg Ala
             130             135             140
Glu Glu Glu Leu Gly Val Trp Gly Pro Gly Pro Glu Glu Asp Leu Tyr
145             150             155             160
Ser Pro Arg Lys Glu Pro Tyr Pro Met Pro Pro Leu Pro Leu Ser Phe
                165             170             175
Asn Glu Gln Thr Ile Lys Ser Ala Leu Asn Gly Tyr Asp Pro Lys Phe
                 180             185             190
His Val Val Thr Glu Pro Val Ala Arg Asn Ser Arg Pro Tyr Asp Gly
                195             200             205
Arg Pro Thr Cys Cys Gly Asn Asn Cys Met Pro Ile Cys Pro Ile
            210             215             220
Gly Ala Met Tyr Asn Gly Ile Val His Val Glu Lys Ala Glu Gln Ala
225             230             235             240
Gly Ala Lys Leu Ile Asp Ser Ala Val Val Tyr Lys Leu Glu Thr Gly
                245             250             255
Pro Asp Lys Arg Ile Thr Ala Ala Val Tyr Lys Asp Lys Thr Gly Ala
                260             265             270
Asp His Arg Val Glu Gly Lys Tyr Phe Val Ile Ala Ala Asn Gly Ile
                275             280             285
Glu Thr Pro Lys Ile Leu Leu Met Ser Ala Asn Arg Asp Phe Pro Asn
                290             295             300
Gly Val Ala Asn Ser Ser Asp Met Val Gly Arg Asn Leu Met Asp His
305             310             315             320
Pro Gly Thr Gly Val Ser Phe Tyr Ala Asn Glu Lys Leu Trp Pro Gly
                325             330             335
Arg Gly Pro Gln Glu Met Thr Ser Leu Ile Gly Phe Arg Asp Gly Pro
                340             345             350
Phe Arg Ala Asn Glu Ala Ala Lys Lys Ile His Leu Ser Asn Met Ser
                355             360             365
Arg Ile Asn Gln Glu Thr Gln Lys Ile Phe Lys Gly Gly Lys Leu Met
                370             375             380
Lys Pro Glu Glu Leu Asp Ala Gln Ile Arg Asp Arg Ser Ala Arg Phe
385             390             395             400
Val Gln Phe Asp Cys Trp His Glu Ile Leu Pro Gln Pro Glu Asn Arg
                405             410             415
Ile Val Pro Ser Lys Thr Ala Thr Asp Ala Val Gly Ile Pro Arg Pro
                420             425             430
Glu Ile Thr Tyr Ala Ile Asp Asp Tyr Val Lys Arg Gly Ala Val His
                435             440             445
```

```
Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val
    530                 535
```

<210> SEQ ID NO 109
<211> LENGTH: 539
<212> TYPE: PRT
<213> ORGANISM: Artificial Sequence
<220> FEATURE:
<223> OTHER INFORMATION: Recombinant sequence

<400> SEQUENCE: 109

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270
```

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Tyr His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
        530                 535

<210> SEQ ID NO 110
<211> LENGTH: 539
<212> TYPE: PRT
<213> ORGANISM: Artificial Sequence
<220> FEATURE:
<223> OTHER INFORMATION: Recombinant sequence

<400> SEQUENCE: 110

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

```
Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
            115                 120                 125

Asp Trp Pro Ile Gln Tyr Asp Asp Leu Glu Pro Tyr Tyr Gln Arg Ala
            130                 135                 140

Glu Glu Glu Leu Gly Val Trp Gly Pro Gly Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
            210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
            355                 360                 365

Arg Ile Asp Gln Glu Thr Gln Lys Ile Phe Lys Ala Gly Lys Leu Met
            370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
            405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
            435                 440                 445

Thr Arg Glu Val Tyr Ala Thr Ala Ala Lys Val Leu Gly Gly Thr Asp
            450                 455                 460

Val Val Phe Asn Asp Glu Phe Ala Pro Asn Asn His Ile Thr Gly Ser
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510
```

```
Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 111
<211> LENGTH: 539
<212> TYPE: PRT
<213> ORGANISM: Artificial Sequence
<220> FEATURE:
<223> OTHER INFORMATION: Recombinant sequence

<400> SEQUENCE: 111

Met Ala Asp Thr Asp Thr Gln Lys Ala Asp Ile Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Ala Asp Lys Thr Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Val Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Leu Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Ala Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Ile Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335
```

```
Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Met Ser
            355                 360                 365

Arg Ile Asn Gln Glu Thr Gln Lys Ile Phe Lys Ala Gly Lys Leu Met
        370                 375                 380

Lys His Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Asp
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
530                 535
```

<210> SEQ ID NO 112
<211> LENGTH: 539
<212> TYPE: PRT
<213> ORGANISM: Artificial Sequence
<220> FEATURE:
<223> OTHER INFORMATION: Recombinant sequence

<400> SEQUENCE: 112

```
Met Ala Asp Thr Asp Thr Gln Lys Ala Asp Ile Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160
```

Ser Pro Arg Lys Glu Pro Tyr Pro Met Pro Pro Leu Pro Leu Ser Phe
        165                 170                 175

Asn Glu Gln Thr Ile Lys Ser Ala Leu Asn Gly Tyr Asp Pro Lys Phe
            180                 185                 190

His Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
        290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
530                 535

<210> SEQ ID NO 113
<211> LENGTH: 539
<212> TYPE: PRT
<213> ORGANISM: Artificial Sequence
<220> FEATURE:
<223> OTHER INFORMATION: Recombinant sequence

<400> SEQUENCE: 113

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Gly Glu Ile
                35                  40                  45

Val Glu Arg Phe Arg Asn Gln Pro Asp Lys Thr Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Val Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Leu Glu His Tyr Tyr Gln Arg Ala
                130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
                210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Val Ala Ala Ile Tyr Lys Asp Lys Thr Gly Ala
                260                 265                 270

Asp His Arg Val Glu Gly Lys Tyr Phe Val Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Asp Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Met Ser
                355                 360                 365

Arg Ile Asn Gln Glu Thr Gln Lys Ile Phe Lys Ala Gly Lys Leu Met
                370                 375                 380

Lys Ser Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg

```
                 405                 410                 415
Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
        450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535
```

<210> SEQ ID NO 114
<211> LENGTH: 539
<212> TYPE: PRT
<213> ORGANISM: Artificial Sequence
<220> FEATURE:
<223> OTHER INFORMATION: Recombinant sequence

<400> SEQUENCE: 114

```
Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Pro Asp Lys Thr Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Ala Arg
        115                 120                 125

Asp Trp Pro Ile Gln Tyr Asp Asp Leu Glu His Trp Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Ala Tyr Pro Met Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
```

```
            225                 230                 235                 240
    Gly Ala Lys Leu Ile Asp Ser Ala Val Val Tyr Lys Leu Glu Thr Gly
                    245                 250                 255
    Pro Asp Lys Arg Ile Val Ala Ala Ile Tyr Lys Asp Lys Thr Gly Ala
                260                 265                 270
    Asp His Arg Val Glu Gly Lys Tyr Phe Val Leu Ala Ala Asn Gly Ile
                275                 280                 285
    Glu Thr Pro Lys Ile Leu Leu Met Ser Ala Asn Arg Asp Phe Pro Asn
            290                 295                 300
    Gly Val Ala Asn Ser Ser Asp Met Val Gly Arg Asn Leu Met Asp His
    305                 310                 315                 320
    Pro Gly Thr Gly Val Ser Phe Tyr Ala Asn Glu Lys Leu Trp Pro Gly
                    325                 330                 335
    Arg Gly Pro Gln Glu Met Thr Ser Leu Ile Gly Phe Arg Asp Gly Pro
                340                 345                 350
    Phe Arg Ala Thr Glu Ala Ala Lys Lys Ile His Leu Ser Asn Met Ser
                355                 360                 365
    Arg Ile Asn Gln Glu Thr Gln Lys Ile Phe Lys Ala Gly Lys Leu Met
            370                 375                 380
    Lys His Glu Glu Leu Asp Ala Gln Ile Arg Asp Arg Ser Ala Arg Tyr
    385                 390                 395                 400
    Val Gln Phe Asp Cys Phe His Glu Ile Leu Pro Gln Pro Glu Asn Arg
                    405                 410                 415
    Ile Val Pro Ser Lys Thr Ala Thr Asp Ala Ile Gly Ile Pro Arg Pro
                420                 425                 430
    Glu Ile Thr Tyr Ala Ile Asp Asp Tyr Val Lys Arg Gly Ala Val His
                435                 440                 445
    Thr Arg Glu Val Tyr Ala Thr Ala Ala Lys Val Leu Gly Gly Thr Asp
            450                 455                 460
    Val Val Phe Asn Asp Glu Phe Ala Pro Asn Asn His Ile Thr Gly Ala
    465                 470                 475                 480
    Thr Ile Met Gly Ala Asp Ala Arg Asp Ser Val Val Asp Lys Asp Cys
                    485                 490                 495
    Arg Thr Phe Asp His Pro Asn Leu Phe Ile Ser Ser Ser Ser Thr Met
                500                 505                 510
    Pro Thr Val Gly Thr Val Asn Val Thr Leu Thr Ile Ala Ala Leu Ala
                515                 520                 525
    Leu Arg Met Ser Asp Thr Leu Lys Lys Glu Val
            530                 535

<210> SEQ ID NO 115
<211> LENGTH: 539
<212> TYPE: PRT
<213> ORGANISM: Artificial Sequence
<220> FEATURE:
<223> OTHER INFORMATION: Recombinant sequence

<400> SEQUENCE: 115

Met Ala Asp Thr Asp Thr Gln Lys Ala Asp Val Val Val Val Gly Ser
1               5                   10                  15
Gly Val Ala Gly Ala Ile Val Ala His Gln Leu Ala Met Ala Gly Lys
                20                  25                  30
Ser Val Ile Leu Leu Glu Ala Gly Pro Arg Met Pro Arg Trp Glu Ile
            35                  40                  45
Val Glu Arg Phe Arg Asn Gln Val Asp Lys Thr Asp Phe Met Ala Pro
```

-continued

```
                50                  55                  60
Tyr Pro Ser Ser Ala Trp Ala Pro His Pro Glu Tyr Gly Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
                130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Thr Glu Ala Ala Lys Lys Ile His Leu Ser Asn Met Ser
                355                 360                 365

Arg Ile Asn Gln Glu Thr Gln Lys Ile Phe Lys Ala Gly Lys Leu Met
                370                 375                 380

Lys Pro Glu Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
                420                 425                 430

Glu Ile Thr Tyr Ala Ile Asp Asp Tyr Val Lys Arg Gly Ala Val His
                435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala
465                 470                 475                 480
```

```
Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ser Thr Met
        500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
        530                 535

<210> SEQ ID NO 116
<211> LENGTH: 535
<212> TYPE: PRT
<213> ORGANISM: Artificial Sequence
<220> FEATURE:
<223> OTHER INFORMATION: Recombinant sequence

<400> SEQUENCE: 116

Asp Thr Gln Gln Ala Asp Val Val Val Gly Ser Gly Val Ala Gly
1               5                   10                  15

Ala Ile Val Ala His Gln Leu Ala Thr Ala Gly Lys Ser Val Ile Leu
            20                  25                  30

Leu Glu Ala Gly Pro Arg Met Pro Arg Trp Glu Ile Val Glu Arg Phe
        35                  40                  45

Arg Asn Gln Pro Asp Lys Met Asp Phe Met Ala Pro Tyr Pro Ser Ser
50                  55                  60

Pro Trp Ala Pro His Pro Glu Tyr Gly Pro Pro Asn Asp Tyr Leu Val
65                  70                  75                  80

Leu Lys Gly Glu His Lys Phe Asn Ser Gln Tyr Ile Arg Ala Val Gly
            85                  90                  95

Gly Thr Thr Trp His Trp Ala Ala Ser Ala Trp Arg Phe Ile Pro Asn
            100                 105                 110

Asp Phe Lys Met Lys Thr Val Tyr Gly Val Gly Arg Asp Trp Pro Ile
        115                 120                 125

Gln Tyr Asp Glu Leu Glu His Tyr Tyr Gln Arg Ala Glu Glu Glu Leu
130                 135                 140

Gly Val Trp Gly Pro Gly Ala Glu Glu Asp Leu Leu Ser Pro Arg Lys
145                 150                 155                 160

Gln Pro Tyr Pro Met Pro Pro Leu Pro Leu Ser Tyr Asn Glu Gln Thr
            165                 170                 175

Ile Lys Thr Ala Leu Asn Asn His Asp Pro Lys Tyr His Val Val Thr
        180                 185                 190

Glu Pro Val Ala Arg Asn Ser Arg Pro Tyr Asp Gly Arg Pro Thr Cys
        195                 200                 205

Cys Gly Asn Asn Asn Cys Met Pro Ile Cys Pro Ile Gly Ala Met Tyr
210                 215                 220

Asn Gly Ile Val His Val Glu Lys Ala Glu Gln Ala Gly Ala Lys Leu
225                 230                 235                 240

Ile Glu Asn Ala Val Val His Lys Leu Glu Val Gly Pro Gln Lys Lys
            245                 250                 255

Ile Val Ala Ala Leu Tyr Lys Asp Pro Lys Gly Val Glu His Arg Val
        260                 265                 270

Glu Gly Lys Tyr Phe Val Leu Ala Ala Asn Gly Ile Glu Thr Pro Lys
        275                 280                 285

Leu Met Leu Met Ser Thr Ser His Asp Phe Pro Asn Gly Val Gly Asn
290                 295                 300
```

```
Arg Ser Asp Met Val Gly Arg Asn Leu Met Asp His Pro Gly Thr Gly
305                 310                 315                 320

Val Ser Phe Tyr Ala Ser Glu Lys Leu Trp Pro Gly Arg Gly Pro Gln
                325                 330                 335

Glu Met Thr Ser Leu Ile Gly Phe Arg Asp Gly Ala Phe Arg Ala Thr
            340                 345                 350

Glu Ala Ala Lys Lys Ile His Leu Ser Asn Leu Ser Arg Ile Asp Gln
        355                 360                 365

Glu Thr Gln Lys Ile Phe Lys Ala Gly Lys Leu Met Lys Pro Ala Glu
    370                 375                 380

Leu Asp Ala Gln Ile Arg Asp Arg Ser Ala Arg Tyr Val Gln Phe Asp
385                 390                 395                 400

Cys Phe His Glu Ile Leu Pro Gln Pro Glu Asn Arg Ile Val Pro Ser
                405                 410                 415

Lys Thr Ala Thr Asp Ala Ile Gly Ile Pro Arg Pro Glu Ile Thr Tyr
            420                 425                 430

Ala Ile Asp Asp Tyr Val Lys Arg Gly Ala Val His Thr Arg Glu Val
        435                 440                 445

Tyr Ala Thr Ala Ala Lys Val Leu Gly Gly Thr Asp Val Ala Phe Asn
    450                 455                 460

Asp Glu Phe Ala Pro Asn Asn His Ile Thr Gly Ala Thr Ile Met Gly
465                 470                 475                 480

Ala Asp Pro Arg Asp Ser Val Val Asp Lys Asp Cys Arg Thr Phe Asp
                485                 490                 495

His Pro Asn Leu Phe Val Ser Ser Ser Ala Thr Met Pro Thr Val Gly
            500                 505                 510

Thr Val Asn Val Thr Leu Thr Ile Ala Ala Leu Ala Leu Arg Ile Ser
        515                 520                 525

Asp Gln Leu Lys Lys Glu Ile
    530                 535

<210> SEQ ID NO 117
<211> LENGTH: 540
<212> TYPE: PRT
<213> ORGANISM: Artificial Sequence
<220> FEATURE:
<223> OTHER INFORMATION: Recombinant sequence

<400> SEQUENCE: 117

Met Ala Asp Lys Gln Gln Ser Thr Glu Gln Ala Asp Ile Val Val Val
1               5                   10                  15

Gly Ser Gly Val Ala Gly Ala Ile Val Ala His Gln Leu Ala Gln Ala
                20                  25                  30

Gly Lys Ser Val Ile Leu Leu Glu Ala Gly Pro Arg Met Pro Arg Trp
            35                  40                  45

Glu Ile Val Glu Arg Phe Arg Asn Gln Ala Asp Lys Met Asp Phe Met
        50                  55                  60

Ala Pro Tyr Pro Pro Ser Lys Trp Ala Pro His Pro Glu Tyr Tyr Pro
65                  70                  75                  80

Pro Asn Asn Tyr Leu Ile Leu Lys Gly Glu His Lys Phe Asn Ser Gln
                85                  90                  95

Tyr Ile Arg Ala Val Gly Gly Thr Thr Trp His Trp Ala Ala Ser Ala
            100                 105                 110

Trp Arg Phe Met Pro Asn Asp Phe Arg Met Lys Thr Val Tyr Gly Val
        115                 120                 125
```

```
Gly Arg Asp Trp Pro Met Gln Tyr Glu Glu Leu Glu Pro Tyr Tyr Gln
        130                 135                 140

Arg Ala Glu Glu Glu Leu Gly Val Trp Gly Pro Thr Asp Glu Glu Leu
145                 150                 155                 160

Gly Ser Pro Arg Ser Gln Pro Tyr Pro Met Ala Pro Leu Pro Leu Ser
                165                 170                 175

Tyr Asn Glu Gln Thr Ile Lys Ser Lys Leu Asn Ala Phe Asp Ser Arg
            180                 185                 190

Tyr His Val Val Thr Glu Pro Val Ala Arg Asn Ser Arg Pro Tyr Asp
        195                 200                 205

Gly Arg Pro Thr Cys Cys Gly Asn Asn Cys Met Pro Ile Cys Pro
210                 215                 220

Ile Gly Ala Met Tyr Asn Gly Ile Val His Val Glu Lys Ala Glu Gln
225                 230                 235                 240

Ala Gly Ala Arg Leu Ile Ala Asn Ala Val Val Tyr Lys Leu Glu Val
                245                 250                 255

Gly Thr Asp Lys Arg Ile Thr Ala Ala Leu Tyr Lys Asp Ala Gln Gly
            260                 265                 270

Asn Glu His Arg Val Glu Gly Lys Tyr Phe Val Leu Ala Ala Asn Gly
        275                 280                 285

Ile Glu Thr Pro Lys Ile Met Leu Met Ser Gln Ser His Asp Phe Pro
290                 295                 300

Asn Gly Val Gly Asn Ser Ser Asp Met Val Gly Arg Asn Leu Met Asp
305                 310                 315                 320

His Pro Gly Thr Gly Val Thr Phe Tyr Ala Asp Glu Lys Leu Trp Pro
                325                 330                 335

Gly Arg Gly Pro Gln Glu Met Thr Ser Leu Ile Gly Phe Arg Asp Gly
            340                 345                 350

Ala Phe Arg Ala Thr Glu Ala Ala Lys Lys Ile His Leu Ser Asn Met
        355                 360                 365

Ser Arg Val Asp Gln Glu Thr Gln Lys Ile Phe Lys Gln Gly Lys Leu
370                 375                 380

Ile Lys Pro Ala Glu Leu Asp Ala Gln Ile Arg Asp Arg Ser Ala Arg
385                 390                 395                 400

Phe Val Glu Phe Asp Cys Phe His Glu Ile Leu Pro Gln Pro Glu Asn
                405                 410                 415

Arg Ile Val Pro Ser Arg Thr Glu Thr Asp Ala Ile Gly Ile Ala Arg
            420                 425                 430

Pro Glu Ile Thr Tyr Arg Ile Asp Asp Tyr Val Lys Arg Gly Ala Ala
        435                 440                 445

His Thr Arg Glu Val Tyr Ala Asn Ala Ala Lys Val Leu Gly Gly Ser
450                 455                 460

Asp Ile Arg Phe Asp Asp Glu Phe Ala Pro Asn Asn His Ile Thr Gly
465                 470                 475                 480

Ala Thr Ile Met Gly Ser Asp Pro Arg Asp Ser Val Val Asp Lys His
                485                 490                 495

Cys Arg Thr Phe Asp His Pro Asn Leu Phe Ile Ser Ser Ala Thr
            500                 505                 510

Met Pro Thr Val Gly Thr Val Asn Val Thr Leu Thr Ile Ala Ala Leu
        515                 520                 525

Ala Leu Arg Met Ala Asp Gln Leu Lys Lys Glu Val
530                 535                 540
```

```
<210> SEQ ID NO 118
<211> LENGTH: 534
<212> TYPE: PRT
<213> ORGANISM: Artificial Sequence
<220> FEATURE:
<223> OTHER INFORMATION: Recombinant sequence

<400> SEQUENCE: 118

Asp Thr Leu Gln Ala Asp Ile Val Val Gly Ser Gly Val Ala Gly
1               5                   10                  15

Ala Leu Val Ala His Gln Leu Ala Leu Ala Gly Lys Ser Val Ile Met
                20                  25                  30

Leu Glu Ala Gly Pro Arg Leu Pro Arg Trp Glu Ile Val Glu Arg Phe
            35                  40                  45

Arg Asn Gln Phe Asp Lys Met Asp Phe Met Ala Pro Tyr Pro Ser Thr
        50                  55                  60

Pro Trp Ala Pro His Pro Glu Tyr Gly Pro Asn Asn Tyr Leu Ile
65              70                  75                  80

Leu Lys Gly Glu His Lys Phe Asn Ser Gln Tyr Ile Arg Ala Val Gly
                85                  90                  95

Gly Thr Thr Trp His Trp Ala Ser Ala Trp Arg Phe Ile Pro Asn
            100                 105                 110

Asp Phe Lys Met Asn Thr Val Tyr Gly Val Ala Arg Asp Trp Pro Ile
        115                 120                 125

Gln Tyr Asp Asp Val Glu Pro Trp Tyr Tyr Arg Ala Glu Gln Glu Leu
    130                 135                 140

Gly Val Trp Gly Pro Asn Asp Glu Asp Leu Tyr Ser Pro Arg Lys Ala
145                 150                 155                 160

Pro Tyr Pro Met Ala Pro Leu Pro Leu Ser Tyr Asn Glu Ala Thr Ile
                165                 170                 175

Lys Ser Lys Leu Asn Ala Tyr Asp Ala Ala Tyr His Val Val Thr Glu
            180                 185                 190

Pro Val Ala Arg Asn Ser Val Pro Tyr Asp Gly Arg Pro Thr Cys Cys
        195                 200                 205

Gly Asn Asn Asn Cys Met Pro Ile Cys Pro Ile Gly Ala Met Tyr Asn
    210                 215                 220

Gly Ile Val His Val Glu Lys Ala Glu Met Ala Gly Ala Lys Leu Ile
225                 230                 235                 240

Asp Asn Ala Val Val Tyr Arg Leu Glu Val Gly Ser Asn Lys Arg Ile
                245                 250                 255

Val Ala Ala Leu Tyr Lys Asp Pro Gln Gly Ile Ser His Arg Val Glu
            260                 265                 270

Gly Lys Tyr Phe Val Leu Ala Ala Asn Gly Ile Glu Thr Pro Lys Ile
        275                 280                 285

Met Leu Met Ser Thr Ser His Asp Phe Pro Asn Gly Val Gly Asn Ser
    290                 295                 300

Ser Asp Met Val Gly Arg Asn Leu Met Asp His Pro Gly Thr Gly Val
305                 310                 315                 320

Ser Phe Tyr Ala Asp Glu Lys Leu Trp Pro Gly Arg Gly Pro Gln Glu
                325                 330                 335

Met Thr Ser Leu Ile Gly Phe Arg Asp Gly Ala Phe Arg Ser Gln Gln
            340                 345                 350

Ala Ala Lys Lys Ile His Leu Ser Asn Leu Ser Arg Ile Asp Gln Glu
        355                 360                 365
```

```
Thr Gln Lys Ile Phe Gly Gln Lys Lys Leu Leu Lys Pro Ala Asp Leu
        370                 375                 380

Asp Ala Gln Ile Arg Asp Arg Ser Ala Arg Tyr Val Gln Phe Asp Cys
385                 390                 395                 400

Phe His Glu Ile Leu Pro Gln Pro Glu Asn Arg Ile Val Pro Ser Arg
                405                 410                 415

Thr Glu Thr Asp Ala Ile Gly Ile Pro Arg Pro Glu Ile Thr Tyr Ala
                420                 425                 430

Ile Gly Asp Tyr Val Lys Arg Gly Ala Ala His Thr Arg Glu Val Tyr
            435                 440                 445

Ala Thr Ala Ala Lys Val Leu Gly Gly Thr Glu Val Glu Phe His Asp
450                 455                 460

Asp Phe Ala Pro Asn Asn His Ile Thr Gly Ser Val Ile Met Gly Ser
465                 470                 475                 480

Asp Pro Arg Asn Ser Val Val Asp Lys Asp Cys Arg Thr Phe Asp His
                485                 490                 495

Pro Asn Leu Phe Val Ser Ser Ser Ala Thr Met Pro Thr Val Gly Thr
                500                 505                 510

Val Asn Val Thr Leu Thr Ile Ala Ala Leu Ala Leu Arg Met Ala Asp
                515                 520                 525

Gln Leu Lys Lys Glu Val
        530
```

```
<210> SEQ ID NO 119
<211> LENGTH: 533
<212> TYPE: PRT
<213> ORGANISM: Artificial Sequence
<220> FEATURE:
<223> OTHER INFORMATION: Recombinant sequence

<400> SEQUENCE: 119

Asp Thr Gln Gln Ala Asp Ile Val Val Gly Ser Gly Val Ala Gly
1               5                   10                  15

Ala Leu Val Ala Tyr Glu Leu Ala Arg Ala Gly Lys Ser Val Leu Met
                20                  25                  30

Leu Glu Ala Gly Pro Arg Leu Pro Arg Trp Glu Ile Val Glu Arg Phe
            35                  40                  45

Arg Asn Gln Ala Asp Lys Met Asp Phe Met Ala Pro Tyr Pro Ser Thr
50                  55                  60

Ser Trp Ala Pro His Pro Glu Tyr Gly Pro Pro Asn Asn Tyr Leu Ile
65                  70                  75                  80

Leu Lys Gly Glu His Lys Phe Asn Ser Gln Tyr Ile Arg Ala Val Gly
                85                  90                  95

Gly Thr Thr Trp His Trp Ala Ser Thr Trp Arg Phe Leu Pro Asn
            100                 105                 110

Asp Phe Lys Leu Arg Ser Val Tyr Gly Ile Ala Arg Asp Trp Pro Leu
            115                 120                 125

Gln Tyr Ser Asp Leu Glu Arg Tyr Tyr Gly Arg Ala Glu Glu Ala Leu
        130                 135                 140

Gly Val Trp Gly Pro Asn Asp Glu Glu Leu Gly Ser Pro Arg Ser Gln
145                 150                 155                 160

Pro Tyr Pro Met Thr Pro Leu Pro Leu Ser Phe Asn Glu Arg Thr Ile
                165                 170                 175

Lys Glu Ala Leu Asn Gly Tyr Asp Pro Asp Phe His Val Thr Glu
                180                 185                 190
```

```
Pro Val Ala Arg Asn Ser Arg Pro Tyr Asp Gly Arg Pro Thr Cys Cys
            195                 200                 205

Gly Asn Asn Asn Cys Met Pro Ile Cys Pro Ile Gly Ala Met Tyr Asn
210                 215                 220

Gly Ile Phe His Val Glu Lys Ala Glu Gln Ala Gly Ala Arg Leu Ile
225                 230                 235                 240

Glu Asn Ala Val Val Phe Lys Leu Glu Val Gly Ala Asn Lys Arg Ile
                245                 250                 255

Val Ala Ala Arg Tyr Lys Asp Ala Lys Gly Val Glu His Arg Val Glu
            260                 265                 270

Gly Lys Trp Phe Val Leu Ala Ala Asn Gly Ile Glu Thr Pro Lys Leu
        275                 280                 285

Met Leu Met Ser Thr Ser Gln Asp Tyr Pro Lys Gly Val Gly Asn Ser
    290                 295                 300

Ser Asp Met Val Gly Arg Asn Leu Met Asp His Pro Gly Thr Gly Val
305                 310                 315                 320

Ser Phe Tyr Ala Asp Arg Lys Leu Trp Pro Gly Arg Gly Pro Gln Glu
                325                 330                 335

Met Thr Ser Leu Ile Gly Phe Arg Asp Gly Pro Phe Arg Ala Thr Gln
            340                 345                 350

Ala Gly Lys Lys Leu His Leu Ser Asn Ile Ser Arg Ile Glu Gln Glu
        355                 360                 365

Thr Gln Arg Ile Phe Lys Glu Gly Lys Leu Ile Lys Pro Ala Glu Leu
    370                 375                 380

Asp Ala Arg Ile Arg Asp Gln Ala Ala Arg Phe Val Glu Phe Asp Ser
385                 390                 395                 400

Phe His Glu Ile Leu Pro Leu Pro Glu Asn Arg Ile Val Pro Ser Ala
                405                 410                 415

Thr Glu Val Asp Ala Ile Gly Ile Pro Arg Pro Glu Ile Thr Tyr Arg
            420                 425                 430

Ile Asp Asp Tyr Val Lys Arg Ser Ala Val His Thr Arg Gln Val Tyr
        435                 440                 445

Ala Thr Ala Ala Lys Val Leu Gly Gly Thr Asp Val Gln Phe Asn Asp
    450                 455                 460

Asp Phe Ala Pro Asn Asn His Ile Thr Gly Ala Thr Ile Met Gly Ala
465                 470                 475                 480

Asp Pro Lys Asp Ser Val Val Asp Lys Asp Cys Arg Thr Phe Asp His
                485                 490                 495

Pro Asn Leu Phe Ile Ser Ser Ser Thr Met Pro Thr Val Gly Thr
            500                 505                 510

Val Asn Val Thr Leu Thr Ile Ala Ala Leu Ala Leu Arg Ile Ala Asp
        515                 520                 525

Gln Leu Lys Lys Glu
    530

<210> SEQ ID NO 120
<211> LENGTH: 533
<212> TYPE: PRT
<213> ORGANISM: Artificial Sequence
<220> FEATURE:
<223> OTHER INFORMATION: Recombinant sequence

<400> SEQUENCE: 120

Asp Thr Gln Gln Ala Asp Ile Val Val Val Gly Ser Gly Val Ala Gly
1               5                   10                  15
```

```
Ala Leu Val Ala Tyr Glu Leu Ala Arg Ala Gly Lys Ser Val Leu Met
         20                  25                  30

Leu Glu Ala Gly Pro Arg Leu Pro Arg Trp Glu Ile Val Glu Arg Phe
     35                  40                  45

Arg Asn Gln Ala Asp Lys Met Asp Phe Met Ala Pro Tyr Pro Ser Thr
 50                  55                  60

Pro Trp Ala Pro His Pro Glu Tyr Gly Pro Pro Asn Asn Tyr Leu Val
65                  70                  75                  80

Leu Lys Gly Glu His Gln Phe Asn Ser Gln Tyr Ile Arg Ala Val Gly
                 85                  90                  95

Gly Thr Thr Trp His Trp Ala Ala Ser Thr Trp Arg Phe Leu Pro Asn
            100                 105                 110

Asp Phe Lys Leu Arg Ser Val Tyr Gly Ile Ala Arg Asp Trp Pro Ile
        115                 120                 125

Gln Tyr Gln Asp Leu Glu Arg Tyr Tyr Gly Arg Ala Glu Glu Ala Leu
    130                 135                 140

Gly Val Trp Gly Pro Asn Asp Glu Asp Leu Gly Ser Pro Arg Ser Gln
145                 150                 155                 160

Pro Tyr Pro Met Ala Pro Leu Pro Leu Ser Phe Ser Glu Arg Thr Ile
                165                 170                 175

Lys Asp Ala Leu Asn Ala His Asp Ala Ser Leu His Val Val Thr Glu
            180                 185                 190

Pro Val Ala Arg Asn Ser Arg Pro Tyr Asp Gly Arg Pro Thr Cys Cys
        195                 200                 205

Gly Asn Asn Asn Cys Met Pro Ile Cys Pro Ile Gly Ala Met Tyr Asn
210                 215                 220

Gly Ile Val His Val Glu Lys Ala Glu Gln Ala Gly Ala Arg Leu Ile
225                 230                 235                 240

Glu Asn Ala Val Val Phe Lys Leu Glu Val Gly Pro Asn Lys Arg Ile
                245                 250                 255

Val Ala Ala Arg Tyr Lys Asp Ser Lys Gly Ala Glu His Arg Val Glu
            260                 265                 270

Gly Lys Trp Phe Val Leu Ala Ala Asn Gly Ile Glu Thr Pro Lys Leu
        275                 280                 285

Met Leu Met Ser Thr Ser Gln Asp Phe Pro Lys Gly Val Gly Asn Ser
    290                 295                 300

Ser Asp Met Val Gly Arg Asn Leu Met Asp His Pro Gly Thr Gly Val
305                 310                 315                 320

Ser Phe Tyr Ala Asp Arg Lys Leu Trp Pro Gly Arg Gly Pro Gln Glu
                325                 330                 335

Met Thr Ser Leu Ile Gly Phe Arg Asp Gly Pro Phe Arg Ala Thr Gln
            340                 345                 350

Ala Gly Lys Lys Leu His Leu Ser Asn Met Ser Arg Ile Glu Gln Glu
        355                 360                 365

Thr Gln Arg Ile Phe Lys Glu Gly Lys Leu Ile Lys Pro Ala Glu Leu
    370                 375                 380

Asp Ala Arg Ile Arg Asp Gln Ala Ala Arg Tyr Val Gln Phe Asp Ser
385                 390                 395                 400

Phe His Glu Ile Leu Pro Leu Pro Glu Asn Arg Ile Val Pro Ser Ala
                405                 410                 415

Ser Glu Val Asp Ala Ile Gly Ile Pro Arg Pro Glu Ile Thr Tyr His
            420                 425                 430

Ile Asp Asp Tyr Val Lys Arg Ser Ala Val His Thr Arg Glu Val Tyr
```

```
            435                 440                 445
Ala Thr Ala Ala Gln Val Met Gly Gly Thr Asn Val Glu Phe His Asp
        450                 455                 460

Asp Phe Ala Pro Asn Asn His Ile Thr Gly Ala Thr Ile Met Gly Ala
465                 470                 475                 480

Asp Pro Lys Asn Ser Val Val Asp Lys Asp Cys Arg Thr Phe Asp His
                485                 490                 495

Pro Asn Leu Phe Ile Ser Ser Ser Thr Met Pro Thr Val Gly Thr
            500                 505                 510

Val Asn Val Thr Leu Thr Ile Ala Ala Leu Ala Leu Arg Ile Ala Asp
                515                 520                 525

Gln Leu Lys Lys Glu
        530

<210> SEQ ID NO 121
<211> LENGTH: 531
<212> TYPE: PRT
<213> ORGANISM: Artificial Sequence
<220> FEATURE:
<223> OTHER INFORMATION: Recombinant sequence

<400> SEQUENCE: 121

Gln Gln Ala Asp Ile Val Val Gly Ser Gly Val Ala Gly Ala Leu
1               5                   10                  15

Val Ala Tyr Glu Leu Ala Arg Ala Gly Lys Ser Val Leu Met Leu Glu
            20                  25                  30

Ala Gly Pro Arg Leu Pro Arg Trp Glu Ile Val Glu Arg Phe Arg Asn
        35                  40                  45

Gln Ala Asp Lys Met Asp Phe Met Ala Pro Tyr Pro Ser Thr Pro Trp
    50                  55                  60

Ala Pro His Pro Glu Tyr Gly Pro Pro Asn Asn Tyr Leu Val Leu Lys
65                  70                  75                  80

Gly Glu His Gln Phe Asn Ser Gln Tyr Ile Arg Ala Val Gly Gly Thr
                85                  90                  95

Thr Trp His Trp Ala Ala Ser Thr Trp Arg Phe Leu Pro Asn Asp Phe
            100                 105                 110

Lys Leu Arg Ser Val Tyr Gly Ile Ala Arg Asp Trp Pro Ile Gln Tyr
        115                 120                 125

Gln Asp Leu Glu Arg Tyr Tyr Gly Leu Ala Glu Glu Ala Leu Gly Val
    130                 135                 140

Trp Gly Pro Asn Asp Glu Asp Leu Gly Ser Pro Arg Ser Gln Pro Tyr
145                 150                 155                 160

Pro Met Thr Pro Leu Pro Leu Ser Phe Ser Glu Arg Thr Ile Lys Asp
                165                 170                 175

Ala Leu Asn Ala His Asp Ala Ser Phe His Val Val Thr Glu Pro Val
            180                 185                 190

Ala Arg Asn Ser Arg Pro Tyr Asp Gly Arg Pro Thr Cys Cys Gly Asn
        195                 200                 205

Asn Asn Cys Met Pro Ile Cys Pro Ile Gly Ala Met Tyr Asn Gly Ile
    210                 215                 220

Val His Val Glu Lys Ala Glu Gln Ala Gly Ala Arg Leu Ile Glu Asn
225                 230                 235                 240

Ala Val Val Phe Lys Leu Glu Val Gly Pro Asn Lys Arg Ile Val Ala
                245                 250                 255

Ala Arg Tyr Lys Asp Ser Lys Gly Ala Glu His Arg Val Glu Gly Lys
```

```
                       260                 265                 270
Trp Phe Val Leu Ala Ala Asn Gly Ile Glu Thr Pro Lys Leu Met Leu
                275                 280                 285

Met Ser Thr Ser Gln Asp Phe Pro Lys Gly Val Gly Asn Ser Ser Asp
        290                 295                 300

Met Val Gly Arg Asn Leu Met Asp His Pro Gly Thr Gly Val Ser Phe
305                 310                 315                 320

Tyr Ala Asp Arg Lys Leu Trp Pro Gly Arg Gly Pro Gln Glu Met Thr
                325                 330                 335

Ser Leu Ile Gly Phe Arg Asp Gly Pro Phe Arg Ala Thr Gln Ala Gly
            340                 345                 350

Lys Lys Leu His Leu Ser Asn Ile Ser Arg Ile Glu Gln Glu Thr Gln
        355                 360                 365

Arg Ile Phe Lys Glu Gly Lys Leu Ile Lys Pro Ala Asp Leu Asp Ala
    370                 375                 380

Arg Ile Arg Asp Gln Ala Ala Arg Tyr Val Gln Phe Asp Ser Phe His
385                 390                 395                 400

Glu Ile Leu Pro Leu Pro Glu Asn Arg Ile Val Pro Ser Ala Thr Glu
                405                 410                 415

Val Asp Ala Ile Gly Ile Pro Arg Pro Glu Ile Thr Tyr His Ile Asp
            420                 425                 430

Asp Tyr Val Lys Arg Ser Ala Val His Thr Arg Glu Val Tyr Ala Thr
        435                 440                 445

Ala Ala Gln Val Met Gly Gly Thr Asn Val Glu Phe His Asp Asp Phe
    450                 455                 460

Ala Pro Asn Asn His Ile Thr Gly Ala Thr Ile Met Gly Ala Asp Pro
465                 470                 475                 480

Lys Asp Ser Val Val Asp Lys Asp Cys Arg Thr Phe Asp His Pro Asn
                485                 490                 495

Leu Phe Ile Ser Ser Ser Ser Ala Met Pro Thr Val Gly Thr Val Asn
            500                 505                 510

Val Thr Leu Thr Ile Ala Ala Leu Ala Leu Arg Ile Ala Asp Gln Leu
        515                 520                 525

Lys Lys Glu
    530

<210> SEQ ID NO 122
<211> LENGTH: 538
<212> TYPE: PRT
<213> ORGANISM: Artificial Sequence
<220> FEATURE:
<223> OTHER INFORMATION: Recombinant sequence

<400> SEQUENCE: 122

Met Ala Asp Thr Arg Gln Ala Glu Gln Ala Asp Ile Val Val Val Gly
1               5                   10                  15

Ser Gly Val Ala Gly Ala Leu Val Ala Tyr Glu Leu Ala Arg Ala Gly
            20                  25                  30

Lys Ser Val Leu Leu Leu Glu Ala Gly Pro Arg Leu Pro Arg Trp Glu
        35                  40                  45

Ile Val Glu Arg Phe Arg Asn Gln Ala Asp Lys Met Asp Phe Met Ala
    50                  55                  60

Pro Tyr Pro Ser Thr Pro Trp Ala Pro His Pro Glu Tyr Gly Pro Pro
65                  70                  75                  80

Asn Asn Tyr Leu Ile Leu Lys Gly Glu His Pro Phe Asp Ser Gln Tyr
```

-continued

```
                85                  90                  95
Ile Arg Ala Val Gly Thr Thr Trp His Trp Ala Ala Ser Thr Trp
            100                 105                 110
Arg Phe Leu Pro Asn Asp Phe Lys Leu Arg Ser Val Tyr Gly Ile Ala
            115                 120                 125
Arg Asp Trp Pro Leu Gln Tyr Asp Asp Leu Glu Arg Tyr Tyr Gly Gln
            130                 135                 140
Ala Glu Ala Ala Leu Gly Val Trp Gly Pro Asn Asp Glu Asp Leu Gly
145                 150                 155                 160
Ser Pro Arg Ser Arg Pro Tyr Pro Met Ala Pro Leu Pro Leu Ser Phe
                165                 170                 175
Asn Glu Arg Thr Ile Lys Glu Ala Leu Asn Ala His Asp Pro Ala Phe
                180                 185                 190
His Val Val Thr Glu Pro Val Ala Arg Asn Ser Arg Pro Tyr Asp Gly
                195                 200                 205
Arg Pro Thr Cys Cys Gly Asn Asn Cys Met Pro Ile Cys Pro Val
            210                 215                 220
Gly Ala Met Tyr Asn Gly Ile Val His Val Glu Lys Ala Glu Gln Ala
225                 230                 235                 240
Gly Ala Arg Leu Ile Glu Asn Ala Val Val Tyr Lys Leu Glu Val Gly
                245                 250                 255
Ala Gly Lys Arg Ile Val Ala Ala His Tyr Lys Asp Pro Lys Gly Val
            260                 265                 270
Asp His Arg Val Glu Gly Lys Trp Phe Val Leu Ala Ala Asn Gly Ile
            275                 280                 285
Glu Thr Pro Lys Leu Met Leu Met Ser Thr Ser Ala Ala Phe Pro Arg
            290                 295                 300
Gly Val Gly Asn Ser Ser Asp Met Val Gly Arg Asn Leu Met Asp His
305                 310                 315                 320
Pro Gly Thr Gly Val Ser Phe Tyr Ala Asp Arg Lys Leu Trp Pro Gly
            325                 330                 335
Arg Gly Pro Gln Glu Met Thr Ser Leu Ile Gly Phe Arg Asp Gly Pro
            340                 345                 350
Phe Arg Ala Thr Gln Ala Gly Lys Lys Leu His Leu Ser Asn Ile Ser
            355                 360                 365
Arg Ile Glu Gln Glu Thr Ala Arg Ile Phe Lys Ala Gly Lys Leu Leu
            370                 375                 380
Lys Pro Ala Glu Leu Asp Ala Arg Ile Arg Asp Gln Ala Ala Arg Tyr
385                 390                 395                 400
Val Gln Phe Asp Ser Phe His Glu Ile Leu Pro Leu Pro Glu Asn Arg
                405                 410                 415
Ile Val Pro Ser Ala Thr Glu Thr Asp Ala Leu Gly Ile Pro Arg Pro
            420                 425                 430
Glu Ile Thr Tyr Arg Ile Asp Asp Tyr Val Lys Arg Ser Ala Val His
            435                 440                 445
Thr Arg Glu Val Tyr Ala Thr Ala Ala Lys Val Leu Gly Gly Thr Asp
            450                 455                 460
Val Gln Phe His Asp Asp Phe Ala Pro Asn Asn His Ile Thr Gly Ala
465                 470                 475                 480
Thr Ile Met Gly Ala Asp Pro Lys Asp Ser Val Val Asp Lys Asn Cys
            485                 490                 495
Arg Thr Phe Asp His Pro Asn Leu Phe Ile Ser Ser Ala Thr Met
            500                 505                 510
```

```
Pro Thr Val Gly Thr Val Asn Val Thr Leu Thr Ile Ala Ala Leu Ala
        515                 520                 525

Leu Arg Ile Ala Asp Gln Leu Lys Lys Glu
    530                 535

<210> SEQ ID NO 123
<211> LENGTH: 528
<212> TYPE: PRT
<213> ORGANISM: Artificial Sequence
<220> FEATURE:
<223> OTHER INFORMATION: Recombinant sequence

<400> SEQUENCE: 123

Ser Asp Ser Leu Asn Ala Asp Val Val Ile Gly Ala Gly Ile Ala
1               5                   10                  15

Gly Ser Leu Ala Ala Leu Lys Met Val Gln Ala Gly Ala Ser Val Leu
                20                  25                  30

Met Leu Glu Ser Gly Pro Glu Ile Lys Arg Asp Glu Ala Val Glu Leu
                35                  40                  45

Phe Arg Asn Ser Pro Phe Lys Gly Asp Phe Thr Glu Pro Phe Pro Pro
        50                  55                  60

Glu Pro Trp Ala Pro Gln Pro Lys Phe Ile Pro Thr Asp Asn Asn Tyr
65                  70                  75                  80

Leu Ile Gln Lys Gly Pro Asp Pro Tyr Arg Ala Gln Tyr Leu Arg Gly
                    85                  90                  95

Val Gly Gly Thr Thr Trp His Trp Ala Gly Gln Ala Phe Arg Leu Leu
                100                 105                 110

Pro Asn Asp Met Arg Met Lys Thr Leu Tyr Gly Val Gly Arg Asp Trp
            115                 120                 125

Pro Ile Gly Tyr Glu Gln Leu Glu Pro Tyr Tyr Cys Glu Ala Glu Tyr
        130                 135                 140

Gln Met Gly Val Ser Gly Asp Ser Glu Leu Asp Ser Pro Arg Ser Arg
145                 150                 155                 160

Pro Tyr Pro Leu Pro Gly Ile Pro Leu Pro Tyr Gly Phe Glu Arg Leu
                165                 170                 175

Lys Gln Arg Ile Ala Gly Leu Gly Tyr Glu Val Gly Ile Gly Pro Gln
            180                 185                 190

Ala Arg Asn Ser Val Pro Tyr Asp Gly Arg Pro Ala Cys Cys Gly Asn
        195                 200                 205

Asn Asn Cys Met Pro Val Cys Pro Ile Asp Ala Gln Tyr His Gly Gly
    210                 215                 220

Ile Ser Ala Asn Lys Ala Leu Ala Ala Gly Ala Arg Ile Ile Ala Asn
225                 230                 235                 240

Ala Val Val His Arg Ile Glu Ala Asn Asp Gln Gly Gln Ile Val Ala
                245                 250                 255

Val His Tyr Leu Asp Arg Asn Lys Val Ser His Arg Val Thr Gly Lys
                260                 265                 270

Arg Phe Val Leu Thr Ala Asn Gly Ile Glu Ser Pro Lys Ile Leu Leu
            275                 280                 285

Ile Ser Thr Ser Glu Arg Tyr Pro Asn Gly Ile Ala Asn Ser Ser Ser
        290                 295                 300

Met Val Gly Arg Asn Leu Met Asp His Pro Gly Ser Ser Val Glu Phe
305                 310                 315                 320

Tyr Ala Asp Glu Pro Val Trp Phe Gly Arg Gly Pro Met Arg Pro Gly
                325                 330                 335
```

```
Ser Ile Asn Asn Leu Arg Asp Gly Ala Phe Arg Ala Glu Arg Ser Ala
                340                 345                 350

Leu Arg Val Asp Val Ser Asn Thr Ser Pro Val Arg Tyr Leu Thr Glu
            355                 360                 365

Arg Leu Ile Arg Gln Gly Tyr Tyr Gly Lys Ala Leu Asn Asp Lys Leu
        370                 375                 380

Ala Phe Gln Ser Glu Arg Tyr Val Gln Leu Lys Cys Leu Leu Glu Met
385                 390                 395                 400

Leu Pro Glu Pro Glu Asn Arg Val Gln Leu Ser Lys Thr Glu Lys Asp
                405                 410                 415

Ala Trp Gly Ile Pro Arg Leu Glu Val Tyr Tyr Lys Phe Pro Glu Tyr
            420                 425                 430

Val His Arg Gly Tyr Asp Gln Ser Met Leu Asp Phe Gln Arg Ile Val
        435                 440                 445

Lys Gln Met Gly Gly Ser Glu Ala Ile Tyr Ser Lys Arg Gly Leu Tyr
    450                 455                 460

Asp Asn Asn Gln His Ile Thr Gly Thr Met Ile Met Gly Arg Ser Gly
465                 470                 475                 480

Ser Asp Ser Val Val Asp Gly Asp Cys Arg Ser His Asp His Pro Asn
                485                 490                 495

Leu Phe Ile Ala Gly Thr Gly Val Met Pro Ser Ala Ser Thr Val Asn
            500                 505                 510

Ser Thr Leu Thr Gly Val Ala Leu Ala Leu His Met Ala Asp Arg Val
        515                 520                 525

<210> SEQ ID NO 124
<211> LENGTH: 542
<212> TYPE: PRT
<213> ORGANISM: Artificial Sequence
<220> FEATURE:
<223> OTHER INFORMATION: Recombinant sequence

<400> SEQUENCE: 124

Met Pro Ser Glu Glu Asn Leu Ser Ala Asp Val Val Ile Val Gly Ser
1               5                   10                  15

Gly Val Ala Gly Ser Ser Ile Ala Asn Glu Leu Ala Arg Ala Gly Ile
            20                  25                  30

Ser Val Ile Val Leu Glu Ala Gly Pro Arg Val Asp Arg Gln His Phe
        35                  40                  45

Val Glu Asn Phe Arg Asn Leu Glu Asn Lys Pro Ser Tyr Gln Gly Pro
    50                  55                  60

Phe Pro Ala Val Pro Trp Ala Arg His Pro Asp Gln Gln Thr Pro
65                  70                  75                  80

Asn Glu Tyr Leu His Thr Ser Gly Pro Asn Ala Glu Ala Tyr Gln Gln
                85                  90                  95

Val Tyr Leu Arg Met Met Gly Gly Thr Thr Trp His Trp Ala Gly Cys
            100                 105                 110

Ala Trp Arg Tyr Leu Pro Ser Asp Phe Glu Leu Lys Thr Arg Tyr Gly
        115                 120                 125

Gln Gly Arg Asp Trp Ala Leu Thr Tyr Asp Asp Leu Glu Pro Phe Tyr
    130                 135                 140

Tyr Gln Ala Glu Val Met Met Gly Val Cys Gly Pro Asp Pro Ala Val
145                 150                 155                 160

Glu Asp Leu Gly Ser Pro Arg Lys Gln Pro Tyr Pro Met Asp Ala Leu
                165                 170                 175
```

```
Pro Ile Ser Tyr Ala Ala Gln Gln Phe Arg Lys Leu Ile Gln Glu Lys
            180                 185                 190

Thr Pro Trp Arg Val Val His Glu Pro Gln Ala Arg Asn Thr Arg Pro
        195                 200                 205

Tyr Asp Asn Arg Pro Thr Cys Glu Gly His Asn Asn Cys Met Pro Ile
    210                 215                 220

Cys Pro Ile Gly Ala Met Tyr Asn Gly Ser Tyr Ser Val Tyr His Ala
225                 230                 235                 240

Glu Ala Ala Gly Ala Lys Phe Ile Pro Asn Ala Val Val Tyr Lys Ile
                245                 250                 255

Glu Arg Asp Ser Ala Asn Lys Arg Val Thr Ala Val His Tyr Phe Asp
            260                 265                 270

Pro Asp Lys Gly Ser His Arg Val Thr Gly Lys Tyr Phe Val Ile Ala
        275                 280                 285

Ala His Cys Ile Glu Thr Ala Lys Leu Leu Leu Ser Ala Asp Glu
    290                 295                 300

Gln Ser Pro Asp Gly Val Ala Asn Ser Ser Gly His Val Gly Arg Asn
305                 310                 315                 320

Met Met Asp His Thr Gly Val Gln Val Thr Phe Val Ser Gly Asp Gln
                325                 330                 335

Ala Leu Trp Pro Gly Arg Gly Pro Leu Glu Thr Asn Val Ile Asp Asn
            340                 345                 350

Phe Arg Asp Gly Asn Trp Arg Thr Asp Arg Gly Ala Tyr Leu Val His
        355                 360                 365

Met Val Asp Asp Asn Gln Val Asp Leu Ala Thr Gln Leu Ala Ile Ser
    370                 375                 380

Lys Gly Tyr Val Gly Arg Glu Leu Glu Glu Gln Ile Arg Tyr Leu Ala
385                 390                 395                 400

Ser His Thr Val Arg Leu Phe Ser His Asn Glu Ala Leu Pro Asp Pro
                405                 410                 415

Asp Asn Arg Leu Thr Leu Ser Lys Asp His Lys Asp Ile Leu Gly Ile
            420                 425                 430

Pro His Pro Glu Val Tyr Tyr Lys Leu Pro Glu Tyr Thr Val Arg Ser
        435                 440                 445

Cys Glu His Thr Arg Tyr Val Phe Arg Asp Leu Ile Lys Leu Met His
    450                 455                 460

Gly Thr Asp Glu Gln Trp Thr Pro Gly Tyr Phe Pro Gln Asp His Pro
465                 470                 475                 480

Ala Gly Ser Thr Ile Met Gly Thr Asp Pro Lys Asp Ser Val Val Asp
                485                 490                 495

Gly His Cys Arg Thr His Asp His Asp Asn Leu Phe Ile Ala Ser Ser
            500                 505                 510

Ser Val Phe Ser Thr Val Gly Thr Gly Asn Ile Thr Leu Thr Val Ala
        515                 520                 525

Ala Leu Ala Leu Arg Val Ala Asp Thr Leu Lys Lys Glu Leu
    530                 535                 540

<210> SEQ ID NO 125
<211> LENGTH: 528
<212> TYPE: PRT
<213> ORGANISM: Artificial Sequence
<220> FEATURE:
<223> OTHER INFORMATION: Recombinant sequence

<400> SEQUENCE: 125
```

-continued

```
Ser Asp Ser Leu Ser Ala Asp Val Val Ile Gly Ala Gly Ile Ala
1               5                   10                  15

Gly Ser Leu Ala Ala Leu Lys Met Ala Lys Ala Gly Ala Ser Val Leu
                20                  25                  30

Met Leu Glu Ser Gly Pro Glu Ile Lys Arg Asp Gln Val Val Glu Tyr
        35                  40                  45

Phe Arg Asn Ser Pro Phe Lys Gly Asp Phe Thr Glu Pro Tyr Pro Pro
    50                  55                  60

Gln Pro Trp Ala Pro Gln Pro Lys Phe Ile Pro Ser Asp Asn Asn Tyr
65                  70                  75                  80

Leu Ile Gln Lys Gly Pro Asp Pro Tyr Arg Ala Gln Tyr Leu Arg Gly
                85                  90                  95

Thr Gly Gly Thr Thr Trp His Trp Ala Gly Gln Ala Phe Arg Leu Leu
                100                 105                 110

Pro Asn Asp Met Arg Ile Gln Ser Leu Tyr Gly Ile Gly Arg Asp Trp
            115                 120                 125

Pro Ile Ser Tyr Asp Glu Leu Glu Pro Tyr Tyr Cys Asp Ala Glu Tyr
        130                 135                 140

Gln Met Gly Val Ser Gly Asp Ser Asp Leu Ala Ser Pro Arg Ser Arg
145                 150                 155                 160

Pro Tyr Pro Leu Pro Gly Ile Pro Leu Pro Tyr Gly Phe Asp Arg Leu
                165                 170                 175

Lys Gln Arg Leu Gly Pro Leu Gly Tyr Glu Val Gly Ile Gly Pro Gln
            180                 185                 190

Ala Arg Asn Ser Ile Ala Tyr Asp Gly Arg Pro Ala Cys Cys Gly Asn
        195                 200                 205

Asn Asn Cys Met Pro Val Cys Pro Ile Asp Ala Gln Tyr His Gly Gly
    210                 215                 220

Ile Ala Ala Arg Lys Ala Leu Asp Ala Gly Val Lys Ile Val Thr Asn
225                 230                 235                 240

Ala Val Val Phe Arg Ile Glu Ala Asp Asp Lys Gly Thr Ile Gln Ala
                245                 250                 255

Val His Tyr Leu Asp Gln Asn Lys Ala Arg His Arg Val Thr Gly Lys
            260                 265                 270

Gln Phe Val Leu Thr Ala Asn Gly Ile Glu Ser Pro Lys Ile Leu Leu
        275                 280                 285

Leu Ser Thr Ser Asp Arg Tyr Pro Asn Gly Ile Ala Asn Ser Ser Gly
    290                 295                 300

Met Val Gly Arg Asn Leu Met Asp His Pro Gly Ser Ser Val Glu Phe
305                 310                 315                 320

Tyr Ala Asp Glu Pro Val Trp Phe Gly Arg Gly Pro Met Arg Pro Gly
                325                 330                 335

Ser Ile Asn Asn Met Arg Asp Gly Asp Phe Arg Gly Glu Arg Ser Ala
            340                 345                 350

Leu Arg Ile Asp Leu Ala Asn Thr Ser Pro Val Arg Tyr Leu Thr Glu
        355                 360                 365

Arg Leu Val Arg Gln Gly Tyr Tyr Gly Lys Ala Leu Asn Asp Lys Leu
370                 375                 380

Ala Phe Gln Ala Glu Arg Phe Val Gln Leu Lys Cys Leu Leu Glu Met
385                 390                 395                 400

Leu Pro Glu Pro Gln Asn Arg Val Thr Leu Ser Lys Thr Glu Lys Asp
                405                 410                 415
```

```
Ala Trp Gly Ile Pro Arg Leu Glu Val Tyr Tyr Ser Phe Pro Glu Tyr
            420                 425                 430

Val His Arg Gly Tyr Asp Gln Ser Met Ile Asp Phe Gln Arg Met Val
            435                 440                 445

Lys Glu Met Gly Gly Thr Glu Ala Val Tyr Ser Lys Arg Gly Val Tyr
450                 455                 460

Asp Asn Asn Gln His Ile Thr Gly Thr Met Ile Met Gly Ser Asn Pro
465                 470                 475                 480

Gln Asp Ser Val Val Asp Gly His Cys Arg Thr His Asp His Pro Asn
                485                 490                 495

Leu Phe Ile Ala Gly Thr Gly Ile Met Pro Ser Ala Ser Thr Val Asn
            500                 505                 510

Ser Thr Leu Thr Gly Thr Ala Leu Ala Leu Arg Met Ala Asp Ser Val
            515                 520                 525

<210> SEQ ID NO 126
<211> LENGTH: 533
<212> TYPE: PRT
<213> ORGANISM: Artificial Sequence
<220> FEATURE:
<223> OTHER INFORMATION: Recombinant sequence

<400> SEQUENCE: 126

Ser Glu Thr Ile Thr Thr Asp Ile Val Ile Gly Ser Gly Val Val
1               5                   10                  15

Gly Ala Leu Thr Ala Arg Lys Leu Ala Leu Ala Gly Arg Gln Val Leu
            20                  25                  30

Met Leu Glu Ala Gly Pro Arg Ile Glu Arg Asp Thr Ile Val Ser Asn
        35                  40                  45

Phe Arg His Ser Ala Arg Lys Asp Asp Phe Ile Ala Pro Tyr Pro Asn
    50                  55                  60

Ser Lys Ile Ala Pro Phe Pro Asp Tyr Lys Pro Glu Asp Asn Gly Tyr
65                  70                  75                  80

Leu Asp Gln Thr Gly Pro Lys Asp Tyr Lys Pro Glu Tyr Leu Arg Val
                85                  90                  95

Val Gly Gly Thr Ser Trp His Trp Ala Ala Gln Ala Trp Arg Leu Val
            100                 105                 110

Pro Ala Asp Phe Arg Leu Lys Ser Gln Tyr Gly Val Gly Arg Asp Trp
        115                 120                 125

Pro Ile Ser Tyr Asp Asp Leu Glu Pro Tyr Tyr Tyr Glu Ala Glu Leu
    130                 135                 140

Leu Trp Gly Val Ser Gly Pro Pro Glu Met Ala Lys Tyr Ser Pro Arg
145                 150                 155                 160

Lys Gln Pro Phe Pro Met Pro Pro Val Thr Lys Ser Trp Leu Glu Gln
                165                 170                 175

Arg Ile Thr Glu Arg Leu Ala Pro Lys Tyr Glu Val Leu Thr Asn Thr
            180                 185                 190

Thr Gly Arg Asn Ser Arg Pro Tyr Asp Gly Arg Pro Gln Cys Cys Gly
        195                 200                 205

Asn Asn Asn Cys Met Pro Ile Cys Pro Ile Asp Ala Gln Tyr His Gly
    210                 215                 220

Gly Ile Ala Ala Asp Ala Ala Glu Lys Ala Gly Val Lys Leu Leu Pro
225                 230                 235                 240

Gln Ala Val Val Tyr Lys Leu Glu Gln Asp Gly Lys Gly Lys Ile Thr
                245                 250                 255
```

```
Ala Val His Tyr Tyr Asp Trp Asn Lys Gln Ser His Arg Val Glu Ala
            260                 265                 270

Glu Ile Val Val Leu Ala Ala Asn Ala Val Glu Thr Pro Lys Ile Leu
        275                 280                 285

Phe Met Ser Ala Asp Ala Lys Asn Pro His Gly Leu Cys Asn Asn Tyr
    290                 295                 300

Asp Gln Leu Gly Arg Asn Leu Met Asp His Pro Ser Asn Ser Val Thr
305                 310                 315                 320

Phe Phe Ala Asp Glu Pro Leu Trp Pro Gly Arg Gly Pro Met Ser Pro
            325                 330                 335

Ser Ser Ile Gln Gln Leu Arg Asp Gly Ala Phe Arg Ser Glu Ser Ala
        340                 345                 350

Ala Phe Arg Ile Asp Ile Ser Asn Ser Ser Arg Val Ala Gly Val Thr
    355                 360                 365

Ala Gly Ala Ile Lys Glu Gly Leu Thr Gly Gln Ala Leu Asp Asp Ala
370                 375                 380

Ile Arg Phe Arg Ala Ser His Glu Leu Ser Phe Lys Asn Val Leu Glu
385                 390                 395                 400

Gln Leu Pro Asp Pro Asn Asn Arg Thr Met Leu Ser Thr Thr Lys Lys
            405                 410                 415

Asp Ala Leu Gly Leu Pro Thr Pro Ala Phe Ser Tyr Ser Phe Asp Ser
        420                 425                 430

Tyr Val Glu Lys Gly Met Gln His Ser Leu Ala Val Tyr Ala Glu Ile
    435                 440                 445

Ala Lys Met Leu Gly Ala Thr Asn Val Arg Tyr Ser Thr Pro Gly Val
450                 455                 460

Tyr Ser Asn Asn Gln His Ile Thr Gly Thr Leu Ala Met Gly Phe Asp
465                 470                 475                 480

Glu Lys Thr Ser Val Thr Asp His His Gly Lys Ala Trp Glu Tyr Asp
            485                 490                 495

Asn Leu Tyr Met Val Ser Thr Gly Val Met Pro Thr Val Ala Thr Ala
        500                 505                 510

Asn Ser Thr Leu Thr Ala Cys Ala Leu Gly Leu Arg Thr Ala Asp Ala
    515                 520                 525

Ile Leu Gly Lys Ile
    530

<210> SEQ ID NO 127
<211> LENGTH: 542
<212> TYPE: PRT
<213> ORGANISM: Artificial Sequence
<220> FEATURE:
<223> OTHER INFORMATION: Recombinant sequence

<400> SEQUENCE: 127

Met Ser Ser Glu His Asn Leu Ser Ala Asp Val Val Ile Val Gly Ser
1               5                   10                  15

Gly Val Ala Gly Ser Ser Ile Ala Asn Glu Leu Ala Arg Ala Gly Ile
            20                  25                  30

Ser Val Ile Val Leu Glu Ala Gly Pro Arg Val Asp Arg Gln His Phe
        35                  40                  45

Val Glu Asn Phe Arg Asn Leu Glu Asn Lys Pro Ser Tyr Gln Gly Pro
    50                  55                  60

Phe Pro Ser Val Pro Trp Ala Ile His Pro Pro Asn Gln Ile Thr Pro
65                  70                  75                  80
```

```
Asn Glu Tyr Leu His Thr Thr Gly Pro Asp Ala Glu Ala Tyr Gln Gln
             85                  90                  95

Val Tyr Leu Arg Met Met Gly Thr Thr Trp His Trp Ala Gly Cys
            100                 105                 110

Ala Trp Arg Tyr Leu Pro Ser Asp Phe Glu Leu Lys Ser Arg Tyr Gly
            115                 120                 125

Gln Gly Arg Asp Trp Ala Leu Lys Tyr Glu Asp Leu Glu Pro Phe Tyr
        130                 135                 140

Tyr Gln Ala Glu Val Met Met Gly Val Cys Gly Pro Asp Pro Ser Val
145                 150                 155                 160

Glu Asp Leu Gly Ser Pro Arg Gln Gln Pro Tyr Pro Met Glu Ala Leu
                165                 170                 175

Pro Ile Ser Tyr Ala Ala Gln Gln Phe Arg Lys Leu Ile Ser Glu Lys
            180                 185                 190

Thr Pro Trp Arg Val Val His Glu Pro Gln Ala Arg Asn Thr Arg Pro
        195                 200                 205

Tyr Asp Asn Arg Pro Thr Cys Glu Gly His Asn Asn Cys Met Pro Ile
210                 215                 220

Cys Pro Ile Gly Ala Met Tyr Asn Gly Ser Tyr Ser Val Tyr His Ala
225                 230                 235                 240

Glu Ala Ala Gly Ala Lys Phe Ile Pro Asn Ala Val Val Tyr Arg Ile
                245                 250                 255

Glu Arg Asp Ser Ala Asn Lys Arg Val Thr Ala Val His Tyr Tyr Asp
                260                 265                 270

Pro Asp Lys Gly Ser His Arg Val Thr Gly Lys Tyr Phe Val Ile Ala
        275                 280                 285

Ala His Cys Ile Glu Thr Ala Lys Leu Leu Leu Val Ser Ala Asp Glu
290                 295                 300

Gln Ser Pro Asp Gly Ile Ala Asn Ser Ser Gly His Val Gly Arg Asn
305                 310                 315                 320

Met Met Asp His Thr Gly Val Gln Val Ser Phe Ile Ser Gly Asp Lys
                325                 330                 335

Ala Leu Trp Pro Gly Arg Gly Pro Leu Glu Thr Asn Val Ile Asp Asn
                340                 345                 350

Phe Arg Asp Gly Ala Trp Arg Asp Thr Arg Gly Ala Tyr Leu Val His
        355                 360                 365

Met Val Asp Asp Asn Gln Val Asp Leu Ala Thr Ala Leu Ala Ile Ser
370                 375                 380

Lys Gly Tyr Val Gly Arg Glu Leu Glu Glu Gln Ile Arg Tyr Leu Ala
385                 390                 395                 400

Ser His Thr Val Arg Leu Phe Ser His Asn Glu Gly Ile Ala Asp Pro
                405                 410                 415

Gln Asn Arg Leu Thr Leu Ser Gln Thr His Lys Asp Val Leu Gly Ile
            420                 425                 430

Pro His Pro Glu Val Tyr Tyr Lys Leu Pro Glu Tyr Thr Val Lys Ser
        435                 440                 445

Cys Glu His Thr Arg Gly Met Phe Arg Glu Leu Ile Gly Leu Met His
        450                 455                 460

Gly Thr Asp Glu Gln Trp Thr Pro Gly Tyr Phe Pro Gln Asp His Pro
465                 470                 475                 480

Ala Gly Ser Thr Ile Met Gly Thr Asp Pro Lys Asp Ser Val Val Asp
                485                 490                 495

Gly Phe Cys Arg Thr His Asp His Glu Asn Leu Phe Met Ala Ser Ser
```

```
                           500                 505                 510
Ser Val Phe Ser Ser Val Gly Thr Gly Asn Ile Thr Leu Thr Val Ala
            515                 520                 525
Ala Leu Ala Leu Arg Val Ala Asp Thr Leu Lys Lys Glu Leu
    530                 535                 540

<210> SEQ ID NO 128
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Ser, Cys, Thr, Met, Val, Tyr, Asn, Pro, Leu,
      Gly, Gln, Ala, Ile, Asp, Trp, His, or Glu
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (29)..(31)
<223> OTHER INFORMATION: Any amino acid
<220> FEATURE:
<221> NAME/KEY: MOD_RES
<222> LOCATION: (33)..(36)
<223> OTHER INFORMATION: Any amino acid
<220> FEATURE:
<221> NAME/KEY: MOD_RES
<222> LOCATION: (38)..(39)
<223> OTHER INFORMATION: Any amino acid
<220> FEATURE:
<221> NAME/KEY: MOD_RES
<222> LOCATION: (41)..(47)
<223> OTHER INFORMATION: Any amino acid
<220> FEATURE:
<221> NAME/KEY: MOD_RES
<222> LOCATION: (49)..(52)
<223> OTHER INFORMATION: Any amino acid
<220> FEATURE:
<221> NAME/KEY: MOD_RES
<222> LOCATION: (54)..(87)
<223> OTHER INFORMATION: Any amino acid
<220> FEATURE:
<221> NAME/KEY: MISC_FEATURE
<222> LOCATION: (54)..(87)
<223> OTHER INFORMATION: This region may encompass 32-34 residues
<220> FEATURE:
<221> NAME/KEY: MOD_RES
<222> LOCATION: (88)..(88)
<223> OTHER INFORMATION: His, Leu, Ser or Val

<400> SEQUENCE: 128

Leu Xaa Xaa Xaa Xaa Xaa Xaa Xaa Xaa Xaa Xaa Xaa Xaa Xaa Xaa Asp
1               5                   10                  15
```

Xaa Xaa Xaa Glu Xaa Xaa Xaa Pro Xaa Asn Arg Xaa Xaa Xaa Ser
         20                  25                  30

Xaa Xaa Xaa Xaa Asp Xaa Xaa Gly Xaa Xaa Xaa Xaa Xaa Xaa Tyr
             35                  40                  45

Xaa Xaa Xaa Xaa Tyr Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
             85

<210> SEQ ID NO 129
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(11)
<223> OTHER INFORMATION: Any amino acid
<220> FEATURE:
<221> NAME/KEY: MISC_FEATURE
<222> LOCATION: (1)..(11)
<223> OTHER INFORMATION: This region may encompass 3-11 residues
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(21)
<223> OTHER INFORMATION: Any amino acid
<220> FEATURE:
<221> NAME/KEY: MOD_RES
<222> LOCATION: (23)..(25)
<223> OTHER INFORMATION: Any amino acid
<220> FEATURE:
<221> NAME/KEY: MOD_RES
<222> LOCATION: (27)..(31)
<223> OTHER INFORMATION: Any amino acid
<220> FEATURE:
<221> NAME/KEY: MOD_RES
<222> LOCATION: (34)..(35)
<223> OTHER INFORMATION: Any amino acid
<220> FEATURE:
<221> NAME/KEY: MOD_RES
<222> LOCATION: (37)..(38)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (44)..(46)
<223> OTHER INFORMATION: Any amino acid
<220> FEATURE:
<221> NAME/KEY: MOD_RES
<222> LOCATION: (48)..(50)
<223> OTHER INFORMATION: Any amino acid
<220> FEATURE:
<221> NAME/KEY: MOD_RES
<222> LOCATION: (52)..(53)
<223> OTHER INFORMATION: Any amino acid

```
<220> FEATURE:
<221> NAME/KEY: MOD_RES
<222> LOCATION: (56)..(59)
<223> OTHER INFORMATION: Any amino acid
<220> FEATURE:
<221> NAME/KEY: MOD_RES
<222> LOCATION: (61)..(65)
<223> OTHER INFORMATION: Any amino acid
<220> FEATURE:
<221> NAME/KEY: MOD_RES
<222> LOCATION: (67)..(67)
<223> OTHER INFORMATION: Any amino acid
<220> FEATURE:
<221> NAME/KEY: MOD_RES
<222> LOCATION: (69)..(72)
<223> OTHER INFORMATION: Any amino acid
<220> FEATURE:
<221> NAME/KEY: MOD_RES
<222> LOCATION: (74)..(75)
<223> OTHER INFORMATION: Any amino acid
<220> FEATURE:
<221> NAME/KEY: MOD_RES
<222> LOCATION: (77)..(82)
<223> OTHER INFORMATION: Any amino acid
<220> FEATURE:
<221> NAME/KEY: MISC_FEATURE
<222> LOCATION: (77)..(82)
<223> OTHER INFORMATION: This region may encompass 5-6 residues
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (87)..(89)
<223> OTHER INFORMATION: Any amino acid
<220> FEATURE:
<221> NAME/KEY: MOD_RES
<222> LOCATION: (91)..(99)
<223> OTHER INFORMATION: Any amino acid
<220> FEATURE:
<221> NAME/KEY: MISC_FEATURE
<222> LOCATION: (91)..(99)
<223> OTHER INFORMATION: This region may encompass 7-9 residues
<220> FEATURE:
<221> NAME/KEY: MOD_RES
<222> LOCATION: (101)..(101)
<223> OTHER INFORMATION: Any amino acid
<220> FEATURE:
<221> NAME/KEY: MOD_RES
<222> LOCATION: (103)..(104)
<223> OTHER INFORMATION: Any amino acid
<220> FEATURE:
<221> NAME/KEY: MOD_RES
<222> LOCATION: (108)..(108)
<223> OTHER INFORMATION: Any amino acid
<220> FEATURE:
<221> NAME/KEY: MOD_RES
<222> LOCATION: (113)..(116)
<223> OTHER INFORMATION: Any amino acid
<220> FEATURE:
<221> NAME/KEY: MOD_RES
<222> LOCATION: (118)..(119)
<223> OTHER INFORMATION: Any amino acid
<220> FEATURE:
<221> NAME/KEY: MOD_RES
<222> LOCATION: (121)..(121)
<223> OTHER INFORMATION: Any amino acid
<220> FEATURE:
<221> NAME/KEY: MOD_RES
<222> LOCATION: (123)..(128)
<223> OTHER INFORMATION: Any amino acid
<220> FEATURE:
<221> NAME/KEY: MOD_RES
<222> LOCATION: (131)..(132)
<223> OTHER INFORMATION: Any amino acid
<220> FEATURE:
<221> NAME/KEY: MOD_RES
<222> LOCATION: (136)..(138)
```

```
<223> OTHER INFORMATION: Any amino acid
<220> FEATURE:
<221> NAME/KEY: MOD_RES
<222> LOCATION: (140)..(142)
<223> OTHER INFORMATION: Any amino acid
<220> FEATURE:
<221> NAME/KEY: MOD_RES
<222> LOCATION: (144)..(145)
<223> OTHER INFORMATION: Any amino acid
<220> FEATURE:
<221> NAME/KEY: MOD_RES
<222> LOCATION: (147)..(148)
<223> OTHER INFORMATION: Any amino acid
<220> FEATURE:
<221> NAME/KEY: MOD_RES
<222> LOCATION: (151)..(153)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (158)..(166)
<223> OTHER INFORMATION: Any amino acid
<220> FEATURE:
<221> NAME/KEY: MISC_FEATURE
<222> LOCATION: (158)..(166)
<223> OTHER INFORMATION: This region may encompass 5-9 residues
<220> FEATURE:
<221> NAME/KEY: MOD_RES
<222> LOCATION: (170)..(173)
<223> OTHER INFORMATION: Any amino acid
<220> FEATURE:
<221> NAME/KEY: MOD_RES
<222> LOCATION: (175)..(199)
<223> OTHER INFORMATION: Any amino acid
<220> FEATURE:
<221> NAME/KEY: MISC_FEATURE
<222> LOCATION: (175)..(199)
<223> OTHER INFORMATION: This region may encompass 23-25 residues
<220> FEATURE:
<221> NAME/KEY: MOD_RES
<222> LOCATION: (201)..(206)
<223> OTHER INFORMATION: Any amino acid
<220> FEATURE:
<221> NAME/KEY: MOD_RES
<222> LOCATION: (209)..(211)
<223> OTHER INFORMATION: Any amino acid
<220> FEATURE:
<221> NAME/KEY: MOD_RES
<222> LOCATION: (214)..(214)
<223> OTHER INFORMATION: Any amino acid
<220> FEATURE:
<221> NAME/KEY: MOD_RES
<222> LOCATION: (217)..(217)
<223> OTHER INFORMATION: Any amino acid
<220> FEATURE:
<221> NAME/KEY: MOD_RES
<222> LOCATION: (219)..(219)
<223> OTHER INFORMATION: Any amino acid
<220> FEATURE:
<221> NAME/KEY: MOD_RES
<222> LOCATION: (221)..(221)
<223> OTHER INFORMATION: Any amino acid
<220> FEATURE:
<221> NAME/KEY: MOD_RES
<222> LOCATION: (227)..(227)
<223> OTHER INFORMATION: Any amino acid
<220> FEATURE:
<221> NAME/KEY: MOD_RES
<222> LOCATION: (230)..(231)
<223> OTHER INFORMATION: Any amino acid
<220> FEATURE:
<221> NAME/KEY: MOD_RES
<222> LOCATION: (233)..(233)
<223> OTHER INFORMATION: Any amino acid
<220> FEATURE:
<221> NAME/KEY: MOD_RES
```

```
<222> LOCATION: (235)..(235)
<223> OTHER INFORMATION: Any amino acid
<220> FEATURE:
<221> NAME/KEY: MOD_RES
<222> LOCATION: (237)..(242)
<223> OTHER INFORMATION: Any amino acid
<220> FEATURE:
<221> NAME/KEY: MOD_RES
<222> LOCATION: (244)..(245)
<223> OTHER INFORMATION: Any amino acid
<220> FEATURE:
<221> NAME/KEY: MOD_RES
<222> LOCATION: (248)..(253)
<223> OTHER INFORMATION: Any amino acid
<220> FEATURE:
<221> NAME/KEY: MOD_RES
<222> LOCATION: (257)..(259)
<223> OTHER INFORMATION: Any amino acid
<220> FEATURE:
<221> NAME/KEY: MOD_RES
<222> LOCATION: (261)..(269)
<223> OTHER INFORMATION: Any amino acid
<220> FEATURE:
<221> NAME/KEY: MISC_FEATURE
<222> LOCATION: (261)..(269)
<223> OTHER INFORMATION: This region may encompass 8-9 residues
<220> FEATURE:
<221> NAME/KEY: MOD_RES
<222> LOCATION: (271)..(272)
<223> OTHER INFORMATION: Any amino acid
<220> FEATURE:
<221> NAME/KEY: MOD_RES
<222> LOCATION: (274)..(274)
<223> OTHER INFORMATION: Any amino acid
<220> FEATURE:
<221> NAME/KEY: MOD_RES
<222> LOCATION: (276)..(280)
<223> OTHER INFORMATION: Any amino acid
<220> FEATURE:
<221> NAME/KEY: MOD_RES
<222> LOCATION: (284)..(288)
<223> OTHER INFORMATION: Any amino acid
<220> FEATURE:
<221> NAME/KEY: MOD_RES
<222> LOCATION: (290)..(291)
<223> OTHER INFORMATION: Any amino acid
<220> FEATURE:
<221> NAME/KEY: MOD_RES
<222> LOCATION: (293)..(295)
<223> OTHER INFORMATION: Any amino acid
<220> FEATURE:
<221> NAME/KEY: MOD_RES
<222> LOCATION: (297)..(298)
<223> OTHER INFORMATION: Any amino acid
<220> FEATURE:
<221> NAME/KEY: MOD_RES
<222> LOCATION: (300)..(303)
<223> OTHER INFORMATION: Any amino acid
<220> FEATURE:
<221> NAME/KEY: MOD_RES
<222> LOCATION: (305)..(309)
<223> OTHER INFORMATION: Any amino acid
<220> FEATURE:
<221> NAME/KEY: MOD_RES
<222> LOCATION: (311)..(311)
<223> OTHER INFORMATION: Any amino acid
<220> FEATURE:
<221> NAME/KEY: MOD_RES
<222> LOCATION: (313)..(314)
<223> OTHER INFORMATION: Any amino acid
<220> FEATURE:
<221> NAME/KEY: MOD_RES
<222> LOCATION: (316)..(320)
<223> OTHER INFORMATION: Any amino acid
<220> FEATURE:
<221> NAME/KEY: MOD_RES
<222> LOCATION: (324)..(324)
<223> OTHER INFORMATION: Any amino acid
<220> FEATURE:
```

```
<221> NAME/KEY: MOD_RES
<222> LOCATION: (328)..(331)
<223> OTHER INFORMATION: Any amino acid
<220> FEATURE:
<221> NAME/KEY: MOD_RES
<222> LOCATION: (333)..(333)
<223> OTHER INFORMATION: Any amino acid
<220> FEATURE:
<221> NAME/KEY: MOD_RES
<222> LOCATION: (335)..(341)
<223> OTHER INFORMATION: Any amino acid
<220> FEATURE:
<221> NAME/KEY: MISC_FEATURE
<222> LOCATION: (335)..(341)
<223> OTHER INFORMATION: This region may encompass 6-7 residues
<220> FEATURE:
<221> NAME/KEY: MOD_RES
<222> LOCATION: (343)..(343)
<223> OTHER INFORMATION: Any amino acid
<220> FEATURE:
<221> NAME/KEY: MOD_RES
<222> LOCATION: (348)..(356)
<223> OTHER INFORMATION: Any amino acid
<220> FEATURE:
<221> NAME/KEY: MOD_RES
<222> LOCATION: (360)..(361)
<223> OTHER INFORMATION: Any amino acid
<220> FEATURE:
<221> NAME/KEY: MOD_RES
<222> LOCATION: (363)..(381)
<223> OTHER INFORMATION: Any amino acid
<220> FEATURE:
<221> NAME/KEY: MOD_RES
<222> LOCATION: (383)..(396)
<223> OTHER INFORMATION: Any amino acid
<220> FEATURE:
<221> NAME/KEY: MISC_FEATURE
<222> LOCATION: (383)..(396)
<223> OTHER INFORMATION: This region may encompass 12-14 residues
<220> FEATURE:
<221> NAME/KEY: MOD_RES
<222> LOCATION: (398)..(411)
<223> OTHER INFORMATION: Any amino acid
<220> FEATURE:
<221> NAME/KEY: MOD_RES
<222> LOCATION: (413)..(413)
<223> OTHER INFORMATION: Any amino acid
<220> FEATURE:
<221> NAME/KEY: MOD_RES
<222> LOCATION: (414)..(414)
<223> OTHER INFORMATION: Ser, Cys, Thr, Met, Val, Tyr, Asn, Pro, Leu,
      Gly, Gln, Ala, Ile, Asp, Trp, His, or Glu
<220> FEATURE:
<221> NAME/KEY: MOD_RES
<222> LOCATION: (415)..(415)
<223> OTHER INFORMATION: Any amino acid
<220> FEATURE:
<221> NAME/KEY: MOD_RES
<222> LOCATION: (417)..(420)
<223> OTHER INFORMATION: Any amino acid
<220> FEATURE:
<221> NAME/KEY: MOD_RES
<222> LOCATION: (422)..(422)
<223> OTHER INFORMATION: Any amino acid
<220> FEATURE:
<221> NAME/KEY: MOD_RES
<222> LOCATION: (425)..(427)
<223> OTHER INFORMATION: Any amino acid
<220> FEATURE:
<221> NAME/KEY: MOD_RES
<222> LOCATION: (429)..(432)
<223> OTHER INFORMATION: Any amino acid
<220> FEATURE:
<221> NAME/KEY: MOD_RES
<222> LOCATION: (434)..(435)
<223> OTHER INFORMATION: Any amino acid
<220> FEATURE:
<221> NAME/KEY: MOD_RES
<222> LOCATION: (437)..(443)
```

```
<223> OTHER INFORMATION: Any amino acid
<220> FEATURE:
<221> NAME/KEY: MOD_RES
<222> LOCATION: (445)..(448)
<223> OTHER INFORMATION: Any amino acid
<220> FEATURE:
<221> NAME/KEY: MOD_RES
<222> LOCATION: (450)..(483)
<223> OTHER INFORMATION: Any amino acid
<220> FEATURE:
<221> NAME/KEY: MISC_FEATURE
<222> LOCATION: (450)..(483)
<223> OTHER INFORMATION: This region may encompass 32-34 residues
<220> FEATURE:
<221> NAME/KEY: MOD_RES
<222> LOCATION: (484)..(484)
<223> OTHER INFORMATION: His, Leu, Ser or Val
<220> FEATURE:
<221> NAME/KEY: MOD_RES
<222> LOCATION: (485)..(486)
<223> OTHER INFORMATION: Any amino acid
<220> FEATURE:
<221> NAME/KEY: MOD_RES
<222> LOCATION: (488)..(489)
<223> OTHER INFORMATION: Any amino acid
<220> FEATURE:
<221> NAME/KEY: MOD_RES
<222> LOCATION: (491)..(493)
<223> OTHER INFORMATION: Any amino acid
<220> FEATURE:
<221> NAME/KEY: MOD_RES
<222> LOCATION: (496)..(500)
<223> OTHER INFORMATION: Any amino acid
<220> FEATURE:
<221> NAME/KEY: MOD_RES
<222> LOCATION: (503)..(503)
<223> OTHER INFORMATION: Any amino acid
<220> FEATURE:
<221> NAME/KEY: MOD_RES
<222> LOCATION: (505)..(513)
<223> OTHER INFORMATION: Any amino acid
<220> FEATURE:
<221> NAME/KEY: MOD_RES
<222> LOCATION: (516)..(527)
<223> OTHER INFORMATION: Any amino acid
<220> FEATURE:
<221> NAME/KEY: MOD_RES
<222> LOCATION: (529)..(529)
<223> OTHER INFORMATION: Any amino acid
<220> FEATURE:
<221> NAME/KEY: MOD_RES
<222> LOCATION: (531)..(531)
<223> OTHER INFORMATION: Any amino acid
<220> FEATURE:
<221> NAME/KEY: MOD_RES
<222> LOCATION: (535)..(536)
<223> OTHER INFORMATION: Any amino acid
<220> FEATURE:
<221> NAME/KEY: MOD_RES
<222> LOCATION: (539)..(539)
<223> OTHER INFORMATION: Any amino acid
<220> FEATURE:
<221> NAME/KEY: MOD_RES
<222> LOCATION: (541)..(543)
<223> OTHER INFORMATION: Any amino acid
<220> FEATURE:
<221> NAME/KEY: MOD_RES
<222> LOCATION: (545)..(550)
<223> OTHER INFORMATION: Any amino acid
<220> FEATURE:
<221> NAME/KEY: MISC_FEATURE
<222> LOCATION: (545)..(550)
<223> OTHER INFORMATION: This region may encompass 2-6 residues

<400> SEQUENCE: 129

Xaa Xaa Xaa Xaa Xaa Xaa Xaa Xaa Xaa Xaa Xaa Asp Xaa Val Xaa Xaa
1               5                   10                  15
```

```
Gly Xaa Gly Xaa Xaa Gly Xaa Xaa Ala Xaa Xaa Xaa Xaa Ala
        20              25              30

Gly Xaa Xaa Val Xaa Xaa Leu Glu Xaa Gly Pro Xaa Xaa Xaa Arg Xaa
        35              40              45

Xaa Xaa Val Xaa Xaa Phe Arg Xaa Xaa Xaa Xaa Lys Xaa Xaa Xaa Xaa
        50              55              60

Xaa Pro Xaa Pro Xaa Xaa Xaa Ala Xaa Xaa Pro Xaa Xaa Xaa Xaa
65              70              75              80

Xaa Xaa Asn Xaa Tyr Leu Xaa Xaa Xaa Gly Xaa Xaa Xaa Xaa Xaa
            85              90              95

Xaa Xaa Xaa Tyr Xaa Arg Xaa Xaa Gly Gly Thr Xaa Trp His Trp Ala
            100             105             110

Xaa Xaa Xaa Xaa Arg Xaa Xaa Pro Xaa Asp Xaa Xaa Xaa Xaa Xaa
            115             120             125

Tyr Gly Xaa Xaa Arg Asp Trp Xaa Xaa Xaa Tyr Xaa Xaa Xaa Glu Xaa
        130             135             140

Xaa Tyr Xaa Xaa Ala Glu Xaa Xaa Xaa Gly Val Xaa Gly Xaa Xaa Xaa
145             150             155             160

Xaa Xaa Xaa Xaa Xaa Xaa Ser Pro Arg Xaa Xaa Xaa Pro Xaa Xaa
            165             170             175

Xaa Xaa Xaa Xaa Xaa Xaa Xaa Xaa Xaa Xaa Xaa Xaa Xaa Xaa Xaa
            180             185             190

Xaa Xaa Xaa Xaa Xaa Val Xaa Xaa Xaa Xaa Xaa Arg Asn
            195             200             205

Xaa Xaa Xaa Tyr Asp Xaa Arg Pro Xaa Cys Xaa Gly Xaa Asn Asn Cys
            210             215             220

Met Pro Xaa Cys Pro Xaa Xaa Ala Xaa Tyr Xaa Gly Xaa Xaa Xaa Xaa
225             230             235             240

Xaa Xaa Ala Xaa Xaa Ala Gly Xaa Xaa Xaa Xaa Xaa Ala Val Val
            245             250             255

Xaa Xaa Xaa Glu Xaa Xaa Xaa Xaa Xaa Xaa Xaa Xaa Ala Xaa Xaa
            260             265             270

Tyr Xaa Asp Xaa Xaa Xaa Xaa Xaa His Arg Val Xaa Xaa Xaa Xaa
        275             280             285

Val Xaa Xaa Ala Xaa Xaa Xaa Glu Xaa Xaa Lys Xaa Xaa Xaa Xaa Ser
290             295             300

Xaa Xaa Xaa Xaa Xaa Pro Xaa Gly Xaa Xaa Asn Xaa Xaa Xaa Xaa
305             310             315             320

Gly Arg Asn Xaa Met Asp His Xaa Xaa Xaa Val Xaa Phe Xaa Xaa
            325             330             335

Xaa Xaa Xaa Xaa Xaa Trp Xaa Gly Arg Gly Pro Xaa Xaa Xaa Xaa
            340             345             350

Xaa Xaa Xaa Xaa Arg Asp Gly Xaa Xaa Arg Xaa Xaa Xaa Xaa Xaa
            355             360             365

Xaa Xaa Xaa Xaa Xaa Xaa Xaa Xaa Xaa Xaa Thr Xaa Xaa
            370             375             380

Xaa Xaa Xaa Xaa Xaa Xaa Xaa Xaa Xaa Xaa Leu Xaa Xaa Xaa
385             390             395             400

Xaa Xaa Xaa Xaa Xaa Xaa Xaa Xaa Xaa Asp Xaa Xaa Xaa Glu
            405             410             415

Xaa Xaa Xaa Xaa Pro Xaa Asn Arg Xaa Xaa Ser Xaa Xaa Xaa Xaa
            420             425             430

Asp Xaa Xaa Gly Xaa Xaa Xaa Xaa Xaa Xaa Xaa Tyr Xaa Xaa Xaa Xaa
```

-continued

```
             435                 440                 445
Tyr Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa
465             470                 475                 480

Xaa Xaa Xaa Xaa Xaa Xaa His Xaa Xaa Gly Xaa Xaa Xaa Met Gly Xaa
            485                 490                 495

Xaa Xaa Xaa Xaa Ser Val Xaa Asp Xaa Xaa Xaa Xaa Xaa Xaa Xaa
        500                 505                 510

Xaa Asn Leu Xaa Xaa Xaa Xaa Xaa Xaa Xaa Xaa Xaa Xaa Xaa Thr
        515                 520                 525

Xaa Asn Xaa Thr Leu Thr Xaa Xaa Ala Leu Xaa Leu Xaa Xaa Xaa Asp
    530                 535                 540

Xaa Xaa Xaa Xaa Xaa Xaa
545             550
```